US008586055B2

(12) United States Patent
Felber et al.

(10) Patent No.: US 8,586,055 B2
(45) Date of Patent: Nov. 19, 2013

(54) DNA IMMUNIZATION PROTOCOLS

(75) Inventors: Barbara Felber, Rockville, MD (US); George N. Pavlakis, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 725 days.

(21) Appl. No.: 12/522,775

(22) PCT Filed: Jan. 14, 2008

(86) PCT No.: PCT/US2008/051004
§ 371 (c)(1),
(2), (4) Date: Jan. 5, 2010

(87) PCT Pub. No.: WO2008/089144
PCT Pub. Date: Jul. 24, 2008

(65) Prior Publication Data
US 2010/0285061 A1    Nov. 11, 2010

Related U.S. Application Data

(63) Continuation-in-part of application No. PCT/US2007/000774, filed on Jan. 12, 2007.

(60) Provisional application No. 60/934,366, filed on Jun. 12, 2007.

(51) Int. Cl.
*A61K 39/21* (2006.01)
*C07H 21/04* (2006.01)
*A01N 37/18* (2006.01)

(52) U.S. Cl.
USPC ..... 424/208.1; 536/23.1; 536/23.2; 536/23.4; 536/23.52; 536/23.72; 514/3.8

(58) Field of Classification Search
None
See application file for complete search history.

(56) References Cited

U.S. PATENT DOCUMENTS

| 8,124,084 B2 | 2/2012 | Lefrancois et al. |
| 2006/0147419 A1 | 7/2006 | Perera et al. |
| 2009/0238791 A1 | 9/2009 | Jacques et al. |

FOREIGN PATENT DOCUMENTS

| WO | WO 00/45823 A | 8/2000 |
| WO | WO 01/08702 A | 2/2001 |
| WO | WO 02/36806 A | 5/2002 |
| WO | WO 2006/010106 A | 1/2006 |
| WO | 2007/095643 A2 | 8/2007 |

OTHER PUBLICATIONS

Chikhlikar et al. DNA Encoding an HIV-1 Gag/Human Lysosome-Associated Membrane Protein-1 Chimera Elicits a Broad Cellular and Humoral Immune Response in *Rhesus macaques*. PLoS One, vol. 1(1), e135.*
Lodolce et al. IL-15 Receptor Maintains Lymphoid Homeostasis by Supporting Lymphocyte Homing and Proliferation. Immunity, Nov. 1998, vol. 9, p. 669-676.*
Kutzler et al. Coimmunization with an Optimized IL-15 Plasmid Results in Enhanced Function and Longevity of CD8 T Cells that Are Partially Independent of CD4 T Cell Help. Journal of Immunology 2005, vol. 175, p. 112-123.*
Altman et al. HIV escape: there and back again. Nature Medicine Mar. 2004 vol. 10, No. 3, p. 229-230.*
Derosiers. Prospects for an AIDS vaccine. Nature Medicine Mar. 2004, vol. 10, No. 3, p. 221-223.*
Feinberg et al. AIDS vaccine models: Challenging challenge viruses. Nature Medicine, Mar. 2002, vol. 8, No. 3, pp. 207-210.*
Haigwood, Predictive Value of Primate Models for AIDS. AIDS Reviews 2004, vol. 6, p. 187-198.*
Klein et al. Examination of the contributions of size and avidity to the neutralization mechanisms of the anti-HIV antibodies b12 and 4E10. Proceedings of the National Academy of Sciences of the United States of America Apr. 16, 2009, electronic publication Early Edition.*
Letvin. Progress toward an HIV vaccine. Annual Review of Medicine 2005, vol. 56, p. 213-223.*
Phogat et al. Inhibition of HIV-1 entry by antibodies: potential viral and cellular targets. Journal of Internal Medicine 2007. vol. 262, p. 26-43.*
Santra et al. Recombinant poxvirus boosting of DNA-primed rhesus monkeys augments peak but not memory T lymphocyte responses. Proceedings from the National Academy of Sciences USA . 2004, vol. 101, p. 11088-11093.*
Sekaly, R. The failed HIV Merck vaccine study: a step back or a launching point for future vaccine development? Journal of Experimental Medicine, Jan. 21, 2008, vol. 205, No. 1, p. 7-12.*
Whitney et al. Live attenuated HIV vaccines: pitfalls and prospects. Current Opinions in Infectious Disease 2004, vol. 17, p. 17-26.*
Yee et al. Prospects for gene therapy using HIV-based vectors. Somatic Cell and Molecular Genetics, Nov. 2001, vol. 26, No. 1/6, pp. 159-174.*
Philipkoski et al. Designer Virus Stalks HIV [online]. Wired News [retrieved on Apr. 20, 2011]. Fetrieved from the Internet: <URL:www.rense.com/general52/design.htm>.*
Otten, G., et al., "Potent immunogenicity of an HIV-1 *gag-pol* fusion DNA vaccine delivered by in vivo electroporation," *Vaccine*, vol. 24(21), pp. 4503-4509 (May 22, 2006).
Rabussay, D., et al., "Toward the Development of Electroporation for Delivery of DNA Vaccines to Humans," *Molecular Therapy*, vol. 9, Supplement 1, p. 209 (May 1, 2004).
Rosati, M., et al., "DNA Vaccines Expressing Different Forms of Simian Immunodeficiency Virus Antigens Decrease Viremia upon SIVmac251 Challenge," *Journal of Virology*, vol. 79(13), pp. 8480-8492 (Jul. 1, 2005).

(Continued)

*Primary Examiner* — Louise Humphrey
(74) *Attorney, Agent, or Firm* — Kilpatrick Townsend & Stockton LLP

(57) ABSTRACT

This invention provides DNA vaccines for the treatment of patients undergoing anti-retroviral therapy. The vaccines are surprisingly effective at controlling viremia.

6 Claims, 14 Drawing Sheets

(56) References Cited

OTHER PUBLICATIONS

Selby, M., et al., "Enhancement of DNA vaccine potency by electroporation in vivo," *Journal of Biotechnology*, vol. 83(1-2), pp. 147-152 (Sep. 29, 2000).

Dubois et al, "IL-15Rα Recycles and Presents IL-15 in trans to Neighboring Cells," *Immunity*, vol. 17, Nov. 2002, 537-547.

Giron-Michel, et al., "Membrane-Bound and Soluble IL-15/IL-15Rα Complexes Display Differential Signalling and Functions on Human Hematopoietic Progenitors," *Blood*, Oct. 1, 2005, vol. 106, No. 7, 2302-2310.

Mortier et al., "Natural, Proteolytic Release of a Soluble Form of Human IL-15 Receptor α-Chain That Behaves as a Specific, High Affinity IL-15 Antagonist," *The Journal of Immunology*, 2004, 173: 1681-1688.

Mortier et al., "Soluble Interleukin-15 Receptor α (IL-15Rα)-sushi as a Selective and Potent Agonist of IL-15 Through IL-15Rβ/γ," *Journal of Biological Chemistry*, vol. 281, No. 3, Jan. 20, 2006, 1612-1619.

Oh, et al., "IL-15/IL-15Rα-Mediated Avidity Maturation of Memory $CD8^+$ T Cells," *PNAS*, Oct. 19, 2004, vol. 101, No. 42, 15154-15159.

Rubinstein et al., "Converting IL-15 to a Superagonist by Binding to Soluble IL-15Rα," *PNAS*, Jun. 13, 2006, vol. 103, No. 24, 9166-9171.

Stoklasek et al., "Combined IL-15/IL-15Rα Immunotherapy Maximizes IL-15 Activity In Vivo," *The Journal of Immunology*, 2006, 177: 6072-6080.

* cited by examiner

Therapeutic DNA Immunization with Modified Forms of SIVmac239 antigens

IFNgamma- and IL2- producing T cells during vaccination and after release for 3 electroporated animals Central Memory and Effector Memory Responses to Gag During Vaccination Induction of antigen-specific IFNg+IL-2+ T cells with both Central and Effector memory phenotype Dramatic increase in Antigen-specific cells in Peripheral Blood after vaccination by electroporation Virus load measurements up to week 14 after release from ART Comparison of virus loads pre and post 2nd Therapeutic Vaccination by Electroporation Comparisons of virus loads during first and second therapeutic immunizations Specific SIV responses in naïve macaques vaccinated by electroporation Electroporation induces stronger and broader immune responses

Figure 12

```
wt     atg aga att tcg aaa cca cat ttg aga agt att tcc atc cag tgc tac ttg tgt tta ctt  60
opt    atg cgg atc tcg aag ccg cac ctg cgg tcg ata tcg atc cag tgc tac atg tgc atg ctg
opt-2  atg agg atc agc aag ccc cac ctg agg agc atc agc atc cag tgc tac ctg tgc atg ctg
       ***  *                **   *               *  *  *  *    **    *  ** wt     cta aac agt cat ttt cta act gaa gct ggc att cat gtc ttc att ttg ggc tgt ttc agt 120
opt    ctg aac tcg cac ttc ctc acg gag gcc ggt ata cac gtc ttc atc ctg ggc tgc ttc tcg
opt-2  ctg aac agc cac ttg ctg acc gag gcc ggt ata cac gtg ttc atc ctg ggc tgc ttt agc
          * wt     gca ggg ctt cct aaa aca gaa gcc aac tgg gtg aat gta ata agt gat ttg aaa aaa att 180
opt    gcg ggg ctg ccg aag acg gag gcg aac tgg gtg aac gtg atc tcg gac ctg aag aag atc
opt-2  gcc gga ctg ccc aag acc gag gcc aat tgg gtg aag gtg atc agc gac ctg aag aag atc
                                 *  *               ** wt     gaa gat ctt att caa tct atg cat att gat gct act tta tat acg gaa agt gat gtt cac 240
opt    gag gac ctc atc cag tcg atg cac atc gac gcg acg gtg tac acg gag tcg gac gtc cac
opt-2  gag gac ctc atc cag agc atg cac atc gac gcc acc gtg tac acc gag agc gat gtg cac
                *              **   *                  * wt     ccc agt tgc aaa gta aca gca atg aag tgc ttt ctc ttg gag tta caa gtt att tca ctt 300
opt    ccg tcg tgc aag gtc acg gcg atg aag tgc ttc ctc ctg gag ctc caa gtc atc tcg ctc
opt-2  ccc agc tgt aag gtg acc gcc atg aag tgc ttt ctg ctg gag ctg caa gtg atc agc ctg
       **    *        **   *                *  *  *          * wt     gag tct gga gat gca agt att cat gat aca gta gaa aat ctg atc atc cta gca aac aac 360
opt    gag tcg ggg gac gcg tcg atc cac gac acg gtg gag aac ctg atc atc ctg gcg aac aac
opt-2  gag agc ggg gac gcc agc atc cac gac acc gtg gag aag ctg atc atc ctg gcc aac aac
       *                                                *  * wt     agt ttg tct tct aat ggg aat gta aca gaa tct gga tgc aaa gaa tgt gag gaa ctg gag 420
opt    tcg ctg tcg tcg aac ggg aac gtc acg gag tcg ggc tgc aag gag tgc gag gag ctg gag
opt-2  agc ctg agc agc aac ggc aat gtg acc gag agc ggc tgt aag gag tgt gag gag ctg gag
                                                        *  * wt     gaa aaa aat att aaa gaa ttt ttg cag agt ttt gta cat att gtc caa atg ttc atc aac 480
opt    gag aag aac atc aag gag ttc ctg cag tcg ttc gtg cac atc gtc cag atg ttc atc aac
opt-2  gag aag aac atc aag gag ttt ctg cag agc ttg gtg cac atc gtg cag atg ttc atc aac
                           *                    *  *  *  *** wt     act tct tga
opt    acg tcg tga
opt-2  acg agc tga
       **      ***
```

Figure 13

```
ATG AGA ATT TCG AAA CCA CAT TTG AGA AGT ATT TCC ATC CAG TGC TAC TGG TGT TTA CTT
::: ::: ::: ::: ::: ::: ::: ::: ::: ::: ::: ::: ::: ::: ::: ::: ::: ::: ::: :::       60
ATG         TCG         CAT         ATA             AAC CAG TAC         CTG         CTG CTC

CTA AAC AGT CAT TTT CTA ACT GAA GCT ATT CAT GTC TTC ATT TTG GGC TGT TTC AGT
::: ::: ::: ::: ::: ::: ::: ::: ::: ::: ::: ::: ::: ::: ::: ::: ::: ::: ::: :::       120
CTG AAC                 TTC         CTC         GTC         TTC         ATC             CTG TGC         TCG

GCA GGG CTT CCT AAA ACA GAA GCC AAC TGG GTG AAT GTA ATA AGT GAT TTG AAA AAA ATT
::: ::: ::: ::: ::: ::: ::: ::: ::: ::: ::: ::: ::: ::: ::: ::: ::: ::: ::: :::       180
GCG         CTG         AAG         GAG         AAC TGG         AAC         CTG ATC         GAC

*Figure 14*

DNA IMMUNIZATION PROTOCOLS

CROSS-REFERENCE TO RELATED APPLICATIONS

This application is a U.S. National Stage Application of PCT/US2008/051004, which is a continuation-in-part application of PCT application no. PCT/US2007/000774, filed Jan. 12, 2007, and claims the benefit of U.S. provisional application no. 60/934,366, filed Jun. 12, 2007, the contents of which applications are herein incorporated by reference.

BACKGROUND OF THE INVENTION

Antiretroviral therapy (ART) to treat HIV has changed the outlook of HIV infection, since well-managed patients can remain free of symptoms for long periods. However, chronic use of the drugs leads to toxicities and virus resistance. Therapy must be continued indefinitely, since HIV (or SIV in macaques) remaining in pharmacological sanctuaries, rebounds rapidly upon treatment interruption.

The administration of nucleic acid-based vaccines, including both naked DNA and viral-based vaccines, to individuals that have undergone ART has been suggested (see, e.g., WO01/08702, WO04/041997). Further, the administration of DNA vaccines in prime boost protocols has been suggested (see, e.g., US application no. 2004/033237; Hel et al., *J. Immunol.* 169:4778-4787, 2002; Barnett et al., AIDS Res. and Human Retroviruses Volume 14, Supplement 3, 1998, pp. S-299-S-309 and Girard et al., C R Acad. Sci III 322:959-966, 1999 for reviews).

DNA immunization followed by administration of another highly attenuated poxvirus has also been tested for the ability to elicit IgG responses, but the interpretation of the results is hampered by the fact that serial challenges were performed (see, e.g., Fuller et al., *Vaccine* 15:924-926, 1997; Barnett et al., supra). In contrast, in a murine model of malaria, DNA vaccination used in conjunction with a recombinant vaccinia virus was promising in protecting from malaria infection (see, e.g., Sedegah et al., *Proc. Natl. Acad. Sci. USA* 95:7648-7653, 1998; Schneider et al., *Nat. Med.* 4:397-402, 1998).

DNA immunization plasmids have been developed that encode fusion proteins that contain a destabilizing amino acid sequence attached to a polypeptide sequence of interest that when administered with a secreted fusion protein containing a secretory peptide attached to a polypeptide of interest enhances the immune response (see. e.g., WO02/36806). Combinations of such DNA immunization plasmids have been administered to animals that have undergone antiretroviral therapy (WO06/010106). The current invention provides further improvements to protocols for administering DNA vaccines to individuals who have received ART that result in improvements in immune responses to the target antigen(s).

BRIEF SUMMARY OF THE INVENTION

The invention is based on the discovery of immunogenic compositions for the treatment of retrovirus infection that are surprisingly effective at controlling viremia in primates that are receiving or will receive antiretroviral therapy (ART), either alone or in conjunction with other therapeutic immunomodulating factors, such as DNA vectors expressing cytokines. These immunogenic compositions can induce potent and long-lasting virus-specific immune responses, which control viremia post-ART. The DNA vaccination regimens of the invention are surprisingly effective and, further, show evidence of triggering a Th1 response with more prominent induction of cellular immune responses.

The invention thus provides a method of treating an individual, preferably a human, infected with a retrovirus, e.g., HIV, the method comprising: administering an immunogenic composition comprising one or more expression vectors, wherein the one or more vectors encode: a fusion protein comprising a degradation polypeptide linked to an immunogenic retrovirus polypeptide, e.g., an HIV polypeptide; a secreted fusion protein comprising a secretory polypeptide linked to the immunogenic retrovirus polypeptide; a cytokine, e.g., a human cytokine where the individual is a human, (such as: an IL-15 polypeptide and IL-15 receptor alpha polypeptide; an IL-12 polypeptide consisting of the p35 and the p40 chains; an IL-2 polypeptide). The DNA vaccine is typically administered by electroporation and is usually administered multiple times, e.g., three times, four times, or more. DNA vaccines have the important property that they produce immune responses only against the desired antigen, and therefore they can be administered multiple times. The inventors have additionally discovered that administration of DNA vaccines to the same animal many times (e.g., 5, 6, 7, 8, or 9 times) continues to result in boosting of immune responses against the encoded antigen. The vaccine is administered while an individual is undergoing ART, or to an individual who has undergone ART. Administration of the DNA vaccine results in a prolonged immune response and control of viremia upon cessation of ART.

In particular embodiments, the invention provides a method of treating an individual infected with a virus, the method comprising: administering antiviral therapy (ART); administering an immunogenic composition by electroporation into a muscle of the individual, wherein the DNA vaccine comprises one or more expression vectors that comprise nucleic acid sequences that encode: a gag polypeptide, e.g., an HIV gag polypeptide, linked to a β-catenin destabilizing sequence; a gag polypeptide, e.g., an HIV gag polypeptide, linked to a secretory polypeptides such as an MCP-3 secretory polypeptide; wherein the DNA vaccine can be administered multiple times and administration of the DNA vaccine results in control of viremia upon cessation of ART. In some embodiments, the immunogenic composition comprises an expression vector that encodes an env polypeptide, e.g., an HIV env polypeptide. The env polypeptide can be linked, e.g., to a secretory signal polypeptide or to a degradation signal. The immunogenic composition can also comprise an expression vector that encodes a polypeptide comprising nef, tat, and vif antigens, e.g., HIV nef, tat, and vif antigens, in any effective order. The polypeptide can be linked to a degradation signal. In some embodiments, the linked epitopes are fusion proteins, such as Gag/Pol fusion proteins.

In some embodiments, the immunogenic composition comprises an expression vector that encodes an IL-15 receptor alpha polypeptide; and an expression vector that encodes an IL-15 polypeptide linked to a secretory signal polypeptide, which can be either a homologous or a heterologous secretory signal to the IL-15 polypeptide. The IL-15 receptor alpha polypeptide and the IL-5 polypeptide can be encoded on the same, or different, expression vectors.

In some embodiments, the immunogenic composition comprises an expression vector that encodes the IL-12 p40 and p35 chains preferably encoded on the same expression vector.

In some embodiments, the immunogenic composition comprises an expression vector that encodes IL-2.

In some embodiments, the immunogenic composition comprises an expression vector that encodes an HIV antigen linked to a lysosome targeting sequence, e.g., a LAMP sequence.

In some embodiments, the immunogenic composition, e.g., comprising expression vectors encoding HIV antigens, comprises an expression vector that encodes: an envelop polypeptide; an envelope polypeptide linked to an secretory signal polypeptide; a polymerase (pol) polypeptide linked to a degradation signal, e.g., a β-catenin degradation signal; a polypeptide comprising nef, tat, and vif antigens, where the polypeptide is linked to a degradation signal; an IL-15 receptor alpha polypeptide; and an IL-15 polypeptide linked to a different secretory signal polypeptide, e.g., tPA or GM-CSF or other signal. The secretory signal polypeptide of the envelope polypeptide linked to a secretory signal polypeptide can be, e.g., an MCP-3 or tPA signal.

In some embodiments, the envelope polypeptide linked to the secretory signal polypeptide is linked to an MCP-3-secretory signal; the pol polypeptide is linked to a LAMP degradation signal; the polypeptide comprising nef, tat, and vif antigens is linked to a LAMP degradation sequence; and the secretory signal polypeptide to which the IL-15 polypeptide is linked is the tPA secretory polypeptide or other secretory signals.

The immunogenic compositions can be administered to the individual while the individual is undergoing ART, or has undergone, ART. Thus, in some embodiments, the invention provides a method of treating an individual infected with a retrovirus, the method comprising: administering antiretroviral therapy (ART); administering an immunogenic composition by electroporation into a muscle of the individual, wherein the immunogenic composition comprises one or more expression vectors that comprise nucleic acid sequences that encode: a gag polypeptide linked to a β-catenin destabilizing sequence; a gag polypeptide linked to a MCP-3 secretory polypeptide; an envelope polypeptide; an envelope polypeptide linked to a MCP-3 secretory polypeptide; a pol polypeptide linked to a LAMP degradation signal; a polypeptide comprising nef, tat, and vif antigens, where the polypeptide is linked to a LAMP degradation signal; an IL-15 receptor alpha polypeptide; and an IL-15 receptor polypeptide linked to a heterologous secretory signal. The immunogenic composition can be administered repeatedly, often at least three times, and administration of the immunogenic composition results in control of viremia upon cessation of ART. Typically, the components of the immunogenic composition are encoded by multiple expression vectors. In some embodiments, combinations of the vector are administered to different sites, although the vectors can also be administered to the same site. The vectors can be administered at the same time, or at different times.

The invention also provides an immunogenic composition comprising least one expression vector that comprise nucleic acid sequences that encode: a gag polypeptide linked to a β-catenin destabilizing sequence; a gag polypeptide linked to a MCP-3 secretory polypeptide; an envelope polypeptide; an envelope polypeptide linked to an MCP-3 secretory polypeptide; a pol polypeptide linked to a LAMP degradation signal; a polypeptide comprising nef, tat, and vif antigens, where the polypeptide is linked to a LAMP degradation signal; an IL-15 receptor alpha polypeptide; and an IL-15 receptor polypeptide linked to a tPA secretory signal polypeptide.

BRIEF DESCRIPTION OF THE DRAWINGS

FIG. 12 illustrates the common positions of nucleotide changes (highlighted) in IL-15opt (SEQ ID NO:56) and IL-15opt2 (SEQ ID NO:57) sequences compared to wild type human IL-15 (SEQ ID NO:54). Changes at the positions of the indicated 115 nucleotides (highlighted) are sufficient for improved mRNA and protein expression of human IL-15 (an approximately 8-fold increase in comparison to wild-type human IL-15).

FIG. 13 illustrates a comparison of the nucleotide changes between wild-type human IL-15 (top; SEQ ID NO:54) and improved human IL-15opt (bottom; SEQ ID NO:56) nucleotide sequences. The improved human IL-15 sequence was changed at 120 of 162 total codons (74%). Forty-two (42) codons were left unchanged in comparison to the wild-type human IL-15 nucleotide sequence. The boxed codons indicate changes to "more preferred" codons according to the classification of Seed (U.S. Pat. No. 5,786,464) (62 codons). The underlined codons indicate codons changed to "less preferred" codons according to the classification of Seed (10 codons), in contradiction to the method of Seed. The grey highlighted codons indicate changes to "not preferred" codons (48 codons), also in contradiction to the method of Seed.

FIG. 14 illustrates a sequence alignment of the nucleic acid sequences of wild-type IL-15 (wt; SEQ ID NO:54), IL-15opt (opt; SEQ ID NO:56), and IL-15opt2 (opt-2; SEQ ID NO:57). Improvement of the coding sequences includes nucleotide changes that use "preferred" codons or "less preferred" codons, as defined in U.S. Pat. No. 5,786,464. IL-15opt has 72 preferred/less preferred codons (grey highlighted), and IL-15opt2 has 105 preferred/less preferred codons (grey highlighted). The boxed codons indicate changes to "not preferred" codons. In addition, improvements of the IL-15 coding sequences include nucleotide changes that are in contradiction to the method defined in U.S. Pat. No. 5,786,464.

DETAILED DESCRIPTION OF THE INVENTION

Definitions

Figure 1:
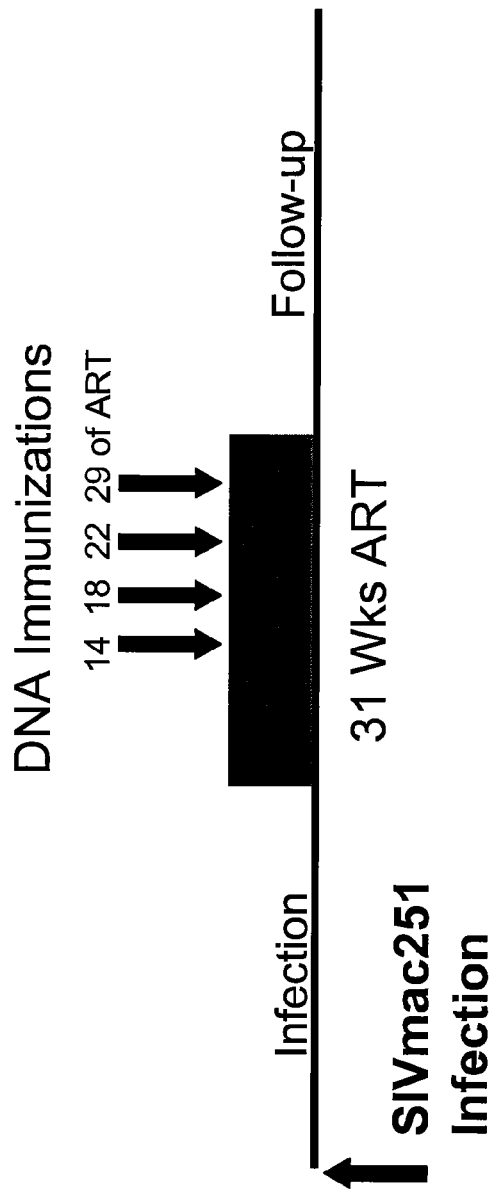
FIG. 1 provides a schematic of immunotherapy of *Rhesus macaques* chronically infected by SIVmac251. Animals received 3-4 immunizations during therapy and were observed for several months after ART termination.

A "nucleic acid vaccine" or "DNA vaccine" refers to a vaccine that includes one or more expression vectors, preferably administered as purified DNA, which enters the cells in the body, and is expressed.

A "destabilizing amino acid sequence" or "destabilization sequence" as used herein refers to a sequence that targets a protein for degradation in the ubiquitin proteosome pathway. Such sequences are well known in the art. Exemplary sequences are described, e.g., in WO 02/36806. A destabilizing sequence that is fused to an antigen of interest comprises the region of the molecule from which the destabilizing sequence is obtained that mediates interaction with the ubiquitin proteosome sequence.

A "secretory polypeptide" as used herein refers to a polypeptide that comprises a secretion signal that directs a molecule to be secreted. Typically, the "secretory polypeptide" that is part of the fusion protein is an immunostimulatory molecule such as a chemokine or cytokine.

A "molecular adjuvant" in the context of this invention refers to a composition that enhances the immune response.

These include molecules such as IL-2, IL-12, and the IL-15 and IL-15Receptor alpha combination.

Introduction

A recurring problem in anti-retroviral therapy is the rebound in viremia when therapy ceases. This invention is based on the discovery that vectors and combinations that produce either secreted or intracellularly degraded antigens are surprisingly effective at controlling viremia when administered to ART-treated subjects. The combination of different vectors is determined by evaluating the specific results for each particular antigen and providing the combination that gives the best results. These vectors can be used for the treatment of viral infections, e.g., for the treatment of HIV infection.

Expression Vectors Encoding Fusion Polypeptides Comprising a Degradation Signal

The nucleic acid vaccines of the invention are typically administered as "naked" DNA, i.e., as plasmid-based vectors. Since the antigens expressed by these DNA vectors are also well expressed in other expression systems, such as recombinant virus vectors, other expression vector systems may also be used either alternatively, or in combination with DNA vectors. These include viral vector systems such as cytomegalovirus, herpes virus, adenovirus, and the like. Such viral vector systems are well known in the art. The constructs of the invention can thus also be administered in viral vectors where the retroviral antigens, e.g., the HIV antigens, are incorporated into the viral genetic material.

Expression vectors encoding a fusion protein comprising a destabilization sequence that targets a protein for degradation linked to the immunogenic protein are used in the invention. Such vectors are described, e.g., in WO02/36806. A variety of sequence elements have been found to confer short lifetime on cellular proteins due to proteasomal degradation.

Targeting to the Proteasome and Other Degradation Signals

Many polypeptide sequences that target a protein for degradation are known in the art. One example of destabilizing sequences are so-called PEST sequences, which are abundant in the amino acids Pro, Asp, Glu, Ser, Thr (they need not be in a particular order), and can occur in internal positions in a protein sequence. A number of proteins reported to have PEST sequence elements are rapidly targeted to the 26S proteasome. A PEST sequence typically correlates with a) predicted surface exposed loops or turns and b) serine phosphorylation sites, e.g. the motif S/TP is the target site for cyclin dependent kinases.

Additional destabilization sequences relate to sequences present in the N-terminal region. In particular the rate of ubiquitination, which targets proteins for degradation, by the 26S proteasome can be influenced by the identity of the N-terminal residue of the protein. Thus, destabilization sequences can also comprise such N-terminal residues, "N-end rule" targeting (see, e.g., Tobery et al., *J. Exp. Med.* 185:909-920.).

Other targeting signals include the destruction box sequence that is present, e.g., in cyclins. Such a destruction box has a motif of 9 amino acids, R1(A/T)2(A)3L4(G)5X6(I/V)7(G/T)8(N)9, in which the only invariable residues are R and L in positions 1 and 4, respectively. The residues shown in brackets occur in most destruction sequences. (see, e.g., Hershko & Ciechanover, Annu. Rev. Biochem. 67:425-79, 1998). In other instances, destabilization sequences lead to phosphorylation of a protein at a serine residue (e.g., Iκbα)

Lysosomal Targeting Sequence

In other embodiments, signals that target proteins to the lysosome may also be employed. For example, the lysosome associated membrane proteins 1 and 2 (LAMP-1 and LAMP- 2) include a region that targets proteins to the lysosome. Examples of lysosome targeting sequences are provided, e.g., in U.S. Pat. Nos. 5,633,234; 6,248,565; and 6,294,378.

Destabilizing sequences present in particular proteins are well known in the art. Exemplary destabilization sequences include c-myc aa 2-120; cyclin A aa 13-91; Cyclin B aa 13-91; IkBα aa 20-45; β-Catenin aa 19-44; β-Catenin aa 18-47, c-Jun aa1-67; and c-Mos aa1-35; and fragments and variants, of those segments that mediate destabilization. Such fragments can be identified using methodology well known in the art. For example, polypeptide half-life can be determined by a pulse-chase assay that detects the amount of polypeptide that is present over a time course using an antibody to the polypeptide, or to a tag linked to the polypeptide. Exemplary assays are described, e.g., in WO02/36806., which is incorporated by reference.

Variants of such sequences, e.g., that have at least 90% identity, usually at least 91%, 92%, 93%, 94%, 95%, 96%, 97%, 98%, 99%, or greater, identity to the sequences noted above, e.g., β-catenin 18-47, can be employed in this invention, e.g., for fusion to a retrovirus antigens, e.g., an HIV or SIV gag antigen.

An exemplary 30 aa of β-catenin destabilization sequence (amino acids 18-47) is:

```
RKAAVSHWQQQSYLDSGIHISGATTTAPSLS.
```

Additional degradation signals that can be used to modify retroviral antigens, e.g., HIV or SIV antigens in accordance with the invention include the F-box degradation signal, such as the F-BOX signal 47aa (182-228) from protein beta-TrCP (Liu, et al., *Biochem Biophys Res Comm.* 313:1023-1029, 2004). Accordingly, in some embodiments, an expression vector for use in the invention may encode a fusion protein where an F-box degradation signal is attached to an HIV antigen, e.g., gag, pol, env, nef, tat, and/or vif.

Expression Vectors that Encode Secreted Fusion Proteins

The vaccines of the invention (naked DNA or viral vector-based nucleic acid vaccines) also comprises expression units that encode a fusion proteins that include a secretory polypeptide. A secretory polypeptide in the context of this invention is a polypeptide signal sequence that results in secretion of the protein to which it is attached. In some embodiments, the secretory polypeptide is a chemokine, cytokine, or lymphokine, or a fragment of the chemokine, cytokine, or lymphokine that retains immunostimulatory activity. Exemplary secretory polypeptides include chemokines such as MCP-3 or LP-10, or cytokines such as GM-CSF, IL-4, IL-15, or IL-2. In other embodiments, the secretory polypeptide is from a secreted protein such as tissue plasminogen activator. Constructs encoding secretory fusion proteins are disclosed, e.g., in WO02/36806.

Many secretory signal peptides are known in the art and can be determined using methods that are conventional in the art. For example, in addition to chemokines, secretory signals such as those from tissue plasminogen activator (tPA) protein, growth hormone, GM-CSF, and immunoglobulin proteins may be used.

In some embodiments, a secretory signal for use in the invention is MCP-3 amino acids 33-109, e.g., linked to IP-10 secretory peptide. Variants of such sequences, e.g., that have at least 90% identity, usually at least 91%, 92%, 93%, 94%, 95%, 96%, 97%, 98%, 99%, or greater, identity to MCP-3 and/or IP-10, can be employed in this invention.

An example of an IP10 sequence linked to MCP3 that could be used is:

The combination of the murine IP10 linker to the mature human MCP3:

M N P S A A V I F C L I L L G L S G T Q G (murine IP10 signal peptide)

I L D M A (linker)

Q P V G I N T S T T C C Y R F I N K K I P K Q R L E S Y R R T T S S

H C P R E A V I F K T K L D K E I C A D P T Q K W V Q D F M K H

L D K K T Q T P K L (mature human MCP3)

The combination of the human IL10 linked to the mature human MCP3:

M N Q T A I L I C C L I F L T L S G I Q G (human IP10 signal peptide)

Q P V G I N T S T T C C Y R F I N K K I P K Q R L E S Y R R T T S S

H C P R E A V I F K T K L D K E I C A D P T Q K W V Q D F M K H

L D K K T Q T P K L (mature human MCP3)

An alternative the human MCP3 using its own signal peptide is used:

M K A S A A L L C L L L T A A A F S P Q G L A (human MCP-3 signal peptide)

Q P V G I N T S T T C C Y R F I N K K I P K Q R L E S Y R R T T S S

H C P R E A V I F K T K L D K E I C A D P T Q K W V Q D F M K H

L D K K T Q T P K L (mature human MCP3)

In other embodiments, tissue plasminogen activator signal peptide and propeptide sequences are known in the art (see, Delogu, et al, Infect Immun (2002) 70:292; GenBank Accession No. E08757). In some embodiments, the tPA secretory signal is:

M D A M K R G L C C V L L L C G A V F V S P (tPA signal aa 1-22)

S Q E I H A R F R R G A R (tPA propeptide aa 23-35)

IL-15/IL-15Rα Sequences

The IL-15 and IL-15Rα nucleic acid constructs employed in the invention are also engineered to improve mRNA trafficking, stability, and expression. Codons are altered to change the overall mRNA AT(AU) content, to minimize or remove potential splice sites and to alter other inhibitory sequences and signals that affect the stability and processing of mRNA, such as runs of A or T/U nucleotides, AATAAA, ATTTA, and closely related variant sequences that are know to negatively influence mRNA stability. Instability sequences are removed using known methods that are described, e.g., in U.S. Pat. Nos. 6,794,498, 6,414,132; 6,291,664; 5,972,596; and 5,965,726.

IL-15 nucleic acid sequences for use in the invention include encoding an interleukin-15 (IL-15) protein having at least 90%, 91%, 92%, 93%, 94%, 95%, 96%, 97%, 98%, 99% sequence identity to a native mammalian IL-15 protein, e.g., a human IL-15, wherein the nucleic acid sequence differs from a nucleic acid sequence encoding the native mammalian IL-15 by at least 50% of the changed nucleotide positions identified in FIG. 12. In some embodiments, the nucleic acid sequence differs from a nucleic acid sequence encoding the native mammalian IL-15 by at least 50% of the changed codon positions identified in FIG. 4 and/or in FIG. 6. In some embodiments, the changed nucleotides and codons are in the mature IL-15 sequence. The native mammalian IL-15 can be any mammalian IL-15, including human IL-15, a primate IL-15, a porcine IL-15, a murine IL-15, and the like.

In some embodiments, the nucleic acid sequence encoding the IL-15 differs from a nucleic acid sequence encoding the native IL-15 by at least about 55% (e.g., 59 nucleotides), 60% (e.g., 64 nucleotides), 65% (e.g., 70 nucleotides), 70% e.g., (75 nucleotides), 75% (e.g., 81 nucleotides), 80% (e.g., 86 nucleotides), 85% (e.g., 91 nucleotides), 90% (e.g., 97 nucleotides), 95% (e.g., 109 nucleotides) of the 115 changed nucleotide positions identified in FIG. 12 (shaded). In some embodiments, the nucleic acid sequence encoding the IL-15 differs from a nucleic acid sequence encoding the native IL-15 by at least about 55% (e.g., 66 codons), 60% (e.g., 73 codons), 65% (e.g., 78 codons), 70% e.g., (85 codons), 75% (e.g., 91 codons), 80% (e.g., 97 codons), 85% (e.g., 103 codons), 90% (e.g., 109 codons), 95% (e.g., 115 codons) of the 121 changed codon positions identified in FIG. 13 (shaded, boxed or underlined).

In some embodiments, the changed nucleotides and codons are in the mature IL-15 sequence. For example, the nucleic acid sequence encoding the improved IL-15 can differ from a nucleic acid sequence encoding the native IL-15 by at least about 65%, 70%, 75%, 80%, 85%, 90%, 95% of the 78 changed nucleotide positions in the mature IL-15 identified in FIG. 8 (shaded). In another embodiment, the nucleic acid sequence encoding the improved IL-15 can differ from a nucleic acid sequence encoding the native IL-15 by at least about 65%, 70%, 75%, 80%, 85%, 90%, 95% of the 84 changed codon positions in the mature IL 15 identified in FIG. 13 (shaded, boxed or underlined).

In some embodiments, the nucleic acid sequence differs from a nucleic acid sequence encoding the native IL-15 at nucleotide positions 6, 9, 15, 18, 21, 22, 27, 30, 33, 49, 54, 55, 57, 60, 63, 69, 72, 75, 78, 81, 84, 87, 90, 93, 96, 105, 106, 114, 120, 123, 129, 132, 135, 138, 141, 156, 159, 162, 165, 168, 169, 174, 177, 180, 183, 186, 189, 192, 195, 198, 204, 207, 210, 213, 216, 217, 219, 222, 228, 231, 237, 246, 252, 255, 258, 261, 277, 283, 285, 291, 294, 297, 300, 306, 309, 312, 315, 318, 321, 324, 327, 330, 333, 336, 339, 351, 354, 363, 364, 369, 372, 375, 384, 387, 390, 393, 396, 402, 405, 414, 423, 426, 429, 432, 435, 438, 442, 450, 453, 456, 459, 462, 468, 483 and 486, wherein the nucleotide positions are as identified in FIG. 12.

In some embodiments, the nucleic acid sequence comprises a guanine (g) or a cytosine (c) nucleotide at nucleotide positions 6, 9, 15, 18, 21, 22, 27, 30, 33, 49, 54, 55, 57, 60, 63, 69, 72, 75, 78, 81, 84, 87, 96, 105, 106, 114, 120, 123, 129, 132, 135, 138, 141, 156, 159, 162, 165, 168, 169, 174, 177, 180, 183, 186, 189, 192, 195, 198, 204, 207, 210, 213, 216, 217, 219, 222, 228, 231, 237, 246, 252, 255, 258, 261, 277, 283, 285, 291, 294, 297, 300, 306, 309, 312, 315, 318, 321, 324, 327, 330, 333, 336, 339, 351, 354, 363, 364, 369, 372, 375, 384, 387, 390, 393, 396, 402, 405, 414, 423, 426, 429, 432, 435, 438, 442, 450, 453, 456, 459, 462, 468, 483 and 486, wherein the nucleotide positions are as identified in FIG. 12.

The codons can differ in any way such that an identical or similar (i.e., conservatively substituted) amino acid is encoded. In some embodiments, the codons are changed to increase GC content. In some embodiments, the improved IL-15 nucleic acid sequences each comprise at least about 50%, 55%, 60%, 65%, 70%, 75% or more GC content (e.g., deoxyguanosine and deoxycytidine residues).

In some embodiments, the nucleic acid sequence encoding an IL-15 signal peptide-propeptide (SIG-PRO) is replaced with a nucleic acid sequence encoding a signal peptide (SIG) or a signal peptide-propeptide (SIG-PRO) from a heterologous protein. In some embodiments, the nucleic acid sequence encoding an IL-15 signal peptide is replaced with a nucleic acid sequence encoding a signal peptide from a heterologous protein. The heterologous protein can be, for example, from tissue plasminogen activator (tPA), growth hormone, granulocyte-macrophage colony stimulating factor (GM-CSF) or an immunoglobulin (e.g., IgE). In one embodiment, the nucleic acid sequence encoding an IL-15 signal peptide-propeptide (SIG-PRO) is replaced with a nucleic acid sequence encoding a tPA SIG PRO having 95% sequence identity to tPA SIG-PRO. In some embodiments, the nucleic acid encoding the IL-15 is operably linked to a nucleic acid encoding an RNA export element, for example a CTE or RTEm26CTE.

In another aspect, the invention provides nucleic acid sequences encoding a signal peptide-propeptide (SIG-PRO) sequence from a protein other than IL-15, for example a tPA SIG-PRO sequence, a growth hormone signal sequence (SIG), an immunoglobulin signal sequence (SIG), operably linked to a nucleic acid encoding an IL-15 protein having at least 90% sequence identity to the native mammalian IL-15 protein, wherein the nucleic acid sequence encoding IL-15 comprises at least 50% GC content. In one embodiment, the SIG PRO sequence is from a protein selected from the group consisting of tPA, GM-CSF, growth hormone and an immunoglobulin family protein. In one embodiment, the SIG-PRO sequence encodes a tPA SIG-PRO having at least 95% amino acid sequence identity to tPA SIG-PRO. Further embodiments are as described above.

In some embodiments, the IL-12 nucleic acid constructs employed in the invention are also engineered to improve mRNA trafficking, stability, and expression. Expression of the p35 and p40 chains are preferred from one plasmid whereby the expression of the p40 chain uses the human CMV promoter and the p35 chain uses the simian CMV promoter.

In some embodiments, the IL-2 nucleic acid construct employed in the invention is also engineered to improve mRNA trafficking, stability, and expression.

Selection of Antigens

Antigenic polypeptide sequences for provoking an immune response selective for a specific retroviral pathogen are known. In some embodiments of the invention, the vaccine regimen is administered to a patient with HIV-1 infection. With minor exceptions, the following discussion of HIV epitopes/immunogenic polypeptides is applicable to other retroviruses, e.g., SIV, except for the differences in sizes of the respective viral proteins. HIV antigens for a multitude of HIV-1 and HIV-2 isolates, including members of the various genetic subtypes of HIV, are known and reported (see, e.g., Myers et al., Los Alamos Database, Los Alamos National Laboratory, Los Alamos, N. Mex. (1992); the updated version of this data base is online and is incorporated herein by reference (http address hiv-web.lanl.gov/content/index) and antigens derived from any of these isolates can be used in the methods of this invention. Immunogenic proteins can be derived from any of the various HIV isolates, including any of the various envelope proteins such as gp120, gp160 and gp41; gag antigens such as p24gag and p55gag, as well as proteins derived from pol, tat, vif, rev, nef, vpr, vpu.

The expression constructs may also contain Rev-independent fragments of genes that retain the desired function (e.g., for antigenicity of Gag or Pol, particle formation (Gag) or enzymatic activity (Pol)), or may also contain Rev-independent variants that have been mutated such that the encoded protein loses function. For example, the gene may be modified to mutate an active site of protease, reverse transcriptase or integrase proteins. Rev-independent fragments of gag and env are described, for example, in WO01/46408 and U.S. Pat. Nos. 5,972,596 and 5,965,726. Typically, rev-independent HIV sequences that are modified to eliminate all enzymatic activities of the encoded proteins are used in the constructs of the invention. All the genes encoding gag, pol, env, tat, nef and vif are made Rev-independent by altering the nucleotide sequence without affecting the protein sequence. The altered nucleotide compositions of the genes also reduce the probability of recombination with wildtype virus.

In some embodiments, the immunogenic compositions of the invention are administered by injection and/or electroporation. Administration by dual routes of injection and electroporation can be done concurrently or sequentially, at the same or different sites.

An immunogenic composition of the invention can be administered as one or more constructs. For example, a vaccine can comprises an HIV antigen fusion protein where multiple HIV polypeptides, structural and/or regulatory polypeptides or immunogenic epitopes thereof, are administered in a single expression vector. In other embodiments, the vaccines are administered as multiple expression vectors, or as one or more expression vectors encoding multiple expression units, e.g., a discistronic, or otherwise multicistronic, expression vectors.

Anti-retroviral Therapy

The vaccines are administered to retrovirus-infected individuals, typically HIV-1-infected humans, who are undergoing or have undergone ART therapy.

Antiviral retroviral treatment typically involves the use of two broad categories of therapeutics. They are reverse transcriptase inhibitors and protease inhibitors. There are two type of reverse transcriptase inhibitors: nucleoside analog reverse transcriptase inhibitors and non-nucleoside reverse transcriptase inhibitors. Both types of inhibitors block infection by blocking the activity of the HIV reverse transcriptase, the viral enzyme that translates HIV RNA into DNA, which can later be incorporated into the host cell chromosomes.

Nucleoside and nucleotide analogs mimic natural nucleotides, molecules that act as the building blocks of DNA and RNA. Both nucleoside and nucleotide analogs must undergo phosphorylation by cellular enzymes to become active; however, a nucleotide analog is already partially phosphorylated and is one step closer to activation when it enters a cell. Following phosphorylation, the compounds compete with the natural nucleotides for incorporation by HIV's reverse transcriptase enzyme into newly synthesized viral DNA chains, resulting in chain termination.

Examples of anti-retroviral nucleoside analogs are: AZT, ddI, ddC, d4T, and 3TC. Combinations of different nucleoside analogs are also available, for example 3TC in combination with AZT (Combivir).

Nonnucleoside reverse transcriptase inhibitors (NNRTIs) are a structurally and chemically dissimilar group of antiretroviral compounds. They are highly selective inhibitors of HIV-1 reverse transcriptase. At present these compounds do not affect other retroviral reverse transcriptase enzymes such as hepatitis viruses, herpes viruses, HIV-2, and mammalian enzyme systems. They are used effectively in triple-therapy regimes. Examples of NNRTIs are Delavirdine and Nevirapine, which have been approved for clinical use in combination with nucleoside analogs for treatment of HIV-infected adults who experience clinical or immunologic deterioration. A detailed review can be found in "Nonnucleoside Reverse Transcriptase Inhibitors" *AIDS Clinical Care* (10/97) Vol. 9, No. 10, p. 75.

Protease inhibitors are compositions that inhibit HIV protease, which is virally encoded and necessary for the infection process to proceed. Clinicians in the United States have a number of clinically effective proteases to use for treating HIV-infected persons. These include: SAQUINAVIR (Invirase); INDINAVIR (Crixivan); and RITONAVIR (Norvir).

Additional classes of antiretroviral drugs are developed for clinical use and include inhibitors of retrovirus entry and integrase inhibitors.

Preparation of Vaccines

In the methods of the invention, the nucleic acid vaccine is directly introduced into the cells of the individual receiving the vaccine regimen. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; and WO 98/04720. Examples of DNA-based delivery technologies include, "naked DNA", facilitated (bupivicaine, polymers, peptide-mediated) delivery, and cationic lipid complexes or liposomes. The nucleic acids can be administered using ballistic delivery as described, for instance, in U.S. Pat. No. 5,204,253 or pressure (see, e.g., U.S. Pat. No. 5,922,687). Using this technique, particles comprised solely of DNA are administered, or in an alternative embodiment, the DNA can be adhered to particles, such as gold particles, for administration.

As is well known in the art, a large number of factors can influence the efficiency of expression of antigen genes and/or the immunogenicity of DNA vaccines. Examples of such factors include the reproducibility of inoculation, construction of the plasmid vector, choice of the promoter used to drive antigen gene expression and stability of the inserted gene in the plasmid. In some embodiments, nucleic acid-based vaccines comprising expression vectors of the invention are viral vectors in which the retroviral antigens for vaccination are included in the viral vector genome.

Within each expression cassette, sequences encoding an antigen for use in the vaccines of the invention will be operably linked to expression regulating sequences. "Operably linked" sequences include both expression control sequences that are contiguous with the nucleic acid of interest and expression control sequences that act in trans or at a distance to control the gene of interest. Expression control sequences include appropriate transcription initiation, termination, promoter and enhancer sequences; efficient RNA processing signals such as splicing and polyadenylation signals; sequences that stabilize cytoplasmic mRNA; sequences that promote RNA export (e.g., a constitutive transport element (CTE), a RNA transport element (RTE), or combinations thereof, including RTEm26CTE); sequences that enhance translation efficiency (e.g., Kozak consensus sequence); sequences that enhance protein stability; and when desired, sequences that enhance protein secretion.

Any of the conventional vectors used for expression in eukaryotic cells may be used for directly introducing DNA into tissue. Expression vectors containing regulatory elements from eukaryotic viruses are typically used in eukaryotic expression vectors, e.g., human CMV, simian CMV, viral LTRs, composition of CMV promoter and HTLV R region providing 5'end of the mRNA and the like. Typical vectors include those with a human CMV promoter, no splice sites, and a bovine growth hormone polyA site and the kanamycin gene for selective growth in bacteria.

In some embodiments, the nucleic acid sequences that encode the polypeptides to be expressed are operably linked to one or more mRNA export sequences. Examples include the constitutive transport element (CTE), which is important for the nucleo-cytoplasmic export of the unspliced RNA of the simian type D retroviruses. Another exemplified RNA export element includes the RNA transport element (RTE), which is present in a subset of rodent intracisternal A particle retroelements. The CTE and RTE elements can be used individually or in combination. In one embodiment, the RTE is an RTEm26 (e.g., WO 04/113547). In one embodiment, the RTEM26 and the CTE are positioned in the 3'-untranslated region of a transcript encoded by the expression cassette. Often, the RTE and the CTE are separated by 100 nucleotides or less. In some embodiments, the RTE and the CTE are separated by 30 nucleotides or less. For example, RTEm26CTE may be used. Such RNA transport elements, and others, are described, for example, in International Patent Publication No. WO 04/113547, the disclosure of which is hereby incorporated by reference.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins. If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, i.e., "naked DNA," is particularly suitable for intramuscular (IM) or intradermal (ID) administration.

Assessment of Immunogenic Response

To assess a patient's immune system during and after treatment and to further evaluate the treatment regimen, various parameters can be measured. Measurements to evaluate vaccine response include: antibody measurements in the plasma, serum, or other body fluids; and analysis of in vitro cell proliferation in response to a specific antigen, indicating the function of CD4+ cells. Such assays are well known in the art. For example, for measuring CD4+ T cells, many laboratories measure absolute CD4+ T-cell levels in whole blood by a multi-platform, three-stage process. The CD4+ T-cell number is the product of three laboratory techniques: the white blood cell (WBC) count; the percentage of WBCs that are lymphocytes (differential); and the percentage of lymphocytes that are CD4+ T-cells. The last stage in the process of measuring the percentage of CD4+ T-lymphocytes in the whole-blood sample is referred to as "immunophenotyping by flow cytometry. Systems for measuring CD4+ cells are commercially available. For example Becton Dickenson's FACSCount System automatically measure absolutes CD4+, CD8+, and CD3+ T lymphocytes.

Other measurements of immune response include assessing CD8+ responses. These techniques are well known. CD8+ T-cell responses can be measured, for example, by using tetramer staining of fresh or cultured PBMC (see, e.g., Altman, et al., *Proc. Natl. Acad. Sci. USA* 90:10330, 1993; Altman, et al., *Science* 274:94, 1996), or γ-interferon release assays such as ELISPOT assays (see, e.g., Lalvani, et al., *J. Exp. Med.* 186:859, 1997; Dunbar, et al., *Curr. Biol.* 8:413, 1998; Murali-Krishna, et al., *Immunity* 8:177, 1998), or by using functional cytotoxicity assays.

Viral Titer

Viremia is measured by assessing viral titer in a patient. There are a variety of methods of perform this. For example, plasma HIV RNA concentrations can be quantified by either target amplification methods (e.g., quantitative RT polymerase chain reaction [RT-PCR], Amplicor HIV Monitor assay, Roche Molecular Systems; or nucleic acid sequence-based amplification [NASBA®] assay, NUCLISENS™ HIV-1 QT quantitative HIV-1 in vitro amplification assay, Organon Teknika) or signal amplification methods (e.g., branched DNA [bDNA], QUANTIPLEX™ HIV RNA bDNA assay signal amplification assay, Chiron Diagnostics). The bDNA signal amplification method amplifies the signal obtained from a captured HIV RNA target by using sequential oligonucleotide hybridization steps, whereas the RT-PCR and NASBA® assays use enzymatic methods to amplify the target HIV RNA into measurable amounts of nucleic acid product. Target HIV RNA sequences are quantitated by comparison with internal or external reference standards, depending upon the assay used.

Administration of vaccine constructs of the invention to individuals undergoing ART controls viremia, e.g., in periods when the patient may stop receiving ART. Controlling viremia refers to lowering of the plasma levels of virus to levels lower than those observed in the period of chronic infection prior to ART, usually to levels to levels one to two logs lower than the set point observed in the period of chronic infection prior to ART. Inclusion of the vaccine constructs described herein results in enhanced control of viremia in comparison to treatment protocols that do not comprise administration of optimized DNA vectors or that do not that encode fusion proteins comprising a destabilization signal/and or secreted fusion proteins.

Administration of DNA Constructs

The DNA vectors are formulated for pharmaceutical administration. While any suitable carrier known to those of ordinary skill in the art may be employed in the pharmaceutical compositions of this invention, the type of carrier will vary depending on the mode of administration. For parenteral administration, including intranasal, intradermal, subcutaneous or intramuscular injection or electroporation, the carrier preferably comprises water, saline, and optionally an alcohol, a fat, a polymer, a wax, one or more stabilizing amino acids or a buffer. General formulation technologies are known to those of skill in the art (see, for example, Remington: The Science and Practice of Pharmacy (20th edition), Gennaro, ed., 2000, Lippincott Williams & Wilkins; Injectable Dispersed Systems: Formulation, Processing And Performance, Burgess, ed., 2005, CRC Press; and Pharmaceutical Formulation Development of Peptides and Proteins, Frkjr et al., eds., 2000, Taylor & Francis).

Naked DNA can be administered in solution (e.g., a phosphate-buffered saline solution) by injection, usually by an intra-arterial, intravenous, subcutaneous or intramuscular route. In general, the dose of a naked nucleic acid composition is from about 10 μg to 10 mg for a typical 70 kilogram patient. Subcutaneous or intramuscular doses for naked nucleic acid (typically DNA encoding a fusion protein) will range from 0.1 mg to 50 mg for a 70 kg patient in generally good health.

DNA vaccinations can be administered once or multiple times. DNA vaccination is performed more than once, for example, 2, 3, 4, 5, 6, 7, 8, 10, 15, 20 or more times as needed to induce the desired response (e.g., specific antigenic response or proliferation of immune cells). Multiple administrations can be administered, for example, bi-weekly, weekly, bi-monthly, monthly, or more or less often, as needed, for a time period sufficient to achieve the desired response.

In some embodiments, the DNA vectors are administered by liposome-based methods, electroporation or biolistic particle acceleration. A delivery apparatus (e.g., a "gene gun") for delivering DNA into cells in vivo can be used. Such an apparatus is commercially available (e.g., BioRad, Hercules, Calif., Chiron Vaccines, Emeryville, Calif.). Naked DNA can also be introduced into cells by complexing the DNA to a cation, such as polylysine, which is coupled to a ligand for a cell-surface receptor (see, for example, Wu, G. and Wu, C. H. (1988) J. Biol. Chem. 263:14621; Wilson et al. (1992) J. Biol. Chem. 267:963-967; and U.S. Pat. Nos. 5,166,320; 6,846,809; 6,733,777; 6,720,001; 6,290,987). Liposome formulations for delivery of naked DNA to mammalian host cells are commercially available from, for example, Encapsula NanoSciences, Nashville, Tenn. An electroporation apparatus for use in delivery of naked DNA to mammalian host cells is commercially available from, for example, Inovio Biomedical Corporation, San Diego, Calif.

The improved nucleic acid vaccine compositions are administered to a mammalian host. The mammalian host usually is a human or a primate. In some embodiments, the mammalian host can be a domestic animal, for example, canine, feline, lagomorpha, rodentia, rattus, hamster, murine. In other embodiment, the mammalian host is an agricultural animal, for example, bovine, ovine, porcine, equine, etc.

The administration procedure for DNA is not critical. Vaccine compositions containing the DNA expression vectors can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular patient, and the route of administration.

In therapeutic applications, the vaccines are administered to a patient in an amount sufficient to elicit a therapeutic effect, e.g., a $CD8^+$, $CD4^+$, and/or antibody response to the HIV-1 antigens encoded by the vaccines that at least partially arrests or slows symptoms and/or complications of HIV infection. An amount adequate to accomplish this is defined as "therapeutically effective dose." Typically, a therapeutically effective dose results in control of viremia upon release from ART, i.e., lower levels of viremia after ART cessation compared to viremia observed prior to ART administration. Amounts effective for this use will depend on, e.g., the particular composition of the vaccine regimen administered, the manner of administration, the stage and severity of the disease, the general state of health of the patient, and the judgment of the prescribing physician.

Suitable quantities of DNA vaccine, e.g., plasmid or naked DNA can be about 1 μg to about 100 mg, preferably 0.1 to 10 mg, but lower levels such as 1-10 μg can be employed. For example, an HIV DNA vaccine, e.g., naked DNA or polynucleotide in an aqueous carrier, can be injected into tissue, e.g., intramuscularly or intradermally, in amounts of from 10 μl per site to about 1 ml per site. The concentration of polynucleotide in the formulation is usually from about 0.1 μg/ml to about 4 mg/ml.

The vaccine may be delivered in a physiologically compatible solution such as sterile PBS in a volume of, e.g., one ml. The vaccines may also be lyophilized prior to delivery. As well known to those in the art, the dose may be proportional to weight.

The compositions included in the vaccine regimen can be administered alone, or can be co-administered or sequentially administered with other immunological, antigenic, vaccine, or therapeutic compositions.

Compositions that may also be administered with the vaccines include other agents to potentiate or broaden the immune response, e.g., IL-2 or CD40 ligand, which can be administered at specified intervals of time, or continuously administered. For example, IL-2 can be administered in a broad range, e.g., from 10,000 to 1,000,000 or more units. Administration can occur continuously following vaccination.

The vaccines can additionally be complexed with other components such as peptides, polypeptides and carbohydrates for delivery. For example, expression vectors, i.e., nucleic acid vectors that are not contained within a viral particle, can be complexed to particles or beads that can be administered to an individual, for example, using a vaccine gun.

Nucleic acid vaccines are administered by methods well known in the art as described in Donnelly et al. (*Ann. Rev. Immunol.* 15:617-648 (1997)); Felgner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), each of which is incorporated herein by reference. One skilled in the art would know that the choice of a pharmaceutically acceptable carrier, including a physiologically acceptable compound, depends, for example, on the route of administration of the expression vector.

For example, naked DNA or polynucleotide in an aqueous carrier can be injected into tissue, such as muscle, in amounts of from 10 μl per site to about 1 ml per site. The concentration of polynucleotide in the formulation is from about 0.1 μg/ml to about 4 mg/ml.

Vaccines can be delivered via a variety of routes. Typical delivery routes include parenteral administration, e.g., intradermal, intramuscular or subcutaneous routes. Other routes include oral administration, intranasal, and intravaginal routes. In such compositions the nucleic acid vector can be in admixture with a suitable carrier, diluent, or excipient such as sterile water, physiological saline, glucose or the like.

The expression vectors of use for the invention can be delivered to the interstitial spaces of tissues of a patient (see, e.g., Feigner et al., U.S. Pat. Nos. 5,580,859, and 5,703,055). Administration of expression vectors of the invention to muscle is a particularly effective method of administration, including intradermal and subcutaneous injections and transdermal administration. Transdermal administration, such as by iontophoresis, is also an effective method to deliver expression vectors of the invention to muscle. Epidermal administration of expression vectors of the invention can also be employed. Epidermal administration involves mechanically or chemically irritating the outermost layer of epidermis to stimulate an immune response to the irritant (Carson et al., U.S. Pat. No. 5,679,647).

The vaccines can also be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. For further discussions of nasal administration of AIDS-related vaccines, references are made to the following patents, U.S. Pat. Nos. 5,846,978, 5,663,169, 5,578,597, 5,502,060, 5,476,874, 5,413,999, 5,308,854, 5,192,668, and 5,187,074.

The vaccines can be incorporated, if desired, into liposomes, microspheres or other polymer matrices (see, e.g., Feigner et al., U.S. Pat. No. 5,703,055; Gregoriadis, *Liposome Technology*, Vols. I to III (2nd ed. 1993). Liposomes, for example, which consist of phospholipids or other lipids, are nontoxic, physiologically acceptable and metabolizable carriers that are relatively simple to make and administer. Liposomes include emulsions, foams, micelles, insoluble monolayers, liquid crystals, phospholipid dispersions, lamellar layers and the like.

Liposome carriers can serve to target a particular tissue or infected cells, as well as increase the half-life of the vaccine. In these preparations the vaccine to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes either filled or decorated with a desired immunogen of the invention can be directed to the site of lymphoid cells, where the liposomes then deliver the immunogen(s).

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), U.S. Pat. Nos. 4,235,871, 4,501,728, 4,837,028, and 5,019,369.

EXAMPLES

Administration of DNA Vaccines to ART-Treated Macaques in Combination with IL-15/IL-15Ra Controls Viremia Upon Release from ART Three macaques enrolled in our immunotherapy protocol were subjected to a second round of ART and DNA vaccination in the presence of optimized plasmids expression IL-15 and IL-15 Receptor alpha (IL-15Rα). Immunization was done by electroporation using the following plasmid mix:

SIV antigens:
gag (2S-CATEgagDX and 21S-MCP-3p39gag);
env (99S-Env and 73S-MCP-3-env);
pol (103S-LAMP-pol);
Nef-tat-vif (147S-LAMP-NTV)

Rhesus macaque IL-15/IL-15 Receptor alpha producing plasmids: rhIL-15tPA6 (AG65) and rhIL-15Rα (AG120)

Two injections of 0.5 ml were performed for each animal. PBMC were isolated at 2 week intervals and analyzed for numbers of SIV-specific cells using 10 parameter flow cytometry. This allowed the enumeration and phenotypical analysis of lymphocytes producing interferon-γ (IFN-γ, IL-2, or TNFα in response to stimulation by peptide pools corresponding to gag, pol, env, nef, and tat proteins of SIV mac259.)

Figure 2:
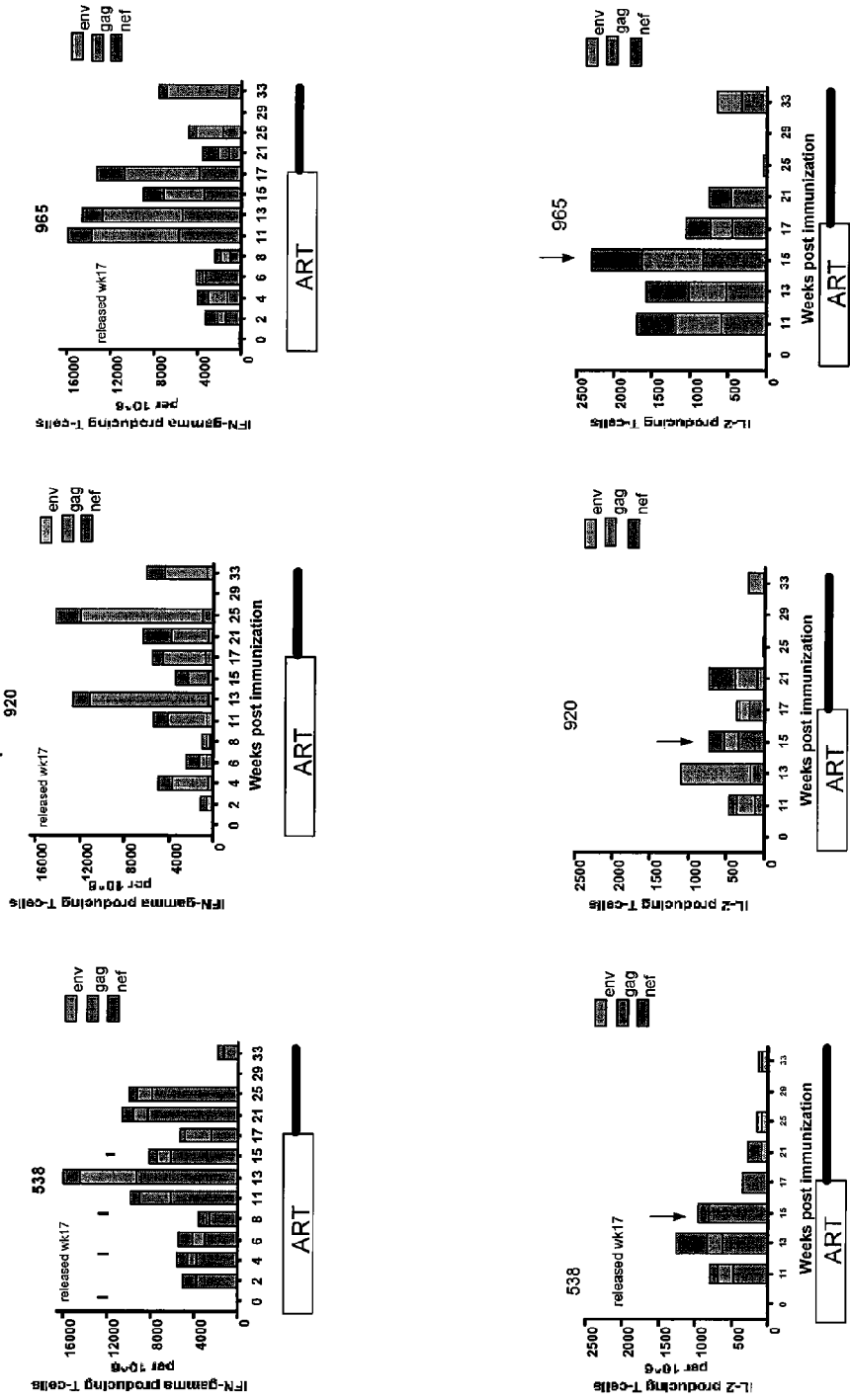
FIG. 2 shows IFNgamma- and IL2-producing T cells during vaccination and after release for 3 electroporated animals 538L, 920L and 965L. The animals were infected with SIVmac251 for 4 years and were then treated with ART (see FIG. 1). Starting week 8 of ART, the animals received 4 vaccinations comprising of plasmids expressing SIV antigens (gag, env, pol, nef-tat-vif: CATEgagDX, MCP-3p39,Env, MCP-3-env, LAMP-pol, LAMP-NTV) together with the rhesus macaque IL-15 and rhesus macaque IL-15Ra expressing plasmids (Rm IL-15tPA6 and Rm IL-15Ra) by in vivo electroporation. Vaccination schedule includes vaccinations at 0, 4, 8, 15 weeks, and at 2 weeks after last vaccination (at week 17) the animals were released from ART. The animals were monitored for SIV-specific (env, gag, nef) immune responses by multicolor FACS (FIGS. 2, 3, 4, 5) and virus loads (FIGS. 7, 8, 9) in the PBMCs.
Figure 5:
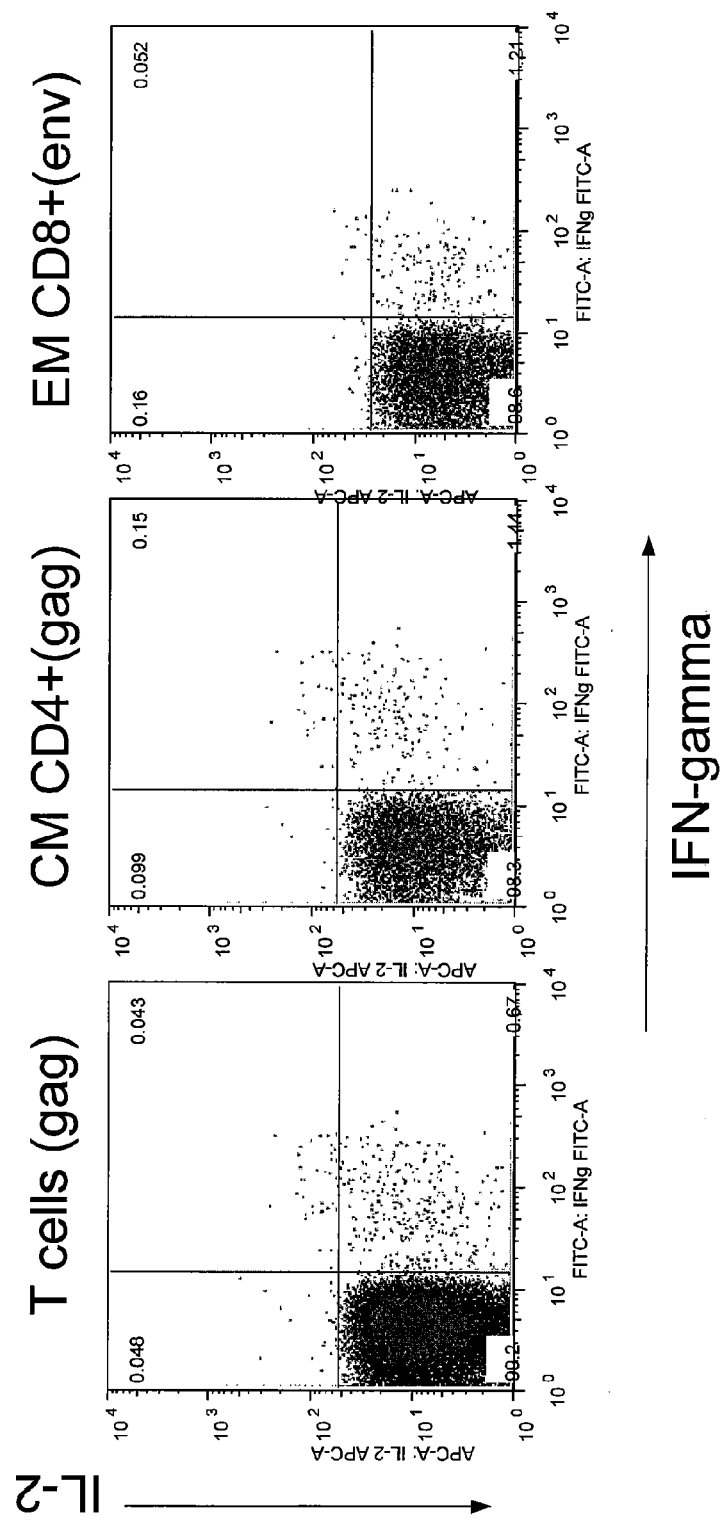
FIG. 5 shows IL-2 and IFNgamma positive cells from the vaccinated animal 965L. The dot plots are from the sample taken at 2 weeks after the 3rd electroporation

The results of this analysis (FIG. 2) show a dramatic increase of average and peak responses of SIV-specific cytokines producing cells. All three animals had low levels of IFN-y producing cells during ART and prior to DNA vaccination. This is expected since ART decreased SIV to undetectable levels in all three animals. Upon vaccination a persistent increase of SIV-specific cells was detected. More importantly, vaccination generated IL-2 secreting cells (FIG. 2) as well as double IFN-γ and IL-2 secreting cells (FIG. 5). This occurred after the third DNA vaccination. In previous determinations these macaques did not have any polyfunctional cytokine-secreting cells in their peripheral blood.

Figure 3:
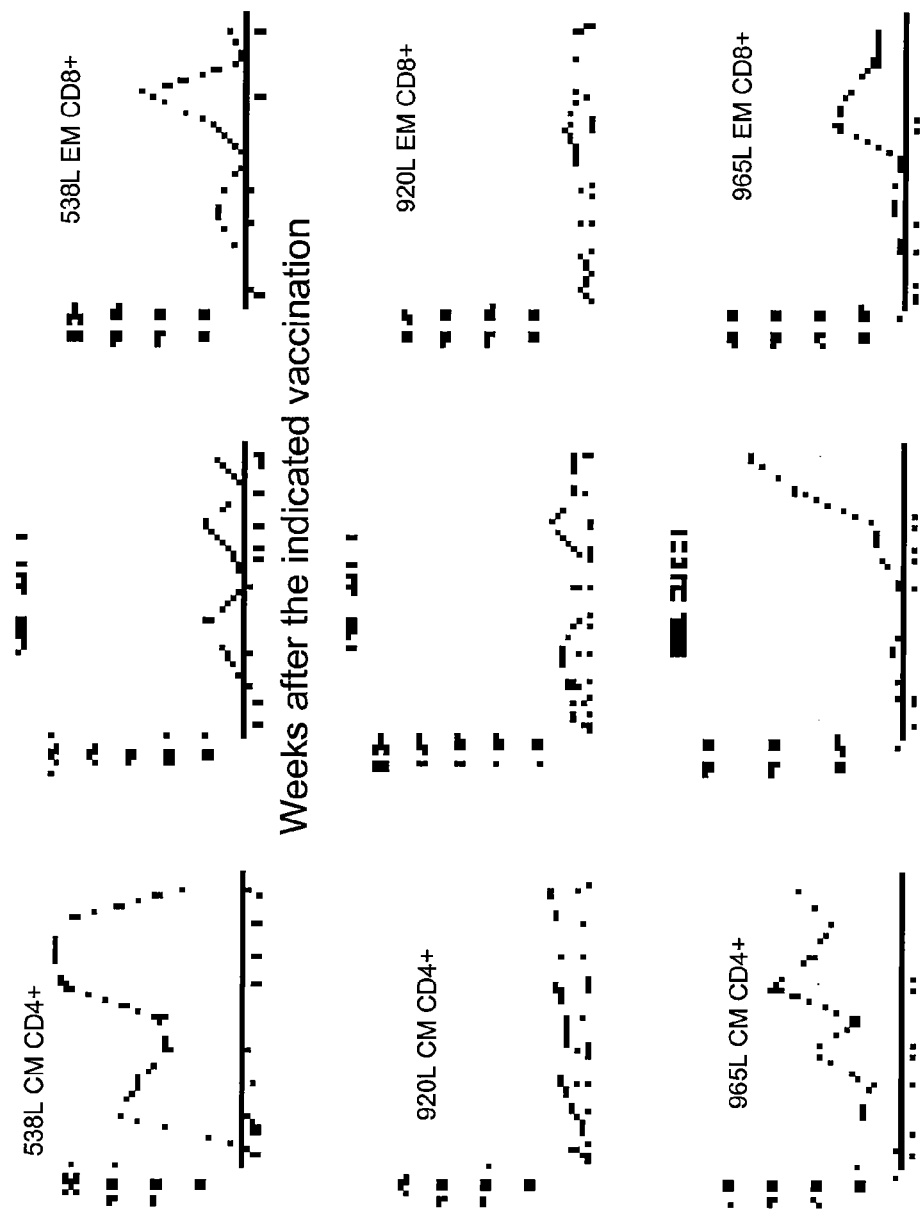
FIG. 3 shows the presence of central memory (CM) and effector memory (EM) responses to Gag in the vaccinated animals 538L, 920L and 965L. Central Memory cells are defined as CD28+, CD45RA− T cells. Effector memory cells are defined as CD28−, CD45RA+ T cells.
Figure 4:
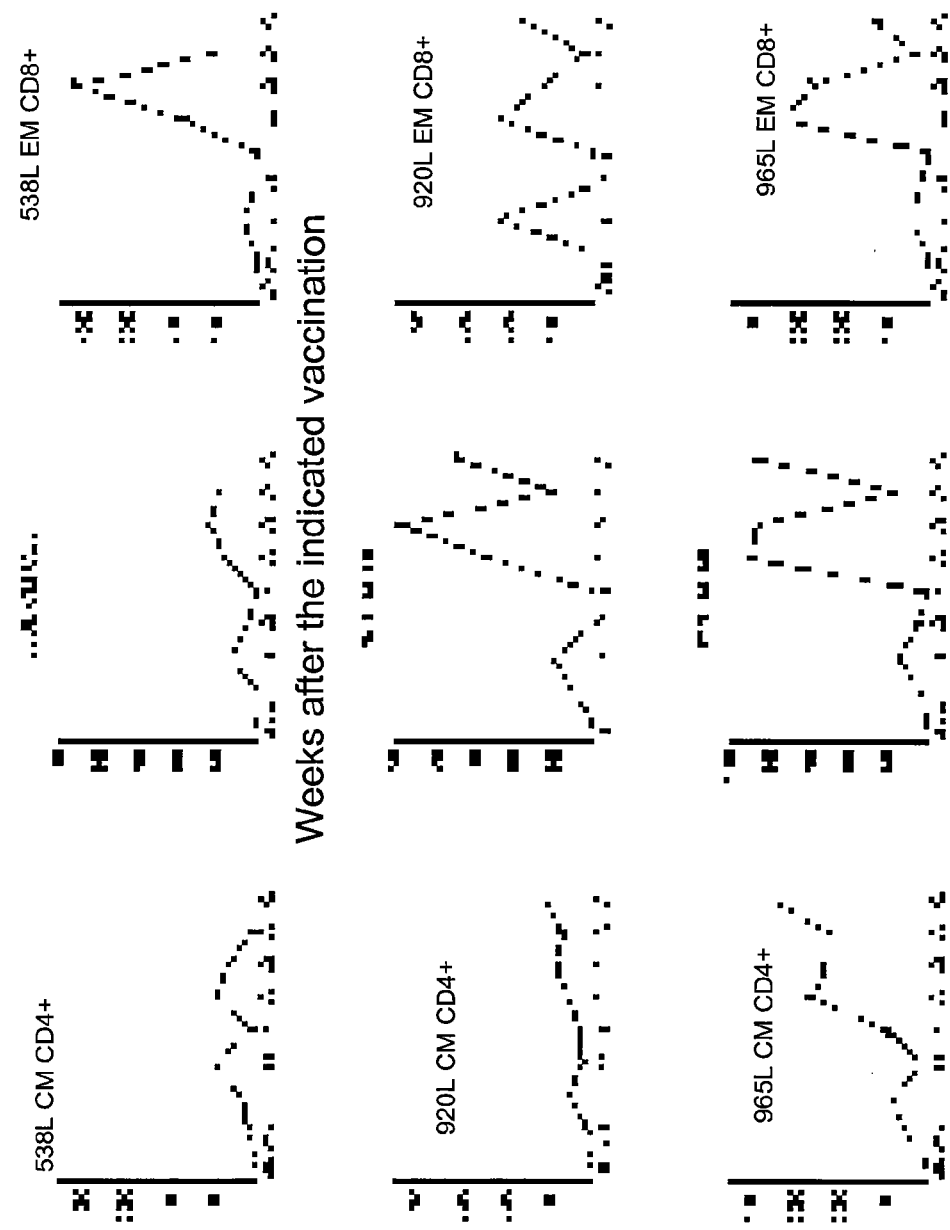
FIG. 4 shows the central memory and effector memory responses to env in the vaccinated animals 538L, 920L and 965L.
Figure 6:
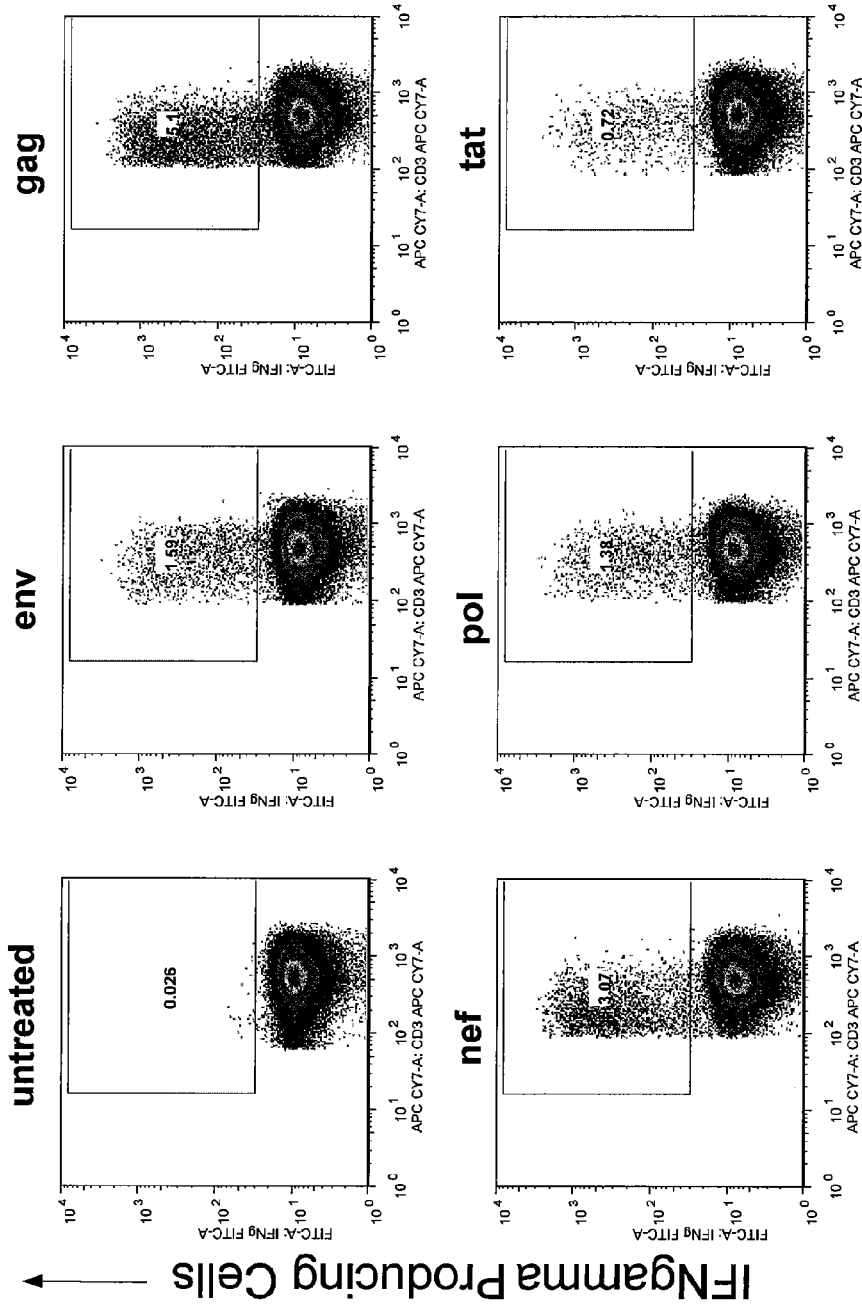
FIG. 6 shows a dramatic increase in antigen-specific cells in peripheral blood after vaccination by electroporation. SIV specific (env, gag, pol, nef, tat) CD3+ T cells were identified by Flow Cytometry after stimulation with pools of overlapping peptides as described in Agneta von Gegerfelt et al., *J Virol.* 2007 February; 81(4):1972-9. The data is from macaque M113, 2 weeks after the 2nd electroporation.
Figure 11:
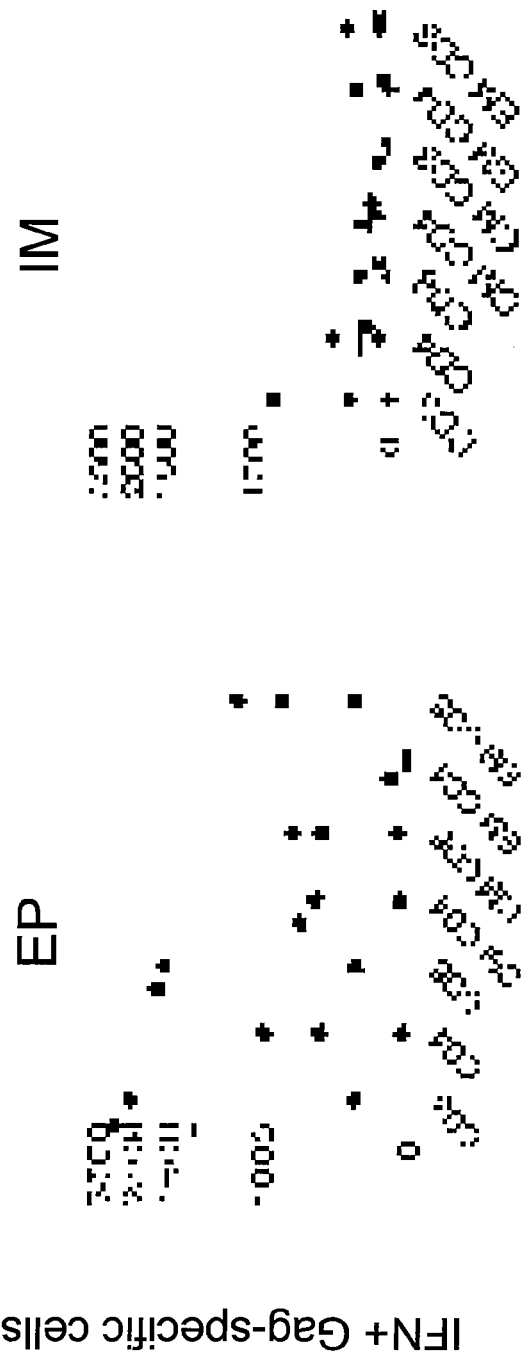
FIG. 11 shows a comparison of HIV gag specific IFN-gamma producing lymphocyte subsets induced by vaccination using electroporation or intramuscular injection. Numbers indicate IFNgamma producing cells after stimulation with gag pool peptides minus spontaneous stimulation expressed per million live lymphocytes. CM, central memory cells, defined as CD28+CD45RA−; EM, effector memory cells, defined as CD28− or low, CD45RA+. ELISPOT assay supports these data and shows also a 2-6 fold increase in the electroporated animals. This figure teaches that electroporation is a more potent method of DNA delivery and results in the induction of both antigen-specific CM and EM T cells.

The three vaccinated macaques showed dramatic increases in the number of SIV-specific cytokine-producing cells in PBMC with either central memory or effector memory phenotype to gag (FIG. 3) and env (FIG. 4). FIG. 5 shows an actual FACS analysis of animal 965L performed 2 weeks after the third immunization. The appearance of increased levels of effector cells in PBMC upon vaccination with the mix of DNAs is in contrast to our previous experiences, where DNA vaccination was able to generate SIV-specific central memory, but not effector cells (FIG. 11). We attribute this to the mix of DNA vaccines, to the improved method of delivery by in vivo electroporation and to the presence of effective levels of IL-15/ILRα cytokines. The improved delivery of the optimized SIV antigens results in great increased immune responses to all the antigens in the vaccine mixture (FIG. 6).

Figure 7:
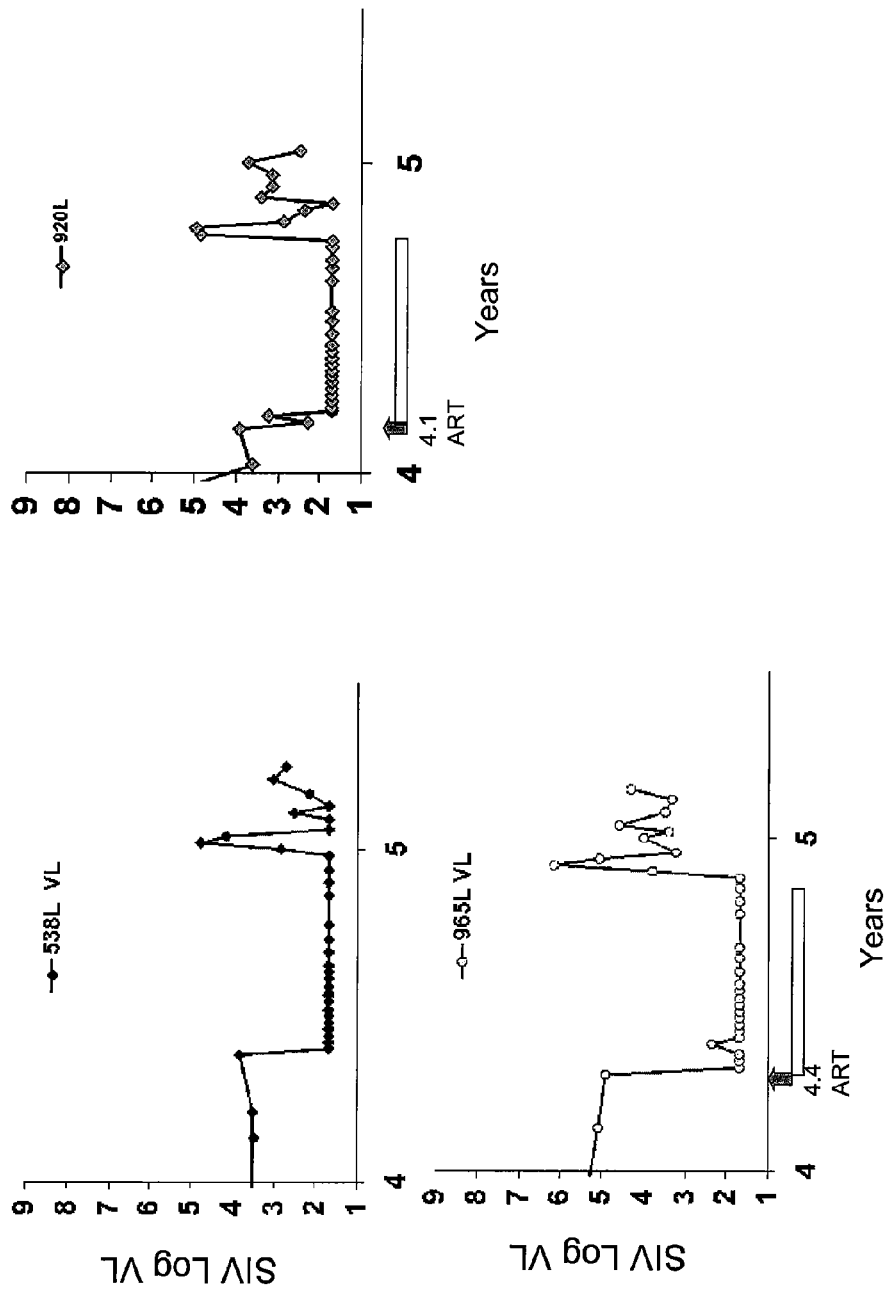
FIG. 7 shows that the animals vaccinated as described in FIG. 2 control viremia after ART release. The animals show the characteristic 'bouncing ball' virus loads after therapeutic vaccination and virus loads stabilize at lower levels.
Figure 8:
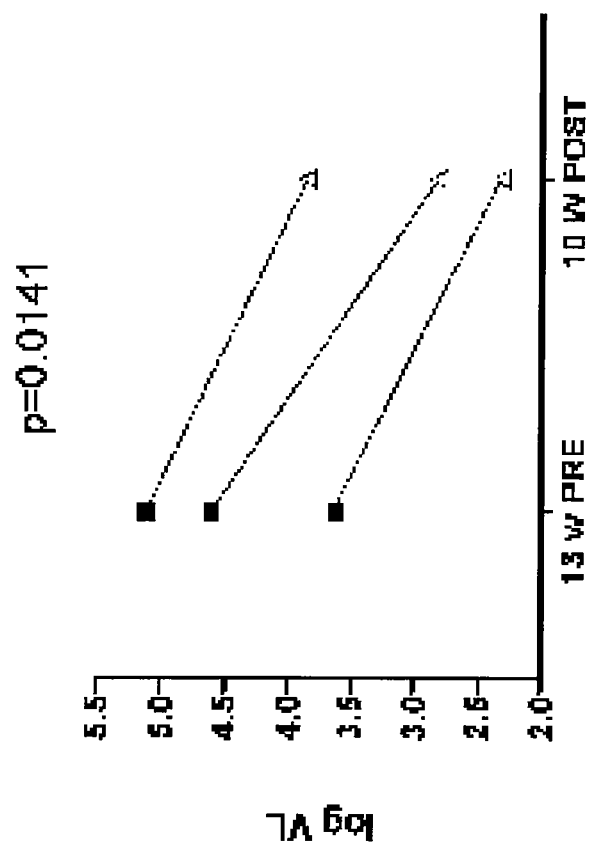
FIG. 8 shows a comparison of virus loads pre and post 2nd therapeutic vaccination by electroporation of animals shown in FIG. 2. The average virus load measurements for the 13 weeks prior to ART treatment were compared to the 4-14 week average virus load after vaccination and release from ART.
Figure 9:
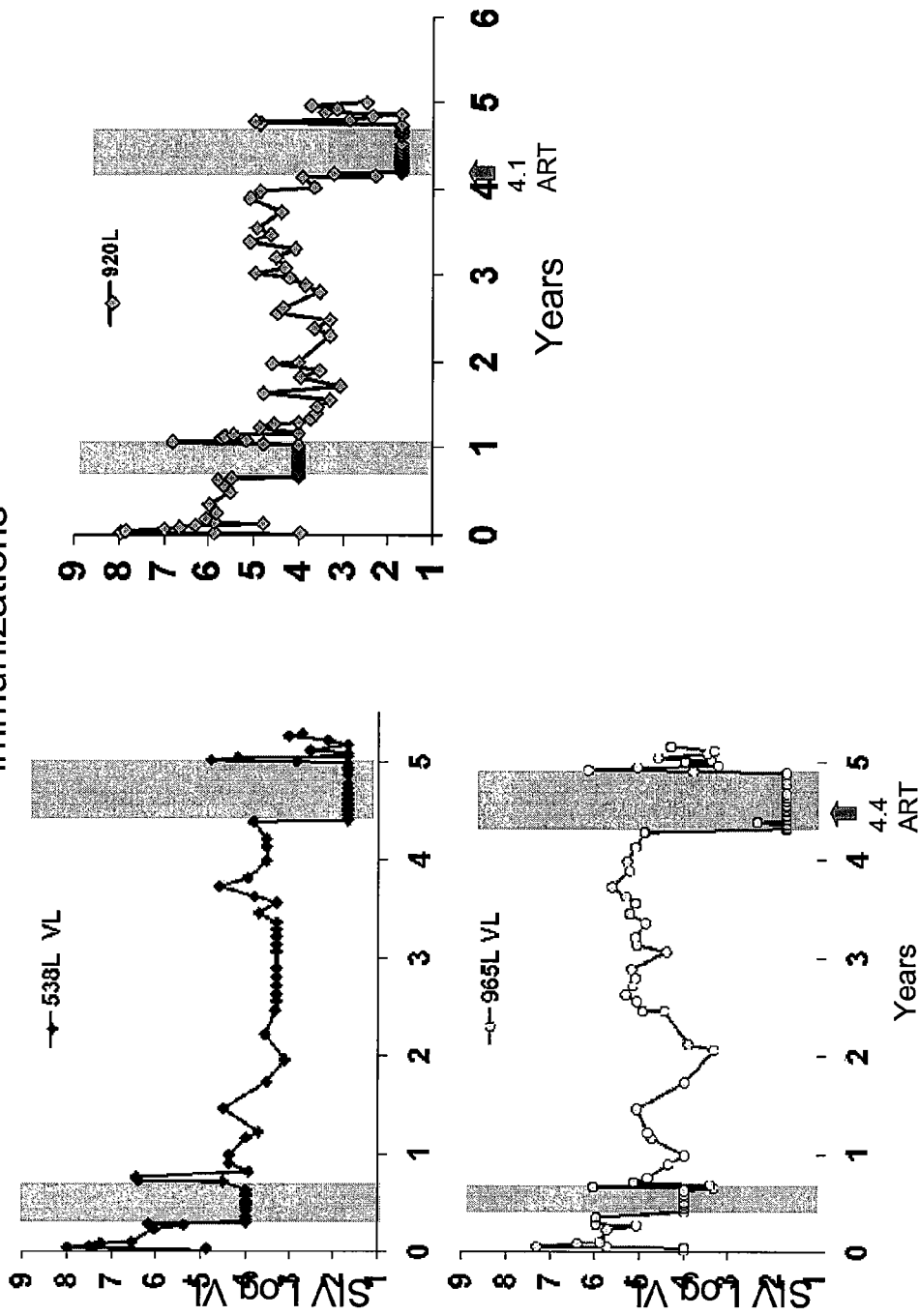
FIG. 9 shows comparisons of virus loads during first and second therapeutic immunizations and teaches that additional ART/vaccination leads to further reduction in virus loads.

The DNA vaccine vector mix and the inclusion of optimized levels of DNAs expressing IL-15 and IL-15Rα resulted in a dramatic increase in antigen-specific cells detected in the peripheral blood. In addition to increased levels, important phenotypic differences were detected by the analysis (FIG. 2-5). The vaccine-generated antigen-specific cells were shown to include IL-2 producing, TNF alpha producing as well as dual IFN-γ and IL-2 producing cells (FIG. 5). Vaccine generated antigen-specific cells having an effector phenotype were also generated, in addition to central memory antigen-specific cells. CD8+ effector cells are expected to be active against virus-infected cells, therefore our results indicate that these macaques better control virus upon release from ART (FIGS. 7 and 8). This dramatic response to DNA vaccination result that approximately 1-2% of circulating lymphocytes are SIV-specific. The results show further the repeated vaccination led to further lowering of virus levels (FIG. 9). This indicates that DNA vaccination alone under the conditions of the invention can generate a strong, diverse, long-lasting and multifunctional repertoire of antigen specific cells.

Figure 10:
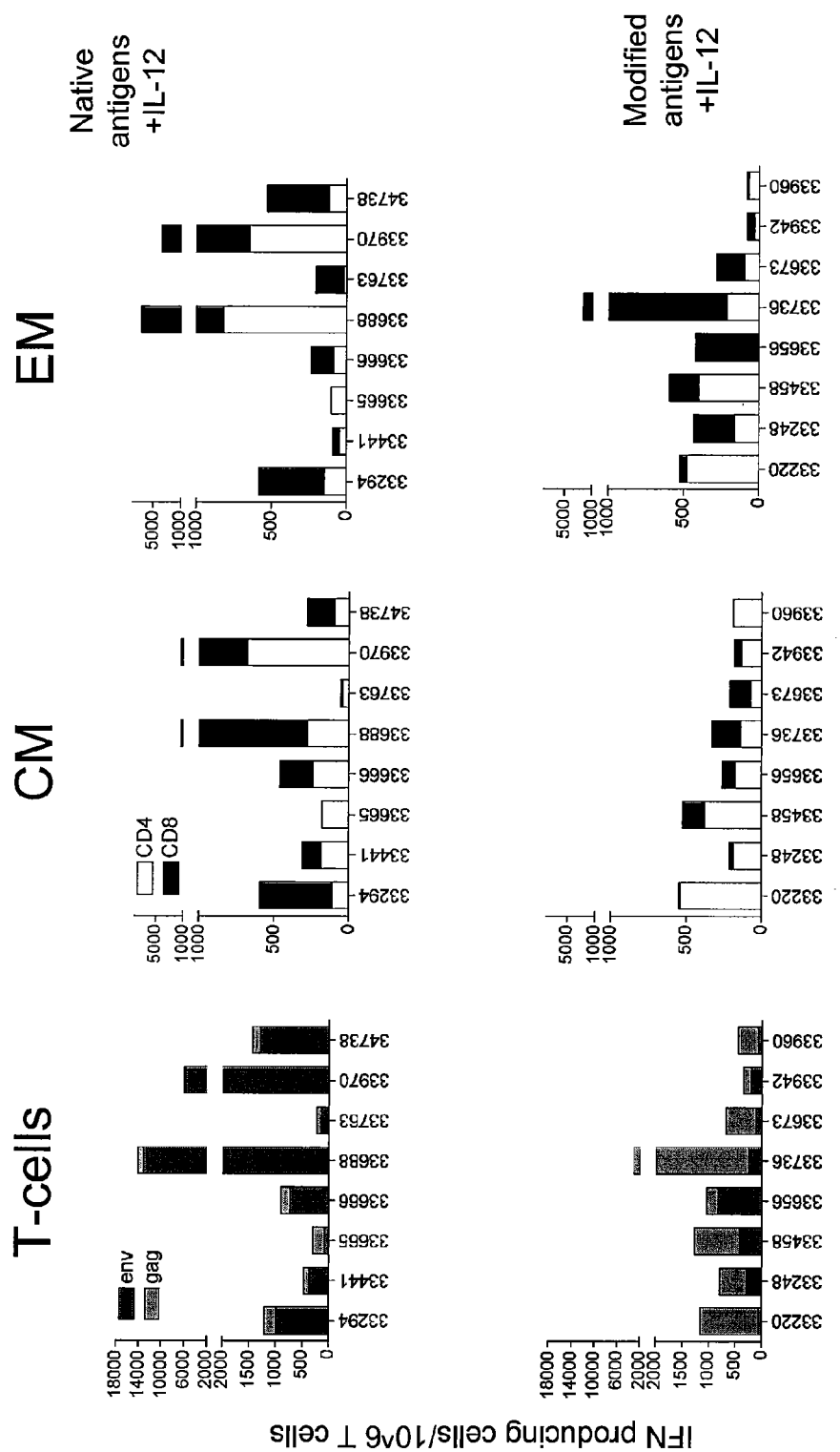
FIG. 10 shows antigen specific responses in naïve macaques (6 animals per group) vaccinated by electroporation at week 2 after 3[rd] vaccination. The animals received SIV expression plasmid for gag. env, pol, nef-tat-vif (NTV) either in their native form or modified form (fusion to CATE, LAMP, MCP-3 signals) and were coinjected with the optimized IL-12 expression plasmids. SIV specific gag and env immune responses were monitored in total T-cells and in central memory (CM) and effector memory (EM) cells. This study teaches that CM and EM cells can also be induced by the IL-12 cytokine. This demonstrates that IL12 and IL-15 cytokines have a positive effect on the induction of SIV specific immune responses.

DNA injection of IL-15/IL-15Rα combination appears to contribute to a great mobilization of effector cells, which are detected in PBMC on their way to peripheral sites. If this is the case, these results suggest the effectiveness of optimized IL-15/IL-15Rα combination as DNA or protein to enhance the mobilization and function of lymphocytes at optimal intervals in vivo. This immunotherapy with IL-15 can be used to enhance the effects of therapeutic vaccination and can also be used to enhance the immune response against the virus in the absence of therapeutic vaccination or for a long time after vaccination. In other studies using IL-12 DNA instead, high levels of effector cells were obtained (FIG. 10) teach that the IL-15 cytokine can be replaced by IL-12.

The DNA vaccine vectors used in this therapeutic vaccination were a mix composed of six SIV antigen-expressing plasmids and 2 rhesus IL-15/IL-15 Receptor alpha expressing plasmids. LAMP-pol and LAMP-NTV plasmids produce protein fusions of pol or NefTatVif, respectively, to human Lysosomal Associated Membrane Protein. The expression plasmids contain the human CMV promoter and the bovine growth hormone polyadenylation signal and the kanamycin resistance gene for selection in bacteria.

2S-CATEgagDX
21S-MCP-3p39gag
99S-Env
73S-MCP-3-env
103S-LAMP-pol
147S-LAMP-NTV

Rhesus IL-15/IL-15 Receptor alpha producing plasmids:
AG65-rhIL-15tPA6
AG120-rhIL-15Rα

Plasmids for use in the combination therapies are disclosed, e.g., in WO02/36806 and WO06/010106.

Lamp:

```
M A P R S A R R P L L L L L L L L L L G L M H C A S A A M F M V K N G N G T A C I

M A N F S A A F S V N Y D T K S G P K N M T L D L P S D A T V V L N R S S C G K E

N T S D P S L V I A F G R G H T L T L N F T R N A T R Y S V Q L M S F V Y N L S D

T H L F P N A S S K E I K T V E S I T D I R A D I D K K Y R C V S G T Q V H M N N V

T V T L H D A T I Q A Y L S N S S F S R G E T R C E Q D R P S P T T A P P A P P S

P S P S P V P K S P S V D K Y N V S G T N G T C L L A S M G L Q L N L T Y E R K D

N T T V T R L L N I N P N K T S A S G S C G A H L V T L E L H S E G T T V L L F Q F

G M N A S S S R F F L Q G I Q L N T I L P D A R D P A F K A A N G S L R A L Q A T

V G N S Y K C N A E E H V R V T K A F S V N I F K V W V Q A F K V E G G Q F G S

V E E C L L D E N S (signal and luminal domain)

xxxx (linker and gene of interest)
T L I P I A V G G A L A G L V L I V L I A Y L V G R K R S H A G Y Q T I • (transmembrane
domain and cytoplasmic tail)
```

The antigens, i.e., pol or the nef-tat-vif fusion proteins were inserted in between the signal/luminal domain and the transmembrane/cytoplasmic tail of human LAMP-1.

The examples provided here show that a method of administering a DNA vaccine to patients undergoing ART including DNA vaccination and IL-15/IL-15Ra to augment antiviral immune responses. The results chow that DNA vaccination can be administered successfully multiple times without adverse effectors. Moreover, the results show that DNA vaccination can be administered repeatedly until it results in the generation of multifunctional T cells.

The above examples are provided to illustrate the invention but not to limit its scope. Other variants of the invention will be readily apparent to one of ordinary skill in the art and are encompassed by the appended claims.

All publications, patents, accession numbers, and patent applications cited herein are hereby incorporated by reference for all purposes.

Exemplary Sequences

SIVCATE-gagDX (2S) nucleic acid sequence    SEQ ID NO: 1

ATGAGAAAAGCGGCTGTTAGTCACTGGCAGCAGCAGTCTTACCTGGACTCTGGAATCCATTC

TGGTGCCACTACCACAGCTCCTTCTCTGAGTGCTAGCGCAGGAGCAGGCGTGAGAAACTCCG

TCTTGTCAGGGAAGAAAGCAGATGAATTAGAAAAAATTAGGCTACGACCCAACGGAAAGAAA

AAGTACATGTTGAAGCATGTAGTATGGGCAGCAAATGAATTAGATAGATTTGGATTAGCAGA

AAGCCTGTTGGAGAACAAAGAAGGATGTCAAAAAATACTTTCGGTCTTAGCTCCATTAGTGC

CAACAGGCTCAGAAAATTTAAAAAGCCTTTATAATACTGTCTGCGTCATCTGGTGCATTCAC

GCAGAAGAGAAAGTGAAACACACTGAGGAAGCAAAACAGATAGTGCAGAGACACCTAGTGGT

GGAAACAGGAACCACCGAAACCATGCCGAAGACCTCTCGACCAACAGCACCATCTAGCGGCA

GAGGAGGAAACTACCCAGTACAGCAGATCGGTGGCAACTACGTCCACCTGCCACTGTCCCCG

AGAACCCTGAACGCTTGGGTCAAGCTGATCGAGGAGAAGAAGTTCGGAGCAGAAGTAGTGCC

AGGATTCCAGGCACTGTCAGAAGGTTGCACCCCCTACGACATCAACCAGATGCTGAACTGCG

TTGGAGACCATCAGGCGGCTATGCAGATCATCCGTGACATCATCAACGAGGAGGCTGCAGAT

TGGGACTTGCAGCACCCACAACCAGCTCCACAACAAGGACAACTTAGGGAGCCGTCAGGATC

AGACATCGCAGGAACCACCTCCTCAGTTGACGAACAGATCCAGTGGATGTACCGTCAGCAGA

ACCCGATCCCAGTAGGCAACATCTACCGTCGATGGATCCAGCTGGGTCTGCAGAAATGCGTC

CGTATGTACAACCCGACCAACATTCTAGATGTAAAACAAGGGCCAAAAGAGCCATTTCAGAG

CTATGTAGACAGGTTCTACAAAAGTTTAAGAGCAGAACAGACAGATGCAGCAGTAAAGAATT

GGATGACTCAAACACTGCTGATTCAAAATGCTAACCCAGATTGCAAGCTAGTGCTGAAGGGG

CTGGGTGTGAATCCCACCCTAGAAGAAATGCTGACGGCTTGTCAAGGAGTAGGGGGGCCGGG

ACAGAAGGCTAGATTAATGGCAGAAGCCCTGAAAGAGGCCCTCGCACCAGTGCCAATCCCTT

TTGCAGCAGCCCAACAGAGGGGACCAAGAAAGCCAATTAAGTGTTGGAATTGTGGGAAAGAG

GGACACTCTGCAAGGCAATGCAGAGCCCCAAGAAGACAGGGATGCTGGAAATGTGGAAAAAT

GGACCATGTTATGGCCAAATGCCCAGACAGACAGGCGGGTTTTTTAGGCCTTGGTCCATGGG

GAAAGAAGCCCCGCAATTTCCCCATGGCTCAAGTGCATCAGGGGCTGATGCCAACTGCTCCC

CCAGAGGACCCAGCTGTGGATCTGCTAAAGAACTACATGCAGTTGGGCAAGCAGCAGAGAGA

AAAGCAGAGAGAAAGCAGAGAGAAGCCTTACAAGGAGGTGACAGAGGATTTGCTGCACCTCA

ATTCTCTCTTTGGAGGAGACCAGTAG

SIVCATE-gagDX (2S) amino acid sequence    SEQ ID NO: 2

<u>M R K A A V S H W Q Q Q S Y L D S G I H S G A T T T A P S L S</u> *a s a g a* G

V R N S V L S G K K A D E L E K I R L R P N G K K K Y M L K H V V W A A

N E L D R F G L A E S L L E N K E G C Q K I L S V L A P L V P T G S E N L

K S L Y N T V C V I W C I H A E E K V K H T E E A K Q I V Q R H L V V E T

G T T E T M P K T S R P T A P S S G R G G N Y P V Q Q I G G N Y V H L P

L S P R T L N A W V K L I E E K K F G A E V V P G F Q A L S E G C T P Y D

I N Q M L N C V G D H Q A A M Q I I R D I I N E E A A D W D L Q H P Q P A

P Q Q G Q L R E P S G S D I A G T T S S V D E Q I Q W M Y R Q Q N P I P

V G N I Y R R W I Q L G L Q K C V R M Y N P T N I L D V K Q G P K E P F Q

S Y V D R F Y K S L R A E Q T D A A V K N W M T Q T L L I Q N A N P D C

K L V L K G L V N P T L E E M L T A C Q G V G G P G Q K A R L M A E A

L K E A L A P V P I P F A A A Q Q R G P R K P I K C W N C G K E G H S A

R Q C R A P R R Q G C W K C G K M D H V M A K C P D R Q A G F L G L G

P W G K K P R N F P M A Q V H Q G L M P T A P P E D P A V D L L K N Y M

Q L G K Q Q R E K Q R E S R E K P Y K E V T E D L L H L N S L F G G D Q *

CATE underlined
Linker lower case, italics
SIVgag bold

SIV MCP-3p39gag (21S) nucleic acid sequence

SEQ ID NO: 3

ATGAACCCAAGTGCTGCCGTCATTTTCTGCCTCATCCTGCTGGGTCTGAGTGGGA

CTCAAGGGATCCTCGACATGGCGCAACCGGTCGGGATCAACACGAGCACGACCT

GCTGCTACCGGTTCATCAACAAGAAGATCCCGAAGCAACGTCTGGAAAGCTATC

GCCGGACCACGTCGAGCCACTGCCCGCGGGAGGCGGTTATCTTCAAGACGAAGC

TGGACAAGGAGATCTGCGCCGACCCGACGCAGAAGTGGGTTCAGGACTTCATGA

AGCACCTGGATAAGAAGACGCAGACGCCGAAGCTGGCTAGCGCAGGAGCAGGC

GTGCGGAACTCCGTCTTGTCGGGGAAGAAAGCGGATGAGTTGGAGAAAATTCGG

CTACGGCCCAACGGGAAGAAGAAGTACATGTTGAAGCATGTAGTATGGGCGGCG

AATGAGTTGGATCGGTTTGGATTGGCGGAGAGCCTGTTGGAGAACAAAGAGGGA

TGTCAGAAGATCCTTTCGGTCTTGGCGCCGTTGGTGCCGACGGGCTCGGAGAACT

TGAAGAGCCTCTACAACACGGTCTGCGTCATCTGGTGCATTCACGCGGAAGAGA

AAGTGAAACACACGGAGGAAGCGAAACAGATAGTGCAGCGGCACCTAGTGGTG

GAAACGGGAACCACCGAAACCATGCCGAAGACCTCGCGGCCGACGGCGCCGTCG

AGCGGCAGGGGAGGAAACTACCCGGTACAGCAGATCGGTGGCAACTACGTCCAC

CTGCCGCTGTCCCCGCGGACCCTGAACGCGTGGGTCAAGCTGATCGAGGAGAAG

AAGTTCGGAGCGGAGGTAGTGCCGGGATTCCAGGCGCTGTCGGAAGGTTGCACC

CCCTACGACATCAACCAGATGCTGAACTGCGTTGGAGACCATCAGGCGGCGATG

CAGATCATCCGGGACATCATCAACGAGGAGGCGGCGGATTGGGACTTGCAGCAC

CCGCAACCGGCGCCGCAACAAGGACAACTTCGGGAGCCGTCGGGATCGGACATC

GCGGGAACCACCTCCTCGGTTGACGAACAGATCCAGTGGATGTACCGGCAGCAG

AACCCGATCCCAGTAGGCAACATCTACCGGCGGTGGATCCAGCTGGGTCTGCAG

AAATGCGTCCGTATGTACAACCCGACCAACATTCTAGATGTAAAACAAGGGCCA

AAGGAGCCGTTCCAGAGCTACGTCGACCGGTTCTACAAGTCGCTGCGGGCGGAG

CAGACGGACGCGGCGGTCAAGAACTGGATGACGCAGACGCTGCTGATCCAGAAC

GCGAACCCAGATTGCAAGCTAGTGCTGAAGGGGCTGGGTGTGAATCCCACCCTA

GAAGAAATGCTGACGGCTTGTCAAGGAGTAGGGGGGCCGGGACAGAAGGCTAG

ATTAATGGGGGCCCATGCGGCCGCGTAG

SIV MCP-3p39gag (21S) amino acid sequence

SEQ ID NO: 4

M N P S A A V I F C L I L L G L S G T Q G *i l d m a* Q P V G I N T S T T C C

Y R F I N K K I P K Q R L E S Y R R T T S S H C P R E A V I F K T K L D K E

I C A D P T Q K W V Q D F M K H L D K K T Q T P K L *a s a g a* G V R N S V

L S G K K A D E L E K I R L R P N G K K K Y M L K H V V W A A N E L D R

F G L A E S L L E N K E G C Q K I L S V L A P L V P T G S E N L K S L Y N

-continued

T V C V I W C I H A E E K V K H T E E A K Q I V Q R H L V V E T G T T E T

M P K T S R P T A P S S G R G G N Y P V Q Q I G G N Y V H L P L S P R T

L N A W V K L I E E K K F G A E V V P G F Q A L S E G C T P Y D I N Q M L

N C V G D H Q A A M Q I I R D I I N E E A A D W D L Q H P Q P A P Q Q G

Q L R E P S G S D I A G T T S S V D E Q I Q W M Y R Q Q N P I P V G N I Y

R R W I Q L G L Q K C V R M Y N P T N I L D V K Q G P K E P F Q S Y V D

R F Y K S L R A E Q T D A A V K N W M T Q L L I Q N A N P D C K L V L

K G L G V N P T L E E M L T A C Q G V G G P G Q K A R L M *G A H A A A* •

IP10 underlined
Linker lower case, italics
MCP-3 underlined
Linker lower case, italics
SIVgaagp39 bold
Linker italics SIV env (99S) nucleic acid sequence

SEQ ID NO: 5

ATGGGCTGCCTGGGGAACCAGCTGCTGATCGCCATCCTGCTGCTGAGCGTCTACG

GGATCTACTGCACCCTCTACGTCACGGTCTTCTACGGCGTCCCGGCTTGGAGGAA

TGCGACAATTCCCCTCTTTTGTGCAACCAAGAATAGGGATACTTGGGGAACAACT

CAGTGCCTACCGGACAACGGGGACTACTCGGAGGTGGCCCTGAACGTGACGGAG

AGCTTCGACGCCTGGAACAACACGGTCACGGAGCAGGCGATCGAGGACGTGTGG

CAGCTGTTCGAGACCTCGATCAAGCCGTGCGTCAAGCTGTCCCCGCTCTGCATCA

CGATGCGGTGCAACAAGAGCGAGACGGATCGGTGGGGGCTGACGAAGTCGATCA

CGACGACGGCGTCGACCACGTCGACGACGGCGTCGGCGAAAGTGGACATGGTCA

ACGAGACCTCGTCGTGCATCGCCCAGGACAACTGCACGGGCCTGGAGCAGGAGC

AGATGATCAGCTGCAAGTTCAACATGACGGGGCTGAAGCGGGACAAGAAGAAG

GAGTACAACGAGACGTGGTACTCGGCGGACCTGGTGTGCGAGCAGGGGAACAAC

ACGGGGAACGAGTCGCGGTGCTACATGAACCACTGCAACACGTCGGTGATCCAG

GAGTCGTGCGACAAGCACTACTGGGACGCGATCCGGTTCCGGTACTGCGCGCCG

CCGGGCTACGCGCTGCTGCGGTGCAACGACACGAACTACTCGGGCTTCATGCCG

AAATGCTCGAAGGTGGTGGTCTCGTCGTGCACGAGGATGATGGAGACGCAGACC

TCGACGTGGTTCGGCTTCAACGGGACGCGGGCGGAGAACCGGACGTACATCTAC

TGGCACGGGCGGGACAACCGGACGATCATCTCGCTGAACAAGTACTACAACCTG

ACGATGAAGTGCCGGCGGCCGGGCAACAAGACGGTGCTCCCGGTCACCATCATG

TCGGGGCTGGTGTTCCACTCGCAGCCGATCAACGACCGGCCGAAGCAGGCGTGG

TGCTGGTTCGGGGGGAAGTGGAAGGACGCGATCAAGGAGGTGAAGCAGACCATC

GTCAAGCACCCCCGCTACACGGGGACGAACAACACGGACAAGATCAACCTGACG

GCGCCGGGCGGGGCGATCCGGAAGTTACCTTCATGTGGACAAATTGCAGAGGA

GAGTTCCTCTACTGCAAGATGAACTGGTTCCTGAACTGGGTGGAGGACAGGAAC

ACGGCGAACCAGAAGCCGAAGGAGCAGCACAAGCGGAACTACGTGCCGTGCCA

CATTCGGCAGATCATCAACACGTGGCACAAAGTGGGCAAGAACGTGTACCTGCC

GCCGAGGGAGGGCGACCTCACGTGCAACTCCACGGTGACCTCCCTCATCGCGAA

CATCGACTGGATCGACGGCAACCAGACGAACATCACCATGTCGGCGGAGGTGGC

GGAGCTGTACCGGCTGGAGCTGGGGGACTACAAGCTGGTGGAGATCACGCCGAT

-continued

CGGCCTGGCCCCCACCGATGTGAAGCGCTACACCACCGGCGGGACGTCGAGAAA
TAAGCGGGGCGTGTTCGTGCTGGGCTTCCTGGGCTTTCTGGCCACCGCCGGCTCC
GCCATGGGAGCCGCCAGCCTGACCCTGACCGCCCAGAGCAGAACCCTGCTGGCC
GGCATCGTGCAGCAGCAGCAACAGCTGCTGGACGTGGTGAAGAGACAGCAGGA
ACTGCTGAGGCTGACAGTGTGGGGCACCAAGAACCTGCAGACCAGGGTGACCGC
CATCGAGAAGTACCTGAAGGACCAGGCCCAGCTGAACGCGTGGGGCTGTGCGTT
CCGCCAAGTCTGCCACACGACGGTCCCGTGGCCCAACGCCTCCCTGACCCCCAAG
TGGAACAACGAGACATGGCAGGAGTGGGAGCGGAAGGTGGACTTCCTGGAGGA
GAACATCACCGCCCTGCTGGAGGAGGCCCAGATCCAGCAAGAGAAGAATATGTA
CGAGCTGCAGAAGCTGAACAGCTGGGACGTGTTCGGCAACTGGTTCGATCTGGC
CAGCTGGATCAAATACATCCAGTACGGCGTGTACATCGTGGTGGGCGTGATCCTG
CTGAGGATCGTGATCTACATCGTGCAGATGCTGGCCAAGCTGAGGCAGGGCTAC
AGACCTGTGTTCAGCAGCCCCCCCAGCTACTTCCAGCAGACCCACATTCAGCAGG
ACCCTGCCCTGCCCACCAGAGAGGGCAAGGAGAGGGACGGCGGCGAGGGCGGA
GGAAACAGCAGCTGGCCCTGGCAGATCGAGTATATCCACTTCCTGATCCGGCAG
CTGATCAGACTGCTGACCTGGCTGTTCAGCAATTGCCGGACCCTGCTGTCCAGAG
TGTACCAGATCCTGCAGCCCATCCTGCAGAGACTGTCCGCGACCCTCCAGCGCAT
CCGGGAGGTGCTGAGAACCGAGCTGACCTACCTGCAGTACGGCTGGTCCTACTTC
CACGAGGCCGTGCAGGCTGTGTGGAGATCCGCCACCGAGACACTGGCCGGAGCC
TGGGGCGACCTGTGGGAGACACTGAGAAGAGGCGGCAGATGGATTCTGGCCATC
CCCCGGAGAATCAGACAGGGCCTGGAGCTGACACTGCTGTGATGA

SIV env (99S) amino acid sequence

SEQ ID NO: 6

M G C L G N Q L L I A I L L L S V Y G I Y C T L Y V T V F Y G V P A W R N A

T I P L F C A T K N R D T W G T T Q C L P D N G D Y S E V A L N V T E S F

D A W N N T V T E Q A I E D V W Q L F E T S I K P C V K L S P L C I T M R

C N K S E T D R W G L T K S I T T T A S T T S T T A S A K V D M V N E T S

S C I A Q D N C T G L E Q E Q M I S C K F N M T G L K R D K K K E Y N E T

W Y S A D L V C E Q G N N T G N E S R C Y M N H C N T S V I Q E S C D K

H Y W D A I R F R Y C A P P G Y A L L R C N D T N Y S G F M P K C S K V

V V S S C T R M M E T Q T S T W F G F N G T R A E N R T Y I Y W H G R D

N R T I I S L N K Y Y N L T M K C R R P G N K T V L P V T I M S G L V F H S

Q P I N D R P K Q A W C W F G G K W K D A I K E V K Q T I V K H P R Y T

G T N N T D K I N L T A P G G G D P E V T F M W T N C R G E F L Y C K M

N W F L N W V E D R N T A N Q K P K E Q H K R N Y V P C H I R Q I I N T W

H K V G K N V Y L P P R E G D L T C N S T V T S L I A N I D W I D G N Q T

N I T M S A E V A E L Y R L E L G D Y K L V E I T P I G L A P T D V K R Y T

T G G T S R N K R G V F V L G F L G F L A T A G S A M G A A S L T L T A Q

S R T L L A G I V Q Q Q Q Q L L D V V K R Q Q E L L R L T V W G T K N L Q

T R V T A I E K Y L K D Q A Q L N A W G C A F R Q V C H T T V P W P N A

S L T P K W N N E T W Q E W E R K V D F L E E N I T A L L E E A Q I Q Q E

KNMYELQKLNSWDVFGNWFDLASWIKYIQYGVYIVVG

VILLRIVIYIVQMLAKLRQGYRPVFSSPPSYFQQTHIQ

QDPALPTREGKERDGGEGGGNSSWPWQIEYIHFLIRQ

LIRLLTWLFSNCRTLLSRVYQILQPILQRLSATLQRIR

EVLRTELTYLQYGWSYFHEAVQAVWRSATETLAGAW

GDLWETLRRGGRWILAIPRRIRQGLELTLL**

SW MCP-3-env (73S) nucleic acid sequence

SEQ ID NO: 7

```
ATGAACCCAAGTGCTGCCGTCATTTTCTGCCTCATCCTGCTGGGTCTGAGTGGGA
CTCAAGGGATCCTCGACATGGCGCAACCGGTAGGTATAAACACAAGCACAACCT
GTTGCTATCGTTTCATAAATAAAAAGATACCGAAGCAACGTCTGGAAAGCTATCG
CCGTACCACTTCTAGCCACTGTCCGCGTGAAGCTGTTATATTCAAAACGAAACTG
GATAAGGAGATCTGCGCCGACCCTACACAGAAATGGGTTCAGGACTTTATGAAG
CACCTGGATAAAAAGACACAGACGCCGAAACTGATCTGCAGCCTGTACGTCACG
GTCTTCTACGGCGTACCAGCTTGGAGGAATGCGACAATTCCCCTCTTTTGTGCAA
CCAAGAATAGGGATACTTGGGGAACAACTCAGTGCCTACCGGACAACGGGGACT
ACTCGGAGGTGGCCCTGAACGTGACGGAGAGCTTCGACGCCTGGAACAACACGG
TCACGGAGCAGGCGATCGAGGACGTGTGGCAGCTGTTCGAGACCTCGATCAAGC
CGTGCGTCAAGCTGTCCCCGCTCTGCATCACGATGCGGTGCAACAAGAGCGAGA
CGGATCGGTGGGGGCTGACGAAGTCGATCACGACGACGGCGTCGACCACGTCGA
CGACGGCGTCGGCGAAAGTGGACATGGTCAACGAGACCTCGTCGTGCATCGCCC
AGGACAACTGCACGGGCCTGGAGCAGGAGCAGATGATCAGCTGCAAGTTCAACA
TGACGGGGCTGAAGCGGGACAAGAAGAAGGAGTACAACGAGACGTGGTACTCG
GCGGACCTGGTGTGCGAGCAGGGGAACAACACGGGGAACGAGTCGCGGTGCTAC
ATGAACCACTGCAACACGTCGGTGATCCAGGAGTCGTGCGACAAGCACTACTGG
GACGCGATCCGGTTCCGGTACTGCGCGCCGCCGGGCTACGCGCTGCTGCGGTGCA
ACGACACGAACTACTCGGGCTTCATGCCGAAATGCTCGAAGGTGGTGGTCTCGTC
GTGCACGAGGATGATGGAGACGCAGACCTCGACGTGGTTCGGCTTCAACGGGAC
GCGGGCGGAGAACCGGACGTACATCTACTGGCACGGGCGGGACAACCGGACGAT
CATCTCGCTGAACAAGTACTACAACCTGACGATGAAGTGCCGGCGGCCGGGCAA
CAAGACGGTGCTCCCGGTCACCATCATGTCGGGGCTGGTGTTCCACTCGCAGCCG
ATCAACGACCGGCCGAAGCAGGCGTGGTGCTGGTTCGGGGGGAAGTGGAAGGAC
GCGATCAAGGAGGTGAAGCAGACCATCGTCAAGCACCCCCGCTACACGGGGACG
AACAACACGGACAAGATCAACCTGACGGCGCCGGGCGGGGCGATCCGGAAGTT
ACCTTCATGTGGACAAATTGCAGAGGAGAGTTCCTCTACTGCAAGATGAACTGGT
TCCTGAACTGGGTGGAGGACAGGAACACGGCGAACCAGAAGCCGAAGGAGCAG
CACAAGCGGAACTACGTGCCGTGCCACATTCGGCAGATCATCAACACGTGGCAC
AAAGTGGGCAAGAACGTGTACCTGCCGCCGAGGGAGGGCGACCTCACGTGCAAC
TCCACGGTGACCTCCCTCATCGCGAACATCGACTGGATCGACGGCAACCAGACG
AACATCACCATGTCGGCGGAGGTGGCGGAGCTGTACCGGCTGGAGCTGGGGGAC
TACAAGCTGGTGGAGATCACGCCGATCGGCCTGGCCCCCACCGATGTGAAGCGC
TACACGACCGGGGGACGTCGCGGAACAAGCGGGGGGTCTTCGTCCTGGGGTTC
```

```
CTGGGGTTCCTCGCGACGGCGGGGTCGGCAATGGGAGCCGCCAGCCTGACCCTC
ACGGCACAGTCCCGAACTTTATTGGCTGGGATCGTCCAACAACAGCAGCAGCTG
CTGGACGTGGTCAAGAGGCAGCAGGAGCTGCTGCGGCTGACCGTCTGGGGCACG
AAGAACCTCCAGACGAGGGTCACGGCCATCGAGAAGTACCTGAAGGACCAGGCG
CAGCTGAACGCGTGGGGCTGTGCGTTTCGACAAGTCTGCCACACGACGGTCCCGT
GGCCGAACGCGTCGCTGACGCCGAAGTGGAACAACGAGACGTGGCAGGAGTGG
GAGCGGAAGGTGGACTTCCTGGAGGAGAACATCACGGCCCTCCTGGAGGAGGCG
CAGATCCAGCAGGAGAAGAACATGTACGAGCTGCAAAAGCTGAACAGCTGGGA
CGTGTTCGGCAACTGGTTCGACCTGGCGTCGTGGATCAAGTACATCCAGTACGGC
GTGTACATCGTGGTGGGGGTGATCCTGCTGCGGATCGTGATCTACATCGTCCAGA
TGCTGGCGAAGCTGCGGCAGGGCTATAGGCCAGTGTTCTCTTCCCCACCCTCTTA
TTTCCAACAAACCCATATCCAACAAGACCCGGCGCTGCCGACCCGGGAGGGCAA
GGAGCGGGACGGCGGGGAGGGCGGCGGCAACAGCTCCTGGCCGTGGCAGATCG
AGTACATCCACTTTCTTATTCGTCAGCTTATTAGACTCCTGACGTGGCTGTTCAGT
AACTGTAGGACTCTGCTGTCGAGGGTGTACCAGATCCTCCAGCCGATCCTCCAGC
GGCTCTCGGCGACCCTCCAGAGGATTCGGGAGGTCCTCCGGACGGAGCTGACCT
ACCTCCAGTACGGGTGGAGCTATTTCCACGAGGCGGTCCAGGCCGTCTGGCGGTC
GGCGACGGAGACGCTGGCGGGCGCGTGGGGCGACCTGTGGGAGACGCTGCGGC
GGGGCGGCCGGTGGATACTCGCGATCCCCCGGCGGATCAGGCAGGGGCTGGAGC
TCACGCTCCTGTGATAA
```

SIV MCP-3-env (73S) amino acid sequence

SEQ ID NO: 8

<u>M N P S A A V I F C L I L L G L S G T Q G</u> i l d m a <u>Q P V G I N T S T T C C</u>
<u>Y R F I N K K I P K Q R L E S Y R R T T S S H C P R E A V I F K T K L D K E</u>
<u>I C A D P T Q K W V Q D F M K H L D K K T Q T P K L</u> I C S L Y V T V F Y G
V P A W R N A T I P L F C A T K N R D T W G T T Q C L P D N G D Y S E V
A L N V T E S F D A W N N T V T E Q A I E D V W Q L F E T S I K P C V K L
S P L C I T M R C N K S E T D R W G L T K S I T T T A S T T S T T A S A K
V D M V N E T S S C I A Q D N C T G L E Q E Q M I S C K F N M T G L K R
D K K K E Y N E T W Y S A D L V C E Q G N N T G N E S R C Y M N H C N T
S V I Q E S C D K H Y W D A I R F R Y C A P P G Y A L L R C N D T N Y S
G F M P K C S K V V V S S C T R M M E T Q T S T W F G F N G T R A E N R
T Y I Y W H G R D N R T I I S L N K Y Y N L T M K C R R P G N K T V L P V
T I M S G L V F H S Q P I N D R P K Q A W C W F G G K W K D A I K E V K
Q T I V K H P R Y T G T N N T D K I N L T A P G G G D P E V T F M W T N C
R G E F L Y C K M N W F L N W V E D R N T A N Q K P K E Q H K R N Y V P
C H I R Q I I N T W H K V G K N V Y L P P R E G D L T C N S T V T S L I A
N I D W I D N Q T N I T M S A E V A E L Y R L E L G D Y K L V E I T P I G
L A P T D V K R Y T T G G T S R N K R G V F V L G F L G F L A T A G S A
M G A A S L T L T A Q S R T L L A G I V Q Q Q Q Q L L D V V K R Q Q E L
L R L T V W G T K N L Q T R V T A I E K Y L K D Q A Q L N A W G C A F R

-continued

QVCHTTVPWPNASLTPKWNNETWQEWERKVDFLEEN

ITALLEEAQIQQEKNMYELQKLNSWDVFGNWFDLAS

WIKYIQYGVYIVVGVILLRIVIYIVQMLAKLRQGYRPV

FSSPPSYFQQTHIQQDPALPTREGKERDGGEGGNS

SWPWQIEYIHFLIRQLIRLLTWLFSNCRTLLSRVYQIL

QPILQRLSATLQRIREVLRTELTYLQYGWSYFHEAVQ

AVWRSATETLAGAWGDLWETLRRGGRWILAIPRRIR

QGLETLL**

IP10 underlined
Linker lower case, italics
MCP-3 underlined
SIVenv bold

SIV LAMP-pol (103S) nucleic acid sequence

SEQ ID NO: 9

ATGGCGCCCCGCAGCGCCCGGCGACCCCTGCTGCTGCTACTGCTGTTGCTGCTGC

TCGGCCTCATGCATTGTGCGTCAGCAGCAATGTTTATGGTGAAAAATGGCAACGG

GACCGCGTGCATAATGGCCAACTTCTCTGCTGCCTTCTCAGTGAACTACGACACC

AAGAGTGGCCCTAAGAACATGACCCTTGACCTGCCATCAGATGCCACAGTGGTG

CTCAACCGCAGCTCCTGTGGAAAAGAGAACACTTCTGACCCCAGTCTCGTGATTG

CTTTTGGAAGAGGACATACACTCACTCTCAATTTCACGAGAAATGCAACACGTTA

CAGCGTCCAGCTCATGAGTTTTGTTTATAACTTGTCAGACACACACCTTTTCCCCA

ATGCGAGCTCCAAAGAAATCAAGACTGTGGAATCTATAACTGACATCAGGGCAG

ATATAGATAAAAAATACAGATGTGTTAGTGGCACCCAGGTCCACATGAACAACG

TGACCGTAACGCTCCATGATGCCACCATCCAGGCGTACCTTTCCAACAGCAGCTT

CAGCAGGGGAGAGACACGCTGTGAACAAGACAGGCCTTCCCCAACCACAGCGCC

CCCTGCGCCACCCAGCCCCTCGCCCTCACCCGTGCCCAAGAGCCCCTCTGTGGAC

AAGTACAACGTGAGCGGCACCAACGGGACCTGCCTGCTGGCCAGCATGGGGCTG

CAGCTGAACCTCACCTATGAGAGGAAGGACAACACGACGGTGACAAGGCTTCTC

AACATCAACCCCAACAAGACCTCGGCCAGCGGGAGCTGCGGCGCCCACCTGGTG

ACTCTGGAGCTGCACAGCGAGGGCACCACCGTCCTGCTCTTCCAGTTCGGGATGA

ATGCAAGTTCTAGCCGGTTTTTCCTACAAGGAATCCAGTTGAATACAATTCTTCCT

GACGCCAGAGACCCTGCCTTTAAAGCTGCCAACGGCTCCCTGCGAGCGCTGCAG

GCCACAGTCGGCAATTCCTACAAGTGCAACGCGGAGGAGCACGTCCGTGTCACG

AAGGCGTTTTCAGTCAATATATTCAAAGTGTGGGTCCAGGCTTTCAAGGTGGAAG

GTGGCCAGTTTGGCTCTGTGGAGGAGTGTCTGCTGGACGAGAACAGCCTCGAGG

ATATCGGGGCCCATCGGGAGGCGTTGCAGGGGGGAGACCGCGGGTTCGCGGCGC

CGCAGTTCTCGCTGTGGCGGCGGCCGGTCGTCACCGCGCACATCGAGGGGCAGC

CGGTGGAGGTGTTGCTGGCGGACGACTCGATCGTGACGGGCATAGAGTTGGGC

CGCACTACACCCCGAAGATCGTAGGGGGGATCGGGGGGTTCATCAACACGAAGG

AGTACAAGAACGTGGAGATCGAGGTCTTGGGCAAGCGGATCAAGGGGACGATCA

TGACCGGGGACACCCCGATCAACATCTTCGGGCGGAACCTGCTGACGGCGCTGG

GGATGTCGCTCAACTTCCCCATCGCGAAGGTGGAGCCCGTCAAGGTCGCCTTGAA

GCCGGGGAAGGATGGGCCGAAGTTGAAGCAGTGGCCGTTGTCCAAGGAGAAGAT

-continued
```
CGTCGCGTTGCGGGAGATCTGCGAGAAGATGGAGAAGGACGGACAGCTGGAGG

AGGCGCCCCGACCAACCCCTACAACACCCCCACCTTCGCTATCAAGAAGAAGG

ACAAGAACAAGTGGCGGATGCTGATCGACTTCCGGGAGTTGAACCGGGTCACGC

AGGACTTCACGGAGGTCCAGTTGGGCATCCCGCACCCGGCGGGGCTGGCGAAGC

GGAAGCGGATCACGGTACTGGACATCGGGGACGCGTACTTCTCCATCCCGCTCG

ACGAGGAGTTCCGGCAGTACACGGCCTTCACGCTCCCGTCCGTCAACAACGCGG

AGCCGGGGAAGCGCTACATCTACAAGGTCCTGCCGCAGGGGTGGAAGGGGTCGC

CGGCCATCTTCCAGTACACGATGCGGCACGTGCTCGAGCCTTTCCGGAAGGCGAA

CCCGGACGTGACCCTGGTCCAGATCTTGATCGCGTCGGACCGGACGGACCTGGA

GCACGATCGGGTCGTGCTGCAGTCGAAGGAGCTGCTGAACAGCATCGGGTTCTC

GACCCCGGAGGAGAAGTTCCAGAAGGACCCCCCGTTCCAGTGGATGGGATACGA

GCTGTGGCCGACGAAGTGGAAGCTGCAGAAGATCGAGCTGCCGCAGCGGGAGAC

TTGGACGGTGAACGACATCCAGAAGCTCGTCGGGGTCCTCAACTGGGCGGCCCA

GATCTACCCGGGGATCAAGACCAAGCACCTCTGTCGGCTGATCCGGGGGAAGAT

GACGCTGACGGAGGAGGTCCAGTGGACGGAGATGGCGGAGGCGGAGTACGAGG

AGAACAAGATCATCCTCTCGCAAGAGCAGGAGGGGTGCTACTACCAGGAGGGCA

AGCCGCTGGAGGCCACGGTCATCAAGTCGCAGGACAACCAGTGGTCGTACAAGA

TCCACCAGGAGGACAAGATCCTGAAGGTCGGGAAGTTCGCGAAGATCAAGAACA

CGCACACCAACGGAGTGCGGCTGCTTGCGCACGTCATCCAGAAGATCGGGAAGG

AGGCGATCGTGATCTGGGGGCAGGTCCCGAAGTTCCACCTTCCGGTCGAGAAGG

ACGTCTGGGAGCAGTGGTGGACGGACTACTGGCAGGTCACCTGGATCCCGGAGT

GGGACTTCATCTCGACGCCGCCGCTCGTCCGGCTTGTGTTCAACCTCGTGAAGGA

CCCGATCGAGGGGAGGAGACATACTACACGGACGGGTCGTGCAACAAGCAGTC

GAAGGAGGGGAAGGCGGGCTACATCACGGACCGGGGCAAGGACAAGGTCAAGG

TGCTTGAGCAGACGACGAACCAGCAGGCGCTGGAGGCGTTCCTCATGGCGTTGA

CGGACTCGGGACCCAAGGCGAACATCATCGTAGACTCGCAATACGTCATGGGGA

TCATCACGGGGTGCCCGACGGAGTCGGAGAGCCGGCTCGTCAACCAGATCATCG

AGGAGATGATCAAGAAGTCGGAGATCTACGTCGCGTGGGTCCCGGCGCACAAGG

GCATCGGCGGCAACCAGGAGATCGACCACCTCGTCTCGCAAGGCATCCGCCAGG

TCCTCTTCCTGGAGAAGATCGAGCCGGCGCAGGAGGAGCACGACAAGTACCATT

CGAACGTCAAGGAGCTGGTGTTCAAGTTCGGGCTCCCCCGGATCGTGGCCCGGC

AGATCGTAGACACCTGCGACAAGTGTCACCAGAAGGGCGAGGCGATCCACGGGC

AGGCGAACTCGGACCTCGGGACCTGGCAGATGTGCACCCATCTCGAGGGGAAGA

TCATCATCGTCGCGGTCCACGTCGCGTCGGGCTTCATCGAGGCGGAGGTCATCCC

GCAGGAAACGGGGCGGCAGACGGCGCTGTTCCTGTTGAAGTTGGCGGGCCGCTG

GCCCATCACGCACCTCCACACGAACGGGGCGAACTTCGCGTCGCAGGAGGTCAA

GATGGTCGCGTGGTGGGCGGGATCGAGCACACCTTCGGGGTCCCGTACAACCC

GCAGTCGCAGGGCGTCGTGGCGATGAACCACCACCTGAAGAACCAGATCGACCG

CATCCGCGAGCAGGCGAACTCCGTCGAGACCATCGTCTTGATGGCGGTCCACTGC

ATGAACTTCAAGCGGCGGGGCGGCATCGGGGACATGACGCCGGCGGAGCGGTTG

ATCAACATGATCACGACGGAGCAGGAGATCCAGTTCCAGCAGTCGAAGAACTCG
```

```
AAGTTCAAGAACTTCCGGGTCTACTACCGGGAGGGCCGGGACCAGCTGTGGAAG
GGACCAGGCGAGCTGCTGTGGAAGGGGGAGGGCGCGGTCATCTTGAAGGTCGGG
ACGGACATCAAGGTCGTCCCCCGGCGGAAGGCGAAGATCATCAAGGACTACGGG
GGCGGGAAGGAGGTGGACAGCTCGTCCCACATGGAGGACACCGGCGAGGCGCG
GGAGGTGGCCCATGCGGCCGCGGGGGAATTCACGCTGATCCCCATCGCTGTGGG
TGGTGCCCTGGCGGGGCTGGTCCTCATCGTCCTCATCGCCTACCTCGTCGGCAGG
AAGAGGAGTCACGCAGGCTACCAGACTATCTAG
```

SIV LAMP-pol (103S) amino acid sequence

SEQ ID NO: 10

<u>M A P R S A R R P L L L L L L L L L L L G L M H C A S A A M F M V K N G N G</u>

<u>T A C I M A N F S A A F S V N Y D T K S G P K N M T L D L P S D A T V V L</u>

<u>N R S S C G K E N T S D P S L V I A F G R G H T L T L N F T R N A T R Y S</u>

<u>V Q L M S F V Y N L S D T H L F P N A S S K E I K T V E S I T D I R A D I D</u>

<u>K K Y R C V S G T Q V H M N N V T V T L H D A T I Q A Y L S N S S F S R G</u>

<u>E T R C E Q D R P S P T T A P P A P P S P S P S P V P K S P S V D K Y N V</u>

<u>S G T N G T C L L A S M G L Q L N L T Y E R K D N T T V T R L L N I N P N</u>

<u>K T S A S G S C G A H L V T L E L H S E G T T V L L F Q F G M N A S S S R</u>

<u>F F L Q G I Q L N T I L P D A R D P A F K A A N G S L R A L Q A T V G N S</u>

<u>Y K C N A E E H V R V T K A F S V N I F K V W V Q A F K V E G G Q F G S V</u>

<u>E E C L L D E N S</u> l e d i g a H R E A L Q G G D R G F A A P Q F S L W R R

P V V T A H I E G Q P V E V L L A D D S I V T G I E L G P H Y T P K I V G G

I G G F I N T K E Y K N V E I E V L G K R I K G T I M T G D T P I N I F G R

N L L T A L G M S L N F P I A K V E P V K V A L K P G K D G P K L K Q W

P L S K E K I V A L R E I C E K M E K D G Q L E E A P P T N P Y N T P T F

A I K K K D K N K W R M L I D F R E L N R V T Q D F T E V Q L G I P H P A

G L A K R K R I T V L D I G D A Y F S I P L D E E F R Q Y T A F T L P S V

N N A E P G K R Y I Y K V L P Q G W K G S P A I F Q Y T M R H V L E P F

R K A N P D V T L V Q I L I A S D R T D L E H D R V V L Q S K E L L N S I

G F S T P E E K F Q K D P P F Q W M G Y E L W P T K W L Q K I E L P Q

R E T W T V N D I Q K L V G V L N W A A Q I Y P G I K T K H L C R L I R G

K M T L T E E V Q W T E M A E A E Y E E N K I I L S Q E Q E G C Y Y Q E

G K P L E A T V I K S Q D N Q W S Y K I H Q E D K I L K V G K F A K I K N

T H T N G V R L L A H V I Q K I G K E A I V I W G Q V P K F H L P V E K D

V W E Q W W T D Y W Q V T W I P E W D F I S T P P L V R L V F N L V K D

P I E G E E T Y Y T D G S C N K Q S K E G K A G Y I T D R G K D K V K V L

E Q T T N Q Q A L E A F L M A L T D S G P K A N I I V D S Q Y V M G I I T

G C P T E S E S R L V N Q I I E E M I K K S E I Y V A W V P A H K G I G G

N Q E I D H L V S Q G I R Q V L F L E K I E P A Q E E H D K Y H S N V K E

L V F K F G L P R I V A R Q I V D T C D K C H Q K G E A I H G Q A N S D L

G T W Q M C T H L E G K I I I V A V H V A S G F I E A E V I P Q E T G R Q

T A L F L L K L A G R W P I T H L H T N G A N F A S Q E V K M V A W W A

-continued

G I E H T F G V P Y N P Q S Q G V V A M N H H L K N Q I D R I R E Q A N S

V E T I V L M A V H C M N F K R R G G I G D M T P A E R L I N M I T T E Q

E I Q F Q Q S K N S K F K N F R V Y Y R E G R D Q L W K G P G E L L W K

G E G A V I L K V G T D I K V V P R R K A K I I K D Y G G G K E V D S S S

H M E D T G E A R E V A H *a a a g e f* <u>T L I P I A V G G A L A G L V L I V L I</u>

<u>A Y L V G R K R S H A G Y Q T I</u> •

LAMP-1 underlined
Linker lower case, italics
SIV pol bold
Linker lower case, italics
LAMP-1 underlined SIV LAMP-NTV (147S) nucleic acid sequence

SEQ ID NO: 11

ATGGCGCCCCGCAGCGCCCGGCGACCCCTGCTGCTGCTACTGCTGTTGCTGCTGC

TCGGCCTCATGCATTGTGCGTCAGCAGCAATGTTTATGGTGAAAAATGGCAACGG

GACCGCGTGCATAATGGCCAACTTCTCTGCTGCCTTCTCAGTGAACTACGACACC

AAGAGTGGCCCTAAGAACATGACCCTTGACCTGCCATCAGATGCCACAGTGGTG

CTCAACCGCAGCTCCTGTGGAAAAGAGAACACTTCTGACCCCAGTCTCGTGATTG

CTTTTGGAAGAGGACATACACTCACTCTCAATTTCACGAGAAATGCAACACGTTA

CAGCGTCCAGCTCATGAGTTTTGTTTATAACTTGTCAGACACACACCTTTTCCCCA

ATGCGAGCTCCAAAGAAATCAAGACTGTGGAATCTATAACTGACATCAGGGCAG

ATATAGATAAAAAATACAGATGTGTTAGTGGCACCCAGGTCCACATGAACAACG

TGACCGTAACGCTCCATGATGCCACCATCCAGGCGTACCTTTCCAACAGCAGCTT

CAGCAGGGGAGAGACACGCTGTGAACAAGACAGGCCTTCCCCAACCACAGCGCC

CCCTGCGCCACCCAGCCCCTCGCCCTCACCCGTGCCCAAGAGCCCCTCTGTGGAC

AAGTACAACGTGAGCGGCACCAACGGGACCTGCCTGCTGGCCAGCATGGGGCTG

CAGCTGAACCTCACCTATGAGAGGAAGGACAACACGACGGTGACAAGGCTTCTC

AACATCAACCCCAACAAGACCTCGGCCAGCGGGAGCTGCGGCGCCCACCTGGTG

ACTCTGGAGCTGCACAGCGAGGGCACCACCGTCCTGCTCTTCCAGTTCGGGATGA

ATGCAAGTTCTAGCCGGTTTTTCCTACAAGGAATCCAGTTGAATACAATTCTTCCT

GACGCCAGAGACCCTGCCTTTAAAGCTGCCAACGGCTCCCTGCGAGCGCTGCAG

GCCACAGTCGGCAATTCCTACAAGTGCAACGCGGAGGAGCACGTCCGTGTCACG

AAGGCGTTTTCAGTCAATATATTCAAAGTGTGGGTCCAGGCTTTCAAGGTGGAAG

GTGGCCAGTTTGGCTCTGTGGAGGAGTGTCTGCTGGACGAGAACAGCCTCGAGG

ATATCGGGCGGCGCGCCATGAGGCGGTCCAGGCCTAGCGGGGACCTGCGGCAGA

GGCTCCTGCGGGCGCGTGGGGAGACCTACGGGAGGCTCCTGGGGGAGGTGGAGG

ACGGGTACTCGCAGTCCCCCGGGGGCCTCGACAAGGGCCTGAGCTCCCTCTCGTG

CGAGGGGCAGAAGTACAACCAGGGGCAGTACATGAACACCCCATGGCGCAACCC

CGCCGAGGAGCGGGAGAAGCTGGCGTACCGGAAGCAGAACATGGACGACATCG

ACGAGGAGGACGACGACCTGGTCGGGGTCTCAGTGCGGCCGAAGGTCCCCCTCC

GGACGATGTCGTACAAGCTGGCGATCGACATGTCGCACTTCATCAAGGAGAAGG

GGGGCCTGGAGGGGATCTACTACTCGGCGCGGCGGCACCGCATCCTCGACATCT

ACCTCGAGAAGGAGGAGGGCATCATCCCGGACTGGCAGGACTACACCTCCGGGC

CCGGGATCAGATATCCCAAGACGTTCGGCTGGCTCTGGAAGCTCGTCCCTGTCAA

-continued

CGTCTCGGACGAGGCGCAGGAGGACGAGGAGCACTACCTCATGCACCCGGCGCA
GACCTCCCAGTGGGACGACCCCTGGGGGAGGTCCTCGCCTGGAAGTTCGACCC
CACGCTGGCCTACACCTACGAGGCCTACGTCCGCTACCCCGAGGAGTTCGGGAG
CAAGTCCGGCCTGTCGGAGGAGGAGGTCCGCCGGCGCCTGACCGCCCGCGGCCT
GCTGAACATGGCCGACAAGAAGGAGACCCGCGGCGCCGAGACCCCCCTGAGGG
AGCAGGAGAACAGCCTGGAGTCCTCCAACGAGCGCAGCAGCTGCATCAGCGAGG
CGGATGCGTCCACCCCCGAGTCGGCCAACCTGGGGGAGGAGATCCTCTCTCAGCT
CTACCGCCCTCTCGAGGCGTGCTACAACACGTGCTACTGCAAGAAGTGCTGCTAC
CACTGCCAGTTCTGCTTCCTCAAGAAGGGCCTGGGGATCTGCTACGAGCAGTCGC
GAAAGCGGCGGCGGACGCCGAAGAAGGCGAAGGCGAACACGTCGTCGGCGTCG
AACAACCGCCCCATCAGCAACCGGACCCGGCACTGCCAGCCCGAGAAGGCCAAG
AAGGAGACGGTGGAGAAGGCGGTGGCCACCGCCCCGGGCCTGGGCCGCGGATCC
GAGGAGGAGAAGCGCTGGATCGCCGTCCCCACGTGGAGGATCCCGGAGAGGCTC
GAGAGGTGGCACAGCCTCATCAAGTACCTGAAGTACAAGACGAAGGACCTCCAG

AAGGTCTGCTACGTGCCCCACTTCAAGGTCGGGTGGGCGTGGTGGACCTGCAGC

AGAGTCATCTTCCCACTTCAAGAGGGCAGCCACTTGGAGGTCCAGGGGTACTGG
CACTTGACGCCGGAGAAGGGGTGGCTGAGCACCTACGCGGTGCGGATCACCTGG
TACTCGAAGAACTTCTGGACGGATGTCACGCCGAACTATGCGGACATCTTGCTGC

ACAGCACTTACTTCCCCTGCTTCACGGCGGGGGAAGTGAGGAGGGCCATCAGGG

GAGAGCAGCTGCTGTCGTGCTGCCGGTTCCCGCGGGCGCACAAGTACCAAGTAC
CGAGCCTACAGTACTTGGCGCTGAAGGTCGTCAGCGACGTCAGGTCCCAGGGGG
AGAACCCCACCTGGAAGCAGTGGCGGCGGGACAACCGGAGGGGCCTTCGAATGG
CGAAGCAGAACTCGCGGGGAGATAAGCAGCGGGGCGGTAAACCACCTACCAAG
GGAGCGAACTTCCCGGGTTTGGCAAAGGTCTTGGGAATACTGGCAGTCGACGCT

AGCGGATCCGAATTCACGCTGATCCCCATCGCTGTGGGTGGTGCCCTGGCGGGGC

TGGTCCTCATCGTCCTCATCGCCTACCTCGTCGGCAGGAAGAGGAGTCACGCAGG
CTACCAGACTATCTAG

SIV LAMP-NTV (147S) amino acid sequence

SEQ ID NO: 12

M A P R S A R RP L L L L L L L L L LG L M H C A S A A M F M V K N G N G

T A C I M A N F S A A F S V N Y D T K S G P K N M T L D L P S D A T V V L

N R S S C G K E N T S D P S L V I A F G R G H T L T L N F T R N A T R Y S

V Q L M S F V Y N L S D T H L F P N A S S K E I K T V E S I T D I R A D I D

K K Y R C V S G T Q V H M N N V T V T L H D A T I Q A Y L S N S S F S R G

E T R C E Q D R P S P T T P P A P P S P S P S P V P K S P S V D K Y N V

S G T N G T C L L A S M G L Q L N L T Y E R K D N T T V T R L L N I N P N

K T S A S G S C G A H L V T L E L H S E G T T V L L F Q F G M N A S S S R

F F L Q G I Q L N T I L P D A R D P A F K A A N G S L R A L Q A T V G N S

Y K C N A E E H V R V T K A F S V N I F K V W V Q A F K V E G G Q F G S V

E E C L L D E N S *l e d i g r r a* M R R S R P S G D L R Q R L L R A R G E T

Y G R L L G E V E D G Y S Q S P G G L D K G L S S L S C E G Q K Y N Q G

-continued

Q Y M N T P W R N P A E E R E K L A Y R K Q N M D D I D E E D D D L V G

V S V R P K V P L R T M S Y K L A I D M S H F I K E K G G L E G I Y Y S A

R R H R I L D I Y L E K E E G I I P D W Q D Y T S G P G I R Y P K T F G W

L W K L V P V N V S D E A Q E D E E H Y L M H P A Q T S Q W D D P W G

E V L A W K F D P T L A Y T Y E A Y V R Y P E E F G S K S G L S E E E V

R R R L T A R G L L N M A D K K E T R G A E T P L R E Q E N S L E S S N

E R S S C I S E A D A S T P E S A N L G E E I L S Q L Y R P L E A C Y N T

C Y C K K C C Y H C Q F C F L K K G L G I C Y E Q S R K R R R T P K K A

K A N T S S A S N N R P I S N R T R H C Q P E K A K K E T V E K A V A T

A P G L G R G S E E E K R W I A V P T W R I P E R L E R W H S L I K Y L K

Y K T K D L Q K V C Y V P H F K V G W A W W T C S R V I F P L Q E G S H

L E V Q G Y W H L T P E K G W L S T Y A V R I T W Y S K N F W T D V T P

N Y A D I L L H S T Y F P C F T A G E V R R A I R G E Q L L S C C R F P R

A H K Y Q V P S L Q Y L A L K V V S D V R S Q G E N P T W K Q W R R D N

R R G L R M A K Q N S R G D K Q R G G K P P T K G A N F P G L A K V L

G I L A *v d a s g s e f* <u>T L I P I A V G G A L A G L V L I V L I A Y L V G R K R S H A G Y Q T I</u> •

LAMP-1 underlined
Linker lower case italics
SIV NTV bold
Linker lower case italics
LAMP-1 underlined rhesus IL-15tPA6 (AG65) nucleic acid sequence
SEQ ID NO: 13

ATGGATGCAATGAAGAGAGGGCTCTGCTGTGTGCTGCTGCTGTGTGGAGCAGTCT

TCGTTTCGCCCAGCCAGGAAATCCATGCCCGATTCAGAAGAGGAGCCAGAAACT

GGGTGAACGTGATCTCGGACCTGAAGAAGATCGAGGACCTCATCCAGTCGATGC

ACATCGACGCGACGCTGTACACGGAGTCGGACGTCCACCCGTCGTGCAAGGTCA

CGGCGATGAAGTGCTTCCTCCTGGAGCTCCAAGTCATCTCGCACGAGTCGGGGGA

CACGGACATCCACGACACGGTGGAGAACCTGATCATCCTGGCGAACAACATCCT

GTCGTCGAACGGGAACATCACGGAGTCGGGCTGCAAGGAGTGCGAGGAGCTGGA

GGAGAAGAACATCAAGGAGTTCCTGCAGTCGTTCGTGCACATCGTCCAGATGTTC

ATCAACACGTCGTGA rhesus IL-15tPA6 (AG65) amino acid sequence

SEQ ID NO: 14

M D A M K R G L C C V L L L C G A V F V S P S Q E I H A R F R R G A R N

W V N V I S D L K K I E D L I Q S M H I D A T L Y T E S D V H P S C K V T

A M K C F L L E L Q V I S H E S G D T D I H D T V E N L I I L A N N I L S S

N G N I T E S G C K E C E E L E E K N I K E F L Q S F V H I V Q M F I N T S • tPA signal and propeptide, underlined
rhesus macaque mature IL-15, bold rhesus IL-15Receptor alpha (AG120) nucleic acid sequence

SEQ ID NO: 15

ATGGCCCCGAGGCGGGCGCGAGGCTCGCGGACCCTCGGTCTCCCGGCGCTGCTA

CTGCTCCTGCTGCTCCGGCCGCCGGCGACGCGGGGCATCACGTGCCCGCCCCCCG

TGTCCGTGGAGCACGCAGACATCCGGGTCAAGAGCTACAGCTTGTACTCCCGGG

```
AGCGGTACATCTGCAACTCGGGTTTCAAGCGGAAGGCCGGCACGTCCAGCCTGA

CGGAGTGCGTGTTGAACAAGGCCACGAATATCGCCCACTGGACGACCCCCTCGC

TCAAGTGCATCCGCGACCCGCTACTGGCCCGGCAGCGGCCCGCGCCACCCTTCAC

CGTAACGACGGCGGGCGTGACCCCGCAGCCGGAGAGCCTCTCCCCGTCGGGAAA

GGAGCCCGCCGCGTCGTCGCCCAGCTCGAACACCACGGCGGCCACAACTGCAGC

GATCGTCCCGTCGTCCCGGCTGATGCCCTCGACGTCGTCGTCCACGGGAACCACG

GAGATCGGCAGTCATGAGTCCTCCCACGGCCCCTCGCAAACGACGGCCAAGACG

TGGGAACTCACGGCGTCCGCCTCCCACCAGCCGCCGGGGGTGTATCCGCAAGGC

CACAGCGACACCACGGTGGCGATCTCCACGTCCACGGTCCTGCTGTGTGGGCTGA

GCGCGGTGTCGCTCCTGGCGTGCTACATCAAGTCGAGGCAGACTCCCCCGCCGGC

CAGCATCGAGATGGAGGCCATGGAGGCTCTGCCGGTGACGGGGGAGACCAGCAG

CAGGGATGAGGACTTGGAGAACTGCTCGCACGACCTATAATGA
``` rhesus IL-15Ra (AG120) amino acid sequence      SEQ ID NO: 16

```
M A P R R A R G S R T L G L P A L L L L L L R P P A T R G I T C P P P V
S V E H A D I R V K S Y S L Y S R E R Y I C N S G F K R K A G T S S L T E
C V L N K A T N I A H W T T P S L K C I R D P L L A R Q R P A P P F T V T
T A G V T P Q P E S L S P S G K E P A A S S P S S N T T A A T T A A I V P
S S R L M P S T S S S T G T T E I G S H E S S H G P S Q T T A K T W E L T
A S A S H Q P P G V Y P Q G H S D T T V A I S T S T V L L C G L S A V S L
L A C Y I K S R Q T P P P A S I E M E A M E A L P V T G E T S S R D E D L
E N C S H D L * *
```

HIVgag (114H) nucleic acid sequence      SEQ ID NO: 17

```
atggggcgcgggcctcggtccttagcggggcgagttggatcggtgggaaaagatccgcttgaggccaggagggaagaagaag
tacaagctaaagcacatcgtctgggcgagcagagagttggagcggttcgcggtcaacccgggcctgcttgagacatcggagggctg
tcggcaaatcctggggcagcttcaaccgtccttgcaaacgggcagcgaggagcttcgatcactatacaacactgtagcaacgctctac
tgcgtgcaccagcggatcgagatcaaggacacgaaggaggctcttgacaagattgaggaagagcagaacaagtccaagaagaag
gcccagcaggcggcggccgacaccggccactccaaccaagtatcacagaactacccgatcgtgcagaacatccagggacagatg
gtccaccaggccatctccccacggacgataacgcgtgggtcaaagtagtggaggagaaggccttcagcccggaagtgatccccat
gttctcggcactttccgagggagccaccccgcaggacctgaacacgatgttgaacaccgtcggcgggcaccaggcggccatgcag
atgcttaaggagaccatcaacgaggaggctgcggagtgggaccgggtccacccggtgcacgcggggcccatcgcgccgggcca
gatgagagagccgcggggatcggacatcgcgggaaccaccagcacccttgcaggagcaaatcggttggatgactaacaacccgcca
atcccggtcggggagatctacaagagatggatcatcctcgggttgaacaagatcgtgaggatgtacagcccgaccagcatcctggac
atccgacagggaccgaaggagccgttcagagactacgtagaccggttctacaagactctccggggcggagcaggcgtcgcaggagg
tcaagaactggatgacggagaccttgaggtccagaacgcgaacccggactgcaagaccatcctgaaggctctcggcccggcggcg
acgttggaagagatgatgacggcgtgccagggagtcgggggacccggccacaaggcgcgggtcttggccgaggcgatgagcca
agtgacgaactcggcgacgatcatgatgcagcggggcaacttccggaaccagcggaagatcgtcaagtgcttcaactgtggcaagg
agggacacaccgccaggaactgccgggccccccggaagaagggctgctggaagtgcggaaaggaggggcaccaaatgaagga
ctgcacggagcggcaggcgaatttcctcgggaagatctggccgtcctacaaggggcggcagggaactttctgcaaagccggccg
gagccgaccgccccgccggaggagtcctttcggtccgggtcgagacgaccacgcccctcagaagcaagagcccatcgacaag
gagttgtaccctcttacctccctccggtcgctcttcggcaacgacccgtcctcgcaatgataa
```

HIVgag (114H) amino acid sequence

-continued

SEQ ID NO: 18
M G A R A S V L S G G E L D R W E K I R L R P G G K K K Y L K H I V W A S R E L
E R F A V N P G L L E T S E G C R Q I L G Q L Q P S L Q T G S E E L R S L Y N T V
A T L Y C V H Q R I E I K D T K E A L D K I E E E Q N K S K K K A Q Q A A A D T G
H S N Q V S Q N Y P I V Q N I Q G Q M V H Q A I S P R T L N A W V K V V E E K A F
S P E V I P M F S A L S E G A T P Q D L N T M L N T V G G H Q A A M Q M L K E T I
N E E A A E W D R V H P V H A G P I A P G Q M R E P R G S D I A G T T S T L Q E
Q I G W M T N N P P I P V G E I Y K R W I I L G L N K I V R M Y S P T S I L D I R Q
G P K E P F R D Y V D R F Y K T L R A E Q A S Q E V K N W M T E T L L V Q N A N
P D C K T I L K A L G P A A T L E E M M T A C Q G V G G P G H K A R V L A E A M S
Q V T N S A T I M M Q R G N F R N Q R K I V K C F N C G K E G H T A R N C R A P
R K K G C W K C G K E G H Q M K D C T E R Q A N F L G K I W P S Y K G R P G N F
L Q S R P E P T A P P E E S F R S G V E T T T P P Q K Q E P I D K E L Y P L T S L
R S L F G N D P S S Q * *

HIV muIP10huMCP-3 gag (122H) nucleic acid sequence

SEQ ID NO: 19

ATGAACCCGAGTGCTGCCGTCATCTTCTGCCTCATCCTGCTGGGGCTGAGCGGGA
CGCAGGGGATCCTCGACGCGCAGCCGGTCGGGATCAACACGAGCACGACCTGCT
GCTACCGGTTCATCAACAAGAAGATCCCGAAGCAGCGTCTGGAGAGCTACCGCC
GGACCACGTCGAGCCACTGCCCGCGGGAGGCGGTCATCTTCAAGACGAAGCTGG
ACAAGGAGATCTGCGCCGACCCGACGCAGAAGTGGGTTCAGGACTTCATGAAGC
ACCTGGACAAGAAGACGCAGACGCCGAAGCTGGCTAGCGGGGCACGTGCCTCGG
TCCTTAGCGGGGGCGAGTTGGATCGGTGGGAAAAGATCCGCTTGAGGCCAGGAG
GGAAGAAGAAGTACAAGCTAAAGCACATCGTCTGGGCGAGCAGAGAGTTGGAG
CGGTTCGCGGTCAACCCGGGCCTGCTTGAGACATCGGAGGGCTGTCGGCAAATC
CTGGGGCAGCTTCAACCGTCCTTGCAAACGGGCAGCGAGGAGCTTCGATCACTAT
ACAACACTGTAGCAACGCTCTACTGCGTGCACCAGCGGATCGAGATCAAGGACA
CGAAGGAGGCTCTTGACAAGATTGAGGAAGAGCAGAACAAGTCCAAGAAGAAG
GCCCAGCAGGCGGCGGCCGACACCGGCCACTCCAACCAAGTATCACAGAACTAC
CCGATCGTGCAGAACATCCAGGGACAGATGGTCCACCAGGCCATCTCCCCACGG
ACGCTTAACGCGTGGGTCAAAGTAGTGGAGGAGAAGGCCTTCAGCCCGGAAGTG
ATCCCCATGTTCTCGGCACTTTCCGAGGGAGCCACCCCGCAGGACCTGAACACGA
TGTTGAACACCGTCGGCGGGCACCAGGCGGCCATGCAGATGCTTAAGGAGACCA
TCAACGAGGAGGCTGCGGAGTGGGACCGGGTCCACCCGGTGCACGCGGGGCCCA
TCGCGCCGGGCCAGATGAGAGAGCCGCGGGGATCGGACATCGCGGGAACCACCA
GCACCTTGCAGGAGCAAATCGGTTGGATGACTAACAACCCGCCAATCCCGGTCG
GGGAGATCTACAAGAGATGGATCATCCTCGGGTTGAACAAGATCGTGAGGATGT
ACAGCCCGACCAGCATCCTGGACATCCGACAGGGACCGAAGGAGCCGTTCAGAG
ACTACGTAGACCGGTTCTACAAGACTCTCCGGGCGGAGCAGGCGTCGCAGGAGG
TCAAGAACTGGATGACGGAGACCTTGTTGGTCCAGAACGCGAACCCGGACTGCA
AGACCATCCTGAAGGCTCTCGGCCCGGCGGCGACGTTGGAAGAGATGATGACGG
CGTGCCAGGGAGTCGGGGGACCCGGCCACAAGGCGCGGGTCTTGGCCGAGGCGA

```
TGAGCCAAGTGACGAACTCGGCGACGATCATGATGCAGCGGGGCAACTTCCGGA

ACCAGCGGAAGATCGTCAAGTGCTTCAACTGTGGCAAGGAGGGACACACCGCCA

GGAACTGCCGGGCCCCCGGAAGAAGGGCTGCTGGAAGTGCGGAAAGGAGGGG

CACCCAAATGAAGGACTGCACGGAGCGGCAGGCGAATTTCCTCGGGAAGATCTGG

CCGTCCTACAAGGGGCGGCCAGGGAACTTTCTGCAAAGCCGGCCGGAGCCGACC

GCCCCGCCGGAGGAGTCCTTTCGGTCCGGGTCGAGACGACCACGCCCCCTCAG

AAGCAAGAGCCCATCGACAAGGAGTTGTACCCTCTTACCTCCCTCCGGTCGCTCT

TCGGCAACGACCCGTCCTCGCAATGATAA
```

HIV muIP10huMCP-3gag (122H) amino acid sequence
SEQ ID NO: 20

<u>M N P S A A V I F C L I L L G L S G T Q G</u> *i l d a* <u>Q P V G I N T S T T C C Y R F I N K</u>
<u>K I P K Q R L E S Y R R T T S S H C P R E A V I F K T K L D K E I C A D P T Q K W V</u>
<u>Q D F M K H L D K K T Q T P K L</u> *a s g* A R A S V L S G G E L D R W E K I R L R P G
G K K K Y L K H I V W A S R E L E R F A V N P G L L E T S E G C R Q I L G Q L Q
P S L Q T G S E E L R S L Y N T V A T L Y C V H Q R I E I K D T K E A L D K I E E E
Q N K S K K K A Q Q A A A D T G H S N Q V S Q N Y P I V Q N I Q G Q M V H Q A I
S P R T L N A W V K V V E E K A F S P E V I P M F S A L S E G A T P Q D L N T M L
N T V G G H Q A A M Q M L K E T I N E E A A E W D R V H P V H A G P I A P G Q M
R E P R G S D I A G T T S T L Q E Q I G W M T N N P P I P V G E I Y K R W I I L G L
N K I V R M Y S P T S I L D I R Q G P K E P F R D Y V D R F Y K T L R A E Q A S Q
E V K N W M T E T L L V Q N A N P D C K T I L K A L G P A A T L E E M M T A C Q
G V G G P G H K A R V L A E A M S Q V T N S A T I M M Q R G N F R N Q R K I V K
C F N C G K E G H T A R N C R A P R K K G C W K C G K E G H Q M K D C T E R Q
A N F L G K I W P S Y K G R P G N F L Q S R P E P T A P P E E S F R S G V E T T T
P P Q K Q E P I D K E L Y P L T S L R S L F G N D P S S Q •• muIP10 underlined
Linker lower case, italics
huMCP-3 mature underlined
Linker lower case italics
HIVgag bold HIV huIP10huMCP-3 gag amino acid sequence
SEQ ID NO: 21

<u>M N Q T A I L I C C L I F L T L S G I Q G</u> *q p v g i n t s t t c c y r f i n k k i*
*p k q r l e s y r r t t s s h c p r e a v i f k t k l d k e i c a d p t q k w v q d f m k h l d k*
*k t q t p k l* *a s g* A R A S V L S G G E L D R W E K I R L R P G G K K K Y K L K H I
V W A S R E L E R F A V N P G L L E T S E G C R Q I L G Q L Q P S L Q T G S E E
L R S L Y N T V A T L Y C V H Q R I E I K D T K E A L D K I E E E Q N K S K K K A
Q Q A A A D T G H S N Q V S Q N Y P I V Q N I Q G Q M V H Q A I S P R T L N A W
V K V V E E K A F S P E V I P M F S A L S E G A T P Q D L N T M L N T V G G H Q
A A M Q M L K E T I N E E A A E W D R V H P V H A G P I A P G Q M R E P R G S D
I A G T T S T L Q E Q I G W M T N N P P I P V G E I Y K R W I I L G L N K I V R M Y
S P T S I L D I R Q G P K E P F R D Y V D R F Y K T L R A E Q A S Q E V K N W M T
E T L L V Q N A N P D C K T I L K A L G P A A T L E E M M T A C Q G V G G P G H
K A R V L A E A M S Q V T N S A T I M M Q R G N F R N Q R K I V K C F N C G K E
G H T A R N C R A P R K K G C W K C G K E G H Q M K D C T E R Q A N F L G K I

W P S Y K G R P G N F L Q S R P E P T A P P E E S F R S G V E T T T P P Q K Q E

P I D K E L Y P L T S L R S L F G N D P S S Q * * huIP10 underlined
huMCP-3 mature lower case, underlined
Linker lower case, italics
HIV gag bold HIV huMCP-3 gag amino acid sequence
SEQ ID NO: 22

<u>M K A S A A L L C L L L T A A A F S P Q G L A G</u> <u>q p v g i n t s t t c c y</u>

<u>r f i n k k i p k a r l e s y r r t t s s h c p r e a v i f k t k l d k e i c a d p t q k w v q d f</u>

<u>m k h l d k k t q t p k i</u> *A S* G A R A S V L S G G E L D R W E K I R L R P G G K K K

Y K L K H I V W A S R E L E R F A V N P G L L E T S E G C R Q I L G Q L Q P S L Q

T G S E E L R S L Y N T V A T L Y C V H Q R I E I K D T K E A L D K I E E E Q N K

S K K K A Q Q A A A D T G H S N Q V S Q N Y P I V Q N I Q G Q M V H Q A I S P R

T L N A W V K V V E E K A F S P E V I P M F S A L S E G A T P Q D L N T M L N T V

G G H Q A A M Q M L K E T I N E E A A E W D R V H P V H A G P I A P G Q M R E P

R G S D I A G T T S T L Q E Q I G W M T N N P P I P V G E I Y K R W I I L G L N K I

V R M Y S P T S I L D I R Q G P K E P F R D Y V D R F Y K T L R A E Q A S Q E V K

N W M T E T L L V Q N A N P D C K T I L K A L G P A A T L E E M M T A C Q G V G

G P G H K A R V L A E A M S Q V T N S A T I M M Q R G N F R N Q R K I V K C F N

C G K E G H T A R N C R A P R K K G C W K C G K E G H Q M K D C T E R Q A N F

L G K I W P S Y K G R P G N F L Q S R P E P T A P P E E S F R S G V E T T T P P Q

K Q E P I D K E L Y P L T S L R S L F G N D P S S Q * * huMCP-3 signal peptide underlined
huMCP-3 mature lower case, underlined
Linker italics
HIVgag bold HIV CATE p37gag (80H) nucleic acid sequence
SEQ ID NO: 23

ATGAGAAAAGCGGCTGTTAGTCACTGGCAGCAGCAGTCTTACCTGGACTCTGGA

ATCCATTCTGGTGCCACTACCACAGCTCCTTCTCTGAGTGCCGGCGCGAGAGCGT

CAGTATTAAGCGGGGGAGAATTAGATCGATGGGAAAAAATTCGGTTAAGGCCAG

GGGGAAAGAAGAAGTACAAGCTAAAGCACATCGTATGGGCAAGCAGGGAGCTA

GAACGATTCGCAGTTAATCCTGGCCTGTTAGAAACATCAGAAGGCTGTAGACAA

ATACTGGGACAGCTACAACCATCCCTTCAGACAGGATCAGAGGAGCTTCGATCA

CTATACAACACAGTAGCAACCCTCTATTGTGTGCACCAGCGGATCGAGATCAAG

GACACCAAGGAAGCTTTAGACAAGATAGAGGAAGAGCAAAACAAGTCCAAGAA

GAAGGCCCAGCAGGCAGCAGCTGACACAGGACACAGCAATCAGGTCAGCCAAA

ATTACCCTATAGTGCAGAACATCCAGGGGCAAATGGTACATCAGGCCATATCAC

CTAGAACTTTAAATGCATGGGTAAAAGTAGTAGAAGAGAAGGCTTTCAGCCCAG

AAGTGATACCCATGTTTTCAGCATTATCAGAAGGAGCCACCCCACAGGACCTGA

ACACGATGTTGAACACCGTGGGGGACATCAAGCAGCCATGCAAATGTTAAAAG

AGACCATCAATGAGGAAGCTGCAGAATGGGATAGAGTGCATCCAGTGCATGCAG

GGCCTATTGCACCAGGCCAGATGAGAGAACCAAGGGGAAGTGACATAGCAGGA

ACTACTAGTACCCTTCAGGAACAAATAGGATGGATGACAAATAATCCACCTATCC

```
CAGTAGGAGAGATCTACAAGAGGTGGATAATCCTGGGATTGAACAAGATCGTGA

GGATGTATAGCCCTACCAGCATTCTGGACATAAGACAAGGACCAAAGGAACCCT

TTAGAGACTATGTAGACCGGTTCTATAAAACTCTAAGAGCTGAGCAAGCTTCACA

GGAGGTAAAAAATTGGATGACAGAAACCTTGTTGGTCCAAAATGCGAACCCAGA

TTGTAAGACCATCCTGAAGGCTCTCGGCCCAGCGGCTACACTAGAAGAAATGAT

GACAGCATGTCAGGGAGTAGGAGGACCCGGCCATAAGGCAAGAGTTTTGTAG
```

HIV HIV CATE p37gag (80H) amino acid sequence    SEQ ID NO: 24

M R K A A V S H W Q Q Q S Y L D S G I H S G A T T T A P S L
S a g A R A S V L S G G E L D R W E K I R L R P G G K K K Y
K L K H I V W A S R E L E R F A V N P G L L E T S E G C R Q I
L G Q L Q P S L Q T G S E E L R S L Y N T V A T L Y C V H Q
R I E I K D T K E A L D K I E E E Q N K S K K K A Q Q A A A D
T G H S N Q V S Q N Y P I V Q N I Q G Q M V H Q A I S P R T L
N A W V K V V E E K A F S P E V I P M F S A L S E G A T P Q
D L N T M L N T V G G H Q A A M Q M L K E T I N E E A A E W
D R V H P V H A G P I A P G Q M R E P R G S D I A G T T S T L
Q E Q I G W M T N N P P I P V G E I Y K R W I I L G L N K I V
R M Y S P T S I L D I R Q G P K E P F R D Y V D R F Y K T L R
A E Q A S Q E V K N W M T E T L L V Q N A N P D C K T I L K
A L G P A A T L E E M M T A C Q G V G G P G H K A R V L •

CATE underlined
Linker lower case, italics
HIVp37gag bold

HIV HIV CATE gag amino acid sequence    SEQ ID NO: 25

M R K A A V S H W Q Q Q S Y L D S G I H S G A T T T A P S L
S a g A R A S V L S G G E L D R W E K I R L R P G G K K K Y
K L K H I V W A S R E L E R F A V N P G L L E T S E G C R Q I
L G Q L Q P S L Q T G S E E L R S L Y N T V A T L Y C V H Q
R I E I K D T K E A L D K I E E E Q N K S K K K A Q Q A A A D
T G H S N Q V S Q N Y P I V Q N I Q G Q M V H Q A I S P R T L
N A W V K V V E E K A F S P E V I P M F S A L S E G A T P Q
D L N T M L N T V G G H Q A A M Q M L K E T I N E E A A E W
D R V H P V H A G P I A P G Q M R E P R G S D I A G T T S T L
Q E Q I G W M T N N P P I P V G E I Y K R W I I L G L N K I V
R M Y S P T S I L D I R Q G P K E P F R D Y V D R F Y K T L R
A E Q A S Q E V K N W M T E T L L V Q N A N P D C K T I L K
A L G P A A T L E E M M T A C Q G V G G P G H K A R V L A E
A M S Q V T N S A T I M M Q R G N F R N Q R K I V K C F N C
G K E G H T A R N C R A P R K K G C W K C G K E G H Q M K
D C T E R Q A N F L G K I W P S Y K G R P G N F L Q S R P E
P T A P P E E S F R S G V E T T T P P Q K Q E P I D K E L Y P
L T S L R S L F G N D P S S Q • •

CATE underlined
Linker lower case, italics
HIVgag (p55) bold

HIV LAMPgag nucleic acid sequence

SEQ ID NO: 26

ATGGCGCCCCGCAGCGCCCGGCGACCCCTGCTGCTGCTACTGCTGTTGCTGCTGC
TCGGCCTCATGCATTGTGCGTCAGCAGCAATGTTTATGGTGAAAAATGGCAACGG
GACCGCGTGCATAATGGCCAACTTCTCTGCTGCCTTCTCAGTGAACTACGACACC
AAGAGTGGCCCTAAGAACATGACCCTTGACCTGCCATCAGATGCCACAGTGGTG
CTCAACCGCAGCTCCTGTGGAAAAGAGAACACTTCTGACCCCAGTCTCGTGATTG
CTTTTGGAAGAGGACATACACTCACTCTCAATTTCACGAGAAATGCAACACGTTA
CAGCGTCCAGCTCATGAGTTTTGTTTATAACTTGTCAGACACACACCTTTTCCCCA
ATGCGAGCTCCAAAGAAATCAAGACTGTGGAATCTATAACTGACATCAGGGCAG
ATATAGATAAAAAATACAGATGTGTTAGTGGCACCCAGGTCCACATGAACAACG
TGACCGTAACGCTCCATGATGCCACCATCCAGGCGTACCTTTCCAACAGCAGCTT
CAGCAGGGGAGAGACACGCTGTGAACAAGACAGGCCTTCCCCAACCACAGCGCC
CCCTGCGCCACCCAGCCCCTCGCCCTCACCCGTGCCCAAGAGCCCCTCTGTGGAC
AAGTACAACGTGAGCGGCACCAACGGGACCTGCCTGCTGGCCAGCATGGGGCTG
CAGCTGAACCTCACCTATGAGAGGAAGGACAACACGACGGTGACAAGGCTTCTC
AACATCAACCCCAACAAGACCTCGGCCAGCGGGAGCTGCGGCGCCCACCTGGTG
ACTCTGGAGCTGCACAGCGAGGGCACCACCGTCCTGCTCTTCCAGTTCGGGATGA
ATGCAAGTTCTAGCCGGTTTTTCCTACAAGGAATCCAGTTGAATACAATTCTTCCT
GACGCCAGAGACCCTGCCTTTAAAGCTGCCAACGGCTCCCTGCGAGCGCTGCAG
GCCACAGTCGGCAATTCCTACAAGTGCAACGCGGAGGAGCACGTCCGTGTCACG
AAGGCGTTTTCAGTCAATATATTCAAAGTGTGGGTCCAGGCTTTCAAGGTGGAAG
GTGGCCAGTTTGGCTCTGTGGAGGAGTGTCTGCTGGACGAGAACAGCCTCGAGG
ATATCGGGGCGCGGGCCTCGGTCCTTAGCGGGGGCGAGTTGGATCGGTGGGAAA
AGATCCGCTTGAGGCCAGGAGGGAAGAAGAAGTACAAGCTAAAGCACATCGTCT
GGGCGAGCAGAGAGTTGGAGCGGTTCGCGGTCAACCCGGGCCTGCTTGAGACAT
CGGAGGGCTGTCGGCAAATCCTGGGGCAGCTTCAACCGTCCTTGCAAACGGGCA
GCGAGGAGCTTCGATCACTATACAACACTGTAGCAACGCTCTACTGCGTGCACCA
GCGGATCGAGATCAAGGACACGAAGGAGGCTCTTGACAAGATTGAGGAAGAGC
AGAACAAGTCCAAGAAGAAGGCCCAGCAGGCGGCGGCCGACACCGGCCACTCC
AACCAAGTATCACAGAACTACCCGATCGTGCAGAACATCCAGGGACAGATGGTC
CACCAGGCCATCTCCCCACGGACGCTTAACGCGTGGGTCAAAGTAGTGGAGGAG
AAGGCCTTCAGCCCGGAAGTGATCCCCATGTTCTCGGCACTTTCCGAGGGAGCCA
CCCCGCAGGACCTGAACACGATGTTGAACACCGTCGGCGGGCACCAGGCGGCCA
TGCAGATGCTTAAGGAGACCATCAACGAGGAGGCTGCGGAGTGGGACCGGGTCC
ACCCGGTGCACGCGGGGCCCATCGCGCCGGGCCAGATGAGAGAGCCGCGGGGAT
CGGACATCGCGGGAACCACCAGCACCTTGCAGGAGCAAATCGGTTGGATGACTA
ACAACCCGCCAATCCCGGTCGGGGAGATCTACAAGAGATGGATCATCCTCGGGT
TGAACAAGATCGTGAGGATGTACAGCCCGACCAGCATCCTGGACATCCGACAGG

```
GACCGAAGGAGCCGTTCAGAGACTACGTAGACCGGTTCTACAAGACTCTCCGGG

CGGAGCAGGCGTCGCAGGAGGTCAAGAACTGGATGACGGAGACCTTGTTGGTCC

AGAACGCGAACCCGGACTGCAAGACCATCCTGAAGGCTCTCGGCCCGGCGGCGA

CGTTGGAAGAGATGATGACGGCGTGCCAGGGAGTCGGGGGACCCGGCCACAAG

GCGCGGGTCTTGGCCGAGGCGATGAGCCAAGTGACGAACTCGGCGACGATCATG

ATGCAGCGGGGCAACTTCCGGAACCAGCGGAAGATCGTCAAGTGCTTCAACTGT

GGCAAGGAGGGACACACCGCCAGGAACTGCCGGGCCCCCCGGAAGAAGGGCTG

CTGGAAGTGCGGAAAGGAGGGGCACCAAATGAAGGACTGCACGGAGCGGCAGG

CGAATTTCCTCGGGAAGATCTGGCCGTCCTACAAGGGGCGGCCAGGGAACTTTCT

GCAAAGCCGGCCGGAGCCGACCGCCCCGCCGAGGAGTCCTTTCGGTCCGGGGT

CGAGACGACCACGCCCCCTCAGAAGCAAGAGCCCATCGACAAGGAGTTGTACCC

TCTTACCTCCCTCCGGTCGCTCTTCGGCAACGACCCGTCCTCGCAAGGGGAATTC

ACGCTGATCCCCATCGCTGTGGGTGGTGCCCTGGCGGGGCTGGTCCTCATCGTCC

TCATCGCCTACCTCGTCGGCAGGAAGAGGAGTCACGCAGGCTACCAGACTATCT

AG
```

HIV LAMPgag amino acid sequence

SEQ ID NO: 27

<u>M A P R S A R R P L L L L L L L L L L G L M H C A S A A M F M V K N G N G</u>

<u>T A C I M A N F S A A F S V N Y D T K S G P K N M T L D L P S D A T V V L</u>

<u>N R S S C G K E N T S D P S L V I A F G R G H T L T L N F T R N A T R Y S</u>

<u>V Q L M S F V Y N L S D T H L F P N A S S K E I K T V E S I T D I R A D I D</u>

<u>K K Y R C V S G T Q V H M N N V T V T L H D A T I Q A Y L S N S S F S R G</u>

<u>E T R C E Q D R P S P T T A P P A P P S P S P S P V P K S P S V D K Y N V</u>

<u>S G T N G T C L L A S M G L Q L N L T Y E R K D N T T V T R L L N I N P N</u>

<u>K T S A S G S C G A H L V T L E L H S E G T T V L L F Q F G M N A S S S R</u>

<u>F F L Q G I Q L N T I L P D A R D P A F K A A N G S L R A L Q A T V G N S</u>

<u>Y K C N A E E H V R V T K A F S V N I F K V W V Q A F K V E G G Q F G S V</u>

<u>E E C L L D E N S</u> *l e d i* G A R A S V L S G G E L D R W E K I R L R P G G

K K K Y K L K H I V W A S R E L E R F A V N P G L L E T S E G C R Q I L G

Q L Q P S L Q T G S E E L R S L Y N T V A T L Y C V H Q R I E I K D T K

A L D K I E E E Q N K S K K K A Q Q A A A D T G H S N Q V S Q N Y P I V

Q N I Q G Q M V H Q A I S P R T L N A W V K V V E E K A F S P E V I P M F

S A L S E G A T P Q D L N T M L N T V G G H Q A A M Q M L K E T I N E E

A A E W D R V H P V H A G P I A P G Q M R E P R G S D I A G T T S T L Q

E Q I G W M T N N P P I P V G E I Y K R W I I L G L N K I V R M Y S P T S I

L D I R Q G P K E P F R D Y V D R F Y K T L R A E Q A S Q E V K N W M T

E T L L V Q N A N P D C K T I L K A L G P A A T L E E M M T A C Q G V G

G P G H K A R V L A E A M S Q V T N S A T I M M Q R G N F R N Q R K I V

K C F N C G K E G H T A R N C R A P R K K G C W K C G K E G H Q M K D

C T E R Q A N F L G K I W P S Y K G R P G N F L Q S R P E P T A P P E E

S F R S G V E T T T P P Q K Q E P I D K E L Y P L T S L R S L F G N D P S

S Q *g e f* <u>T L I P I A V G G A L A G L V L I V L I A Y L V G R K R S</u>

H A G Y Q T I.

LAMP-1 underlined
Linker lower case italics
HIV gag bold
Linker lower case italics
LAMP-1 underlined HIV gagpol fusion nucleic acid sequence
SEQ ID NO: 28

ATGGGTGCGAGAGCGTCAGTATTAAGCGGGGGAGAATTAGATCGATGGGAAAAA

ATTCGGTTAAGGCCAGGGGGAAAGAAGAAGTACAAGCTAAAGCACATCGTATGG

GCAAGCAGGGAGCTAGAACGATTCGCAGTTAATCCTGGCCTGTTAGAAACATCA

GAAGGCTGTAGACAAATACTGGGACAGCTACAACCATCCCTTCAGACAGGATCA

GAGGAGCTTCGATCACTATACAACACAGTAGCAACCCTCTATTGTGTGCACCAGC

GGATCGAGATCAAGGACACCAAGGAAGCTTTAGACAAGATAGAGGAAGAGCAA

AACAAGTCCAAGAAGAAGGCCCAGCAGGCAGCAGCTGACACAGGACACAGCAA

TCAGGTCAGCCAAAATTACCCTATAGTGCAGAACATCCAGGGGCAAATGGTACA

TCAGGCCATATCACCTAGAACTTTAAATGCATGGGTAAAAGTAGTAGAAGAGAA

GGCTTTCAGCCCAGAAGTGATACCCATGTTTTCAGCATTATCAGAAGGAGCCACC

CCACAGGACCTGAACACGATGTTGAACACCGTGGGGGGACATCAAGCAGCCATG

CAAATGTTAAAAGAGACCATCAATGAGGAAGCTGCAGAATGGGATAGAGTGCAT

CCAGTGCATGCAGGGCCTATTGCACCAGGCCAGATGAGAGAACCAAGGGGAAGT

GACATAGCAGGAACTACTAGTACCCTTCAGGAACAAATAGGATGGATGACAAAT

AATCCACCTATCCCAGTAGGAGAGATCTACAAGAGGTGGATAATCCTGGGATTG

AACAAGATCGTGAGGATGTATAGCCCTACCAGCATTCTGGACATAAGACAAGGA

CCAAAGGAACCCTTTAGAGACTATGTAGACCGGTTCTATAAAACTCTAAGAGCTG

AGCAAGCTTCACAGGAGGTAAAAAATTGGATGACAGAAACCTTGTTGGTCCAAA

ATGCGAACCCAGATTGTAAGACCATCCTGAAGGCTCTCGGCCCAGCGGCTACACT

AGAAGAAATGATGACAGCATGTCAGGGAGTAGGAGGACCCGGCCATAAGGCAA

GAGTTTTGGCCGAGGCGATGAGCCAGGTGACGAACTCGGCGACCATAATGATGC

AGAGAGGCAACTTCCGGAACCAGCGGAAGATCGTCAAGTGCTTCAATTGTGGCA

AAGAAGGGCACACCGCCAGGAACTGCCGGGCCCCCCGGAAGAAGGGCTGCTGG

AAGTGCGGGAAGGAGGGGCACCAGATGAAGGACTGCACGGAGCGGCAGGCGAA

CTTCCTGGGGAAGATATGGCCGAGTTACAAGGGAAGACCCGACCGGCAGGGGAC

GGTGTCGTTCAACTTCCCTCAGATCACGCTCTGGCAGCGGCCGCTCGTCACAATA

AAGATCGGGGGGCAACTCAAGGAGGCGCTGCTCGCGGACGACACGGTCTTGGAG

GAGATGTCGTTGCCGGGCGGTGGAAGCCGAAGATGATCGGGGGGATCGGGGGC

TTCATCAAGGTGCGGCAGTACGACCAGATCCTCATCGAGATCTGCGGGCACAAG

GCGATCGGGACGGTCCTCGTCGGCCCGACGCCGGTCAACATCATCGGGCGGAAC

CTGTTGACCCAGATCGGCTGCACCTTGAACTTCCCCATCAGCCCTATTGAGACGG

TGCCCGTGAAGTTGAAGCCGGGGATGGACGGCCCCAAGGTCAAGCAATGGCCAT

TGACGGAGGAGAAGATCAAGGCCTTAGTCGAAATCTGTACAGAGATGGAGAAGG

AAGGGAAGATCAGCAAGATCGGGCCTGAGAACCCCTACAACACTCCAGTCTTCG

CAATCAAGAAGAAGGACAGTACCAAGTGGAGAAAGCTGGTGGACTTCAGAGAG

```
                               -continued
CTGAACAAGAGAACTCAGGACTTCTGGGAAGTTCAGCTGGGCATCCCACATCCC

GCTGGGTTGAAGAAGAAGAAGTCAGTGACAGTGCTGGATGTGGGTGATGCCTAC

TTCTCCGTTCCCTTGGACGAGGACTTCAGGAAGTACACTGCCTTCACGATACCTA

GCATCAACAACGAGACACCAGGCATCCGCTACCAGTACAACGTGCTGCCACAGG

GATGGAAGGGATCACCAGCCATCTTTCAATCGTCGATGACCAAGATCCTGGAGC

CCTTCCGCAAGCAAAACCCAGACATCGTGATCTATCAGCTCTACGTAGGAAGTGA

CCTGGAGATCGGGCAGCACAGGACCAAGATCGAGGAGCTGAGACAGCATCTGTT

GAGGTGGGGACTGACCACACCAGACAAGAAGCACCAGAAGGAACCTCCCTTCCT

GTGGATGGGCTACGAACTGCATCCTGACAAGTGGACAGTGCAGCCCATCGTGCT

GCCTGAGAAGGACAGCTGGACTGTGAACGACATACAGAAGCTCGTGGGCAAGTT

GAACTGGGCAAGCCAGATCTACCCAGGCATCAAAGTTAGGCAGCTGTGCAAGCT

GCTTCGAGGAACCAAGGCACTGACAGAAGTGATCCCACTGACAGAGGAAGCAGA

GCTAGAACTGGCAGAGAACCGAGAGATCCTGAAGGAGCCAGTACATGGAGTGTA

CTACGACCCAAGCAAGGACCTGATCGCAGAGATCCAGAAGCAGGGGCAAGGCC

AATGGACCTACCAAATCTACCAGGAGCCCTTCAAGAACCTGAAGACAGGCAAGT

ACGCAAGGATGAGGGGTGCCCACACCAACGATGTGAAGCAGCTGACAGAGGCA

GTGCAGAAGATCACCACAGAGAGCATCGTGATCTGGGGCAAGACTCCCAAGTTC

AAGCTGCCCATACAGAAGGAGACATGGGAGACATGGTGGACCGAGTACTGGCAA

GCCACCTGGATCCCTGAGTGGGAGTTCGTGAACACCCCTCCCTTGGTGAAACTGT

GGTATCAGCTGGAGAAGGAACCCATCGTGGGAGCAGAGACCTTCTACGTGGATG

GGGCAGCCAACAGGGAGACCAAGCTGGGCAAGGCAGGCTACGTGACCAACCGA

GGACGACAGAAAGTGGTGACCCTGACTGACACCACCAACCAGAAGACTCTGCAA

GCCATCTACCTAGCTCTGCAAGACAGCGGACTGGAAGTGAACATCGTGACAGAC

TCACAGTACGCACTGGGCATCATCCAAGCACAACCAGACCAATCCGAGTCAGAG

CTGGTGAACCAGATCATCGAGCAGCTGATCAAGAAGGAGAAAGTGTACCTGGCA

TGGGTCCCGGCGCACAAGGGGATCGGGGGAACGAGCAGGTCGACAAGTTGGTC

TCGGCGGGATCCGGAAGGTGCTGTTCCTGGACGGGATCGATAAGGCCCAAGAT

GAACATGAGAAGTACCACTCCAACTGGCGCGCTATGGCCAGCGACTTCAACCTG

CCGCCGGTCGTCGCGAAGGAGATCGTCGCCAGCTGCGACAAGTGCCAGCTCAAG

GGGGAGGCCATGCACGGGCAAGTCGACTGCAGTCCGGGGATCTGGCAGCTGTGC

ACGCACCTGGAGGGGAAGGTGATCCTGGTCGCGGTCCACGTCGCCAGCGGGTAT

ATCGAGGCGGAGGTCATCCCGGCTGAGACGGGGCAGGAGACGGCGTACTTCCTC

TTGAAGCTCGCGGGGCGGTGGCCGGTCAAGACGATCCACACGAACGGGAGCAAC

TTCACGGGGGCGACGGTCAAGGCCGCCTGTTGGTGGGCGGGAATCAAGCAGGAA

TTTGGAATTCCCTACAATCCCCAATCGCAAGGAGTCGTGAGCATGAACAAGGAG

CTGAAGAAGATCATCGGACAAAGGGATCAGGCTGAGCACCTGAAGACAGCAGTG

CAGATGGCAGTGTTCATCCACAACTTCAAAAGAAAAGGGGGGATTGGGGGGTAC

AGTGCGGGGAACGGATCGTGGACATCATCGCCACCGACATCCAAACCAAGGAG

CTGCAGAAGCAGATCACCAAGATCCAGAACTTCCGGGTGTACTACCGCGACAGC

CGCAACCCACTGTGGAAGGGACCAGCAAAGCTCCTCTGGAAGGGAGAGGGGGC

AGTGGTGATCCAGGACAACAGTGACATCAAAGTGGTGCCAAGGCGCAAGGCCAA
```

GATCATCCGCGACTATGGAAAACAGATGGCAGGGGATGATTGTGTGGCAAGTAG

ACAGGATGAGGATGGCGCCTAG

HIV gagpol fusion amino acid sequence

SEQ ID NO: 29

M G A R A S V L S G G E L D R W E K I R L R P G G K K K Y K L K H I V W A

S R E L E R F A V N P G L L E T S E G C R Q I L G Q L Q P S L Q T G S E E

L R S L Y N T V A T L Y C V H Q R I E I K D T K E A L D K I E E E Q N K S K

K K A Q Q A A A D T G H S N Q V S Q N Y P I V Q N I Q G Q M V H Q A I S P

R T L N A W V K V V E E K A F S P E V I P M F S A L S E G A T P Q D L N T

M L N T V G G H Q A A M Q M L K E T I N E E A A E W D R V H P V H A G P

I A P G Q M R E P R G S D I A G T T S T L Q E Q I G W M T N N P P I P V G

E I Y K R W I I L G L N K I V R M Y S P T S I L D I R Q G P K E P F R D Y V

D R F Y K T L R A E Q A S Q E V K N W M T E T L L V Q N A N P D C K T I L

K A L G P A A T L E E M M T A C Q G V G G P G H K A R V L A E A M S Q V

T N S A T I M M Q R G N F R N Q R K I V K C F N C G K E G H T A R N C R

A P R K K G C W K C G K E G H Q M K D C T E R Q A N F L G K I W P S Y K

G R P *D R Q G T V S F N F* P Q I T L W Q R P L V T I K I G G Q L K E A L L

A D D T V L E E M S L P G R W K P K M I G G I G G F I K V R Q Y D Q I L I

E I C G H K A I G T V L V G P T P V N I I G R N L L T Q I G C T L N F P I S P

I E T V P V K L K P G M D G P K V K Q W P L T E E K I K A L V E I C T E M

E K E G K I S K I G P E N P Y N T P V F A I K K K D S T K W R K L V D F R

E L N K R T Q D F W E V Q L G I P H P A G L K K K K S V T V L D V G D A Y

F S V P L D E D F R K Y T A F T I P S I N N E T P G I R Y Q Y N V L P Q G

W K G S P A I F Q S S M T K I L E P F R K Q N P D I V I Y Q L Y V G S D L E

I G Q H R T K I E E L R Q H L L R W G L T T P D K K H Q K E P P F L W M G

Y E L H P D K W T V Q P I V L P E K D S W T V N D I Q K L V G K L N W A S

Q I Y P G I K V R Q L C K L L R G T K A L T E V I P L T E E A E L E L A E N

R E I L K E P V H G V Y Y D P S K D L I A E I Q K Q G Q G Q W T Y Q I Y Q

E P F K N L K T G K Y A R M R G A H T N D V K Q L T E A V Q K I T T E S I

V I W G K T P K F K L P I Q K E T W E T W W T E Y W Q A T W I P E W E F

V N T P P L V K L W Y Q L E K E P I V G A E T F Y V D G A A N R E T K L G

K A G Y V T N R G R Q K V V T L T D T T N Q K T L Q A I Y L A L Q D S G L

E V N I V T D S Q Y A L G I I Q A Q P D Q S E S E L V N Q I I E Q L I K K E

K V Y L A W V P A H K G I G G N E Q V D K L V S A G I R K V L F L D G I D

K A Q D E H E K Y H S N W R A M A S D F N L P P V V A K E I V A S C D K

C Q L K G E A M H G Q V D C S P G I W Q L C T H L E G K V I L V A V H V A

S G Y I E A E V I P A E T G Q E T A Y F L L K L A G R W P V K T I H T N G S

N F T G A T V K A A C W W A G I K Q E F G I P Y N P Q S Q G V V S M N K

E L K K I I G Q R D Q A E H L K T A V Q M A V F I H N F K R K G G I G G Y

S A G E R I V D I I A T D I Q T K E L Q K Q I T K I Q N F R V Y Y R D S R N

P L W K G P A K L L W K G E G A V V I Q D N S D I K V V P R R K A K I I R
D Y G K Q M A G D D C V A S R Q D E D G A •

Gag underlined
Linker italics
Pol (inactive) underlined

HIV env (98H) nucleic acid sequence

SEQ ID NO: 30

```
ATGAGGGCCAAGGAGATGAGGAAGAGCTGCCAGCACCTGAGAAAGTGGGGCAT
CCTGCTGTTCGGCGTGCTGATGATCTGCAGCGCCGAGGAGAAGCTGTGGGTGAC
AGTGTACTACGGCGTGCCTGTGTGGAAGGAGGCCACCACCACCCTGTTCTGTGCC
TCGGACGCCAAGGCCCACCACGCCGAGGCCCATAATGTGTGGGCTACCCACGCC
TGTGTGCCCACCGATCCCAATCCTCAGGAGGTGATCCTGGAGAACGTGACCGAG
AAGTACAACATGTGGAAGAACAACATGGTGGACCAGATGCACGAGGACATCATC
AGCCTGTGGGACCAGAGCCTGAAGCCCTGTGTGAAGCTGACCCCCCTGTGTGTGA
CCCTGAACTGTACCAACGCCACCTACACCAACAGCGACAGCAAGAACAGCACCA
GCAACAGCAGCCTGGAGGACAGCGGCAAGGGCGACATGAACTGTAGCTTCGACG
TGACCACCTCCATCGACAAGAAGAAGAAAACCGAGTACGCCATCTTCGACAAGC
TGGACGTGATGAACATCGGCAACGGCCGCTACACCCTGCTGAACTGTAACACCA
GCGTGATCACCCAGGCCTGCCCCAAGATGAGCTTCGAGCCCATCCCCATCCACTA
CTGTACCCCTGCCGGCTACGCCATCCTGAAGTGTAACGACAACAAGTTCAACGGC
ACCGGCCCCTGTACCAACGTCAGCACCATCCAGTGTACCCACGGCATCAAGCCTG
TGGTGTCCACCCAGCTGCTGCTGAACGGCAGCCTGGCCGAGGGCGGCGAGGTGA
TCATCAGGAGCGAGAACCTGACCGACAACGCCAAGACCATCATCGTGCAGCTGA
AGGAGCCCGTGGAGATCAACTGTACCCGGCCCAACAACAACACCCGGAAGAGCA
TCCACATGGGCCCTGGAGCCGCCTTCTACGCTCGGGGCGAAGTGATCGGCGACAT
CAGACAGGCCCACTGTAACATCAGCCGGGGCAGGTGGAATGATACCCTGAAGCA
GATCGCCAAGAAGCTGAGGGAGCAGTTCAACAAGACCATCTCCCTGAACCAGAG
CAGCGGCGGAGACCTGGAGATCGTGATGCACACCTTCAACTGTGGCGGCGAGTT
CTTCTACTGTAACACAACCCAGCTGTTCAACTCCACCTGGAACGAGAACGACACC
ACCTGGAATAATACCGCCGGCAGCAACAACAACGAGACCATCACACTGCCCTGC
CGGATCAAGCAGATCATCAACCGGTGGCAGGAAGTGGGCAAGGCTATGTACGCC
CCTCCCATCAGCGGCCCTATCAACTGCCTGAGCAACATCACCGGCCTGCTGCTGA
CCAGAGATGGCGGCGACAACAACAATACCATCGAGACCTTCAGACCTGGCGGCG
GAGATATGAGAGACAACTGGCGGAGCGAGCTGTACAAGTACAAGGTTGTGAGGA
TCGAGCCCCTGGGCATCGCCCCCACCAAGGCCAAGAGAAGAGTGGTGCAGCGGG
AGAAGAGAGCTGTGGGCATCGGCGCCATGTTTCTGGGCTTTCTGGGAGCCGCCG
GAAGCACAATGGGAGCCGCCTCGGTGACCCTGACCGTGCAGGCCAGACTGCTGC
TGTCCGGCATTGTGCAGCAGCAGAACAACCTGCTGAGAGCCATCGAGGCCCAGC
AGCACCTGCTCCAGCTGACAGTGTGGGGCATCAAGCAGCTCCAGGCCAGGGTGC
TGGCCATGGAGAGATACCTGAAGGACCAGCAACTGCTCGGCATCTGGGGCTGTA
GCGGCAAGCTGATCTGTACCACCAACGTGCCCTGGAACGCCAGCTGGAGCAACA
AGAGCCTGGACAAGATCTGGCACAACATGACCTGGATGGAGTGGGACCGGGAGA
```

```
TCGACAACTACACAAAGCTGATCTACACCCTGATCGAGGCCAGCCAGATCCAGC

AGGAGAAGAACGAGCAGGAGCTGCTGGAGCTGGACAGCTGGGCCAGCCTGTGG

AGCTGGTTCGACATCAGCAAGTGGCTGTGGTACATCGGCGTGTTCATCATCGTGA

TCGGCGGCCTGGTTGGTCTGAAGATCGTGTTCGCCGTGCTGTCCATCGTGAACAG

AGTGAGGCAGGGCTACAGCCCCCTGAGCTTCCAGACCAGACTGCCTGCTCCGCG

GGGCCCCGATAGACCCGAGGGCATCGAGGAGGGCGGAGGAGAGAGAGACAGGG

ACAGGAGCGACCAGCTGGTGACAGGCTTCCTGGCCCTGATCTGGGACGATCTGA

GGAGCCTGTGCCTGTTCAGCTACCACCGGCTGAGAGATCTGCTGCTGATCGTGGC

CAGAATCGTGGAACTGCTGGGCAGAAGAGGCTGGGAGGCCCTGAAGTACTGGTG

GAATCTGCTCCAGTACTGGATTCAGGAGCTGAAGAACAGCGCCGTGTCCCTGCTG

AATGCCACCGCCATCGCCGTGGCCGAGGGAACCGACAGAATCATCGAGGTGGTG

CAGAGAATCGGCAGAGCCATCCTGCACATCCCCCGGAGAATCAGACAGGGCCTG

GAAAGAGCCCTGCTGTGATGA
```

HIV env (98H) amino acid sequence

SEQ ID NO: 31

```
M R A K E M R K S C Q H L R K W G I L L F G V L M I C S A E E K L W V T V
Y Y G V P V W K E A T T T L F C A S D A K A H H A E A H N V W A T H A C
V P T D P N P Q E V I L E N V T E K Y N M W K N N M V D Q M H E D I I S L
W D Q S L K P C V K L T P L C V T L N C T N A T Y T N S D S K N S T S N S
S L E D S G K G D M N C S F D V T T S I D K K K K T E Y A I F D K L D V M
N I G N G R Y T L L N C N T S V I T Q A C P K M S F E P I P I H Y C T P A G
Y A I L K C N D N K F N G T G P C T N V S T I Q C T H G I K P V V S T Q L L
L N G S L A E G G E V I I R S E N L T D N A K T I I V Q L K E P V E I N C T
R P N N N T R K S I H M G P G A A F Y A R G E V I G D I R Q A H C N I S R
G R W N D T L K Q I A K K L R E Q F N K T I S L N Q S S G G D L E I V M H
T F N C G G E F F Y C N T T Q L F N S T W N E N D T T W N N T A G S N N
N E T I T L P C R I K Q I I N R W Q E V G K A M Y A P P I S G P I N C L S N
I T G L L L T R D G G D N N N T I E T F R P G G G D M R D N W R S E L Y K
Y K V V R I E P L G I A P T K A K R R V V Q R E K R A V G I G A M F L G F
L G A A G S T M G A A S V T L T V Q A R L L L S G I V Q Q Q N N L L R A I
E A Q Q H L L Q L T V W G I K Q L Q A R V L A M E R Y L K D Q Q L L G I W
G C S G K L I C T T N V P W N A S W S N K S L D K I W H N M T W M E W D
R E I D N Y T K L I Y T L I E A S Q I Q Q E K N E Q E L L E L D S W A S L W
S W F D I S K W L W Y I G V F I I V I G G L V G L K I V F A V L S I V N R V
R Q G Y S P L S F Q T R L P A P R G P D R P E G I E E G G G E R D R D R
S D Q L V T G F L A L I W D D L R S L C L F S Y H R L R D L L L I V A R I V
E L L G R R G W E A L K Y W W N L L Q Y W I Q E L K N S A V S L L N A T
A I A V A E G T D R I I E V V Q R I G R A I L H I P R R I R Q G L E R A L L • •
```

SEQ ID NOs: 32 and 33 are derived from clade B. Similar Env sequences can be derived from other clades.
HIV mIP10hMCP-3 env amino acid sequence

SEQ ID NO: 32

<u>M N P S A A V I F C L I L L G L S G T Q G</u> *i l d a* <u>Q P V G I N T S T T C C Y R F I N K</u>

<u>K I P K Q R L E S Y R R T T S S H C P R E A V I F K T K L D K E I C A D P T Q K W V</u>

<u>Q D F M K H L D K K T Q T P K L</u> *a s g* R A K E M R K S C Q H L R K W G I L L

F G V L M I C S A E E K L W V T V Y Y G V P V W K E A T T T L F C A S D

A K A H H A E A H N V W A T H A C V P T D P N P Q E V I L E N V T E K Y

N M W K N N M V D Q M H E D I I S L W D Q S L K P C V K L T P L C V T L

N C T N A T Y T N S D K N S T S N S S L E D S G K G D M N C S F D V T

T S I D K K K K T E Y A I F D K L D V M N I G N G R Y T L L N C N T S V I T

Q A C P K M S F E P I P I H Y C T P A G Y A I L K C N D N K F N G T G P C

T N V S T I Q C T H G I K P V V S T Q L L L N G S L A E G G E V I I R S E N

L T D N A K T I I V Q L K E P V E I N C T R P N N N T R K S I H M G P G A

A F Y A R G E V I G D I R Q A H C N I S R G R W N D T L K Q I A K K L R E

Q F N K T I S L N Q S S G G D L E I V M H T F N C G G E F F Y C N T T Q L

F N S T W N E N D T T W N N T A G S N N N E T I T L P C R I K Q I I N R W

Q E V G K A M Y A P P I S G P I N C L S N I T G L L L T R D G G D N N N T

I E T F R P G G G D M R D N W R S E L Y K Y K V V R I E P L G I A P T K A

K R R V V Q R E K R A V G I G A M F L G F L G A A G S T M G A A S V T L

T V Q A R L L L S G I V Q Q Q N N L L R A I E A Q Q H L L Q L T V W G I K

Q L Q A R V L A M E R Y L K D Q Q L L G I W G C S G K L I C T T N V P W

N A S W S N K S L D K I W H N M T W M E W D R E I D N Y T K L I Y T L I E

A S Q I Q Q E K N E Q E L L E L D S W A S L W S W F D I S K W L W Y I G

V F I I V I G G L V G L K I V F A V L S I V N R V R Q G Y S P L S F Q T R L

P A P R G P D R P E G I E E G G G E R D R D R S D Q L V T G F L A L I W

D D L R S L C L F S Y H R L R D L L L I V A R I V E L L G R R G W E A L K

Y W W N L L Q Y W I Q E L K N S A V S L L N A T A I A V A E G T D R I I E

V V Q R I G R A I L H I P R R I R Q G L E R A L L * * muIP10 underlined
Linker lower case, italics
huMCP-3 mature underlined
Linker lower case italics
HIVenv bold HIV hIP10hMCP-3 env amino acid sequence

SEQ ID NO: 33

<u>M N Q T A I L I C C L I F L T L S G I Q G</u> *q p v g i n t s t t c c v r f i n k k i*

*p k q r l e s y r r t t s s h c p r e a v i f k t k l d k e i c a d p t q k w v q d f m k h l d k*

*k t q t p k l* *a s g* R A K E M R K S C Q H L R K W G I L L F G V L M I C S A E

E K L W V T V Y Y G V P V W K E A T T T L F C A S D A K A H H A E A H N

V W A T H A C V P T D P N P Q E V I L E N V T E K Y N M W K N N M V D Q

M H E D I I S L W Q S L K P C V K L T P L C V T L N C T N A T Y T N S D

S K N S T S N S S L E D S G K G D M N C S F D V T T S I D K K K K T E Y

A I F D K L D V M N I G N G R Y T L L N C N T S V I T Q A C P K M S F E P

I P I H Y C T P A G Y A I L K C N D N K F N G T G P C T N V S T I Q C T H

G I K P V V S T Q L L L N G S L A E G G E V I I R S E N L T D N A K T I I V

```
QLKEPVEINCTRPNNNTRKSIHMGPGAAFYARGEVIG

DIRQAHCNISRGRWNDTLKQIAKKLREQFNKTISLNQ

SSGGDLEIVMHTFNCGGEFFYCNTTQLFNSTWNEND

TTWNNTAGSNNNETITLPCRIKQIINRWQEVGKAMYA

PPISGPINCLSNITGLLLTRDGGDNNNTIETFRPGGG

DMRDNWRSELYKYKVVRIEPLGIAPTKAKRRVVQRE

KRAVGIGAMFLGFLGAAGSTMGAASVTLTVQARLLL

SGIVQQQNNLLRAIEAQQHLLQLTVWGIKQLQARVLA

MERYLKDQQLLGIWGCSGKLICTTNVPWNASWSNKS

LDKIWHNMTWMEWDREIDNYTKLIYTLIEASQIQQEK

NEQELLELDSWASLWSWFDISKWLWYIGVFIIVIGGL

VGLKIVFAVLSIVNRVRQGYSPLSFQTRLPAPRGPDR

PEGIEEGGGERDRDRSDQLVTGFLALIWDDLRSLCLF

SYHRLRDLLLIVARIVELLGRRGWEALKYWWNLLQY

WIQELKNSAVSLLNATAIAVAEGTDRIIEVVQRIGRAI

LHIPRRIRQGLERALL**
``` huIP10 underlined
huMCP-3 mature lower case, underlined
Linker lower case, italics
HIVenv bold HIV huMCP-3 env amino acid sequence

SEQ ID NO: 34

```
MKASAALLCLLLTAAAFSPQGLAGqpvgintsttccy rfinkkipkqrlesyrrttsshcpreavifktkldkeicadptqkwvqdf mkhldkktqtpklASRAKEMRKSCQHLRKWGILLFGVLMI

CSAEEKLWVTVYYGVPVWKEATTTLFCASDAKAHHA

EAHNVWATHACVPTDPNPQEVILENVTEKYNMWKNN

MVDQMHEDIISLWDQSLKPCVKLTPLCVTLNCTNATY

TNSDSKNSTSNSSLEDSGKGDMNCSFDVTTSIDKKK

KTEYAIFDKLDVMNIGNGRYTLLNCNTSVITQACPKM

SFEPIPIHYCTPAGYAILKCNDKFNGTGPCTNVSTIQ

CTHGIKPVVSTQLLLNGSLAEGGEVIIRSENLTDNAK

TIIVQLKEPVEINCTRPNNNTRKSIHMGPGAAFYARG

EVIGDIRQAHCNISRGRWNDTLKQIAKKLREQFNKTI

SLNQSSGGDLEIVMHTFNCGGEFFYCNTTQLFNSTW

NENDTTWNNTAGSNNNETITLPCRIKQIINRWQEVGK

AMYAPPISGPINCLSNITGLLLTRDGGDNNNTIETFRP

GGGDMRDNWRSELYKYKVVRIEPLGIAPTKAKRRVV

QREKRAVGIGAMFLGFLGAAGSTMGAASVTLTVQAR

LLLSGIVQQQNNLLRAIEAQQHLLQLTVWGIKQLQAR

VLAMERYLKDQQLLGIWGCSGKLICTTNVPWNASWS

NKSLDKIWHNMTWMEWDREIDNYTKLIYTLIEASQIQ

QEKNEQELLELDSWASLWSWFDISKWLWYIGVFIIVI
```

-continued

GGLVGLKIVFAVLSIVNRVRQGYSPLSFQTRLPAPRG

PDRPEGIEEGGGERDRDRSDQLVTGFLALIWDDLRSL

CLFSYHRLRDLLLIVARIVELLGRRGWEALKYWWNLL

QYWIQELKNSAVSLLNATAIAVAEGTDRIIEVVQRIG

RAILHIPRRIRQGLERALL·· huMCP-3 signal peptide underlined
huMCP-3 mature lower case, underlined
Linker italics
HIVenv bold HIV LAMPpol nucleic acid sequence    SEQ ID NO: 35

ATGGCGCCCCGCAGCGCCCGGCGACCCCTGCTGCTGCTACTGCTGTTGCTGCTGC

TCGGCCTCATGCATTGTGCGTCAGCAGCAATGTTTATGGTGAAAAATGGCAACGG

GACCGCGTGCATAATGGCCAACTTCTCTGCTGCCTTCTCAGTGAACTACGACACC

AAGAGTGGCCCTAAGAACATGACCcTTGACCTGCCATCAGATGCCACAGTGGTGC

TCAACCGCAGCTCCTGTGGAAAAGAGAACACTTCTGACCCCAGTCTCGTGATTGC

TTTTGGAAGAGGACATACACTCACTCTCAATTTCACGAGAAATGCAACACGTTAC

AGCGTcCAGCTCATGAGTTTTGTTTATAACTTGTCAGACACACACCTTTTCCCCAA

TGCGAGCTCCAAAGAAATCAAGACTGTGGAATCTATAACTGACATCAGGGCAGA

TATAGATAAAAAATACAGATGTGTTAGTGGCACCCAGGTCCACATGAACAACGT

GACCGTAACGCTCCATGATGCCACCATCCAGGCGTACCTTTCCAACAGCAGCTTC

AGCAGGGGAGAGACACGCTGTGAACAAGACAGGCCTTCCCCAACCACAGCGCCC

CCTGCGCCACCCAGCCCCTCGCCCTCACCCGTGCCCAAGAGCCCCTCTGTGGACA

AGTACAACGTGAGCGGCACCAACGGGACCTGCCTGCTGGCCAGCATGGGGCTGC

AGCTGAACCTCACCTATGAGAGGAAGGACAACACGACGGTGACAAGGCTTCTCA

ACATCAACCCCAACAAGACCTCGGCCAGCGGGAGCTGCGGCGCCCACCTGGTGA

CTCTGGAGCTGCACAGCGAGGGCACCACCGTCCTGCTCTTCCAGTTCGGGATGAA

TGCAAGTTCTAGCCGGTTTTTCCTACAAGGAATCCAGTTGAATACAATTCTTCCTG

ACGCCAGAGACCCTGCCTTTAAAGCTGCCAACGGCTCCCTGCGAGCGCTGCAGG

CCACAGTCGGCAATTCCTACAAGTGCAACGCGGAGGAGCACGTCCGTGTCACGA

AGGCGTTTTCAGTCAATATATTCAAAGTGTGGGTCCAGGCTTTCAAGGTGGAAGG

TGGCCAGTTTGGCTCTGTGGAGGAGTGTCTGCTGGACGAGAACAGCCTCGAGGA

TATCGGCCCTCAGATCACGCTCTGGCAGCGGCCGCTCGTCACAGTACGGATCGGG

GGGCAACTCAAGGAGGCGCTGCTCGCGGACGACACGGTCTTGGAGGAGATGTCG

TTGCCGGGGCGGTGGAAGCCGAAGATGATCGGGGGGATCGGGGGCTTCATCAAG

GTGCGGCAGTACGACCAGATCCTCATCGAGATCTGCGGGCACAAGGCGATCGGG

ACGGTCCTCGTCGGCCCGACGCCGGTCAACATCATCGGGCGGAACCTGTTGACCC

AGATCGGCTGCACCTTGAACTTCCCCATCAGCCCTATTGAGACGGTGCCCGTGAA

GTTGAAGCCGGGGATGGACGGCCCCAAGGTCAAGCAATGGCCATTGACGAAAGA

GAAGATCAAGGCCTTAGTCGAAATCTGTACAGAGATGGAGAAGGAAGGGAAGA

TCAGCAAGATCGGGCCTGAGAACCCCTACAACACTCCAGTCTTCGCAATCAAGA

AGAAGGACAGTACCAAGTGGAGAAAGCTGGTGGACTTCAGAGAGCTGAACAAG

AGAACTCAGGACTTCTGGGAAGTTCAGCTGGGCATCCCACATCCCGCTGGGTTGA

-continued

```
AGAAGAAGAAGTCAGTGACAGTGCTGGATGTGGGTGATGCCTACTTCTCCGTTCC
CTTGGACGAGGACTTCAGGAAGTACACTGCCTTCACGATACCTAGCATCAACAAC
GAGACACCAGGCATCCGCTACCAGTACAACGTGCTGCCACAGGGATGGAAGGGA
TCACCAGCCATCTTTCAATCGTCGATGACCAAGATCCTGGAGCCCTTCCGCAAGC
AAAACCCAGACATCGTGATCTATCAGCTCTACGTAGGAAGTGACCTGGAGATCG
GGCAGCACAGGACCAAGATCGAGGAGCTGAGACAGCATCTGTTGAGGTGGGGAC
TGACCACACCAGACAAGAAGCACCAGAAGGAACCTCCCTTCCTGTGGATGGGCT
ACGAACTGCATCCTGACAAGTGGACAGTGCAGCCCATCGTGCTGCCTGAGAAGG
ACAGCTGGACTGTGAACGACATACAGAAGCTCGTGGGCAAGTTGAACTGGGCAA
GCCAGATCTACCCAGGCATCAAAGTTAGGCAGCTGTGCAAGCTGCTTCGAGGAA
CCAAGGCACTGACAGAAGTGATCCCACTGACAGAGGAAGCAGAGCTAGAACTGG
CAGAGAACCGAGAGATCCTGAAGGAGCCAGTACATGGAGTGTACTACGACCCAA
GCAAGGACCTGATCGCAGAGATCCAGAAGCAGGGGCAAGGCCAATGGACCTACC
AAATCTACCAGGAGCCCTTCAAGAACCTGAAGACAGGCAAGTACGCAAGGATGA
GGGGTGCCCACACCAACGATGTGAAGCAGCTGACAGAGGCAGTGCAGAAGATCA
CCACAGAGAGCATCGTGATCTGGGGCAAGACTCCCAAGTTCAAGCTGCCCATAC
AGAAGGAGACATGGGAGACATGGTGGACCGAGTACTGGCAAGCCACCTGGATCC
CTGAGTGGGAGTTCGTGAACACCCCTCCCTTGGTGAAACTGTGGTATCAGCTGGA
GAAGGAACCCATCGTGGGAGCAGAGACCTTCTACGTGGATGGGGCAGCCAACAG
GGAGACCAAGCTGGGCAAGGCAGGCTACGTGACCAACCGAGGACGACAGAAAG
TGGTGACCCTGACTGACACCACCAACCAGAAGACTCTGCAAGCCATCTACCTAGC
TCTGCAAGACAGCGGACTGGAAGTGAACATCGTGACAGACTCACAGTACGCACT
GGGCATCATCCAAGCACAACCAGACCAATCCGAGTCAGAGCTGGTGAACCAGAT
CATCGAGCAGCTGATCAAGAAGGAGAAAGTGTACCTGGCATGGGTCCCGGCGCA
CAAGGGGATCGGGGGGAACGAGCAGGTCGACAAGTTGGTCTCGGCGGGGATCCG
GAAGGTGCTGTTCCTGGACGGGATCGATAAGGCCCAAGATGAACATGAGAAGTA
CCACTCCAACTGGCGCGCTATGGCCAGCGACTTCAACCTGCCGCCGGTCGTCGCG
AAGGAGATCGTCGCCAGCTGCGACAAGTGCCAGCTCAAGGGGGAGGCCATGCAC
GGGCAAGTCGACTGCAGTCCGGGGATCTGGCAGCTGTGCACGCACCTGGAGGGG
AAGGTGATCCTGGTCGCGGTCCACGTCGCCAGCGGGTATATCGAGGCGGAGGTC
ATCCCGGCTGAGACGGGGCAGGAGACGGCGTACTTCCTCTTGAAGCTCGCGGGG
CGGTGGCCGGTCAAGACGATCCACACGAACGGGAGCAACTTCACGGGGGCGACG
GTCAAGGCCGCCTGTTGGTGGGCGGGAATCAAGCAGGAATTTGGAATTCCCTAC
AATCCCCAATCGCAAGGAGTCGTGAGCATGAACAAGGAGCTGAAGAAGATCATC
GGACAAAGGGATCAGGCTGAGCACCTGAAGACAGCAGTGCAGATGGCAGTGTTC
ATCCACAACTTCAAAAGAAAAGGGGGGATTGGGGGGTACAGTGCGGGGGAACG
GATCGTGGACATCATCGCCACCGACATCCAAACCAAGGAGCTGCAGAAGCAGAT
CACCAAGATCCAGAACTTCCGGGTGTACTACCGCGACAGCCGCAACCCACTGTG
GAAGGGACCAGCAAAGCTCCTCTGGAAGGGAGAGGGGGCAGTGGTGATCCAGG
ACAACAGTGACATCAAAGTGGTGCCAAGGCGCAAGGCCAAGATCATCCGCGACT
ATGGAAAACAGATGGCAGGGGATGATTGTGTGGCAAGTAGACAGGATGAGGAT
```

```
GCTAGCGGATCCGAATTCACGCTGATCCCCATCGCTGTGGGTGGTGCCCTGGCGG

GGCTGGTCCTCATCGTCCTCATCGCCTACCTCGTCGGCAGGAAGAGGAGTCACGC

AGGCTACCAGACTATCTAG
```

HIV LAMPpol amino acid sequence

SEQ ID NO: 36

<u>M A P R S A R R P L L L L L L L L L L G L M H C A S A A M F M V K N G N G</u>

<u>T A C I M A N F S A A F S V N Y D T K S G P K N M T L D L P S D A T V V L</u>

<u>N R S S C G K E N T S D P S L V I A F G R G H T L T L N F T R N A T R Y S</u>

<u>V Q L M S F V Y N L S D T H L F P N A S S K E I K T V E S I T D I R A D I D</u>

<u>K K Y R C V S G T Q V H M N N V T V T L H D A T I Q A Y L S N S S F S R G</u>

<u>E T R C E Q D R P S P T T A P P A P P S P S P S P V P K S P S V D K Y N V</u>

<u>S G T N G T C L L A S M G L Q L N L T Y E R K D N T T V T R L L N I N P N</u>

<u>K T S A S G S C G A H L V T L E L H S E G T T V L L F Q F G M N A S S S R</u>

<u>F F L Q G I Q L N T I L P D A R D P A F K A A N G S L R A L Q A T V G N S</u>

<u>Y K C N A E E H V R V T K A F S V N I F K V W V Q A F K V E G G Q F G S V</u>

<u>E E C L L D E N S</u> l e d i g P Q I T L W Q R P L V T V R I G G Q L K E A L L

A D D T V L E E M S L P G R W K P K M I G G I G G F I K V R Q Y D Q I L I

E I C G H K A I G T V L V G P T P V N I I G R N L L T Q I G C T L N F P I S

P I E T V P V K L K P G M D G P K V K Q W P L T K E K I K A L V E I C T E

M E K E G K I S K I G P E N P Y N T P V F A I K K K D S T K W R K L V D F

R E L N K R T Q D F W E V Q L G I P H P A G L K K K K S V T V L D V G D

A Y F S V P L D E D F R K Y T A F T I P S I N N E T P G I R Y Q Y N V L P

Q G W K G S P A I F Q S S M T K I L E P F R K Q N P D I V I Y Q Y V G S

D L E I G Q H R T K I E E L R Q H L L R W G L T T P D K K H Q K E P P F L

W M G Y E L H P D K W T V Q P I V L P E K D S W T V N D I Q K L V G K L

N W A S Q I Y P G I K V R Q L C K L L R G T K A L T E V I P L T E E A E L

E L A E N R E I L K E P V H G V Y Y D P S K D L I A E I Q K Q G Q G Q W T

Y Q I Y Q E P F K N L K T G K Y A R M R G A H T N D V K Q L T E A V Q K

I T T E S I V I W G K T P K F K L P I Q K E T W E T W W T E Y W Q A T W I

P E W E F V N T P P L V K L W Y Q L E K E P I V G A E T F Y V D G A A N

R E T K L G K A G Y V T N R G R Q K V V T L T D T T N Q K T L Q A I Y L A

L Q D S G L E V N I V T D S Q Y A L G I I Q A Q P D Q S E S E L V N Q I I E

Q L I K K E K V Y L A W V P A H K G I G G N E Q V D K L V S A G I R K V L

F L D G I D K A Q D E H E K Y H S N W R A M A S D F N L P P V V A K E I

V A S C D K C Q L K G E A M H G Q V D C S P G I W Q L C T H L E G K V I

L V A V H V A S G Y I E A E V I P A E T G Q E T A Y F L L K L A G R W P V

K T I H T N G S N F T G A T V K A A C W W A G I K Q E F G I P Y N P Q S

Q G V V S M N K E L K K I I G Q R D Q A E H L K T A V Q M A V F I H N F K

R K G G I G G Y S A G E R I V D I I A T D I Q T K E L Q K Q I T K I Q N F R

V Y Y R D S R N P L W K G P A K L L W K G E G A V V I Q D N S D I K V V

P R R K A K I I R D Y G K Q M A G D D C V A S R Q D E D a s g s e f <u>T L I P</u>
<u>I A V G G A L A G L V L I V L I A Y L V G R K R S H A G Y Q T I</u>•

LAMP-1 underlined
Linker lower case
HIVpol bold
Linker lower case
LAMP-1 underlined HIV LAMP-NTV nucleic acid sequence

SEQ ID NO: 37

```
ATGGCGCCCCGCAGCGCCCGGCGACCCCTGCTGCTGCTACTGCTGTTGCTGCTGC
TCGGCCTCATGCATTGTGCGTCAGCAGCAATGTTTATGGTGAAAAATGGCAACGG
GACCGCGTGCATAATGGCCAACTTCTCTGCTGCCTTCTCAGTGAACTACGACACC
AAGAGTGGCCCTAAGAACATGACCcTTGACCTGCCATCAGATGCCACAGTGGTGC
TCAACCGCAGCTCCTGTGGAAAAGAGAACACTTCTGACCCCAGTCTCGTGATTGC
TTTTGGAAGAGGACATACACTCACTCTCAATTTCACGAGAAATGCAACACGTTAC
AGCGTcCAGCTCATGAGTTTTGTTTATAACTTGTCAGACACACACCTTTTCCCCAA
TGCGAGCTCCAAAGAAATCAAGACTGTGGAATCTATAACTGACATCAGGGCAGA
TATAGATAAAAAATACAGATGTGTTAGTGGCACCCAGGTCCACATGAACAACGT
GACCGTAACGCTCCATGATGCCACCATCCAGGCGTACCTTTCCAACAGCAGCTTC
AGCAGGGGAGAGACACGCTGTGAACAAGACAGGCCTTCCCCAACCACAGCGCCC
CCTGCGCCACCCAGCCCCTCGCCCTCACCCGTGCCCAAGAGCCCCTCTGTGGACA
AGTACAACGTGAGCGGCACCAACGGGACCTGCCTGCTGGCCAGCATGGGGCTGC
AGCTGAACCTCACCTATGAGAGGAAGGACAACACGACGGTGACAAGGCTTCTCA
ACATCAACCCCAACAAGACCTCGGCCAGCGGGAGCTGCGGCGCCCACCTGGTGA
CTCTGGAGCTGCACAGCGAGGGCACCACCGTCCTGCTCTTCCAGTTCGGGATGAA
TGCAAGTTCTAGCCGGTTTTTCCTACAAGGAATCCAGTTGAATACAATTCTTCCTG
ACGCCAGAGACCCTGCCTTTAAAGCTGCCAACGGCTCCCTGCGAGCGCTGCAGG
CCACAGTCGGCAATTCCTACAAGTGCAACGCGGAGGAGCACGTCCGTGTCACGA
AGGCGTTTTCAGTCAATATATTCAAAGTGTGGGTCCAGGCTTTCAAGGTGGAAGG
TGGCCAGTTTGGCTCTGTGGAGGAGTGTCTGCTGGACGAGAACAGCCTCGAGGA
TATCGGgAAGTGGTCGAAGTCGTCGGTGATCGGGTGGCCGACTGTTCGGGAGCGG
ATGCGGCGGCGGAGCCGGCGGCGATCGGGTGGGAGCGGCGTCGCGGGACCTT
GAGAAGCACGGGGCGATCACGTCGAGCAACACGGCGGCGACGAATGCGGCGTG
TGCCTGGCTAGAGGCGCAAGAGGAGGAGGAAGTGGGTTTTCCGGTCACGCCGCA
GGTCCCGCTTCGGCCGATGACGTACAAGGCAGCGGTCGACCTCAGCCACTTCCTC
AAGGAGAAGGGGGGACTGGAGGGGCTCATCCACTCCCAGCGGCGGCAGGACAT
CCTTGACCTGTGGATCTACCACACACAAGGCTACTTCCCGGATTGGCAGAACTAC
ACGCCGGGGCCGGGGGTCCGGTATCCGCTGACCTTTGGATGGTGCTACAAGCTA
GTACCGGTTGAGCCGGATAAGATCGAGGAGGCCAACAAGGGAGAGAACACCAG
CTTGTTGCACCCTGTGAGCCTGCATGGAATGGATGACCCGGAGCGGGAGGTGCTT
GAGTGGCGGTTTGACAGCCGCCTAGCGTTTCATCACGTGGCCCGAGAGCTGCATC
CGGAGTACTTCAAGAACTGCGGATCCGAGCCAGTAGATCCTAGACTAGAGCCCT
GGAAGCATCCAGGATCGCAGCCGAAGACGGCGTGCACCAACTGCTACTGCAAGA
```

-continued

```
AGTGCTTCCACCAGGTCTGCTTCATGACGAAGGCCTTGGGCATCTCCTATGGCCG

GAAGAAGCGGAGACAGCGACGAAGAGCTCATCAGAACTCGCAGACGCACCAGG

CGTCGCTATCGAAGCAACCCACCTCCCAATCCCGAGGGGACCCGACAGGCCCGA

AGGAATCGAAGAAGGAGGTGGAGAGAGAGACAGAGACAGATCCGTTCGACTGG

TCTAGAGAGAACCGGTGGCAGGTGATGATTGTGTGGCAGGTCGACCGGATGCGG

ATTCGGACGTGGAAGTCGCTTGTCAAGCACCACATGTACATCTCGGGGAAGGCG

AAGGGGTGGTTCTACCGGCACCACTATGAGTCGACGCACCCGCGGATCTCGTCG

GAGGTCCACATCCCGCTAGGGGACGCGAAGCTTGTCATCACGACGTACTGGGGT

CTGCATACGGGAGAGCGGGACTGGCATTTGGGTCAGGGAGTCTCCATAGAGTGG

AGGAAAAAGCGGTATAGCACGCAAGTAGACCCGGACCTAGCGGACCAGCTAATC

CACCTGTACTACTTCGACTCGTTCTCGGAGTCGGCGATACGGAATACCATCCTTG

GGCGGATCGTTTCGCCGCGGAGTGAGTATCAAGCGGGGCACAACAAGGTCGGGT

CGCTACAGTACTTGGCGCTCGCGGCGTTGATCACGCCGAAGCAGATAAAGCCGC

CGTTGCCGTCGGTTACGAAACTGACGGAGGACCGGTGGAACAAGCCCCAGAAGA

CCAAGGGCCACCGGGGGAGCCACACAATGAACGGGCACGAATTCACGCTGATCC

CCATCGCTGTGGGTGGTGCCCTGGCGGGGCTGGTCCTCATCGTCCTCATCGCCTA

CCTCGTCGGCAGGAAGAGGAGTCACGCAGGCTACCAGACTATCTAG
```

HIV LAMP-NTV amino acid sequence

SEQ ID NO: 38

<u>M A P R S A R R P L L L L L L L L L L G L M H C A S A A M F M V K N G N G</u>

<u>T A C I M A N F S A A F S V N Y D T K S G P K N M T L D L P S D A T V V L</u>

<u>N R S S C G K E N T S D P S L V I A F G R G H T L T L N F T R N A T R Y S</u>

<u>V Q L M S F V Y N L S D T H L F P N A S S K E I K T V E S I T D I R A D I D</u>

<u>K K Y R C V S G T Q V H M N N V T V T L H D A T I Q A Y L S N S S F S R G</u>

<u>E T R C E Q D R P S P T T A P P A P P S P S P S P V P K S P S V D K Y N V</u>

<u>S G T N G T C L L A S M G L Q L N L T Y E R K D N T T V T R L L N I N P N</u>

<u>K T S A S G S C G A H L V T L E L H S E G T T V L L F Q F G M N A S S S R</u>

<u>F F L Q G I Q L N T I L P D A R D P A F K A A N G S L R A L Q A T V G N S</u>

<u>Y K C N A E E H V R V T K A F S V N I F K V W V Q A F K V E G G Q F G S V</u>

<u>E E C L L D E N S</u> l e d i g K W S K S S V I G W P T V R E R M R R A E P A

A D R V G A A S R D L E K H G A I T S S N T A A T N A A C A W L E A Q E

E E E V G F P V T P Q V P L R P M T Y K A A V D L S H F L K E K G G L E

G L I H S Q R R Q D I L D L W I Y H T Q G Y F P D W Q N Y T P G P G V R Y

P L T F G W C Y K L V P V E P D K I E E A N K G E N T S L L H P V S L H G

M D D P E R E V L E W R F D S R L A F H H V A R E L H P E Y F K N C G S

E P V D P R L E P W K H G S Q P K T A C T N C Y C K K C F H Q V C F M

T K A L G I S Y G R K K R R Q R R A H Q N S Q T H Q A S L S K Q P T S

Q S R G D P T G P K E S K K E V E R E T E T D P F D W S R E N R W Q V M

I V W Q V D R M R I R T W K S L V K H H M Y I S G K A K G W F Y R H H Y

E S T H P R I S S E V H I P L G D A K L V I T T Y W G L H T G E R D W H L

G Q G V S I E W R K K R Y S T Q V D P D L A D Q L I H L Y Y F D S F S E S

A I R N T I L G R I V S P R S E Y Q A G H N K V G S L Q Y L A L A A L I T

P K Q I K P P L P S V T K L T E D R W N K P Q K T K G H R G S H T M N G

H e f <u>T L I P I A V G G A L A G L V L I V L I A Y L V G R K R S H A G Y Q T I</u> •

LAMP-1 underlined
Linker lower case
HIVNTV bold
Linker lower case
LAMP-1 underlined Human IL-15tPA6 opt (AG59) nucleic acid sequence  SEQ ID NO: 39

ATGGATGCAATGAAGAGAGGGCTCTGCTGTGTGCTGCTGCTGTGTGGAGCAGTCT

TCGTTTCGCCCAGCCAGGAAATCCATGCCCGATTCAGAAGAGGAGCCAGAAACT

GGGTGAACGTGATCTCGGACCTGAAGAAGATCGAGGACCTCATCCAGTCGATGC

ACATCGACGCGACGCTGTACACGGAGTCGGACGTCCACCCGTCGTGCAAGGTCA

CGGCGATGAAGTGCTTCCTCCTGGAGCTCCAAGTCATCTCGCTCGAGTCGGGGGA

CGCGTCGATCCACGACACGGTGGAGAACCTGATCATCCTGGCGAACAACTCGCT

GTCGTCGAACGGGAACGTCACGGAGTCGGGCTGCAAGGAGTGCGAGGAGCTGGA

GGAGAAGAACATCAAGGAGTTCCTGCAGTCGTTCGTGCACATCGTCCAGATGTTC

ATCAACACGTCGTGA

Human IL-15tPA6 amino acid sequence  SEQ ID NO: 40

<u>M D A M K R G L C C V L L L C G A V F V S P S Q E I H A R F R R</u>

<u>G A R</u> N W V N V I S D L K K I E D L I Q S M H I D A T L Y T E S D V H P S

C K V T A M K C F L L E L Q V I S L E S G D A S I H D T V E N L I I L A N N

S L S S N G N V T E S G C K E C E E L E E K N I K E F L Q S F V H I V Q M

F I N T S • tPA signal and propeptide underlined

HIV MCP-3env amino acid sequence  SEQ ID NO: 41

<u>M N P S A A V I F C L I L L G L S G T Q G</u> *I L D A* Q P V G I N T S T T C C Y R F I N

K K I P K Q R L E S Y R R T T S S H C P R E A V I F K T K L D K E I C A D P T Q K W

V Q D F M K H L D K K T Q T P K L *I C* S A E E K L W V T V Y Y G V P V W K E

A T T T L F C A S D A K A H H A E A H N V W A T H A C V P T D P N P Q E

V I L E N V T E K Y N M W K N N M V D Q M H E D I I S L W D Q S L K P C

V K L T P L C V T L N C T N A T Y T N S D S K N S T S N S S L E D S G K G

D M N C S F D V T T S I D K K K K T E Y A I F D K L D V M N I G N G R Y T

L L N C N T S V I T Q A C P K M S F E P I P I H Y C T P A G Y A I L K C N D

N K F N G T G P C T N V S T I Q C T H G I K P V V S T Q L L L N G S L A E

G G E V I I R S E N L T D N A K T I I V Q L K E P V E I N C T R P N N N T R

K S I H M G P G A A F Y A R G E V I G D I R Q A H C N I S R G R W N D T L

K Q I A K K L R E Q F N K T I S L N Q S S G G D L E I V M H T F N C G G E

F F Y C N T T Q L F N S T W N E N D T T W N N T A G S N N N E T I T L P C

R I K Q I I N R W Q E V G K A M Y A P P I S G P I N C L S N I T G L L L T R

D G G D N N N T I E T F R P G G G D M R D N W R S E L Y K Y K V V R I E

P L G I A P T K A K R R V V Q R E K R A V G I G A M F L G F L G A A G S

T M G A A S V T L T V Q A R L L L S G I V Q Q Q N N L L R A I E A Q Q H L

```
L Q L T V W G I K Q L Q A R V L A M E R Y L K D Q Q L L G I W G C S G K

L I C T T N V P W N A S W S N K S L D K I W H N M T W M E W D R E I D N

Y T K L I Y T L I E A S Q I Q Q E K N E Q E L L E L D S W A S L W S W F D

I S K W L W Y I G V F I I V I G G L V G L K I V F A V L S I V N R V R Q G Y

S P L S F Q T R L P A P R G P D R P E G I E E G G G E R D R D R S D Q L

V T G F L A L I W D D L R S L C F S Y H R L R D L L L I V A R I V E L L G

R R G W E A L K Y W W N L L Q Y W I Q E L K N S A V S L L N A T A I A V

A E G T D R I I E V V Q R I G R A I L H I P R R I R Q G L E R A L L * *
``` muIP10 underlined
Linker italics
huMCP-3 mature underlined
Linker italics
HIVenv bold Human IL-12 p35opt nucleic acid sequence

SEQ ID NO: 42

ATGTGCCCGGCGCGCTCCCTGCTGCTCGTGGCGACGCTGGTCCTGCTCGACCACC

TGAGCCTGGCGCGGAACCTGCCGGTGGCGACGCCGGACCCGGGGATGTTCCCGT

GCCTGCACCACAGCCAGAACCTGCTGCGGGCGGTGTCGAACATGCTGCAGAAGG

CGCGGCAGACGCTGGAGTTCTACCCGTGCACGAGCGAGGAGATCGACCACGAGG

ACATCACGAAGGACAAGACCAGCACGGTGGAGGCGTGCCTGCCGCTGGAGCTGA

CGAAGAACGAGTCGTGCCTGAACTCGAGGGAGACGTCGTTCATCACGAACGGGT

CGTGCCTGGCGTCGCGGAAGACGTCGTTCATGATGGCGCTGTGCCTGTCGTCGAT

CTACGAGGACCTGAAGATGTACCAGGTGGAGTTCAAGACGATGAACGCGAAGCT

GCTGATGGACCCGAAGCGGCAGATCTTCCTCGACCAGAACATGCTGGCGGTGAT

CGACGAGCTCATGCAGGCGCTCAACTTCAACAGCGAGACGGTGCCGCAGAAGTC

GTCGCTCGAGGAGCCGGACTTCTACAAGACGAAGATCAAGCTCTGCATCCTGCTG

CACGCTTTCCGGATCCGGGCGGTGACGATCGACCGGGTGATGTCGTACCTGAACG

CTTCGTAA

Human IL-12 p35 amino acid sequence

SEQ ID NO: 43

M C P A R S L L L V A T L V L L D H L S L A R N L P V A T P D P G M F P C

L H H S Q N L L R A V S N M L Q K A R Q T L E F Y P C T S E E I D H E D I

T K D K T S T V E A C L P L E L T K N E S C L N S R E T S F I T N G S C L A

S R K T S F M M A L C L S S I Y E D L K M Y Q V E F K T M N A K L L M D P

K R Q I F L D Q N M L A V I D E L M Q A L N F N S E T V P Q K S S L E E P

D F Y K T K I K L C I L L H A F R I R A V T I D R V M S Y L N A S •

Human IL-12 p40opt nucleic acid sequence

SEQ ID NO: 44

ATGTGCCACCAGCAGCTGGTCATCAGCTGGTTCAGCCTCGTTTTCCTCGCCTCGCC

GCTGGTCGCCATATGGGAGCTCAAGAAGGACGTATACGTGGTGGAGCTGGACTG

GTACCCCGACGCGCCGGGCGAGATGGTCGTCCTGACGTGCGACACGCCGGAGGA

GGACGGCATCACGTGGACGCTGGACCAGTCCAGCGAGGTCCTCGGCTCCGGCAA

GACGCTGACGATCCAGGTCAAGGAGTTCGGCGACGCGGGCCAGTACACGTGCCA

CAAGGGCGGCGAGGTCCTGAGCCACTCCCTCCTCCTGCTACACAAGAAGGAGGA

CGGGATCTGGAGCACGGACATCCTCAAGGACCAGAAGGAGCCGAAGAACAAGA

CCTTCCTGCGCTGCGAGGCGAAGAATTACTCGGGCCGGTTCACGTGCTGGTGGCT

```
CACCACGATCAGCACGGACCTGACGTTCTCGGTCAAGTCGTCGCGGGGCTCGTCG

GACCCCCAGGGGGTGACCTGCGGCGCGGCGACGCTGTCGGCGGAGCGGGTGCGG

GGCGACAACAAGGAGTACGAGTACTCGGTCGAGTGCCAGGAGGACTCGGCGTGC

CCGGCGGCGGAGGAGTCGCTGCCGATCGAGGTGATGGTCGACGCGGTCCACAAG

CTGAAGTACGAGAACTACACGTCGTCGTTCTTCATCCGGGACATCATCAAGCCGG

ACCCGCCGAAGAACCTGCAGCTGAAGCCGCTGAAGAACTCGCGGCAGGTCGAGG

TCTCGTGGGAGTACCCGGACACGTGGTCGACGCCGCACTCGTACTTCTCGCTGAC

GTTCTGCGTCCAAGTGCAGGGCAAGTCGAAGCGGGAGAAGAAGGACCGGGTGTT

CACCGACAAGACGAGCGCGACGGTGATCTGCCGGAAGAACGCGTCGATCTCGGT

GCGGGCGCAGGACCGGTACTACTCGTCGTCGTGGTCGGAGTGGGCGTCGGTGCC

GTGCAGCTAG
```

Human IL-12 p40 amino acid sequence     SEQ ID NO: 45

```
M C H Q Q L V I S W F S L V F L A S P L V A I W E L K K D V Y V V E L D W
Y P D A P G E M V V L T C D T P E E D G I T W T L D Q S S E V L G S G K T
L T I Q V K E F G D A G Q Y T C H K G G E V L S H S L L L L H K K E D G I
W S T D I L K D Q K E P K N K T F L R C E A K N Y S G R F T C W L T T I
S T D L T F S V K S S R G S S D P Q G V T C G A A T L S A E R V R G D N
K E Y E Y S V E C Q E D S A C P A A E E S L P I E V M V D A V H K L K Y E
N Y T S S F F I R D I I K P D P P K N L Q L K P L K N S R Q V E V S W E Y P
D T W S T P H S Y F S L T F C V Q V Q G K S K R E K K D R V F T D K T S A
T V I C R K N A S I S V R A Q D R Y Y S S S W S E W A S V P C S •
```

Human IL-2opt nucleic acid sequence     SEQ ID NO: 46

```
ATGTACCGCATGCAGCTGCTCTCGTGCATCGCGCTCAGCCTCGCGCTGGTGACGA

ACTCGGCGCCCACGTCCTCGTCCACGAAGAAGACCCAGCTGCAGCTGGAGCACC

TGCTCCTGGACCTCCAGATGATCCTGAACGGCATCAACAACTACAAGAACCCCA

AGCTCACCCGGATGCTGACGTTCAAGTTCTACATGCCGAAGAAGGCCACGGAGC

TGAAGCACCTTCAGTGCTTGGAGGAGGAGTTGAAGCCCCTGGAGGAGGTCCTCA

ACCTGGCCCAGAGCAAGAACTTCCACCTGAGGCCCCGGGACCTCATCTCCAACAT

CAACGTGATCGTCCTGGAGTTGAAGGGCAGCGAGACGACCTTCATGTGCGAGTA

CGCCGACGAGACGGCGACCATCGTCGAGTTCCTGAACCGGTGGATCACCTTCTGC

CAGTCGATCATCAGCACGCTGACCTGATAA
```

Human IL-2 amino acid sequence     SEQ ID NO: 47

```
M Y R M Q L L S C I A L S L A L V T N S A P T S S S T K K T Q L Q L E H L
L L D L Q M I L N G I N N Y K N P K L T R M L T F K F Y M P K K A T E L K
H L Q C L E E E L K P L E E V L N L A Q S K N F H L R P R D L I S N I N V I
V L E L K G S E T T F M C E Y A D E T A T I V E F L N R W I T F C Q S I I S
T L T • •
```

Human IL-15GMCSF opt (AG146) nucleic acid sequence     SEQ ID NO: 48

```
ATGTGGCTCCAGGGCCTGCTACTCCTGGGGACGGTGGCCTGCAGCATCTCGAACT

GGGTGAACGTGATCTCGGACCTGAAGAAGATCGAGGACCTCATCCAGTCGATGC
```

-continued

ACATCGACGCGACGCTGTACACGGAGTCGGACGTCCACCCGTCGTGCAAGGTCA

CGGCGATGAAGTGCTTCCTCCTGGAGCTCCAAGTCATCTCGCTCGAGTCGGGGA

CGCGTCGATCCACGACACGGTGGAGAACCTGATCATCCTGGCGAACAACTCGCT

GTCGTCGAACGGGAACGTCACGGAGTCGGGCTGCAAGGAGTGCGAGGAGCTGGA

GGAGAAGAACATCAAGGAGTTCCTGCAGTCGTTCGTGCACATCGTCCAGATGTTC

ATCAACACGTCGTGA

Human IL-15GM-CSF opt amino acid sequence

SEQ ID NO: 49

<u>M W L Q G L L L L L G T V A C S I S</u> N W V N V I S D L K K I E D L I Q S M H I

D A T L Y T E S D V H P S C K V T A M K C F L L E L Q V I S L E S G D A S I

H D T V E N L I I L A N N S L S S N G N V T E S G C K E C E E L E E K N I K

E F L Q S F V H I V Q M F I N T S •

GM-CSF secretory signal underlined

Human IL-15IgE opt (AG54) nucleic acid sequence

SEQ ID NO: 50

ATGGACTGGACGTGGATCCTTTTCCTTGTCGCGGCGGCGACGCGGGTCCACTCGA

ACTGGGTGAACGTGATCTCGGACCTGAAGAAGATCGAGGACCTCATCCAGTCGA

TGCACATCGACGCGACGCTGTACACGGAGTCGGACGTCCACCCGTCGTGCAAGG

TCACGGCGATGAAGTGCTTCCTCCTGGAGCTCCAAGTCATCTCGCTCGAGTCGGG

GGACGCGTCGATCCACGACACGGTGGAGAACCTGATCATCCTGGCGAACAACTC

GCTGTCGTCGAACGGGAACGTCACGGAGTCGGGCTGCAAGGAGTGCGAGGAGCT

GGAGGAGAAGAACATCAAGGAGTTCCTGCAGTCGTTCGTGCACATCGTCCAGAT

GTTCATCAACACGTCGTGA

Human IL-15IgE opt (AG54) amino acid sequence

SEQ ID NO: 51

<u>M D W T W I L F L V A A A T R V H S</u> N W V N V I S D L K K I E D L I Q S M

H I D A T L Y T E S D V H P S C K V T A M K C F L L E L Q V I S L E S G D A

S I H D T V E N L I I L A N N S L S S N G N V T E S G C K E C E E L E E K N

I K E F L Q S F V H I V Q M F I N T S •

IgE secretory signal underlined.

Human IL-12tPA6 opt (AG59) nucleic acid sequence

SEQ ID NO: 52

ATGGCCCCGAGGCGGGCGCGAGGCTGCCGGACCCTCGGTCTCCCGGCGCTGCTA

CTGCTCCTGCTGCTCCGGCCGCCGGCGACGCGGGGCATCACGTGCCCGCCCCCA

TGTCCGTGGAGCACGCAGACATCTGGGTCAAGAGCTACAGCTTGTACTCCCGGG

AGCGGTACATCTGCAACTCGGGTTTCAAGCGGAAGGCCGGCACGTCCAGCCTGA

CGGAGTGCGTGTTGAACAAGGCCACGAATGTCGCCCACTGGACGACCCCCTCGC

TCAAGTGCATCCGCGACCCGGCCCTGGTTCACCAGCGGCCCGCGCCACCCTCCAC

CGTAACGACGGCGGGGGTGACCCCGCAGCCGGAGAGCCTCTCCCCGTCGGGAAA

GGAGCCCGCCGCGTCGTCGCCCAGCTCGAACAACACGGCGGCCACAACTGCAGC

GATCGTCCCGGGCTCCCAGCTGATGCCGTCGAAGTCGCCGTCCACGGGAACCAC

GGAGATCAGCAGTCATGAGTCCTCCCACGGCACCCCCTCGCAAACGACGGCCAA

GAACTGGGAACTCACGGCGTCCGCCTCCCACCAGCCGCCGGGGGTGTATCCGCA

AGGCCACAGCGACACCACGGTGGCGATCTCCACGTCCACGGTCCTGCTGTGTGG

GCTGAGCGCGGTGTCGCTCCTGGCGTGCTACCTCAAGTCGAGGCAGACTCCCCCG

CTGGCCAGCGTTGAGATGGAGGCCATGGAGGCTCTGCCGGTGACGTGGGGGACC

AGCAGCAGGGATGAGGACTTGGAGAACTGCTCGCACCACCTATAATGA

Human IL-15Receptor alpha amino acid sequence

SEQ ID NO: 53

M A P R R A R G C R T L G L P A L L L L L L R P P A T R G I T C P P P M

S V E H A D I W V K S Y S L Y S R E R Y I C N S G F K R K A G T S S L T E

C V L N K A T N V A H W T T P S L K C I R D P A L V H Q R P A P P S T V T

T A G V T P Q P E S L S P S G K E P A A S S P S S N N T A A T T A A I V P

G S Q L M P S K S P S T G T T E I S S H E S S H G T P S Q T T A K N W E L

T A S A S H Q P P G V Y P Q G H S D T T V A I S T S T V L L C G L S A V S

L L A C Y L K S R Q T P P L A S V E M E A M E A L P V T W G T S S R D E D

L E N C S H H L • •

Human wild-type IL-15 nucleic acid sequence

SEQ ID NO: 54

ATGAGAATTTCGAAACCACATTTGAGAAGTATTTCCATCCAGTGCTACTTGTGTTTACTTCT

AAACAGTCATTTTCTAACTGAAGCTGGCATTCATGTCTTCATTTTGGGCTGTTTCAGTGCAG

GGCTTCCTAAAACAGAAGCCAACTGGGTGAATGTAATAAGTGATTTGAAAAAAATTGAAGAT

CTTATTCAATCTATGCATATTGATGCTACTTTATATACGGAAAGTGATGTTCACCCCAGTTG

CAAAGTAACAGCAATGAAGTGCTTTCTCTTGGAGTTACAAGTTATTTCACTTGAGTCTGGAG

ATGCAAGTATTCATGATACAGTAGAAAATCTGATCATCCTAGCAAACAACAGTTTGTCTTCT

AATGGGAATGTAACAGAATCTGGATGCAAAGAATGTGAGGAACTGGAGGAAAAAAATATTAA

AGAATTTTTGCAGAGTTTTGTACATATTGTCCAAATGTTCATCAACACTTCTTGA

Human wild-type IL-15 amino acid sequence

SEQ ID NO: 55

M R I S K P H L R S I S I Q C Y L C L L L

N S H F L T E A G I H V F I L G C F S A G

L P K T E A N W V N V I S D L K K I E D L

I Q S M H I D A T L Y T E S D V H P S C K

V T A M K C F L L E L Q V I S L E S G D A

S I H D T V E N L I I L A N N S L S S N G

N V T E S G C K E C E E L E E K N I K E F

L Q S F V H I V Q M F I N T S •

Human improved IL-15 nucleic acid sequence (opt)

SEQ ID NO: 56

ATGCGGATCTCGAAGCCGCACCTGCGGTCGATATCGATCCAGTGCTACCTGTGCCTGCTCCT

GAACTCGCACTTCCTCACGGAGGCCGGTATACACGTCTTCATCCTGGGCTGCTTCTCGGCGG

GGCTGCCGAAGACGGAGGCGAACTGGGTGAACGTGATCTCGGACCTGAAGAAGATCGAGGAC

CTCATCCAGTCGATGCACATCGACGCGACGCTGTACACGGAGTCGGACGTCCACCCGTCGTG

CAAGGTCACGGCGATGAAGTGCTTCCTCCTGGAGCTCCAAGTCATCTCGCTCGAGTCGGGGG

ACGCGTCGATCCACGACACGGTGGAGAACCTGATCATCCTGGCGAACAACTCGCTGTCGTCG

AACGGGAACGTCACGGAGTCGGGCTGCAAGGAGTGCGAGGAGCTGGAGGAGAAGAACATCAA

GGAGTTCCTGCAGTCGTTCGTGCACATCGTCCAGATGTTCATCAACACGTCGTGA

Human improved IL-15 nucleic acid sequence (opt2)

-continued

SEQ ID NO: 57

```
ATGAGGATCAGCAAGCCCCACCTGAGGAGCATCAGCATCCAGTGCTACCTGTGCCTGCTGCT
GAACAGCCACTTCCTGACCGAGGCCGGTATACACGTGTTCATCCTGGGCTGCTTTAGCGCCG
GACTGCCCAAGACCGAGGCCAATTGGGTGAACGTGATCAGCGACCTGAAGAAGATCGAGGAC
CTCATCCAGAGCATGCACATCGACGCCACCCTGTACACCGAGAGCGATGTGCACCCCAGCTG
TAAGGTGACCGCCATGAAGTGCTTTCTGCTGGAGCTGCAAGTGATCAGCCTGGAGAGCGGCG
ACGCCAGCATCCACGACACCGTGGAGAACCTGATCATCCTGGCCAACAACAGCCTGAGCAGC
AACGGCAATGTGACCGAGAGCGGCTGTAAGGAGTGTGAGGAGCTGGAGGAGAAGAACATCAA
GGAGTTTCTGCAGAGCTTCGTGCACATCGTGCAGATGTTCATCAACACCAGCTGA

What is claimed is:

1. A method of inducing an immune response in an individual infected with a retrovirus, the method comprising:
administering antiretroviral therapy (ART);
administering an immunogenic composition by electroporation into a muscle of the individual, wherein the immunogenic composition comprises one or more expression vectors that comprise nucleic acid sequences that encode:
a Gag polypeptide linked to a β-catenin destabilizing sequence;
a Gag polypeptide linked to a MCP-3 secretory polypeptide;
an Env polypeptide;
an Env polypeptide linked to an MCP-3 secretory polypeptide;
a Pol polypeptide linked to a LAMP degradation signal;
a polypeptide comprising Nef, Tat, and Vif antigens, where the polypeptide is linked to a LAMP degradation signal;
an IL-15 receptor alpha polypeptide;
and an IL-15 polypeptide linked to a secretory signal polypeptide;
wherein the immunogenic composition is administered at least three times and administration of the immunogenic composition results in control of viremia upon cessation of ART.

2. The method of claim 1, wherein the components of the immunogenic composition are administered in a sequential manner.

3. The method of claim 1, wherein the IL-15 receptor alpha polypeptide and the IL-15 polypeptide are encoded on separate expression vectors.

4. The method of claim 1, wherein the IL-15 receptor alpha polypeptide and the IL-15 polypeptide are encoded on the same expression vector.

5. The method of claim 1, wherein the immunogenic composition is administered to the individual while the individual is undergoing ART.

6. The method of claim 1, wherein the IL-15 polypeptide is linked to a tPA secretory polypeptide, an IgE secretory signal polypeptide, or a GM-CSF secretory polypeptide.

* * * * *

```

SEQUENCE LISTING

<160> NUMBER OF SEQ ID NOS: 65

<210> SEQ ID NO 1
<211> LENGTH: 1638
<212> TYPE: DNA
<213> ORGANISM: Artificial Sequence
<220> FEATURE:
<223> OTHER INFORMATION: Description of Artificial Sequence:fusion
      protein SIVCATE-gagDX (2S)

<400> SEQUENCE: 1

```
atgagaaaag cggctgttag tcactggcag cagcagtctt acctggactc tggaatccat      60
tctggtgcca ctaccacagc tccttctctg agtgctagcg caggagcagg cgtgagaaac     120
tccgtcttgt cagggaagaa agcagatgaa ttagaaaaaa ttaggctacg acccaacgga     180
aagaaaaagt acatgttgaa gcatgtagta tgggcagcaa atgaattaga tagatttgga     240
ttagcagaaa gcctgttgga gaacaaagaa ggatgtcaaa aatactttc ggtcttagct      300
ccattagtgc aacaggctc agaaaattta aaaagccttt ataatactgt ctgcgtcatc      360
tggtgcattc acgcagaaga gaaagtgaaa cacactgagg aagcaaaaca gatagtgcag     420
agacacctag tggtggaaac aggaaccacc gaaaccatgc cgaagacctc tcgaccaaca     480
gcaccatcta gcggcagagg aggaaactac ccagtacagc agatcggtgg caactacgtc     540
cacctgccac tgtccccgag aaccctgaac gcttgggtca agctgatcga ggagaagaag     600
ttcggagcag aagtagtgcc aggattccag gcactgtcag aaggttgcac ccctacgac      660
atcaaccaga tgctgaactg cgttggagac catcaggcgg ctatgcagat catccgtgac     720
atcatcaacg aggaggctgc agattgggac ttgcagcacc cacaaccagc tccacaacaa     780
ggacaactta gggagccgtc aggatcagac atcgcaggaa ccacctcctc agttgacgaa     840
cagatccagt ggatgtaccg tcagcagaac ccgatcccag taggcaacat ctaccgtcga     900
tggatccagc tgggtctgca gaaatgcgtc cgtatgtaca cccgaccaa cattctagat      960
gtaaaacaag gccaaaaga gccatttcag agctatgtag acaggttcta caaaagttta    1020
agagcagaac agacagatgc agcagtaaag aattggatga ctcaaacact gctgattcaa    1080
aatgctaacc cagattgcaa gctagtgctg aaggggctgg gtgtgaatcc caccctagaa    1140
gaaatgctga cggcttgtca aggagtaggg gggccgggac agaaggctag attaatggca    1200
gaagccctga aagaggccct cgcaccagtg ccaatccctt ttgcagcagc ccaacagagg    1260
ggaccaagaa agccaattaa gtgttggaat tgtgggaaag agggacactc tgcaaggcaa    1320
tgcagagccc caagaagaca gggatgctgg aaatgtggaa aaatggacca tgttatggcc    1380
```

```
aaatgcccag acagacaggc gggtttttta ggccttggtc catggggaaa gaagccccgc    1440
aatttcccca tggctcaagt gcatcagggg ctgatgccaa ctgctccccc agaggaccca    1500
gctgtggatc tgctaaagaa ctacatgcag ttgggcaagc agcagagaga aaagcagaga    1560
gaaagcagag agaagcctta caaggaggtg acagaggatt tgctgcacct caattctctc    1620
tttggaggag accagtag                                                  1638

<210> SEQ ID NO 2
<211> LENGTH: 545
<212> TYPE: PRT
<213> ORGANISM: Artificial Sequence
<220> FEATURE:
<223> OTHER INFORMATION: Description of Artificial Sequence:fusion
      protein SIVCATE-gagDX (2S)

<400> SEQUENCE: 2

Met Arg Lys Ala Ala Val Ser His Trp Gln Gln Gln Ser Tyr Leu Asp
  1               5                  10                  15

Ser Gly Ile His Ser Gly Ala Thr Thr Thr Ala Pro Ser Leu Ser Ala
                 20                  25                  30

Ser Ala Gly Ala Gly Val Arg Asn Ser Val Leu Ser Gly Lys Lys Ala
             35                  40                  45

Asp Glu Leu Glu Lys Ile Arg Leu Arg Pro Asn Gly Lys Lys Lys Tyr
         50                  55                  60

Met Leu Lys His Val Val Trp Ala Ala Asn Glu Leu Asp Arg Phe Gly
 65                  70                  75                  80

Leu Ala Glu Ser Leu Leu Glu Asn Lys Glu Gly Cys Gln Lys Ile Leu
                 85                  90                  95

Ser Val Leu Ala Pro Leu Val Pro Thr Gly Ser Glu Asn Leu Lys Ser
            100                 105                 110

Leu Tyr Asn Thr Val Cys Val Ile Trp Cys Ile His Ala Glu Glu Lys
        115                 120                 125

Val Lys His Thr Glu Glu Ala Lys Gln Ile Val Gln Arg His Leu Val
    130                 135                 140

Val Glu Thr Gly Thr Thr Glu Thr Met Pro Lys Thr Ser Arg Pro Thr
145                 150                 155                 160

Ala Pro Ser Ser Gly Arg Gly Gly Asn Tyr Pro Val Gln Gln Ile Gly
                165                 170                 175

Gly Asn Tyr Val His Leu Pro Leu Ser Pro Arg Thr Leu Asn Ala Trp
            180                 185                 190

Val Lys Leu Ile Glu Glu Lys Lys Phe Gly Ala Glu Val Val Pro Gly
        195                 200                 205

Phe Gln Ala Leu Ser Glu Gly Cys Thr Pro Tyr Asp Ile Asn Gln Met
    210                 215                 220

Leu Asn Cys Val Gly Asp His Gln Ala Ala Met Gln Ile Ile Arg Asp
225                 230                 235                 240

Ile Ile Asn Glu Glu Ala Ala Asp Trp Asp Leu Gln His Pro Gln Pro
                245                 250                 255

Ala Pro Gln Gln Gly Gln Leu Arg Glu Pro Ser Gly Ser Asp Ile Ala
            260                 265                 270

Gly Thr Thr Ser Ser Val Asp Glu Gln Ile Gln Trp Met Tyr Arg Gln
        275                 280                 285

Gln Asn Pro Ile Pro Val Gly Asn Ile Tyr Arg Arg Trp Ile Gln Leu
    290                 295                 300

Gly Leu Gln Lys Cys Val Arg Met Tyr Asn Pro Thr Asn Ile Leu Asp
```

```
               305                 310                 315                 320
Val Lys Gln Gly Pro Lys Glu Pro Phe Gln Ser Tyr Val Asp Arg Phe
                325                 330                 335

Tyr Lys Ser Leu Arg Ala Glu Gln Thr Asp Ala Ala Val Lys Asn Trp
                340                 345                 350

Met Thr Gln Thr Leu Leu Ile Gln Asn Ala Asn Pro Asp Cys Lys Leu
                355                 360                 365

Val Leu Lys Gly Leu Gly Val Asn Pro Thr Leu Glu Glu Met Leu Thr
        370                 375                 380

Ala Cys Gln Gly Val Gly Gly Pro Gly Gln Lys Ala Arg Leu Met Ala
385                 390                 395                 400

Glu Ala Leu Lys Glu Ala Leu Ala Pro Val Pro Ile Pro Phe Ala Ala
                405                 410                 415

Ala Gln Gln Arg Gly Pro Arg Lys Pro Ile Lys Cys Trp Asn Cys Gly
                420                 425                 430

Lys Glu Gly His Ser Ala Arg Gln Cys Arg Ala Pro Arg Arg Gln Gly
                435                 440                 445

Cys Trp Lys Cys Gly Lys Met Asp His Val Met Ala Lys Cys Pro Asp
        450                 455                 460

Arg Gln Ala Gly Phe Leu Gly Leu Gly Pro Trp Gly Lys Lys Pro Arg
465                 470                 475                 480

Asn Phe Pro Met Ala Gln Val His Gln Gly Leu Met Pro Thr Ala Pro
                485                 490                 495

Pro Glu Asp Pro Ala Val Asp Leu Leu Lys Asn Tyr Met Gln Leu Gly
                500                 505                 510

Lys Gln Gln Arg Glu Lys Gln Arg Glu Ser Arg Glu Lys Pro Tyr Lys
                515                 520                 525

Glu Val Thr Glu Asp Leu Leu His Leu Asn Ser Leu Phe Gly Gly Asp
        530                 535                 540

Gln
545

<210> SEQ ID NO 3
<211> LENGTH: 1431
<212> TYPE: DNA
<213> ORGANISM: Artificial Sequence
<220> FEATURE:
<223> OTHER INFORMATION: Description of Artificial Sequence:fusion
      protein SIV MCP-3p39gag (21S)

<400> SEQUENCE: 3
atgaacccaa gtgctgccgt cattttctgc ctcatcctgc tgggtctgag tgggactcaa        60
gggatcctcg acatggcgca accggtcggg atcaacacga gcacgacctg ctgctaccgg       120
ttcatcaaca agaagatccc gaagcaacgt ctggaaagct atcgccggac cacgtcgagc       180 cactgccccgc gggaggcggt tatcttcaag acgaagctgg acaaggagat ctgcgccgac       240
ccgacgcaga gtgggttca ggacttcatg aagcacctgg ataagaagac gcagacgccg        300
aagctggcta gcgcaggagc aggcgtgcgg aactccgtct tgtcggggaa gaaagcggat       360
gagttggaga aaattcggct acggcccaac gggaagaaga gtacatgttg aagcatgta        420 gtatgggcgg cgaatgagtt ggatcggttt tggattggcgg agagcctgtt ggagaacaaa      480
gagggatgtc agaagatcct ttcggtcttg gcgccgttgg tgccgacggg ctcggagaac       540
ttgaagagcc tctacaacac ggtctgcgtc atctggtgca ttcacgcgga agagaaagtg       600
aaacacacgg aggaagcgaa acagatagtg cagcggcacc tagtggtgga aacgggaacc       660
```

```
accgaaacca tgccgaagac ctcgcggccg acggcgccgt cgagcggcag gggaggaaac    720
tacccggtac agcagatcgg tggcaactac gtccacctgc cgctgtcccc gcggacccctg   780 aacgcgtggg tcaagctgat cgaggagaag aagttcggag cggaggtagt gccgggattc    840
caggcgctgt cggaaggttg cacccccctac gacatcaacc agatgctgaa ctgcgttgga   900
gaccatcagg cggcgatgca gatcatccgg gacatcatca cgaggaggc ggcggattgg     960 gacttgcagc acccgcaacc ggcgccgcaa caaggacaac ttcgggagcc gtcgggatcg   1020
gacatcgcgg gaaccacctc ctcggttgac gaacagatcc agtggatgta ccggcagcag  1080
aacccgatcc cagtaggcaa catctaccgg cggtggatcc agctgggtct gcagaaatgc  1140
gtccgtatgt acaacccgac caacattcta gatgtaaaac aagggccaaa ggagccgttc  1200
cagagctacg tcgaccggtt ctacaagtcg ctgcgggcgg agcagacgga cgcggcggtc  1260
aagaactgga tgacgcagac gctgctgatc cagaacgcga acccagattg caagctagtg  1320 ctgaagggc tgggtgtgaa tcccaccccta gaagaaatgc tgacggcttg tcaaggagta   1380
ggggggccgg acagaaggc tagattaatg ggggcccatg cggccgcgta g             1431
```

<210> SEQ ID NO 4
<211> LENGTH: 476
<212> TYPE: PRT
<213> ORGANISM: Artificial Sequence
<220> FEATURE:
<223> OTHER INFORMATION: Description of Artificial Sequence:fusion
      protein SIV MCP-3p39gag (21S)

<400> SEQUENCE: 4

```
Met Asn Pro Ser Ala Ala Val Ile Phe Cys Leu Ile Leu Leu Gly Leu
 1               5                   10                  15

Ser Gly Thr Gln Gly Ile Leu Asp Met Ala Gln Pro Val Gly Ile Asn
            20                  25                  30

Thr Ser Thr Thr Cys Cys Tyr Arg Phe Ile Asn Lys Lys Ile Pro Lys
        35                  40                  45

Gln Arg Leu Glu Ser Tyr Arg Arg Thr Thr Ser Ser His Cys Pro Arg
    50                  55                  60

Glu Ala Val Ile Phe Lys Thr Lys Leu Asp Lys Glu Ile Cys Ala Asp
65                  70                  75                  80

Pro Thr Gln Lys Trp Val Gln Asp Phe Met Lys His Leu Asp Lys Lys
                85                  90                  95

Thr Gln Thr Pro Lys Leu Ala Ser Ala Gly Ala Gly Val Arg Asn Ser
            100                 105                 110

Val Leu Ser Gly Lys Lys Ala Asp Glu Leu Glu Lys Ile Arg Leu Arg
        115                 120                 125

Pro Asn Gly Lys Lys Lys Tyr Met Leu Lys His Val Val Trp Ala Ala
    130                 135                 140

Asn Glu Leu Asp Arg Phe Gly Leu Ala Glu Ser Leu Leu Glu Asn Lys
145                 150                 155                 160

Glu Gly Cys Gln Lys Ile Leu Ser Val Leu Ala Pro Leu Val Pro Thr
                165                 170                 175

Gly Ser Glu Asn Leu Lys Ser Leu Tyr Asn Thr Val Cys Val Ile Trp
            180                 185                 190

Cys Ile His Ala Glu Glu Lys Val Lys His Thr Glu Glu Ala Lys Gln
        195                 200                 205

Ile Val Gln Arg His Leu Val Val Glu Thr Gly Thr Thr Glu Thr Met
    210                 215                 220

Pro Lys Thr Ser Arg Pro Thr Ala Pro Ser Ser Gly Arg Gly Gly Asn
```

```
                    225                 230                 235                 240
Tyr Pro Val Gln Gln Ile Gly Gly Asn Tyr Val His Leu Pro Leu Ser
                245                 250                 255

Pro Arg Thr Leu Asn Ala Trp Val Lys Leu Ile Glu Glu Lys Lys Phe
            260                 265                 270

Gly Ala Glu Val Val Pro Gly Phe Gln Ala Leu Ser Glu Gly Cys Thr
        275                 280                 285

Pro Tyr Asp Ile Asn Gln Met Leu Asn Cys Val Gly Asp His Gln Ala
    290                 295                 300

Ala Met Gln Ile Ile Arg Asp Ile Ile Asn Glu Glu Ala Ala Asp Trp
305                 310                 315                 320

Asp Leu Gln His Pro Gln Pro Ala Pro Gln Gln Gly Gln Leu Arg Glu
                325                 330                 335

Pro Ser Gly Ser Asp Ile Ala Gly Thr Thr Ser Ser Val Asp Glu Gln
            340                 345                 350

Ile Gln Trp Met Tyr Arg Gln Gln Asn Pro Ile Pro Val Gly Asn Ile
        355                 360                 365

Tyr Arg Arg Trp Ile Gln Leu Gly Leu Gln Lys Cys Val Arg Met Tyr
    370                 375                 380

Asn Pro Thr Asn Ile Leu Asp Val Lys Gln Gly Pro Lys Glu Pro Phe
385                 390                 395                 400

Gln Ser Tyr Val Asp Arg Phe Tyr Lys Ser Leu Arg Ala Glu Gln Thr
                405                 410                 415

Asp Ala Ala Val Lys Asn Trp Met Thr Gln Thr Leu Leu Ile Gln Asn
            420                 425                 430

Ala Asn Pro Asp Cys Lys Leu Val Leu Lys Gly Leu Gly Val Asn Pro
        435                 440                 445

Thr Leu Glu Glu Met Leu Thr Ala Cys Gln Gly Val Gly Gly Pro Gly
    450                 455                 460

Gln Lys Ala Arg Leu Met Gly Ala His Ala Ala Ala
465                 470                 475

<210> SEQ ID NO 5
<211> LENGTH: 2643
<212> TYPE: DNA
<213> ORGANISM: Simian immunodeficiency virus
<220> FEATURE:
<223> OTHER INFORMATION: SIV envelope protein env (99S)

<400> SEQUENCE: 5
atgggctgcc tggggaacca gctgctgatc gccatcctgc tgctgagcgt ctacgggatc      60
tactgcaccc tctacgtcac ggtcttctac ggcgtcccgg cttggaggaa tgcgacaatt     120
cccctctttt gtgcaaccaa gaatagggat acttggggaa caactcagtg cctaccggac     180
aacggggact actcggaggt ggccctgaac gtgacggaga gcttcgacgc ctggaacaac     240
acggtcacgg agcaggcgat cgaggacgtg tggcagctgt tcgagacctc gatcaagccg     300
tgcgtcaagc tgtccccgct ctgcatcacg atgcggtgca acaagagcga cgggatcgg      360 tgggggctga cgaagtcgat cacgacgacg gcgtcgacca cgtcgacgac ggcgtcggcg     420
aaagtggaca tggtcaacga cctcgtcg tgcatcgccc aggacaactg cacgggcctg      480
gagcaggagc agatgatcag ctgcaagttc aacatgacgg gctgaagcg ggacaagaag      540 aaggagtaca cgagacgtg gtactcggcg gacctggtgt gcgagcaggg gaacaacacg     600
gggaacgagt cgcggtgcta catgaaccac tgcaacacgt cggtgatcca ggagtcgtgc     660
gacaagcact actgggacgc gatccggttc cggtactgcg cgccgccggg ctacgcgctg     720
```

-continued

| | |
|---|---|
| ctgcggtgca acgacacgaa ctactcgggc ttcatgccga aatgctcgaa ggtggtggtc | 780 |
| tcgtcgtgca cgaggatgat ggagacgcag acctcgacgt ggttcggctt caacgggacg | 840 |
| cgggcggaga accggacgta catctactgg cacgggcggg acaaccggac gatcatctcg | 900 |
| ctgaacaagt actacaacct gacgatgaag tgccggcggc cgggcaacaa gacggtgctc | 960 |
| ccggtcacca tcatgtcggg gctggtgttc cactcgcagc cgatcaacga ccggccgaag | 1020 |
| caggcgtggt gctggttcgg ggggaagtgg aaggacgcga tcaaggaggt gaagcagacc | 1080 |
| atcgtcaagc accccgcta cacggggacg aacaacacgg acaagatcaa cctgacggcg | 1140 |
| ccgggcgggg gcgatccgga agttaccttc atgtggacaa attgcagagg agagttcctc | 1200 |
| tactgcaaga tgaactggtt cctgaactgg gtggaggaca ggaacacggc gaaccagaag | 1260 |
| ccgaaggagc agcacaagcg gaactacgtg ccgtgccaca ttcggcagat catcaacacg | 1320 |
| tggcacaaag tgggcaagaa cgtgtacctg ccgccgaggg agggcgacct cacgtgcaac | 1380 |
| tccacggtga cctccctcat cgcgaacatc gactggatcg acggcaacca gacgaacatc | 1440 |
| accatgtcgg cggaggtggc ggagctgtac cggctggagc tgggggacta caagctggtg | 1500 |
| gagatcacgc cgatcggcct ggcccccacc gatgtgaagc gctacaccac cggcgggacg | 1560 |
| tcgagaaata gcggggcgt gttcgtgctg ggcttcctgg gctttctggc caccgccggc | 1620 |
| tccgccatgg gagccgccag cctgaccctg accgccagga gcagaaccct gctgccggc | 1680 |
| atcgtgcagc agcagcaaca gctgctggac gtggtgaaga cagcagga actgctgagg | 1740 |
| ctgacagtgt ggggcaccaa gaacctgcag accaggtga ccgccatcga gaagtacctg | 1800 |
| aaggaccagg cccagctgaa cgcgtggggc tgtgcgttcc gccaagtctg ccacacgacg | 1860 |
| gtcccgtggc ccaacgcctc cctgaccccc aagtggaaca acgagacatg gcaggagtgg | 1920 |
| gagcggaagg tggacttcct ggaggagaac atcaccgccc tgctggagga ggcccagatc | 1980 |
| cagcaagaga agaatatgta cgagctgcag aagctgaaca gctgggacgt gttcggcaac | 2040 |
| tggttcgatc tggccagctg gatcaaatac atccagtacg gcgtgtacat cgtggtgggc | 2100 |
| gtgatcctgc tgaggatcgt gatctacatc gtgcagatgc tggccaagct gaggcagggc | 2160 |
| tacagacctg tgttcagcag ccccccagc tacttccagc agacccacat tcagcaggac | 2220 |
| cctgccctgc ccaccagaga gggcaaggag agggacggcg gcgagggcgg aggaaacagc | 2280 |
| agctggccct ggcagatcga gtatatccac ttcctgatcc ggcagctgat cagactgctg | 2340 |
| acctggctgt tcagcaattg ccggaccctg ctgtccagag tgtaccagat cctgcagccc | 2400 |
| atcctgcaga gactgtccgc gaccctccag cgcatccggg aggtgctgag aaccgagctg | 2460 |
| acctacctgc agtacggctg gtcctacttc cacgaggccg tgcaggctgt gtggagatcc | 2520 |
| gccaccgaga cactggccgg agcctggggc gacctgtggg agacactgag aagaggcggc | 2580 |
| agatggattc tggccatccc ccggagaatc agacagggcc tggagctgac actgctgtga | 2640 |
| tga | 2643 |

<210> SEQ ID NO 6
<211> LENGTH: 879
<212> TYPE: PRT
<213> ORGANISM: Simian immunodeficiency virus
<220> FEATURE:
<223> OTHER INFORMATION: SIV envelope protein env (99S)

<400> SEQUENCE: 6

Met Gly Cys Leu Gly Asn Gln Leu Leu Ile Ala Ile Leu Leu Leu Ser
1               5                   10                  15

-continued

Val Tyr Gly Ile Tyr Cys Thr Leu Tyr Val Thr Val Phe Tyr Gly Val
                20                  25                  30

Pro Ala Trp Arg Asn Ala Thr Ile Pro Leu Phe Cys Ala Thr Lys Asn
         35                  40                  45

Arg Asp Thr Trp Gly Thr Thr Gln Cys Leu Pro Asp Asn Gly Asp Tyr
     50                  55                  60

Ser Glu Val Ala Leu Asn Val Thr Glu Ser Phe Asp Ala Trp Asn Asn
 65                  70                  75                  80

Thr Val Thr Glu Gln Ala Ile Glu Asp Val Trp Gln Leu Phe Glu Thr
                 85                  90                  95

Ser Ile Lys Pro Cys Val Lys Leu Ser Pro Leu Cys Ile Thr Met Arg
            100                 105                 110

Cys Asn Lys Ser Glu Thr Asp Arg Trp Gly Leu Thr Lys Ser Ile Thr
        115                 120                 125

Thr Thr Ala Ser Thr Thr Ser Thr Thr Ala Ser Ala Lys Val Asp Met
    130                 135                 140

Val Asn Glu Thr Ser Ser Cys Ile Ala Gln Asp Asn Cys Thr Gly Leu
145                 150                 155                 160

Glu Gln Glu Gln Met Ile Ser Cys Lys Phe Asn Met Thr Gly Leu Lys
                165                 170                 175

Arg Asp Lys Lys Lys Glu Tyr Asn Glu Thr Trp Tyr Ser Ala Asp Leu
            180                 185                 190

Val Cys Glu Gln Gly Asn Asn Thr Gly Asn Glu Ser Arg Cys Tyr Met
        195                 200                 205

Asn His Cys Asn Thr Ser Val Ile Gln Glu Ser Cys Asp Lys His Tyr
    210                 215                 220

Trp Asp Ala Ile Arg Phe Arg Tyr Cys Ala Pro Pro Gly Tyr Ala Leu
225                 230                 235                 240

Leu Arg Cys Asn Asp Thr Asn Tyr Ser Gly Phe Met Pro Lys Cys Ser
                245                 250                 255

Lys Val Val Val Ser Ser Cys Thr Arg Met Met Glu Thr Gln Thr Ser
            260                 265                 270

Thr Trp Phe Gly Phe Asn Gly Thr Arg Ala Glu Asn Arg Thr Tyr Ile
        275                 280                 285

Tyr Trp His Gly Arg Asp Asn Arg Thr Ile Ile Ser Leu Asn Lys Tyr
    290                 295                 300

Tyr Asn Leu Thr Met Lys Cys Arg Arg Pro Gly Asn Lys Thr Val Leu
305                 310                 315                 320

Pro Val Thr Ile Met Ser Gly Leu Val Phe His Ser Gln Pro Ile Asn
                325                 330                 335

Asp Arg Pro Lys Gln Ala Trp Cys Trp Phe Gly Gly Lys Trp Lys Asp
            340                 345                 350

Ala Ile Lys Glu Val Lys Gln Thr Ile Val Lys His Pro Arg Tyr Thr
        355                 360                 365

Gly Thr Asn Asn Thr Asp Lys Ile Asn Leu Thr Ala Pro Gly Gly Gly
    370                 375                 380

Asp Pro Glu Val Thr Phe Met Trp Thr Asn Cys Arg Gly Glu Phe Leu
385                 390                 395                 400

Tyr Cys Lys Met Asn Trp Phe Leu Asn Trp Val Glu Asp Arg Asn Thr
                405                 410                 415

Ala Asn Gln Lys Pro Lys Glu Gln His Lys Arg Asn Tyr Val Pro Cys
            420                 425                 430

His Ile Arg Gln Ile Ile Asn Thr Trp His Lys Val Gly Lys Asn Val
        435                 440                 445

```
Tyr Leu Pro Pro Arg Glu Gly Asp Leu Thr Cys Asn Ser Thr Val Thr
    450                 455                 460

Ser Leu Ile Ala Asn Ile Asp Trp Ile Asp Gly Asn Gln Thr Asn Ile
465                 470                 475                 480

Thr Met Ser Ala Glu Val Ala Glu Leu Tyr Arg Leu Glu Leu Gly Asp
                485                 490                 495

Tyr Lys Leu Val Glu Ile Thr Pro Ile Gly Leu Ala Pro Thr Asp Val
            500                 505                 510

Lys Arg Tyr Thr Thr Gly Gly Thr Ser Arg Asn Lys Arg Gly Val Phe
        515                 520                 525

Val Leu Gly Phe Leu Gly Phe Leu Ala Thr Ala Gly Ser Ala Met Gly
    530                 535                 540

Ala Ala Ser Leu Thr Leu Thr Ala Gln Ser Arg Thr Leu Leu Ala Gly
545                 550                 555                 560

Ile Val Gln Gln Gln Gln Leu Leu Asp Val Val Lys Arg Gln Gln
                565                 570                 575

Glu Leu Leu Arg Leu Thr Val Trp Gly Thr Lys Asn Leu Gln Thr Arg
            580                 585                 590

Val Thr Ala Ile Glu Lys Tyr Leu Lys Asp Gln Ala Gln Leu Asn Ala
        595                 600                 605

Trp Gly Cys Ala Phe Arg Gln Val Cys His Thr Thr Val Pro Trp Pro
    610                 615                 620

Asn Ala Ser Leu Thr Pro Lys Trp Asn Asn Glu Thr Trp Gln Glu Trp
625                 630                 635                 640

Glu Arg Lys Val Asp Phe Leu Glu Glu Asn Ile Thr Ala Leu Leu Glu
                645                 650                 655

Glu Ala Gln Ile Gln Gln Glu Lys Asn Met Tyr Glu Leu Gln Lys Leu
            660                 665                 670

Asn Ser Trp Asp Val Phe Gly Asn Trp Phe Asp Leu Ala Ser Trp Ile
        675                 680                 685

Lys Tyr Ile Gln Tyr Gly Val Tyr Ile Val Gly Val Ile Leu Leu
    690                 695                 700

Arg Ile Val Ile Tyr Ile Val Gln Met Leu Ala Lys Leu Arg Gln Gly
705                 710                 715                 720

Tyr Arg Pro Val Phe Ser Ser Pro Pro Ser Tyr Phe Gln Gln Thr His
                725                 730                 735

Ile Gln Gln Asp Pro Ala Leu Pro Thr Arg Glu Gly Lys Glu Arg Asp
            740                 745                 750

Gly Gly Glu Gly Gly Gly Asn Ser Ser Trp Pro Trp Gln Ile Glu Tyr
        755                 760                 765

Ile His Phe Leu Ile Arg Gln Leu Ile Arg Leu Leu Thr Trp Leu Phe
    770                 775                 780

Ser Asn Cys Arg Thr Leu Leu Ser Arg Val Tyr Gln Ile Leu Gln Pro
785                 790                 795                 800

Ile Leu Gln Arg Leu Ser Ala Thr Leu Gln Arg Ile Arg Glu Val Leu
                805                 810                 815

Arg Thr Glu Leu Thr Tyr Leu Gln Tyr Gly Trp Ser Tyr Phe His Glu
            820                 825                 830

Ala Val Gln Ala Val Trp Arg Ser Ala Thr Glu Thr Leu Ala Gly Ala
        835                 840                 845

Trp Gly Asp Leu Trp Glu Thr Leu Arg Arg Gly Gly Arg Trp Ile Leu
    850                 855                 860

Ala Ile Pro Arg Arg Ile Arg Gln Gly Leu Glu Leu Thr Leu Leu
```

<210> SEQ ID NO 7
<211> LENGTH: 2889
<212> TYPE: DNA
<213> ORGANISM: Artificial Sequence
<220> FEATURE:
<223> OTHER INFORMATION: Description of Artificial Sequence:fusion protein SIV MCP-3-env (73S)

<400> SEQUENCE: 7

| | |
|---|---|
| atgaacccaa gtgctgccgt cattttctgc ctcatcctgc tgggtctgag tgggactcaa | 60 |
| gggatcctcg acatggcgca accggtaggt ataaacacaa gcacaacctg ttgctatcgt | 120 |
| ttcataaata aaaagatacc gaagcaacgt ctggaaagct atcgccgtac cacttctagc | 180 |
| cactgtccgc gtgaagctgt tatattcaaa acgaaactgg ataaggagat ctgcgccgac | 240 |
| cctacacaga aatgggttca ggactttatg aagcacctgg ataaaaagac acagacgccg | 300 |
| aaactgatct gcagcctgta cgtcacggtc ttctacggcg taccagcttg gaggaatgcg | 360 |
| acaattcccc tcttttgtgc aaccaagaat agggatactt ggggaacaac tcagtgccta | 420 |
| ccggacaacg gggactactc ggaggtggcc ctgaacgtga cggagagctt cgacgcctgg | 480 |
| aacaacacgg tcacggagca ggcgatcgag gacgtgtggc agctgttcga gacctcgatc | 540 |
| aagccgtgcg tcaagctgtc cccgctctgc atcacgatgc ggtgcaacaa gagcgagacg | 600 |
| gatcggtggg ggctgacgaa gtcgatcacg acgacggcgt cgaccacgtc gacgacggcg | 660 |
| tcggcgaaag tggacatggt caacgagacc tcgtcgtgca tcgcccagga caactgcacg | 720 |
| ggcctggagc aggagcagat gatcagctgc aagttcaaca tgacggggct gaagcgggac | 780 |
| aagaagaagg agtacaacga cgtggtgtac tcggcggacc tggtgtgcga gcaggggaac | 840 |
| aacacgggga acgagtcgcg gtgctacatg aaccactgca acacgtcggt gatccaggag | 900 |
| tcgtgcgaca gcactactg gacgcgatc cggttccggt actgcgcgcc gccgggctac | 960 |
| gcgctgctgc ggtgcaacga cacgaactac tcgggcttca tgccgaaatg ctcgaaggtg | 1020 |
| gtggtctcgt cgtgcacgag gatgatggag acgcagacct cgacgtggtt cggcttcaac | 1080 |
| gggacgcggg cggagaaccg gacgtacatc tactggcacg gcgggacaa ccggacgatc | 1140 |
| atctcgctga caagtacta caacctgacg atgaagtgcc ggcggccggg caacaagacg | 1200 |
| gtgctcccgg tcaccatcat gtcggggctg gtgttccact cgcagccgat caacgaccgg | 1260 |
| ccgaagcagg cgtggtgctg gttcgggggg aagtggaagg acgcgatcaa ggaggtgaag | 1320 |
| cagaccatcg tcaagcaccc ccgctacacg gggacgaaca cacggacaa gatcaacctg | 1380 |
| acggcgccgg cgggggcga tccggaagtt accttcatgt ggacaaattg cagaggagag | 1440 |
| ttcctctact gcaagatgaa ctggttcctg aactgggtgg aggacaggaa cacggcgaac | 1500 |
| cagaagccga aggagcagca caagcggaac tacgtgccgt gccacattcg gcagatcatc | 1560 |
| aacacgtggc acaaagtggg caagaacgtg tacctgccgc cgagggaggg cgacctcacg | 1620 |
| tgcaactcca cggtgaccct cctcatcgcg aacatcgact ggatcgacgg caaccagacg | 1680 |
| aacatcacca tgtcggcgga ggtggcggag ctgtaccggc tggagctggg ggactacaag | 1740 |
| ctggtggaga tcacgccgat cggcctggcc ccaccgatg tgaagcgcta cacgaccggg | 1800 |
| gggacgtcgc ggaacaagcg gggggtcttc gtcctggggt tcctgggtt cctcgcgacg | 1860 |
| gcggggtcgg caatgggagc cgccagcctg accctcacgg cacagtcccg aactttattg | 1920 |
| gctgggatcg tccaacaaca gcagcagctg ctggacgtgg tcaagaggca gcaggagctg | 1980 |
| ctgcggctga ccgtctgggg cacgaagaac ctccagacga gggtcacggc catcgagaag | 2040 |

```
tacctgaagg accaggcgca gctgaacgcg tggggctgtg cgtttcgaca agtctgccac      2100
acgacggtcc cgtggccgaa cgcgtcgctg acgccgaagt ggaacaacga gacgtggcag      2160
gagtgggagc ggaaggtgga cttcctggag gagaacatca cggccctcct ggaggaggcg      2220
cagatccagc aggagaagaa catgtacgag ctgcaaaagc tgaacagctg ggacgtgttc      2280
ggcaactggt tcgacctggc gtcgtggatc aagtacatcc agtacggcgt gtacatcgtg      2340 gtggggtga tcctgctgcg gatcgtgatc tacatcgtcc agatgctggc gaagctgcgg      2400
cagggctata ggccagtgtt ctcttcccca ccctcttatt tccaacaaac ccatatccaa      2460
caagacccgg cgctgccgac ccgggagggc aaggagcggg acgcggggga gggcggcggc      2520
aacagctcct ggccgtggca gatcgagtac atccactttc ttattcgtca gcttattaga      2580
ctcctgacgt ggctgttcag taactgtagg actctgctgt cgagggtgta ccagatcctc      2640
cagccgatcc tccagcggct ctcggcgacc ctccagagga ttcgggaggt cctccggacg      2700
gagctgacct acctccagta cggggtggagc tatttccacg aggcggtcca ggccgtctgg      2760
cggtcggcga cggagacgct ggcgggcgcg tggggcgacc tgtgggagac gctgcggcgg      2820
ggcggccggt ggatactcgc gatccccgg cggatcaggc aggggctgga gctcacgctc      2880
ctgtgataa                                                              2889
```

<210> SEQ ID NO 8
<211> LENGTH: 961
<212> TYPE: PRT
<213> ORGANISM: Artificial Sequence
<220> FEATURE:
<223> OTHER INFORMATION: Description of Artificial Sequence:fusion protein SIV MCP-3-env (73S)

<400> SEQUENCE: 8

Met Asn Pro Ser Ala Ala Val Ile Phe Cys Leu Ile Leu Leu Gly Leu
1 5 10 15

Ser Gly Thr Gln Gly Ile Leu Asp Met Ala Gln Pro Val Gly Ile Asn
20 25 30

Thr Ser Thr Thr Cys Cys Tyr Arg Phe Ile Asn Lys Lys Ile Pro Lys
35 40 45

Gln Arg Leu Glu Ser Tyr Arg Arg Thr Thr Ser Ser His Cys Pro Arg
50 55 60

Glu Ala Val Ile Phe Lys Thr Lys Leu Asp Lys Glu Ile Cys Ala Asp
65 70 75 80

Pro Thr Gln Lys Trp Val Gln Asp Phe Met Lys His Leu Asp Lys Lys
85 90 95

Thr Gln Thr Pro Lys Leu Ile Cys Ser Leu Tyr Val Thr Val Phe Tyr
100 105 110

Gly Val Pro Ala Trp Arg Asn Ala Thr Ile Pro Leu Phe Cys Ala Thr
115 120 125

Lys Asn Arg Asp Thr Trp Gly Thr Thr Gln Cys Leu Pro Asp Asn Gly
130 135 140

Asp Tyr Ser Glu Val Ala Leu Asn Val Thr Glu Ser Phe Asp Ala Trp
145 150 155 160

Asn Asn Thr Val Thr Glu Gln Ala Ile Glu Asp Val Trp Gln Leu Phe
165 170 175

Glu Thr Ser Ile Lys Pro Cys Val Lys Leu Ser Pro Leu Cys Ile Thr
180 185 190

Met Arg Cys Asn Lys Ser Glu Thr Asp Arg Trp Gly Leu Thr Lys Ser
195 200 205

```
Ile Thr Thr Thr Ala Ser Thr Thr Ser Thr Thr Ala Ser Ala Lys Val
    210                 215                 220

Asp Met Val Asn Glu Thr Ser Ser Cys Ile Ala Gln Asp Asn Cys Thr
225                 230                 235                 240

Gly Leu Glu Gln Glu Gln Met Ile Ser Cys Lys Phe Asn Met Thr Gly
                245                 250                 255

Leu Lys Arg Asp Lys Lys Glu Tyr Asn Glu Thr Trp Tyr Ser Ala
        260                 265                 270

Asp Leu Val Cys Glu Gln Gly Asn Asn Thr Gly Asn Glu Ser Arg Cys
                275                 280                 285

Tyr Met Asn His Cys Asn Thr Ser Val Ile Gln Glu Ser Cys Asp Lys
    290                 295                 300

His Tyr Trp Asp Ala Ile Arg Phe Arg Tyr Cys Ala Pro Pro Gly Tyr
305                 310                 315                 320

Ala Leu Leu Arg Cys Asn Asp Thr Asn Tyr Ser Gly Phe Met Pro Lys
                325                 330                 335

Cys Ser Lys Val Val Val Ser Ser Cys Thr Arg Met Met Glu Thr Gln
                340                 345                 350

Thr Ser Thr Trp Phe Gly Phe Asn Gly Thr Arg Ala Glu Asn Arg Thr
            355                 360                 365

Tyr Ile Tyr Trp His Gly Arg Asp Asn Arg Thr Ile Ile Ser Leu Asn
    370                 375                 380

Lys Tyr Tyr Asn Leu Thr Met Lys Cys Arg Arg Pro Gly Asn Lys Thr
385                 390                 395                 400

Val Leu Pro Val Thr Ile Met Ser Gly Leu Val Phe His Ser Gln Pro
                405                 410                 415

Ile Asn Asp Arg Pro Lys Gln Ala Trp Cys Trp Phe Gly Gly Lys Trp
                420                 425                 430

Lys Asp Ala Ile Lys Glu Val Lys Gln Thr Ile Val Lys His Pro Arg
        435                 440                 445

Tyr Thr Gly Thr Asn Asn Thr Asp Lys Ile Asn Leu Thr Ala Pro Gly
    450                 455                 460

Gly Gly Asp Pro Glu Val Thr Phe Met Trp Thr Asn Cys Arg Gly Glu
465                 470                 475                 480

Phe Leu Tyr Cys Lys Met Asn Trp Phe Leu Asn Trp Val Glu Asp Arg
                485                 490                 495

Asn Thr Ala Asn Gln Lys Pro Lys Glu Gln His Lys Arg Asn Tyr Val
                500                 505                 510

Pro Cys His Ile Arg Gln Ile Ile Asn Thr Trp His Lys Val Gly Lys
            515                 520                 525

Asn Val Tyr Leu Pro Pro Arg Glu Gly Asp Leu Thr Cys Asn Ser Thr
530                 535                 540

Val Thr Ser Leu Ile Ala Asn Ile Asp Trp Ile Asp Gly Asn Gln Thr
545                 550                 555                 560

Asn Ile Thr Met Ser Ala Glu Val Ala Glu Leu Tyr Arg Leu Glu Leu
                565                 570                 575

Gly Asp Tyr Lys Leu Val Glu Ile Thr Pro Ile Gly Leu Ala Pro Thr
            580                 585                 590

Asp Val Lys Arg Tyr Thr Thr Gly Gly Thr Ser Arg Asn Lys Arg Gly
            595                 600                 605

Val Phe Val Leu Gly Phe Leu Gly Phe Leu Ala Thr Ala Gly Ser Ala
    610                 615                 620

Met Gly Ala Ala Ser Leu Thr Leu Thr Ala Gln Ser Arg Thr Leu Leu
```

-continued

```
                625               630               635               640
Ala Gly Ile Val Gln Gln Gln Gln Leu Leu Asp Val Val Lys Arg
                    645               650               655
Gln Gln Glu Leu Leu Arg Leu Thr Val Trp Gly Thr Lys Asn Leu Gln
                660               665               670
Thr Arg Val Thr Ala Ile Glu Lys Tyr Leu Lys Asp Gln Ala Gln Leu
            675               680               685
Asn Ala Trp Gly Cys Ala Phe Arg Gln Val Cys His Thr Thr Val Pro
        690               695               700
Trp Pro Asn Ala Ser Leu Thr Pro Lys Trp Asn Asn Glu Thr Trp Gln
705               710               715               720
Glu Trp Glu Arg Lys Val Asp Phe Leu Glu Glu Asn Ile Thr Ala Leu
                725               730               735
Leu Glu Glu Ala Gln Ile Gln Gln Glu Lys Asn Met Tyr Glu Leu Gln
                740               745               750
Lys Leu Asn Ser Trp Asp Val Phe Gly Asn Trp Phe Asp Leu Ala Ser
            755               760               765
Trp Ile Lys Tyr Ile Gln Tyr Gly Val Tyr Ile Val Val Gly Val Ile
    770               775               780
Leu Leu Arg Ile Val Ile Tyr Ile Val Gln Met Leu Ala Lys Leu Arg
785               790               795               800
Gln Gly Tyr Arg Pro Val Phe Ser Ser Pro Ser Tyr Phe Gln Gln
                805               810               815
Thr His Ile Gln Gln Asp Pro Ala Leu Pro Thr Arg Glu Gly Lys Glu
            820               825               830
Arg Asp Gly Gly Glu Gly Gly Gly Asn Ser Ser Trp Pro Trp Gln Ile
        835               840               845
Glu Tyr Ile His Phe Leu Ile Arg Gln Leu Ile Arg Leu Leu Thr Trp
    850               855               860
Leu Phe Ser Asn Cys Arg Thr Leu Leu Ser Arg Val Tyr Gln Ile Leu
865               870               875               880
Gln Pro Ile Leu Gln Arg Leu Ser Ala Thr Leu Gln Arg Ile Arg Glu
                885               890               895
Val Leu Arg Thr Glu Leu Thr Tyr Leu Gln Tyr Gly Trp Ser Tyr Phe
            900               905               910
His Glu Ala Val Gln Ala Val Trp Arg Ser Ala Thr Glu Thr Leu Ala
        915               920               925
Gly Ala Trp Gly Asp Leu Trp Glu Thr Leu Arg Arg Gly Gly Arg Trp
    930               935               940
Ile Leu Ala Ile Pro Arg Arg Ile Arg Gln Gly Leu Glu Leu Thr Leu
945               950               955               960
Leu
```

```
<210> SEQ ID NO 9
<211> LENGTH: 4152
<212> TYPE: DNA
<213> ORGANISM: Artificial Sequence
<220> FEATURE:
<223> OTHER INFORMATION: Description of Artificial Sequence:fusion
      protein SIV LAMP-pol (103S)

<400> SEQUENCE: 9
atggcgcccc gcagcgcccg gcgacccctg ctgctgctac tgctgttgct gctgctcggc     60
ctcatgcatt gtgcgtcagc agcaatgttt atggtgaaaa atggcaacgg gaccgcgtgc    120
ataatggcca acttctctgc tgccttctca gtgaactacg acaccaagag tggccctaag    180
```

```
aacatgaccc ttgacctgcc atcagatgcc acagtggtgc tcaaccgcag ctcctgtgga    240
aaagagaaca cttctgaccc cagtctcgtg attgcttttg gaagaggaca tacactcact    300
ctcaatttca cgagaaatgc aacacgttac agcgtccagc tcatgagttt tgtttataac    360
ttgtcagaca cacaccttt ccccaatgcg agctccaaag aaatcaagac tgtggaatct    420
ataactgaca tcagggcaga tatagataaa aaatacagat gtgttagtgg cacccaggtc    480
cacatgaaca acgtgaccgt aacgctccat gatgccacca tccaggcgta cctttccaac    540
agcagcttca gcaggggaga gacacgctgt gaacaagaca ggccttcccc aaccacagcg    600 cccctgcgc cacccagccc ctcgccctca cccgtgccca agagcccctc tgtggacaag    660
tacaacgtga gcggcaccaa cgggacctgc ctgctggcca gcatggggct gcagctgaac    720
ctcacctatg agaggaagga caacacgacg gtgacaaggc ttctcaacat caaccccaac    780
aagacctcgg ccagcgggag ctgcggcgcc cacctggtga ctctggagct gcacagcgag    840
ggcaccaccg tcctgctctt ccagttcggg atgaatgcaa gttctagccg gttttcctta    900
caaggaatcc agttgaatac aattcttcct gacgccagag accctgcctt taaagctgcc    960 aacgctccc tgcgagcgct gcaggccaca gtcggcaatt cctacaagtg caacgcggag   1020
gagcacgtcc gtgtcacgaa ggcgttttca gtcaatatat tcaaagtgtg gtccaggct   1080 ttcaaggtgg aagtggcca gtttggctct gtggaggagt gtctgctgga cgagaacagc   1140
ctcgaggata tcgggcccca tcgggaggcg ttgcagggg gagaccgcgg gttcgcggcg   1200
ccgcagttct cgctgtggcg gcggccggtc gtcaccgcgc acatcgaggg gcagccggtg   1260
gaggtgttgc tggcggacga ctcgatcgtg acgggcatag agttggggcc gcactacacc   1320
ccgaagatcg taggggggat cggggggttc atcaacacga aggagtacaa gaacgtggag   1380
atcgaggtct tgggcaagcg gatcaagggg acgatcatga ccggggacac cccgatcaac   1440
atcttcgggc ggaacctgct gacggcgctg gggatgtcgc tcaacttccc catcgcgaag   1500
gtggagcccg tcaaggtcgc cttgaagccg gggaaggatg ggccgaagtt gaagcagtgg   1560
ccgttgtcca aggagaagat cgtcgcgttg cgggagatct gcgagaagat ggagaaggac   1620
ggacagctgg aggaggcgcc cccgaccaac ccctacaaca cccccacctt cgctatcaag   1680
aagaaggaca gaacaagtg gcggatgctg atcgacttcc gggagttgaa ccgggtcacg   1740
caggacttca cggaggtcca gttgggcatc ccgcacccgg cggggctggc gaagcggaag   1800
cggatcacgg tactggacat cggggacgcg tacttctcca tcccgctcga cgaggagttc   1860
cggcagtaca cggccttcac gctcccgtcc gtcaacaacg cggagccggg gaagcgctac   1920
atctacaagg tcctgccgca ggggtggaag gggtcgccgg ccatcttcca gtacacgatg   1980
cggcacgtgc tcgagccttt ccggaaggcg aacccggacg tgaccctggt ccagatcttg   2040
atcgcgtcgg accggacgga cctggagcac gatcgggtcg tgctgcagtc gaaggagctg   2100
ctgaacagca tcgggttctc gaccccggag gagaagttcc agaaggaccc cccgttccag   2160
tggatgggat acgagctgtg gccgacgaag tggaagctgc agaagatcga gctgccgcag   2220
cgggagactt ggacggtgaa cgacatccag aagctcgtcg ggtcctcaa ctgggcggcc   2280 cagatctacc cggggatcaa gaccaagcac ctctgtcggc tgatccgggg gaagatgacg   2340
ctgacggagg aggtccagtg gacggagatg gcggaggcg agtacgagga gaacaagatc   2400
atcctctcgc aagagcagga ggggtgctac taccaggagg gcaagccgct ggaggccacg   2460
gtcatcaagt cgcaggacaa ccagtggtcg tacaagatcc accaggagga caagatcctg   2520
aaggtcggga agttcgcgaa gatcaagaac acgcacacca acggagtgcg gctgcttgcg   2580
```

```
cacgtcatcc agaagatcgg gaaggaggcg atcgtgatct gggggcaggt cccgaagttc    2640
caccttccgg tcgagaagga cgtctgggag cagtggtgga cggactactg gcaggtcacc    2700
tggatcccgg agtgggactt catctcgacg ccgccgctcg tccggcttgt gttcaacctc    2760
gtgaaggacc cgatcgaggg ggaggagaca tactacacgg acgggtcgtg caacaagcag    2820
tcgaaggagg ggaaggcggg ctacatcacg gaccggggca aggacaaggt caaggtgctt    2880
gagcagacga cgaaccagca ggcgctggag gcgttcctca tggcgttgac ggactcggga    2940
cccaaggcga acatcatcgt agactcgcaa tacgtcatgg ggatcatcac ggggtgcccg    3000
acggagtcgg agagccggct cgtcaaccag atcatcgagg agatgatcaa gaagtcggag    3060
atctacgtcg cgtgggtccc ggcgcacaag ggcatcggcg gcaaccagga gatcgaccac    3120
ctcgtctcgc aaggcatccg ccaggtcctc ttcctggaga agatcgagcc ggcgcaggag    3180
gagcacgaca agtaccattc gaacgtcaag gagctggtgt tcaagttcgg gctcccccgg    3240
atcgtggccc ggcagatcgt agacacctgc gacaagtgtc accagaaggg cgaggcgatc    3300
cacgggcagg cgaactcgga cctcgggacc tggcagatgt gcacccatct cgaggggaag    3360
atcatcatcg tcgcggtcca cgtcgcgtcg ggcttcatcg aggcggaggt catcccgcag    3420
gaaacggggc ggcagacggc gctgttcctg ttgaagttgg cgggccgctg gcccatcacg    3480
cacctccaca cgaacggggc gaacttcgcg tcgcaggagg tcaagatggt cgcgtggtgg    3540
gcggggatcg agcacacctt cggggtcccg tacaacccgc agtcgcaggg cgtcgtggcg    3600
atgaaccacc acctgaagaa ccagatcgac cgcatccgcg agcaggcgaa ctccgtcgag    3660
accatcgtct tgatggcggt ccactgcatg aacttcaagc ggcgggggcgg catcggggac    3720 atgacgccgg cggagcggtt gatcaacatg atcacgacgg agcaggagat ccagttccag    3780
cagtcgaaga actcgaagtt caagaacttc cgggtctact accgggaggg ccgggaccag    3840 ctgtgtggaagg gaccaggcga gctgctgtgg aaggggggag gcgcggtcat cttgaaggtc    3900
gggacggaca tcaaggtcgt cccccggcgg aaggcgaaga tcatcaagga ctacgggggc    3960
gggaaggagg tggacagctc gtcccacatg gaggacaccg cgaggcgcg ggaggtggcc    4020 catgcggccg cggggggaatt cacgctgatc cccatcgctg tgggtggtgc cctggcgggg    4080
ctggtcctca tcgtcctcat cgcctacctc gtcggcagga agaggagtca cgcaggctac    4140
cagactatct ag                                                        4152
```

<210> SEQ ID NO 10
<211> LENGTH: 1383
<212> TYPE: PRT
<213> ORGANISM: Artificial Sequence
<220> FEATURE:
<223> OTHER INFORMATION: Description of Artificial Sequence:fusion
    protein SIV LAMP-pol (103S)

<400> SEQUENCE: 10

```
Met Ala Pro Arg Ser Ala Arg Arg Pro Leu Leu Leu Leu Leu Leu
  1               5                  10                  15

Leu Leu Leu Gly Leu Met His Cys Ala Ser Ala Ala Met Phe Met Val
             20                  25                  30

Lys Asn Gly Asn Gly Thr Ala Cys Ile Met Ala Asn Phe Ser Ala Ala
         35                  40                  45

Phe Ser Val Asn Tyr Asp Thr Lys Ser Gly Pro Lys Asn Met Thr Leu
     50                  55                  60

Asp Leu Pro Ser Asp Ala Thr Val Val Leu Asn Arg Ser Ser Cys Gly
 65                  70                  75                  80
```

```
Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Asp Ile
370                 375                 380

Gly Ala His Arg Glu Ala Leu Gln Gly Gly Asp Arg Gly Phe Ala Ala
385                 390                 395                 400

Pro Gln Phe Ser Leu Trp Arg Arg Pro Val Val Thr Ala His Ile Glu
                405                 410                 415

Gly Gln Pro Val Glu Val Leu Leu Ala Asp Asp Ser Ile Val Thr Gly
            420                 425                 430

Ile Glu Leu Gly Pro His Tyr Thr Pro Lys Ile Val Gly Gly Ile Gly
        435                 440                 445

Gly Phe Ile Asn Thr Lys Glu Tyr Lys Asn Val Glu Ile Glu Val Leu
450                 455                 460

Gly Lys Arg Ile Lys Gly Thr Ile Met Thr Gly Asp Thr Pro Ile Asn
465                 470                 475                 480

Ile Phe Gly Arg Asn Leu Leu Thr Ala Leu Gly Met Ser Leu Asn Phe
                485                 490                 495

Pro Ile Ala Lys Val Glu Pro Val Lys Val Ala Leu Lys Pro Gly Lys
```

```
                500                 505                 510
Asp Gly Pro Lys Leu Lys Gln Trp Pro Leu Ser Lys Glu Lys Ile Val
            515                 520                 525

Ala Leu Arg Glu Ile Cys Glu Lys Met Glu Lys Asp Gly Gln Leu Glu
            530                 535                 540

Glu Ala Pro Pro Thr Asn Pro Tyr Asn Thr Pro Thr Phe Ala Ile Lys
545                 550                 555                 560

Lys Lys Asp Lys Asn Lys Trp Arg Met Leu Ile Asp Phe Arg Glu Leu
            565                 570                 575

Asn Arg Val Thr Gln Asp Phe Thr Glu Val Gln Leu Gly Ile Pro His
            580                 585                 590

Pro Ala Gly Leu Ala Lys Arg Lys Arg Ile Thr Val Leu Asp Ile Gly
            595                 600                 605

Asp Ala Tyr Phe Ser Ile Pro Leu Asp Glu Glu Phe Arg Gln Tyr Thr
            610                 615                 620

Ala Phe Thr Leu Pro Ser Val Asn Asn Ala Glu Pro Gly Lys Arg Tyr
625                 630                 635                 640

Ile Tyr Lys Val Leu Pro Gln Gly Trp Lys Gly Ser Pro Ala Ile Phe
            645                 650                 655

Gln Tyr Thr Met Arg His Val Leu Glu Pro Phe Arg Lys Ala Asn Pro
            660                 665                 670

Asp Val Thr Leu Val Gln Ile Leu Ile Ala Ser Asp Arg Thr Asp Leu
            675                 680                 685

Glu His Asp Arg Val Val Leu Gln Ser Lys Glu Leu Leu Asn Ser Ile
            690                 695                 700

Gly Phe Ser Thr Pro Glu Glu Lys Phe Gln Lys Asp Pro Pro Phe Gln
705                 710                 715                 720

Trp Met Gly Tyr Glu Leu Trp Pro Thr Lys Trp Lys Leu Gln Lys Ile
            725                 730                 735

Glu Leu Pro Gln Arg Glu Thr Trp Thr Val Asn Asp Ile Gln Lys Leu
            740                 745                 750

Val Gly Val Leu Asn Trp Ala Ala Gln Ile Tyr Pro Gly Ile Lys Thr
            755                 760                 765

Lys His Leu Cys Arg Leu Ile Arg Gly Lys Met Thr Leu Thr Glu Glu
            770                 775                 780

Val Gln Trp Thr Glu Met Ala Glu Ala Glu Tyr Glu Glu Asn Lys Ile
785                 790                 795                 800

Ile Leu Ser Gln Glu Gln Glu Gly Cys Tyr Tyr Gln Glu Gly Lys Pro
            805                 810                 815

Leu Glu Ala Thr Val Ile Lys Ser Gln Asp Asn Gln Trp Ser Tyr Lys
            820                 825                 830

Ile His Gln Glu Asp Lys Ile Leu Lys Val Gly Lys Phe Ala Lys Ile
            835                 840                 845

Lys Asn Thr His Thr Asn Gly Val Arg Leu Leu Ala His Val Ile Gln
            850                 855                 860

Lys Ile Gly Lys Glu Ala Ile Val Ile Trp Gly Gln Val Pro Lys Phe
865                 870                 875                 880

His Leu Pro Val Glu Lys Asp Val Trp Glu Gln Trp Trp Thr Asp Tyr
            885                 890                 895

Trp Gln Val Thr Trp Ile Pro Glu Trp Asp Phe Ile Ser Thr Pro Pro
            900                 905                 910

Leu Val Arg Leu Val Phe Asn Leu Val Lys Asp Pro Ile Glu Gly Glu
            915                 920                 925
```

-continued

```
Glu Thr Tyr Tyr Thr Asp Gly Ser Cys Asn Lys Gln Ser Lys Glu Gly
    930                 935                 940

Lys Ala Gly Tyr Ile Thr Asp Arg Gly Lys Asp Lys Val Lys Val Leu
945                 950                 955                 960

Glu Gln Thr Thr Asn Gln Gln Ala Leu Glu Ala Phe Leu Met Ala Leu
                965                 970                 975

Thr Asp Ser Gly Pro Lys Ala Asn Ile Ile Val Asp Ser Gln Tyr Val
            980                 985                 990

Met Gly Ile Ile Thr Gly Cys Pro Thr Glu Ser Glu Ser Arg Leu Val
        995                 1000                1005

Asn Gln Ile Ile Glu Glu Met Ile Lys Lys Ser Glu Ile Tyr Val Ala
    1010                1015                1020

Trp Val Pro Ala His Lys Gly Ile Gly Gly Asn Gln Glu Ile Asp His
1025                1030                1035                1040

Leu Val Ser Gln Gly Ile Arg Gln Val Leu Phe Leu Glu Lys Ile Glu
                1045                1050                1055

Pro Ala Gln Glu Glu His Asp Lys Tyr His Ser Asn Val Lys Glu Leu
            1060                1065                1070

Val Phe Lys Phe Gly Leu Pro Arg Ile Val Ala Arg Gln Ile Val Asp
        1075                1080                1085

Thr Cys Asp Lys Cys His Gln Lys Gly Glu Ala Ile His Gly Gln Ala
    1090                1095                1100

Asn Ser Asp Leu Gly Thr Trp Gln Met Cys Thr His Leu Glu Gly Lys
1105                1110                1115                1120

Ile Ile Ile Val Ala Val His Val Ala Ser Gly Phe Ile Glu Ala Glu
                1125                1130                1135

Val Ile Pro Gln Glu Thr Gly Arg Gln Thr Ala Leu Phe Leu Leu Lys
            1140                1145                1150

Leu Ala Gly Arg Trp Pro Ile Thr His Leu His Thr Asn Gly Ala Asn
        1155                1160                1165

Phe Ala Ser Gln Glu Val Lys Met Val Ala Trp Trp Ala Gly Ile Glu
    1170                1175                1180

His Thr Phe Gly Val Pro Tyr Asn Pro Gln Ser Gln Gly Val Val Ala
1185                1190                1195                1200

Met Asn His His Leu Lys Asn Gln Ile Asp Arg Ile Arg Glu Gln Ala
                1205                1210                1215

Asn Ser Val Glu Thr Ile Val Leu Met Ala Val His Cys Met Asn Phe
            1220                1225                1230

Lys Arg Arg Gly Gly Ile Gly Asp Met Thr Pro Ala Glu Arg Leu Ile
        1235                1240                1245

Asn Met Ile Thr Thr Glu Gln Glu Ile Gln Phe Gln Gln Ser Lys Asn
    1250                1255                1260

Ser Lys Phe Lys Asn Phe Arg Val Tyr Tyr Arg Glu Gly Arg Asp Gln
1265                1270                1275                1280

Leu Trp Lys Gly Pro Gly Glu Leu Leu Trp Lys Gly Glu Gly Ala Val
                1285                1290                1295

Ile Leu Lys Val Gly Thr Asp Ile Lys Val Val Pro Arg Arg Lys Ala
            1300                1305                1310

Lys Ile Ile Lys Asp Tyr Gly Gly Gly Lys Glu Val Asp Ser Ser Ser
        1315                1320                1325

His Met Glu Asp Thr Gly Glu Ala Arg Glu Val Ala His Ala Ala Ala
    1330                1335                1340

Gly Glu Phe Thr Leu Ile Pro Ile Ala Val Gly Gly Ala Leu Ala Gly
1345                1350                1355                1360
```

-continued

Leu Val Leu Ile Val Leu Ile Ala Tyr Leu Val Gly Arg Lys Arg Ser
                1365                1370                1375

His Ala Gly Tyr Gln Thr Ile
        1380

<210> SEQ ID NO 11
<211> LENGTH: 3111
<212> TYPE: DNA
<213> ORGANISM: Artificial Sequence
<220> FEATURE:
<223> OTHER INFORMATION: Description of Artificial Sequence:fusion
      protein SIV LAMP-NTV (147S)

<400> SEQUENCE: 11

| | | | | | |
|---|---|---|---|---|---|
| atggcgcccc | gcagcgcccg | gcgacccctg | ctgctgctac | tgctgttgct | gctgctcggc | 60 |
| ctcatgcatt | gtgcgtcagc | agcaatgttt | atggtgaaaa | atggcaacgg | gaccgcgtgc | 120 |
| ataatggcca | acttctctgc | tgccttctca | gtgaactacg | acaccaagag | tggccctaag | 180 |
| aacatgaccc | ttgacctgcc | atcagatgcc | acagtggtgc | tcaaccgcag | ctcctgtgga | 240 |
| aaagagaaca | cttctgaccc | cagtctcgtg | attgcttttg | gaagaggaca | tacactcact | 300 |
| ctcaatttca | cgagaaatgc | aacacgttac | agcgtccagc | tcatgagttt | tgtttataac | 360 |
| ttgtcagaca | cacaccttttt | ccccaatgcg | agctccaaag | aaatcaagac | tgtggaatct | 420 |
| ataactgaca | tcagggcaga | tatagataaa | aaatacagat | gtgttagtgg | cacccaggtc | 480 |
| cacatgaaca | acgtgaccgt | aacgctccat | gatgccacca | tccaggcgta | cctttccaac | 540 |
| agcagcttca | gcaggggaga | gacacgctgt | gaacaagaca | ggccttcccc | aaccacagcg | 600 |
| cccccctgcgc | cacccagccc | ctcgccctca | ccgtgccca | agagccctc | tgtggacaag | 660 |
| tacaacgtga | gcggcaccaa | cgggacctgc | ctgctggcca | gcatgggct | gcagctgaac | 720 |
| ctcacctatg | agaggaagga | caacacgacg | gtgacaaggc | ttctcaacat | caaccccaac | 780 |
| aagacctcgg | ccagcgggag | ctgcggcgcc | cacctggtga | ctctggagct | gcacagcgag | 840 |
| ggcaccaccg | tcctgctctt | ccagttcggg | atgaatgcaa | gttctagccg | gttttttccta | 900 |
| caaggaatcc | agttgaatac | aattcttcct | gacgccagag | accctgcctt | taaagctgcc | 960 |
| aacggctccc | tgcgagcgct | gcaggccaca | gtcggcaatt | cctacaagtg | caacgcggag | 1020 |
| gagcacgtcc | gtgtcacgaa | ggcgttttca | gtcaatatat | tcaaagtgtg | ggtccaggct | 1080 |
| ttcaaggtgg | aagtggccca | gtttggctct | gtggaggagt | gtctgctgga | cgagaacagc | 1140 |
| ctcgaggata | tcgggcggcg | cgccatgagg | cggtccaggc | ctagcgggga | cctgcggcag | 1200 |
| aggctcctgc | gggcgcgtgg | ggagacctac | gggaggctcc | tgggggaggt | ggaggacggg | 1260 |
| tactcgcagt | cccccggggg | cctgacaag | ggcctgagct | ccctctcgtg | cgaggggcag | 1320 |
| aagtacaacc | aggggcagta | catgaacacc | ccatggcgca | ccccgccga | ggagcgggag | 1380 |
| aagctggcgt | accggaagca | gaacatggac | gacatcgacg | aggaggacga | cgacctggtc | 1440 |
| ggggtctcag | tgcggccgaa | ggtccccctc | cggacgatgt | cgtacaagct | ggcgatcgac | 1500 |
| atgtcgcact | tcatcaagga | gaaggggggc | ctggagggga | tctactactc | ggcgcggcgg | 1560 |
| caccgcatcc | tcgacatcta | cctcgagaag | gaggagggca | tcatcccgga | ctggcaggac | 1620 |
| tacacctccg | ggcccgggat | cagatatccc | aagacgttcg | gctggctctg | gaagctcgtc | 1680 |
| cctgtcaacg | tctcggacga | ggcgcaggag | gacgaggagc | actacctcat | gcaccggcg | 1740 |
| cagacctccc | agtgggacga | cccctggggg | gaggtcctcg | cctggaagtt | cgaccccacg | 1800 |
| ctggcctaca | cctacgaggc | ctacgtccgc | taccccgagg | agttcgggag | caagtccggc | 1860 |

```
ctgtcggagg aggaggtccg ccggcgcctg accgcccgcg gcctgctgaa catggccgac    1920
aagaaggaga cccgcggcgc cgagacccc ctgagggagc aggagaacag cctggagtcc    1980
tccaacgagc gcagcagctg catcagcgag gcggatgcgt ccaccccga gtcggccaac    2040 ctgggggagg agatcctctc tcagctctac cgccctctcg aggcgtgcta acacgtgc     2100 tactgcaaga agtgctgcta ccactgccag ttctgcttcc tcaagaaggg cctggggatc    2160
tgctacgagc agtcgcgaaa gcggcggcgg acgccgaaga aggcgaaggc gaacacgtcg    2220
tcggcgtcga caaccgccc catcagcaac cggacccggc actgccagcc cgagaaggcc    2280
aagaaggaga cggtggagaa gcggtggcc accgccccgg gcctgggccg cggatccgag    2340
gaggagaagc gctggatcgc cgtccccacg tggaggatcc cggagaggct cgagaggtgg    2400
cacagcctca tcaagtacct gaagtacaag acgaaggacc tccagaaggt ctgctacgtg    2460
ccccacttca aggtcgggtg ggcgtggtgg acctgcagca gagtcatctt cccacttcaa    2520
gagggcagcc acttggaggt ccaggggtac tggcacttga cgccggagaa ggggtggctg    2580
agcacctacg cggtgcggat cacctggtac tcgaagaact tctggacgga tgtcacgccg    2640
aactatgcgg acatcttgct gcacagcact tacttcccct gcttcacggc ggggaagtg    2700 aggagggcca tcagggagaa gcagctgctg tcgtgctgcc ggttcccgcg ggcgcacaag    2760
taccaagtac cgagcctaca gtacttggcg ctgaaggtcg tcagcgacgt caggtcccag    2820
ggggagaacc ccacctggaa gcagtggcgg cgggacaacc ggaggggcct tcgaatggcg    2880
aagcagaact cgcggggaga taagcagcgg ggcggtaaac cacctaccaa gggagcgaac    2940
ttcccgggtt tggcaaaggt cttgggaata ctggcagtcg acgctagcgg atccgaattc    3000
acgctgatcc ccatcgctgt gggtggtgcc ctggcggggc tggtcctcat cgtcctcatc    3060
gcctacctcg tcgcaggaa gaggagtcac gcaggctacc agactatcta g              3111
```

<210> SEQ ID NO 12
<211> LENGTH: 1036
<212> TYPE: PRT
<213> ORGANISM: Artificial Sequence
<220> FEATURE:
<223> OTHER INFORMATION: Description of Artificial Sequence:fusion
      protein SIV LAMP-NTV (147S)

<400> SEQUENCE: 12

```
Met Ala Pro Arg Ser Ala Arg Arg Pro Leu Leu Leu Leu Leu Leu
  1               5                  10                  15

Leu Leu Leu Gly Leu Met His Cys Ala Ser Ala Ala Met Phe Met Val
             20                  25                  30

Lys Asn Gly Asn Gly Thr Ala Cys Ile Met Ala Asn Phe Ser Ala Ala
         35                  40                  45

Phe Ser Val Asn Tyr Asp Thr Lys Ser Gly Pro Lys Asn Met Thr Leu
     50                  55                  60

Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140
```

```
Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Val Thr Arg Leu Leu Asn
                245                 250                 255

Ile Asn Pro Asn Lys Thr Ser Ala Ser Gly Ser Cys Gly Ala His Leu
                260                 265                 270

Val Thr Leu Glu Leu His Ser Glu Gly Thr Thr Val Leu Leu Phe Gln
            275                 280                 285

Phe Gly Met Asn Ala Ser Ser Ser Arg Phe Phe Leu Gln Gly Ile Gln
290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
                355                 360                 365

Gly Ser Val Glu Glu Cys Leu Leu Asp Glu Asn Ser Leu Glu Asp Ile
370                 375                 380

Gly Arg Arg Ala Met Arg Arg Ser Arg Pro Ser Gly Asp Leu Arg Gln
385                 390                 395                 400

Arg Leu Leu Arg Ala Arg Gly Glu Thr Tyr Gly Arg Leu Leu Gly Glu
                405                 410                 415

Val Glu Asp Gly Tyr Ser Gln Ser Pro Gly Gly Leu Asp Lys Gly Leu
                420                 425                 430

Ser Ser Leu Ser Cys Glu Gly Gln Lys Tyr Asn Gln Gly Gln Tyr Met
            435                 440                 445

Asn Thr Pro Trp Arg Asn Pro Ala Glu Glu Arg Glu Lys Leu Ala Tyr
                450                 455                 460

Arg Lys Gln Asn Met Asp Asp Ile Asp Glu Glu Asp Asp Leu Val
465                 470                 475                 480

Gly Val Ser Val Arg Pro Lys Val Pro Leu Arg Thr Met Ser Tyr Lys
                485                 490                 495

Leu Ala Ile Asp Met Ser His Phe Ile Lys Glu Lys Gly Gly Leu Glu
                500                 505                 510

Gly Ile Tyr Tyr Ser Ala Arg Arg His Arg Ile Leu Asp Ile Tyr Leu
                515                 520                 525

Glu Lys Glu Glu Gly Ile Ile Pro Asp Trp Gln Asp Tyr Thr Ser Gly
                530                 535                 540

Pro Gly Ile Arg Tyr Pro Lys Thr Phe Gly Trp Leu Trp Lys Leu Val
545                 550                 555                 560

Pro Val Asn Val Ser Asp Glu Ala Gln Glu Asp Glu Glu His Tyr Leu
                565                 570                 575
```

```
Met His Pro Ala Gln Thr Ser Gln Trp Asp Asp Pro Trp Gly Glu Val
            580                 585                 590

Leu Ala Trp Lys Phe Asp Pro Thr Leu Ala Tyr Thr Tyr Glu Ala Tyr
        595                 600                 605

Val Arg Tyr Pro Glu Glu Phe Gly Ser Lys Ser Gly Leu Ser Glu Glu
    610                 615                 620

Glu Val Arg Arg Arg Leu Thr Ala Arg Gly Leu Leu Asn Met Ala Asp
625                 630                 635                 640

Lys Lys Glu Thr Arg Gly Ala Glu Thr Pro Leu Arg Glu Gln Glu Asn
                645                 650                 655

Ser Leu Glu Ser Ser Asn Glu Arg Ser Ser Cys Ile Ser Glu Ala Asp
            660                 665                 670

Ala Ser Thr Pro Glu Ser Ala Asn Leu Gly Glu Glu Ile Leu Ser Gln
        675                 680                 685

Leu Tyr Arg Pro Leu Glu Ala Cys Tyr Asn Thr Cys Tyr Cys Lys Lys
    690                 695                 700

Cys Cys Tyr His Cys Gln Phe Cys Phe Leu Lys Lys Gly Leu Gly Ile
705                 710                 715                 720

Cys Tyr Glu Gln Ser Arg Lys Arg Arg Thr Pro Lys Lys Ala Lys
                725                 730                 735

Ala Asn Thr Ser Ser Ala Ser Asn Asn Arg Pro Ile Ser Asn Arg Thr
            740                 745                 750

Arg His Cys Gln Pro Glu Lys Ala Lys Lys Glu Thr Val Glu Lys Ala
        755                 760                 765

Val Ala Thr Ala Pro Gly Leu Gly Arg Gly Ser Glu Glu Glu Lys Arg
    770                 775                 780

Trp Ile Ala Val Pro Thr Trp Arg Ile Pro Glu Arg Leu Glu Arg Trp
785                 790                 795                 800

His Ser Leu Ile Lys Tyr Leu Lys Tyr Lys Thr Lys Asp Leu Gln Lys
                805                 810                 815

Val Cys Tyr Val Pro His Phe Lys Val Gly Trp Ala Trp Thr Cys
            820                 825                 830

Ser Arg Val Ile Phe Pro Leu Gln Glu Gly Ser His Leu Glu Val Gln
        835                 840                 845

Gly Tyr Trp His Leu Thr Pro Glu Lys Gly Trp Leu Ser Thr Tyr Ala
    850                 855                 860

Val Arg Ile Thr Trp Tyr Ser Lys Asn Phe Trp Thr Asp Val Thr Pro
865                 870                 875                 880

Asn Tyr Ala Asp Ile Leu Leu His Ser Thr Tyr Phe Pro Cys Phe Thr
                885                 890                 895

Ala Gly Glu Val Arg Arg Ala Ile Arg Gly Glu Gln Leu Leu Ser Cys
            900                 905                 910

Cys Arg Phe Pro Arg Ala His Lys Tyr Gln Val Pro Ser Leu Gln Tyr
        915                 920                 925

Leu Ala Leu Lys Val Val Ser Asp Val Arg Ser Gln Gly Glu Asn Pro
    930                 935                 940

Thr Trp Lys Gln Trp Arg Arg Asp Asn Arg Arg Gly Leu Arg Met Ala
945                 950                 955                 960

Lys Gln Asn Ser Arg Gly Asp Lys Gln Arg Gly Gly Lys Pro Pro Thr
                965                 970                 975

Lys Gly Ala Asn Phe Pro Gly Leu Ala Lys Val Leu Gly Ile Leu Ala
            980                 985                 990

Val Asp Ala Ser Gly Ser Glu Phe Thr Leu Ile Pro Ile Ala Val Gly
```

```
                 995                 1000                1005

Gly Ala Leu Ala Gly Leu Val Leu Ile Val Leu Ile Ala Tyr Leu Val
    1010                1015                1020

Gly Arg Lys Arg Ser His Ala Gly Tyr Gln Thr Ile
1025                1030                1035

<210> SEQ ID NO 13
<211> LENGTH: 450
<212> TYPE: DNA
<213> ORGANISM: Artificial Sequence
<220> FEATURE:
<223> OTHER INFORMATION: Description of Artificial Sequence:fusion
      protein rhesus IL-15tPA6 (AG65)

<400> SEQUENCE: 13
atggatgcaa tgaagagagg gctctgctgt gtgctgctgc tgtgtggagc agtcttcgtt     60
tcgcccagcc aggaaatcca tgcccgattc agaagaggag ccagaaactg ggtgaacgtg    120
atctcggacc tgaagaagat cgaggacctc atccagtcga tgcacatcga cgcgacgctg    180
tacacggagt cggacgtcca cccgtcgtgc aaggtcacgg cgatgaagtg cttcctcctg    240
gagctccaag tcatctcgca cgagtcgggg gacacggaca tccacgacac ggtggagaac    300
ctgatcatcc tggcgaacaa catcctgtcg tcgaacggga acatcacgga gtcgggctgc    360
aaggagtgcg aggagctgga ggagaagaac atcaaggagt tcctgcagtc gttcgtgcac    420
atcgtccaga tgttcatcaa cacgtcgtga                                    450

<210> SEQ ID NO 14
<211> LENGTH: 149
<212> TYPE: PRT
<213> ORGANISM: Artificial Sequence
<220> FEATURE:
<223> OTHER INFORMATION: Description of Artificial Sequence:fusion
      protein rhesus IL-15tPA6 (AG65)

<400> SEQUENCE: 14

Met Asp Ala Met Lys Arg Gly Leu Cys Cys Val Leu Leu Leu Cys Gly
  1               5                  10                  15

Ala Val Phe Val Ser Pro Ser Gln Glu Ile His Ala Arg Phe Arg Arg
             20                  25                  30

Gly Ala Arg Asn Trp Val Asn Val Ile Ser Asp Leu Lys Lys Ile Glu
         35                  40                  45

Asp Leu Ile Gln Ser Met His Ile Asp Ala Thr Leu Tyr Thr Glu Ser
     50                  55                  60

Asp Val His Pro Ser Cys Lys Val Thr Ala Met Lys Cys Phe Leu Leu
 65                  70                  75                  80

Glu Leu Gln Val Ile Ser His Glu Ser Gly Asp Thr Asp Ile His Asp
                 85                  90                  95

Thr Val Glu Asn Leu Ile Ile Leu Ala Asn Asn Ile Leu Ser Ser Asn
            100                 105                 110

Gly Asn Ile Thr Glu Ser Gly Cys Lys Glu Cys Glu Glu Leu Glu Glu
        115                 120                 125

Lys Asn Ile Lys Glu Phe Leu Gln Ser Phe Val His Ile Val Gln Met
    130                 135                 140

Phe Ile Asn Thr Ser
145

<210> SEQ ID NO 15
<211> LENGTH: 804
<212> TYPE: DNA
```

<213> ORGANISM: Macaca mulatta
<220> FEATURE:
<223> OTHER INFORMATION: rhesus macaque interleukin-15 receptor alpha
      (IL-15Ra) (AG120)

<400> SEQUENCE: 15

```
atggccccga ggcgggcgcg aggctcgcgg accctcggtc tcccggcgct gctactgctc    60
ctgctgctcc ggccgccggc gacgcggggc atcacgtgcc cgcccccgt gtccgtggag    120
cacgcagaca tccgggtcaa gagctacagc ttgtactccc gggagcggta catctgcaac    180
tcgggtttca gcggaaggc cggcacgtcc agcctgacgg agtgcgtgtt gaacaaggcc    240
acgaatatcg cccactggac gacccctcg ctcaagtgca tccgcgaccc gctactggcc    300
cggcagcggc ccgcgccacc cttcaccgta cgacggcgg cgtgacccc gcagccggag    360
agcctctccc cgtcgggaaa ggagcccgcc gcgtcgtcgc ccagctcgaa caccacggcg    420
gccacaactg cagcgatcgt cccgtcgtcc cggctgatgc cctcgacgtc gtcgtccacg    480
ggaaccacgg agatcggcag tcatgagtcc tcccacggcc cctcgcaaac gacggccaag    540
acgtgggaac tcacggcgtc cgcctcccac cagccgccgg gggtgtatcc gcaaggccac    600
agcgacacca cggtggcgat ctccacgtcc acggtcctgc tgtgtgggct gagcgcggtg    660
tcgctcctgg cgtgctacat caagtcgagg cagactcccc cgccggccag catcgagatg    720
gaggccatgg aggctctgcc ggtgacgggg gagaccagca gcaggatga ggacttggag    780
aactgctcgc acgacctata atga                                        804
```

<210> SEQ ID NO 16
<211> LENGTH: 266
<212> TYPE: PRT
<213> ORGANISM: Macaca mulatta
<220> FEATURE:
<223> OTHER INFORMATION: rhesus macaque interleukin-15 receptor alpha
      (IL-15Ra) (AG120)

<400> SEQUENCE: 16

```
Met Ala Pro Arg Arg Ala Arg Gly Ser Arg Thr Leu Gly Leu Pro Ala
1               5                   10                  15

Leu Leu Leu Leu Leu Leu Arg Pro Pro Ala Thr Arg Gly Ile Thr
            20                  25                  30

Cys Pro Pro Pro Val Ser Val Glu His Ala Asp Ile Arg Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Ile Ala His Trp Thr Thr Pro Ser Leu Lys Cys Ile Arg Asp
                85                  90                  95

Pro Leu Leu Ala Arg Gln Arg Pro Ala Pro Pro Phe Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Thr Thr Ala Ala Thr Thr Ala
    130                 135                 140

Ala Ile Val Pro Ser Ser Arg Leu Met Pro Ser Thr Ser Ser Ser Thr
145                 150                 155                 160

Gly Thr Thr Glu Ile Gly Ser His Glu Ser Ser His Gly Pro Ser Gln
                165                 170                 175

Thr Thr Ala Lys Thr Trp Glu Leu Thr Ala Ser Ala Ser His Gln Pro
```

|    |    |    |    | 180 |    |    |    |    | 185 |    |    |    |    | 190 |    |
|----|----|----|----|-----|----|----|----|----|-----|----|----|----|----|-----|----|
| Pro | Gly | Val | Tyr | Pro | Gln | Gly | His | Ser | Asp | Thr | Thr | Val | Ala | Ile | Ser |
|    |    | 195 |    |    |    |    | 200 |    |    |    |    | 205 |    |    |    |

Thr Ser Thr Val Leu Leu Cys Gly Leu Ser Ala Val Ser Leu Leu Ala
        210                 215                 220

Cys Tyr Ile Lys Ser Arg Gln Thr Pro Pro Ala Ser Ile Glu Met
225             230                 235                 240

Glu Ala Met Glu Ala Leu Pro Val Thr Gly Glu Thr Ser Ser Arg Asp
                245                 250                 255

Glu Asp Leu Glu Asn Cys Ser His Asp Leu
            260                 265

<210> SEQ ID NO 17
<211> LENGTH: 1506
<212> TYPE: DNA
<213> ORGANISM: Human immunodeficiency virus
<220> FEATURE:
<223> OTHER INFORMATION: HIV gag (114H)

<400> SEQUENCE: 17

```
atggggcgc gggcctcggt ccttagcggg ggcgagttgg atcggtggga aaagatccgc    60
ttgaggccag gagggaagaa gaagtacaag ctaaagcaca tcgtctgggc gagcagagag   120
ttggagcggt tcgcggtcaa cccgggcctg cttgagacat cggagggctg tcggcaaatc   180
ctggggcagc ttcaaccgtc cttgcaaacg ggcagcgagg agcttcgatc actatacaac   240
actgtagcaa cgctctactg cgtgcaccag cggatcgaga tcaaggacac gaaggaggct   300
cttgacaaga ttgaggaaga gcagaacaag tccaagaaga aggcccagca ggcggcggcc   360
gacaccggcc actccaacca gtatcacag aactacccga tcgtgcagaa catccaggga   420
cagatggtcc accaggccat ctccccacgg acgcttaacg cgtgggtcaa agtagtggag   480
gagaaggcct tcagcccgga agtgatcccc atgttctcgg cactttccga gggagccacc   540
ccgcaggacc tgaacacgat gttgaacacc gtcggcgggc accaggcggc catgcagatg   600
cttaaggaga ccatcaacga ggaggctgcg gagtgggacc gggtccaccc ggtgcacgcg   660
gggcccatcg cgccgggcca gatgagagag ccgcggggat cggacatcgc gggaaccacc   720
agcaccttgc aggagcaaat cggttggatg actaacaacc cgccaatccc ggtcggggag   780
atctacaaga gatggatcat cctcgggttg aacaagatcg tgaggatgta cagcccgacc   840
agcatcctgg acatccgaca gggaccgaag gagccgttca gagactacgt agaccggttc   900
tacaagactc tccgggcgga gcaggcgtcg caggaggtca gaactggat gacggagacc   960
ttgttggtcc agaacgcgaa cccggactgc aagaccatcc tgaaggctct cggcccggcg  1020
gcgacgttgg aagagatgat gacggcgtgc cagggagtcg ggggacccgg ccacaaggcg  1080
cgggtcttgg ccgaggcgat gagccaagtg acgaactcgg cgacgatcat gatgcagcgg  1140
ggcaacttcc ggaaccagcg gaagatcgtc aagtgcttca ctgtggcaa ggaggggacac  1200
accgccagga actgccgggc cccccggaag aagggctgct ggaagtgcgg aaaggagggg  1260
caccaaatga aggactgcac ggagcggcag gcgaatttcc tcgggaagat ctggccgtcc  1320
tacaaggggc ggccagggaa ctttctgcaa agcggccgg agccgaccgc cccgccggag  1380
gagtcctttc ggtccgggt cgagacgacc acgcccctc agaagcaaga gcccatcgac  1440
aaggagttgt accctcttac ctccctccgg tcgctcttcg gcaacgaccc gtcctcgcaa  1500
tgataa                                                              1506
```

```
<210> SEQ ID NO 18
<211> LENGTH: 500
<212> TYPE: PRT
<213> ORGANISM: Human immunodeficiency virus
<220> FEATURE:
<223> OTHER INFORMATION: HIV gag (114H)

<400> SEQUENCE: 18
```

| | | | | | | | | | | | | | | | |
|---|---|---|---|---|---|---|---|---|---|---|---|---|---|---|---|
|Met|Gly|Ala|Arg|Ala|Ser|Val|Leu|Ser|Gly|Gly|Glu|Leu|Asp|Arg|Trp|
|1| | | |5| | | | |10| | | | |15| |
|Glu|Lys|Ile|Arg|Leu|Arg|Pro|Gly|Gly|Lys|Lys|Tyr|Lys|Leu|Lys| |
| | | |20| | | | |25| | | | |30| | |
|His|Ile|Val|Trp|Ala|Ser|Arg|Glu|Leu|Glu|Arg|Phe|Ala|Val|Asn|Pro|
| | | |35| | | | |40| | | | |45| | |
|Gly|Leu|Leu|Glu|Thr|Ser|Glu|Gly|Cys|Arg|Gln|Ile|Leu|Gly|Gln|Leu|
| |50| | | | |55| | | | |60| | | | |
|Gln|Pro|Ser|Leu|Gln|Thr|Gly|Ser|Glu|Glu|Leu|Arg|Ser|Leu|Tyr|Asn|
|65| | | | |70| | | | |75| | | | |80|
|Thr|Val|Ala|Thr|Leu|Tyr|Cys|Val|His|Gln|Arg|Ile|Glu|Ile|Lys|Asp|
| | | | |85| | | | |90| | | | |95| |
|Thr|Lys|Glu|Ala|Leu|Asp|Lys|Ile|Glu|Glu|Glu|Gln|Asn|Lys|Ser|Lys|
| | | |100| | | | |105| | | | |110| | |
|Lys|Lys|Ala|Gln|Gln|Ala|Ala|Ala|Asp|Thr|Gly|His|Ser|Asn|Gln|Val|
| | | |115| | | | |120| | | | |125| | |
|Ser|Gln|Asn|Tyr|Pro|Ile|Val|Gln|Asn|Ile|Gln|Gly|Gln|Met|Val|His|
| |130| | | | |135| | | | |140| | | | |
|Gln|Ala|Ile|Ser|Pro|Arg|Thr|Leu|Asn|Ala|Trp|Val|Lys|Val|Val|Glu|
|145| | | | |150| | | | |155| | | | |160|
|Glu|Lys|Ala|Phe|Ser|Pro|Glu|Val|Ile|Pro|Met|Phe|Ser|Ala|Leu|Ser|
| | | | |165| | | | |170| | | | |175| |
|Glu|Gly|Ala|Thr|Pro|Gln|Asp|Leu|Asn|Thr|Met|Leu|Asn|Thr|Val|Gly|
| | | |180| | | | |185| | | | |190| | |
|Gly|His|Gln|Ala|Ala|Met|Gln|Met|Leu|Lys|Glu|Thr|Ile|Asn|Glu|Glu|
| | | |195| | | | |200| | | | |205| | |
|Ala|Ala|Glu|Trp|Asp|Arg|Val|His|Pro|Val|His|Ala|Gly|Pro|Ile|Ala|
| |210| | | | |215| | | | |220| | | | |
|Pro|Gly|Gln|Met|Arg|Glu|Pro|Arg|Gly|Ser|Asp|Ile|Ala|Gly|Thr|Thr|
|225| | | | |230| | | | |235| | | | |240|
|Ser|Thr|Leu|Gln|Glu|Gln|Ile|Gly|Trp|Met|Thr|Asn|Asn|Pro|Pro|Ile|
| | | | |245| | | | |250| | | | |255| |
|Pro|Val|Gly|Glu|Ile|Tyr|Lys|Arg|Trp|Ile|Ile|Leu|Gly|Leu|Asn|Lys|
| | | |260| | | | |265| | | | |270| | |
|Ile|Val|Arg|Met|Tyr|Ser|Pro|Thr|Ser|Ile|Leu|Asp|Ile|Arg|Gln|Gly|
| | | |275| | | | |280| | | | |285| | |
|Pro|Lys|Glu|Pro|Phe|Arg|Asp|Tyr|Val|Asp|Arg|Phe|Tyr|Lys|Thr|Leu|
| |290| | | | |295| | | | |300| | | | |
|Arg|Ala|Glu|Gln|Ala|Ser|Gln|Glu|Val|Lys|Asn|Trp|Met|Thr|Glu|Thr|
|305| | | | |310| | | | |315| | | | |320|
|Leu|Leu|Val|Gln|Asn|Ala|Asn|Pro|Asp|Cys|Lys|Thr|Ile|Leu|Lys|Ala|
| | | | |325| | | | |330| | | | |335| |
|Leu|Gly|Pro|Ala|Ala|Thr|Leu|Glu|Glu|Met|Met|Thr|Ala|Cys|Gln|Gly|
| | | |340| | | | |345| | | | |350| | |
|Val|Gly|Gly|Pro|Gly|His|Lys|Ala|Arg|Val|Leu|Ala|Glu|Ala|Met|Ser|
| | | |355| | | | |360| | | | |365| | |
|Gln|Val|Thr|Asn|Ser|Ala|Thr|Ile|Met|Met|Gln|Arg|Gly|Asn|Phe|Arg|
| |370| | | | |375| | | | |380| | | | |

```
Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500

<210> SEQ ID NO 19
<211> LENGTH: 1812
<212> TYPE: DNA
<213> ORGANISM: Artificial Sequence
<220> FEATURE:
<223> OTHER INFORMATION: Description of Artificial Sequence:fusion
      protein HIV muIP10huMCP-3 gag (122H)

<400> SEQUENCE: 19
atgaacccga gtgctgccgt catcttctgc ctcatcctgc tggggctgag cgggacgcag      60
gggatcctcg acgcgcagcc ggtcgggatc aacacgagca cgacctgctg ctaccgttc     120 atcaacaaga agatcccgaa gcagcgtctg gagagctacc gccggaccac gtcgagccac    180
tgcccgcggg aggcggtcat cttcaagacg aagctggaca aggagatctg cgccgacccg    240
acgcagaagt gggttcagga cttcatgaag cacctggaca agaagacgca gacgccgaag    300
ctggctagcg gggcacgtgc ctcggtcctt agcggggggcg agttggatcg gtgggaaaag    360
atccgcttga ggccaggagg gaagaagaag tacaagctaa agcacatcgt ctgggcgagc    420
agagagttgg agcggttcgc ggtcaacccg ggcctgcttg agacatcgga gggctgtcgg    480
caaatcctgg ggcagcttca accgtccttg caaacgggca gcgaggagct tcgatcacta    540
tacaacactg tagcaacgct ctactgcgtg caccagcgga tcgagatcaa ggacacgaag    600
gaggctcttg acaagattga ggaagagcag aacaagtcca agaagaaggc ccagcaggcg    660
gcggccgaca ccggccactc aaccaagta tcacagaact acccgatcgt gcagaacatc    720
caggacagga tggtccacca ggccatctcc cacggacgc ttaacgcgtg ggtcaaagta    780
gtggaggaga aggccttcag cccggaagtg atccccatgt tctcggcact ttccgaggga    840
gccaccccgc aggacctgaa cacgatgttg aacaccgtcg cgggcacca gcggccatg    900 cagatgctta aggagaccat caacgaggag gctgcggagt gggaccgggt ccacccggtg    960
cacgcggggc ccatcgcgcc gggccagatg agagagccgc ggggatcgga catcgcggga   1020
accaccagca ccttgcagga gcaaatcggt tggatgacta caacccgcc aatcccggtc   1080 ggggagatct acaagagatg gatcatcctc ggggttaaca agatcgtgag gatgtacagc   1140
ccgaccagca tcctggacat ccgacaggga ccgaaggagc cgttcagaga ctacgtagac   1200
cggttctaca agactctccg ggcggagcag gcgtcgcagg aggtcaagaa ctggatgacg   1260
gagaccttgt tggtccagaa cgcgaacccg gactgcaaga ccatcctgaa ggctctcggc   1320
```

-continued

```
ccggcggcga cgttggaaga gatgatgacg gcgtgccagg gagtcggggg acccggccac    1380
aaggcgcggg tcttggccga ggcgatgagc caagtgacga actcggcgac gatcatgatg    1440
cagcggggca acttccggaa ccagcggaag atcgtcaagt gcttcaactg tggcaaggag    1500
ggacacaccg ccaggaactg ccgggccccc cggaagaagg gctgctggaa gtgcggaaag    1560
gagggcaccc aaatgaagga ctgcacggag cggcaggcga atttcctcgg gaagatctgg    1620
ccgtcctaca aggggcggcc aggaactttt ctgcaaagcc ggccggagcc gaccgccccg    1680
ccggaggagt cctttcggtc cggggtcgag acgaccacgc cccctcagaa gcaagagccc    1740
atcgacaagg agttgtaccc tcttacctcc ctccggtcgc tcttcggcaa cgacccgtcc    1800
tcgcaatgat aa                                                        1812
```

<210> SEQ ID NO 20
<211> LENGTH: 602
<212> TYPE: PRT
<213> ORGANISM: Artificial Sequence
<220> FEATURE:
<223> OTHER INFORMATION: Description of Artificial Sequence:fusion
      protein HIV muIP10huMCP-3 gag (122H)

<400> SEQUENCE: 20

```
Met Asn Pro Ser Ala Ala Val Ile Phe Cys Leu Ile Leu Leu Gly Leu
  1               5                  10                  15

Ser Gly Thr Gln Gly Ile Leu Asp Ala Gln Pro Val Gly Ile Asn Thr
             20                  25                  30

Ser Thr Thr Cys Cys Tyr Arg Phe Ile Asn Lys Lys Ile Pro Lys Gln
         35                  40                  45

Arg Leu Glu Ser Tyr Arg Arg Thr Thr Ser Ser His Cys Pro Arg Glu
     50                  55                  60

Ala Val Ile Phe Lys Thr Lys Leu Asp Lys Glu Ile Cys Ala Asp Pro
 65                  70                  75                  80

Thr Gln Lys Trp Val Gln Asp Phe Met Lys His Leu Asp Lys Lys Thr
                 85                  90                  95

Gln Thr Pro Lys Leu Ala Ser Gly Ala Arg Ala Ser Val Leu Ser Gly
            100                 105                 110

Gly Glu Leu Asp Arg Trp Glu Lys Ile Arg Leu Arg Pro Gly Gly Lys
        115                 120                 125

Lys Lys Tyr Lys Leu Lys His Ile Val Trp Ala Ser Arg Glu Leu Glu
    130                 135                 140

Arg Phe Ala Val Asn Pro Gly Leu Leu Glu Thr Ser Glu Gly Cys Arg
145                 150                 155                 160

Gln Ile Leu Gly Gln Leu Gln Pro Ser Leu Gln Thr Gly Ser Glu Glu
                165                 170                 175

Leu Arg Ser Leu Tyr Asn Thr Val Ala Thr Leu Tyr Cys Val His Gln
            180                 185                 190

Arg Ile Glu Ile Lys Asp Thr Lys Glu Ala Leu Asp Lys Ile Glu Glu
        195                 200                 205

Glu Gln Asn Lys Ser Lys Lys Lys Ala Gln Gln Ala Ala Ala Asp Thr
    210                 215                 220

Gly His Ser Asn Gln Val Ser Gln Asn Tyr Pro Ile Val Gln Asn Ile
225                 230                 235                 240

Gln Gly Gln Met Val His Gln Ala Ile Ser Pro Arg Thr Leu Asn Ala
                245                 250                 255

Trp Val Lys Val Val Glu Glu Lys Ala Phe Ser Pro Glu Val Ile Pro
            260                 265                 270
```

```
Met Phe Ser Ala Leu Ser Glu Gly Ala Thr Pro Gln Asp Leu Asn Thr
            275                 280                 285

Met Leu Asn Thr Val Gly Gly His Gln Ala Ala Met Gln Met Leu Lys
        290                 295                 300

Glu Thr Ile Asn Glu Glu Ala Ala Glu Trp Asp Arg Val His Pro Val
305                 310                 315                 320

His Ala Gly Pro Ile Ala Pro Gly Gln Met Arg Glu Pro Arg Gly Ser
                325                 330                 335

Asp Ile Ala Gly Thr Thr Ser Thr Leu Gln Glu Gln Ile Gly Trp Met
            340                 345                 350

Thr Asn Asn Pro Pro Ile Pro Val Gly Glu Ile Tyr Lys Arg Trp Ile
        355                 360                 365

Ile Leu Gly Leu Asn Lys Ile Val Arg Met Tyr Ser Pro Thr Ser Ile
370                 375                 380

Leu Asp Ile Arg Gln Gly Pro Lys Glu Pro Phe Arg Asp Tyr Val Asp
385                 390                 395                 400

Arg Phe Tyr Lys Thr Leu Arg Ala Glu Gln Ala Ser Gln Glu Val Lys
                405                 410                 415

Asn Trp Met Thr Glu Thr Leu Leu Val Gln Asn Ala Asn Pro Asp Cys
            420                 425                 430

Lys Thr Ile Leu Lys Ala Leu Gly Pro Ala Ala Thr Leu Glu Glu Met
        435                 440                 445

Met Thr Ala Cys Gln Gly Val Gly Gly Pro Gly His Lys Ala Arg Val
450                 455                 460

Leu Ala Glu Ala Met Ser Gln Val Thr Asn Ser Ala Thr Ile Met Met
465                 470                 475                 480

Gln Arg Gly Asn Phe Arg Asn Gln Arg Lys Ile Val Lys Cys Phe Asn
                485                 490                 495

Cys Gly Lys Glu Gly His Thr Ala Arg Asn Cys Arg Ala Pro Arg Lys
            500                 505                 510

Lys Gly Cys Trp Lys Cys Gly Lys Glu Gly His Gln Met Lys Asp Cys
        515                 520                 525

Thr Glu Arg Gln Ala Asn Phe Leu Gly Lys Ile Trp Pro Ser Tyr Lys
530                 535                 540

Gly Arg Pro Gly Asn Phe Leu Gln Ser Arg Pro Glu Pro Thr Ala Pro
545                 550                 555                 560

Pro Glu Glu Ser Phe Arg Ser Gly Val Glu Thr Thr Thr Pro Pro Gln
                565                 570                 575

Lys Gln Glu Pro Ile Asp Lys Glu Leu Tyr Pro Leu Thr Ser Leu Arg
            580                 585                 590

Ser Leu Phe Gly Asn Asp Pro Ser Ser Gln
        595                 600

<210> SEQ ID NO 21
<211> LENGTH: 598
<212> TYPE: PRT
<213> ORGANISM: Artificial Sequence
<220> FEATURE:
<223> OTHER INFORMATION: Description of Artificial Sequence:fusion
      protein HIV huIP10huMCP-3 gag

<400> SEQUENCE: 21

Met Asn Gln Thr Ala Ile Leu Ile Cys Cys Leu Ile Phe Leu Thr Leu
1               5                   10                  15

Ser Gly Ile Gln Gly Gln Pro Val Gly Ile Asn Thr Ser Thr Thr Cys
            20                  25                  30
```

-continued

```
Cys Tyr Arg Phe Ile Asn Lys Lys Ile Pro Lys Gln Arg Leu Glu Ser
             35                  40                  45

Tyr Arg Arg Thr Thr Ser Ser His Cys Pro Arg Glu Ala Val Ile Phe
 50                  55                  60

Lys Thr Lys Leu Asp Lys Glu Ile Cys Ala Asp Pro Thr Gln Lys Trp
 65                  70                  75                  80

Val Gln Asp Phe Met Lys His Leu Asp Lys Lys Thr Gln Thr Pro Lys
                 85                  90                  95

Leu Ala Ser Gly Ala Arg Ala Ser Val Leu Ser Gly Gly Glu Leu Asp
                100                 105                 110

Arg Trp Glu Lys Ile Arg Leu Arg Pro Gly Gly Lys Lys Lys Tyr Lys
            115                 120                 125

Leu Lys His Ile Val Trp Ala Ser Arg Glu Leu Glu Arg Phe Ala Val
130                 135                 140

Asn Pro Gly Leu Leu Glu Thr Ser Glu Gly Cys Arg Gln Ile Leu Gly
145                 150                 155                 160

Gln Leu Gln Pro Ser Leu Gln Thr Gly Ser Glu Glu Leu Arg Ser Leu
                165                 170                 175

Tyr Asn Thr Val Ala Thr Leu Tyr Cys Val His Gln Arg Ile Glu Ile
            180                 185                 190

Lys Asp Thr Lys Glu Ala Leu Asp Lys Ile Glu Glu Glu Gln Asn Lys
        195                 200                 205

Ser Lys Lys Lys Ala Gln Gln Ala Ala Ala Asp Thr Gly His Ser Asn
210                 215                 220

Gln Val Ser Gln Asn Tyr Pro Ile Val Gln Asn Ile Gln Gly Gln Met
225                 230                 235                 240

Val His Gln Ala Ile Ser Pro Arg Thr Leu Asn Ala Trp Val Lys Val
                245                 250                 255

Val Glu Glu Lys Ala Phe Ser Pro Glu Val Ile Pro Met Phe Ser Ala
            260                 265                 270

Leu Ser Glu Gly Ala Thr Pro Gln Asp Leu Asn Thr Met Leu Asn Thr
        275                 280                 285

Val Gly Gly His Gln Ala Ala Met Gln Met Leu Lys Glu Thr Ile Asn
290                 295                 300

Glu Glu Ala Ala Glu Trp Asp Arg Val His Pro Val His Ala Gly Pro
305                 310                 315                 320

Ile Ala Pro Gly Gln Met Arg Glu Pro Arg Gly Ser Asp Ile Ala Gly
                325                 330                 335

Thr Thr Ser Thr Leu Gln Glu Gln Ile Gly Trp Met Thr Asn Asn Pro
            340                 345                 350

Pro Ile Pro Val Gly Glu Ile Tyr Lys Arg Trp Ile Ile Leu Gly Leu
        355                 360                 365

Asn Lys Ile Val Arg Met Tyr Ser Pro Thr Ser Ile Leu Asp Ile Arg
370                 375                 380

Gln Gly Pro Lys Glu Pro Phe Arg Asp Tyr Val Asp Arg Phe Tyr Lys
385                 390                 395                 400

Thr Leu Arg Ala Glu Gln Ala Ser Gln Glu Val Lys Asn Trp Met Thr
                405                 410                 415

Glu Thr Leu Leu Val Gln Asn Ala Asn Pro Asp Cys Lys Thr Ile Leu
            420                 425                 430

Lys Ala Leu Gly Pro Ala Ala Thr Leu Glu Glu Met Met Thr Ala Cys
        435                 440                 445

Gln Gly Val Gly Gly Pro Gly His Lys Ala Arg Val Leu Ala Glu Ala
450                 455                 460
```

```
Met Ser Gln Val Thr Asn Ser Ala Thr Ile Met Met Gln Arg Gly Asn
465                 470                 475                 480

Phe Arg Asn Gln Arg Lys Ile Val Lys Cys Phe Asn Cys Gly Lys Glu
            485                 490                 495

Gly His Thr Ala Arg Asn Cys Arg Ala Pro Arg Lys Lys Gly Cys Trp
            500                 505                 510

Lys Cys Gly Lys Glu Gly His Gln Met Lys Asp Cys Thr Glu Arg Gln
            515                 520                 525

Ala Asn Phe Leu Gly Lys Ile Trp Pro Ser Tyr Lys Gly Arg Pro Gly
530                 535                 540

Asn Phe Leu Gln Ser Arg Pro Glu Pro Thr Ala Pro Pro Glu Glu Ser
545                 550                 555                 560

Phe Arg Ser Gly Val Glu Thr Thr Thr Pro Pro Gln Lys Gln Glu Pro
                565                 570                 575

Ile Asp Lys Glu Leu Tyr Pro Leu Thr Ser Leu Arg Ser Leu Phe Gly
            580                 585                 590

Asn Asp Pro Ser Ser Gln
            595

<210> SEQ ID NO 22
<211> LENGTH: 601
<212> TYPE: PRT
<213> ORGANISM: Artificial Sequence
<220> FEATURE:
<223> OTHER INFORMATION: Description of Artificial Sequence:fusion
      protein HIV huMCP-3 gag

<400> SEQUENCE: 22

Met Lys Ala Ser Ala Ala Leu Leu Cys Leu Leu Leu Thr Ala Ala Ala
1               5                   10                  15

Phe Ser Pro Gln Gly Leu Ala Gly Gln Pro Val Gly Ile Asn Thr Ser
            20                  25                  30

Thr Thr Cys Cys Tyr Arg Phe Ile Asn Lys Lys Ile Pro Lys Gln Arg
        35                  40                  45

Leu Glu Ser Tyr Arg Arg Thr Thr Ser Ser His Cys Pro Arg Glu Ala
    50                  55                  60

Val Ile Phe Lys Thr Lys Leu Asp Lys Glu Ile Cys Ala Asp Pro Thr
65                  70                  75                  80

Gln Lys Trp Val Gln Asp Phe Met Lys His Leu Asp Lys Lys Thr Gln
                85                  90                  95

Thr Pro Lys Leu Ala Ser Gly Ala Arg Ala Ser Val Leu Ser Gly Gly
            100                 105                 110

Glu Leu Asp Arg Trp Glu Lys Ile Arg Leu Arg Pro Gly Gly Lys Lys
            115                 120                 125

Lys Tyr Lys Leu Lys His Ile Val Trp Ala Ser Arg Glu Leu Glu Arg
130                 135                 140

Phe Ala Val Asn Pro Gly Leu Leu Glu Thr Ser Glu Gly Cys Arg Gln
145                 150                 155                 160

Ile Leu Gly Gln Leu Gln Pro Ser Leu Gln Thr Gly Ser Glu Glu Leu
                165                 170                 175

Arg Ser Leu Tyr Asn Thr Val Ala Thr Leu Tyr Cys Val His Gln Arg
            180                 185                 190

Ile Glu Ile Lys Asp Thr Lys Glu Ala Leu Asp Lys Ile Glu Glu Glu
            195                 200                 205

Gln Asn Lys Ser Lys Lys Lys Ala Gln Gln Ala Ala Ala Asp Thr Gly
210                 215                 220
```

His Ser Asn Gln Val Ser Gln Asn Tyr Pro Ile Val Gln Asn Ile Gln
225                 230                 235                 240

Gly Gln Met Val His Gln Ala Ile Ser Pro Arg Thr Leu Asn Ala Trp
            245                 250                 255

Val Lys Val Val Glu Glu Lys Ala Phe Ser Pro Glu Val Ile Pro Met
                260                 265                 270

Phe Ser Ala Leu Ser Glu Gly Ala Thr Pro Gln Asp Leu Asn Thr Met
            275                 280                 285

Leu Asn Thr Val Gly Gly His Gln Ala Ala Met Gln Met Leu Lys Glu
    290                 295                 300

Thr Ile Asn Glu Glu Ala Ala Glu Trp Asp Arg Val His Pro Val His
305                 310                 315                 320

Ala Gly Pro Ile Ala Pro Gly Gln Met Arg Glu Pro Arg Gly Ser Asp
                325                 330                 335

Ile Ala Gly Thr Thr Ser Thr Leu Gln Glu Gln Ile Gly Trp Met Thr
            340                 345                 350

Asn Asn Pro Pro Ile Pro Val Gly Glu Ile Tyr Lys Arg Trp Ile Ile
            355                 360                 365

Leu Gly Leu Asn Lys Ile Val Arg Met Tyr Ser Pro Thr Ser Ile Leu
    370                 375                 380

Asp Ile Arg Gln Gly Pro Lys Glu Pro Phe Arg Asp Tyr Val Asp Arg
385                 390                 395                 400

Phe Tyr Lys Thr Leu Arg Ala Glu Gln Ala Ser Gln Glu Val Lys Asn
                405                 410                 415

Trp Met Thr Glu Thr Leu Leu Val Gln Asn Ala Asn Pro Asp Cys Lys
            420                 425                 430

Thr Ile Leu Lys Ala Leu Gly Pro Ala Ala Thr Leu Glu Glu Met Met
            435                 440                 445

Thr Ala Cys Gln Gly Val Gly Gly Pro Gly His Lys Ala Arg Val Leu
    450                 455                 460

Ala Glu Ala Met Ser Gln Val Thr Asn Ser Ala Thr Ile Met Met Gln
465                 470                 475                 480

Arg Gly Asn Phe Arg Asn Gln Arg Lys Ile Val Lys Cys Phe Asn Cys
                485                 490                 495

Gly Lys Glu Gly His Thr Ala Arg Asn Cys Arg Ala Pro Arg Lys Lys
            500                 505                 510

Gly Cys Trp Lys Cys Gly Lys Glu Gly His Gln Met Lys Asp Cys Thr
    515                 520                 525

Glu Arg Gln Ala Asn Phe Leu Gly Lys Ile Trp Pro Ser Tyr Lys Gly
530                 535                 540

Arg Pro Gly Asn Phe Leu Gln Ser Arg Pro Glu Pro Thr Ala Pro Pro
545                 550                 555                 560

Glu Glu Ser Phe Arg Ser Gly Val Glu Thr Thr Thr Pro Pro Gln Lys
                565                 570                 575

Gln Glu Pro Ile Asp Lys Glu Leu Tyr Pro Leu Thr Ser Leu Arg Ser
            580                 585                 590

Leu Phe Gly Asn Asp Pro Ser Ser Gln
    595                 600

<210> SEQ ID NO 23
<211> LENGTH: 1185
<212> TYPE: DNA
<213> ORGANISM: Artificial Sequence
<220> FEATURE:
<223> OTHER INFORMATION: Description of Artificial Sequence:fusion protein HIV CATE p37gag (80H)

<400> SEQUENCE: 23

```
atgagaaaag cggctgttag tcactggcag cagcagtctt acctggactc tggaatccat    60
tctggtgcca ctaccacagc tccttctctg agtgccggcg cgagagcgtc agtattaagc   120
gggggagaat tagatcgatg ggaaaaaatt cggttaaggc cagggggaaa gaagaagtac   180
aagctaaagc acatcgtatg ggcaagcagg gagctagaac gattcgcagt taatcctggc   240
ctgttagaaa catcagaagg ctgtagacaa atactgggac agctacaacc atcccttcag   300
acaggatcag aggagcttcg atcactatac aacacagtag caaccctcta ttgtgtgcac   360
cagcggatcg agatcaagga caccaaggaa gctttagaca gatagagga agagcaaaac   420
aagtccaaga agaaggccca gcaggcagca gctgacacag gacacagcaa tcaggtcagc   480
caaaattacc ctatagtgca gaacatccag ggcaaatgg tacatcaggc catatcacct   540
agaactttaa atgcatgggt aaagtagta agagagaagg ctttcagccc agaagtgata   600
cccatgtttt cagcattatc agaaggagcc accccacagg acctgaacac gatgttgaac   660
accgtggggg gacatcaagc agccatgcaa atgttaaaag agaccatcaa tgaggaagct   720
gcagaatggg atagagtgca tccagtgcat gcagggccta ttgcaccagg ccagatgaga   780
gaaccaaggg gaagtgacat agcaggaact actagtaccc ttcaggaaca aataggatgg   840
atgacaaata atccacctat cccagtagga gagatctaca gaggtggat aatcctggga   900
ttgaacaaga tcgtgaggat gtatagccct accagcattc tggacataag acaaggacca   960
aaggaaccct ttagagacta tgtagaccgg ttctataaaa ctctaagagc tgagcaagct  1020
tcacaggagg taaaaaattg gatgacagaa accttgttgg tccaaaatgc gaacccagat  1080
tgtaagacca tcctgaaggc tctcggccca gcggctacag taagaaaat gatgacagca  1140
tgtcagggag taggaggacc cggccataag gcaagagttt tgtag                  1185
```

<210> SEQ ID NO 24
<211> LENGTH: 394
<212> TYPE: PRT
<213> ORGANISM: Artificial Sequence
<220> FEATURE:
<223> OTHER INFORMATION: Description of Artificial Sequence:fusion
    protein HIV CATE p37gag (80H)

<400> SEQUENCE: 24

```
Met Arg Lys Ala Ala Val Ser His Trp Gln Gln Gln Ser Tyr Leu Asp
  1               5                  10                  15

Ser Gly Ile His Ser Gly Ala Thr Thr Thr Ala Pro Ser Leu Ser Ala
             20                  25                  30

Gly Ala Arg Ala Ser Val Leu Ser Gly Gly Glu Leu Asp Arg Trp Glu
         35                  40                  45

Lys Ile Arg Leu Arg Pro Gly Gly Lys Lys Tyr Lys Leu Lys His
     50                  55                  60

Ile Val Trp Ala Ser Arg Glu Leu Glu Arg Phe Ala Val Asn Pro Gly
 65                  70                  75                  80

Leu Leu Glu Thr Ser Glu Gly Cys Arg Gln Ile Leu Gly Gln Leu Gln
                 85                  90                  95

Pro Ser Leu Gln Thr Gly Ser Glu Glu Leu Arg Ser Leu Tyr Asn Thr
            100                 105                 110

Val Ala Thr Leu Tyr Cys Val His Gln Arg Ile Glu Ile Lys Asp Thr
        115                 120                 125

Lys Glu Ala Leu Asp Lys Ile Glu Glu Glu Gln Asn Lys Ser Lys Lys
```

```
                130                 135                 140
Lys Ala Gln Gln Ala Ala Ala Asp Thr Gly His Ser Asn Gln Val Ser
145                 150                 155                 160

Gln Asn Tyr Pro Ile Val Gln Asn Ile Gln Gly Gln Met Val His Gln
                165                 170                 175

Ala Ile Ser Pro Arg Thr Leu Asn Ala Trp Val Lys Val Val Glu Glu
                180                 185                 190

Lys Ala Phe Ser Pro Glu Val Ile Pro Met Phe Ser Ala Leu Ser Glu
                195                 200                 205

Gly Ala Thr Pro Gln Asp Leu Asn Thr Met Leu Asn Thr Val Gly Gly
210                 215                 220

His Gln Ala Ala Met Gln Met Leu Lys Glu Thr Ile Asn Glu Glu Ala
225                 230                 235                 240

Ala Glu Trp Asp Arg Val His Pro Val His Ala Gly Pro Ile Ala Pro
                245                 250                 255

Gly Gln Met Arg Glu Pro Arg Gly Ser Asp Ile Ala Gly Thr Thr Ser
                260                 265                 270

Thr Leu Gln Glu Gln Ile Gly Trp Met Thr Asn Asn Pro Pro Ile Pro
                275                 280                 285

Val Gly Glu Ile Tyr Lys Arg Trp Ile Ile Leu Gly Leu Asn Lys Ile
290                 295                 300

Val Arg Met Tyr Ser Pro Thr Ser Ile Leu Asp Ile Arg Gln Gly Pro
305                 310                 315                 320

Lys Glu Pro Phe Arg Asp Tyr Val Asp Arg Phe Tyr Lys Thr Leu Arg
                325                 330                 335

Ala Glu Gln Ala Ser Gln Glu Val Lys Asn Trp Met Thr Glu Thr Leu
                340                 345                 350

Leu Val Gln Asn Ala Asn Pro Asp Cys Lys Thr Ile Leu Lys Ala Leu
                355                 360                 365

Gly Pro Ala Ala Thr Leu Glu Glu Met Met Thr Ala Cys Gln Gly Val
                370                 375                 380

Gly Gly Pro Gly His Lys Ala Arg Val Leu
385                 390

<210> SEQ ID NO 25
<211> LENGTH: 531
<212> TYPE: PRT
<213> ORGANISM: Artificial Sequence
<220> FEATURE:
<223> OTHER INFORMATION: Description of Artificial Sequence:fusion
      protein HIV CATE gag

<400> SEQUENCE: 25

Met Arg Lys Ala Ala Val Ser His Trp Gln Gln Gln Ser Tyr Leu Asp
 1                  5                  10                  15

Ser Gly Ile His Ser Gly Ala Thr Thr Thr Ala Pro Ser Leu Ser Ala
                20                  25                  30

Gly Ala Arg Ala Ser Val Leu Ser Gly Gly Glu Leu Asp Arg Trp Glu
                35                  40                  45

Lys Ile Arg Leu Arg Pro Gly Gly Lys Lys Lys Tyr Lys Leu Lys His
        50                  55                  60

Ile Val Trp Ala Ser Arg Glu Leu Glu Arg Phe Ala Val Asn Pro Gly
 65                 70                  75                  80

Leu Leu Glu Thr Ser Glu Gly Cys Arg Gln Ile Leu Gly Gln Leu Gln
                85                  90                  95

Pro Ser Leu Gln Thr Gly Ser Glu Glu Leu Arg Ser Leu Tyr Asn Thr
```

-continued

```
                100                 105                 110
Val Ala Thr Leu Tyr Cys Val His Gln Arg Ile Glu Ile Lys Asp Thr
            115                 120                 125
Lys Glu Ala Leu Asp Lys Ile Glu Glu Gln Asn Lys Ser Lys Lys
        130                 135                 140
Lys Ala Gln Gln Ala Ala Ala Asp Thr Gly His Ser Asn Gln Val Ser
145                 150                 155                 160
Gln Asn Tyr Pro Ile Val Gln Asn Ile Gln Gly Gln Met Val His Gln
                165                 170                 175
Ala Ile Ser Pro Arg Thr Leu Asn Ala Trp Val Lys Val Val Glu Glu
            180                 185                 190
Lys Ala Phe Ser Pro Glu Val Ile Pro Met Phe Ser Ala Leu Ser Glu
        195                 200                 205
Gly Ala Thr Pro Gln Asp Leu Asn Thr Met Leu Asn Thr Val Gly Gly
    210                 215                 220
His Gln Ala Ala Met Gln Met Leu Lys Glu Thr Ile Asn Glu Glu Ala
225                 230                 235                 240
Ala Glu Trp Asp Arg Val His Pro Val His Ala Gly Pro Ile Ala Pro
                245                 250                 255
Gly Gln Met Arg Glu Pro Arg Gly Ser Asp Ile Ala Gly Thr Thr Ser
            260                 265                 270
Thr Leu Gln Glu Gln Ile Gly Trp Met Thr Asn Asn Pro Pro Ile Pro
        275                 280                 285
Val Gly Glu Ile Tyr Lys Arg Trp Ile Ile Leu Gly Leu Asn Lys Ile
    290                 295                 300
Val Arg Met Tyr Ser Pro Thr Ser Ile Leu Asp Ile Arg Gln Gly Pro
305                 310                 315                 320
Lys Glu Pro Phe Arg Asp Tyr Val Asp Arg Phe Tyr Lys Thr Leu Arg
                325                 330                 335
Ala Glu Gln Ala Ser Gln Glu Val Lys Asn Trp Met Thr Glu Thr Leu
            340                 345                 350
Leu Val Gln Asn Ala Asn Pro Asp Cys Lys Thr Ile Leu Lys Ala Leu
        355                 360                 365
Gly Pro Ala Ala Thr Leu Glu Glu Met Met Thr Ala Cys Gln Gly Val
    370                 375                 380
Gly Gly Pro Gly His Lys Ala Arg Val Leu Ala Glu Ala Met Ser Gln
385                 390                 395                 400
Val Thr Asn Ser Ala Thr Ile Met Met Gln Arg Gly Asn Phe Arg Asn
                405                 410                 415
Gln Arg Lys Ile Val Lys Cys Phe Asn Cys Gly Lys Glu Gly His Thr
            420                 425                 430
Ala Arg Asn Cys Arg Ala Pro Arg Lys Lys Gly Cys Trp Lys Cys Gly
        435                 440                 445
Lys Glu Gly His Gln Met Lys Asp Cys Thr Glu Arg Gln Ala Asn Phe
    450                 455                 460
Leu Gly Lys Ile Trp Pro Ser Tyr Lys Gly Arg Pro Gly Asn Phe Leu
465                 470                 475                 480
Gln Ser Arg Pro Glu Pro Thr Ala Pro Pro Glu Glu Ser Phe Arg Ser
                485                 490                 495
Gly Val Glu Thr Thr Thr Pro Pro Gln Lys Gln Glu Pro Ile Asp Lys
            500                 505                 510
Glu Leu Tyr Pro Leu Thr Ser Leu Arg Ser Leu Phe Gly Asn Asp Pro
        515                 520                 525
```

Ser Ser Gln
    530

<210> SEQ ID NO 26
<211> LENGTH: 2769
<212> TYPE: DNA
<213> ORGANISM: Artificial Sequence
<220> FEATURE:
<223> OTHER INFORMATION: Description of Artificial Sequence:fusion
      protein HIV LAMPgag

<400> SEQUENCE: 26

| | |
|---|---|
| atggcgcccc gcagcgcccg gcgacccctg ctgctgctac tgctgttgct gctgctcggc | 60 |
| ctcatgcatt gtgcgtcagc agcaatgttt atggtgaaaa atggcaacgg accgcgtgc | 120 |
| ataatggcca acttctctgc tgccttctca gtgaactacg acaccaagag tggccctaag | 180 |
| aacatgaccc ttgacctgcc atcagatgcc acagtggtgc tcaaccgcag ctcctgtgga | 240 |
| aaagagaaca cttctgaccc cagtctcgtg attgcttttg aagaggaca tacactcact | 300 |
| ctcaatttca cgagaaatgc aacacgttac agcgtccagc tcatgagttt tgtttataac | 360 |
| ttgtcagaca cacacccttttt ccccaatgcg agctccaaag aaatcaagac tgtgaatct | 420 |
| ataactgaca tcagggcaga tatagataaa aaatacagat gtgttagtgg caccccaggtc | 480 |
| cacatgaaca acgtgaccgt aacgctccat gatgccacca tccaggcgta cctttccaac | 540 |
| agcagcttca gcaggggaga gacacgctgt gaacaagaca ggccttcccc aaccacagcg | 600 |
| cccctgcgc cacccagccc ctcgccctca ccgtgcccca gagcccctc tgtggacaag | 660 |
| tacaacgtga gcggcaccaa cgggacctgc ctgctggcca gcatggggct gcagctgaac | 720 |
| ctcacctatg agaggaagga caacacgacg gtgacaaggc ttctcaacat caaccccaac | 780 |
| aagacctcgg ccagcgggag ctgcggcgcc cacctggtga ctctggagct gcacagcgag | 840 |
| ggcaccaccg tcctgctctt ccagttcggg atgaatgcaa gttctagccg gttttttccta | 900 |
| caaggaatcc agttgaatac aattcttcct gacgccagag accctgcctt taaagctgcc | 960 |
| aacggctccc tgcgagcgct gcaggccaca gtcggcaatt cctacaagtg caacgcggag | 1020 |
| gagcacgtcc gtgtcacgaa ggcgttttca gtcaatatat tcaaagtgtg ggtccaggct | 1080 |
| ttcaaggtgg aaggtggcca gtttggctct gtggaggagt gtctgctgga cgagaacagc | 1140 |
| ctcgaggata tcggggcgcg ggcctcggtc cttagcgggg cgagttgga tcggtgggaa | 1200 |
| aagatccgct tgaggccagg agggaagaag agtacaagc taaagcacat cgtctgggcg | 1260 |
| agcagagagt tggagcggtt cgcggtcaac ccgggcctgc ttgagacatc ggagggctgt | 1320 |
| cggcaaatcc tggggcagct tcaaccgtcc ttgcaaacgg gcagcgagga gcttcgatca | 1380 |
| ctatacaaca ctgtagcaac gctctactgc gtgcaccagc ggatcgagat caaggacacg | 1440 |
| aaggaggctc ttgacaagat tgaggaagag cagaacaagt ccaagaagaa ggcccagcag | 1500 |
| gcggcggccg acaccggcca ctccaaccaa gtatcacaga actacccgat cgtgcagaac | 1560 |
| atccagggac agatggtcca ccaggccatc tcccacgga cgcttaacgc gtgggtcaaa | 1620 |
| gtagtggagg agaaggcctt cagcccggaa gtgatcccca tgttctcggc actttccgag | 1680 |
| ggagccaccc cgcaggacct gaacacgatg ttgaacaccg tcggcgggca ccaggcggcc | 1740 |
| atgcagatgc ttaaggagac catcaacgag gaggctgcgg agtgggaccg ggtccacccg | 1800 |
| gtgcacgcgg ggcccatcgc gccgggccag atgagagagc cgcgggatc ggacatcgcg | 1860 |
| ggaaccacca gcaccttgca ggagcaaatc ggttggatga ctaacaaccc gccaatcccg | 1920 |
| gtcggggaga tctacaagag atggatcatc ctcgggttga acaagatcgt gaggatgtac | 1980 |

```
agcccgacca gcatcctgga catccgacag ggaccgaagg agccgttcag agactacgta   2040
gaccggttct acaagactct ccgggcggag caggcgtcgc aggaggtcaa gaactggatg   2100
acggagacct tgttggtcca gaacgcgaac ccggactgca agaccatcct gaaggctctc   2160
ggcccggcgg cgacgttgga agagatgatg acggcgtgcc agggagtcgg gggacccggc   2220
cacaaggcgc gggtcttggc cgaggcgatg agccaagtga cgaactcggc gacgatcatg   2280
atgcagcggg gcaacttccg gaaccagcgg aagatcgtca agtgcttcaa ctgtggcaag   2340
gagggacaca ccgccaggaa ctgccgggcc cccggaagag agggctgctg gaagtgcgga   2400
aaggaggggc accaaatgaa ggactgcacg gagcggcagg cgaatttcct cgggaagatc   2460
tggccgtcct acaaggggcg gccagggaac tttctgcaaa gccggccgga gccgaccgcc   2520
ccgccggagt agtcctttcg gtccggggtc gagacgacca cgccccctca gaagcaagag   2580
cccatcgaca aggagttgta ccctcttacc tccctccggt cgctcttcgg caacgacccg   2640
tcctcgcaag gggaattcac gctgatcccc atcgctgtgg gtggtgccct ggcggggctg   2700
gtcctcatcg tcctcatcgc ctacctcgtc ggcaggaaga ggagtcacgc aggctaccag   2760
actatctag                                                          2769

<210> SEQ ID NO 27
<211> LENGTH: 922
<212> TYPE: PRT
<213> ORGANISM: Artificial Sequence
<220> FEATURE:
<223> OTHER INFORMATION: Description of Artificial Sequence:fusion
      protein HIV LAMPgag

<400> SEQUENCE: 27

Met Ala Pro Arg Ser Ala Arg Arg Pro Leu Leu Leu Leu Leu Leu Leu
 1               5                  10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
        50                  55                  60

Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Ser Pro Ser
        195                 200                 205

Pro Ser Pro Val Pro Lys Ser Pro Ser Val Asp Lys Tyr Asn Val Ser
    210                 215                 220
```

```
Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
            245                 250                 255

Ile Asn Pro Asn Lys Thr Ser Ala Ser Gly Ser Cys Gly Ala His Leu
                260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
                340                 345                 350

Ile Phe Lys Val Trp Val Gln Ala Phe Lys Val Glu Gly Gly Gln Phe
            355                 360                 365

Gly Ser Val Glu Glu Cys Leu Leu Asp Glu Asn Ser Leu Glu Asp Ile
    370                 375                 380

Gly Ala Arg Ala Ser Val Leu Ser Gly Gly Glu Leu Asp Arg Trp Glu
385                 390                 395                 400

Lys Ile Arg Leu Arg Pro Gly Gly Lys Lys Lys Tyr Lys Leu Lys His
                405                 410                 415

Ile Val Trp Ala Ser Arg Glu Leu Glu Arg Phe Ala Val Asn Pro Gly
            420                 425                 430

Leu Leu Glu Thr Ser Glu Gly Cys Arg Gln Ile Leu Gly Gln Leu Gln
                435                 440                 445

Pro Ser Leu Gln Thr Gly Ser Glu Glu Leu Arg Ser Leu Tyr Asn Thr
450                 455                 460

Val Ala Thr Leu Tyr Cys Val His Gln Arg Ile Glu Ile Lys Asp Thr
465                 470                 475                 480

Lys Glu Ala Leu Asp Lys Ile Glu Glu Glu Gln Asn Lys Ser Lys Lys
                485                 490                 495

Lys Ala Gln Gln Ala Ala Ala Asp Thr Gly His Ser Asn Gln Val Ser
                500                 505                 510

Gln Asn Tyr Pro Ile Val Gln Asn Ile Gln Gly Gln Met Val His Gln
            515                 520                 525

Ala Ile Ser Pro Arg Thr Leu Asn Ala Trp Val Lys Val Val Glu Glu
            530                 535                 540

Lys Ala Phe Ser Pro Glu Val Ile Pro Met Phe Ser Ala Leu Ser Glu
545                 550                 555                 560

Gly Ala Thr Pro Gln Asp Leu Asn Thr Met Leu Asn Thr Val Gly Gly
                565                 570                 575

His Gln Ala Ala Met Gln Met Leu Lys Glu Thr Ile Asn Glu Glu Ala
            580                 585                 590

Ala Glu Trp Asp Arg Val His Pro Val His Ala Gly Pro Ile Ala Pro
            595                 600                 605

Gly Gln Met Arg Glu Pro Arg Gly Ser Asp Ile Ala Gly Thr Thr Ser
            610                 615                 620

Thr Leu Gln Glu Gln Ile Gly Trp Met Thr Asn Asn Pro Pro Ile Pro
625                 630                 635                 640

Val Gly Glu Ile Tyr Lys Arg Trp Ile Ile Leu Gly Leu Asn Lys Ile
```

```
                    645                 650                 655
Val Arg Met Tyr Ser Pro Thr Ser Ile Leu Asp Ile Arg Gln Gly Pro
                660                 665                 670

Lys Glu Pro Phe Arg Asp Tyr Val Asp Arg Phe Tyr Lys Thr Leu Arg
            675                 680                 685

Ala Glu Gln Ala Ser Gln Glu Val Lys Asn Trp Met Thr Glu Thr Leu
        690                 695                 700

Leu Val Gln Asn Ala Asn Pro Asp Cys Lys Thr Ile Leu Lys Ala Leu
705                 710                 715                 720

Gly Pro Ala Ala Thr Leu Glu Glu Met Met Thr Ala Cys Gln Gly Val
                725                 730                 735

Gly Gly Pro Gly His Lys Ala Arg Val Leu Ala Glu Ala Met Ser Gln
            740                 745                 750

Val Thr Asn Ser Ala Thr Ile Met Met Gln Arg Gly Asn Phe Arg Asn
        755                 760                 765

Gln Arg Lys Ile Val Lys Cys Phe Asn Cys Gly Lys Glu Gly His Thr
770                 775                 780

Ala Arg Asn Cys Arg Ala Pro Arg Lys Lys Gly Cys Trp Lys Cys Gly
785                 790                 795                 800

Lys Glu Gly His Gln Met Lys Asp Cys Thr Glu Arg Gln Ala Asn Phe
                805                 810                 815

Leu Gly Lys Ile Trp Pro Ser Tyr Lys Gly Arg Pro Gly Asn Phe Leu
            820                 825                 830

Gln Ser Arg Pro Glu Pro Thr Ala Pro Pro Glu Glu Ser Phe Arg Ser
        835                 840                 845

Gly Val Glu Thr Thr Thr Pro Pro Gln Lys Gln Glu Pro Ile Asp Lys
850                 855                 860

Glu Leu Tyr Pro Leu Thr Ser Leu Arg Ser Leu Phe Gly Asn Asp Pro
865                 870                 875                 880

Ser Ser Gln Gly Glu Phe Thr Leu Ile Pro Ile Ala Val Gly Gly Ala
                885                 890                 895

Leu Ala Gly Leu Val Leu Ile Val Leu Ile Ala Tyr Leu Val Gly Arg
            900                 905                 910

Lys Arg Ser His Ala Gly Tyr Gln Thr Ile
        915                 920

<210> SEQ ID NO 28
<211> LENGTH: 4179
<212> TYPE: DNA
<213> ORGANISM: Artificial Sequence
<220> FEATURE:
<223> OTHER INFORMATION: Description of Artificial Sequence:fusion
      protein HIV gagpol

<400> SEQUENCE: 28
atgggtgcga gagcgtcagt attaagcggg ggagaattag atcgatggga aaaaattcgg      60
ttaaggccag ggggaaagaa gaagtacaag ctaaagcaca tcgtatgggc aagcagggag     120
ctagaacgat tcgcagttaa tcctggcctg ttagaaacat cagaaggctg tagacaaata     180
ctgggacagc tacaaccatc ccttcagaca ggatcagagg agcttcgatc actatacaac     240
acagtagcaa ccctctattg tgtgcaccag cggatcgaga tcaaggacac caaggaagct     300
ttagacaaga tagaggaaga gcaaaacaag tccaagaaga aggcccagca ggcagcagct     360
gacacaggac acagcaatca ggtcagccaa aattacccta tagtgcagaa catccagggg     420
caaatggtac atcaggccat atcacctaga actttaaatg catgggtaaa agtagtagaa     480
```

-continued

```
gagaaggctt tcagcccaga agtgatacccc atgtttttcag cattatcaga aggagccacc    540
ccacaggacc tgaacacgat gttgaacacc gtgggggac atcaagcagc catgcaaatg      600
ttaaaagaga ccatcaatga ggaagctgca gaatgggata gagtgcatcc agtgcatgca     660
gggcctattg caccaggcca gatgagagaa ccaaggggaa gtgacatagc aggaactact    720
agtacccttc aggaacaaat aggatggatg acaaataatc cacctatccc agtaggagag   780
atctacaaga ggtggataat cctgggattg aacaagatcg tgaggatgta tagccctacc   840
agcattctgg acataagaca aggaccaaag gaaccctttta gagactatgt agaccggttc   900
tataaaactc taagagctga gcaagcttca caggaggtaa aaaattggat gacagaaacc    960
ttgttggtcc aaaatgcgaa cccagattgt aagaccatcc tgaaggctct cggcccagcg   1020
gctacactag aagaaatgat gacagcatgt caggagtag gaggacccgg ccataaggca    1080
agagttttgg ccgaggcgat gagccaggtg acgaactcgg cgaccataat gatgcagaga   1140
ggcaacttcc ggaaccagcg gaagatcgtc aagtgcttca attgtggcaa agaagggcac   1200
accgccagga actgccgggc cccccggaag aagggctgct ggaagtgcgg gaaggagggg    1260
caccagatga aggactgcac ggagcggcag gcgaacttcc tggggaagat atggccgagt   1320
tacaagggaa gacccgaccg gcaggggacg gtgtcgttca acttccctca gatcacgctc   1380
tggcagcggc cgctcgtcac aataaagatc gggggggcaac tcaaggaggc gctgctcgcg   1440
gacgacacgg tcttggagga gatgtcgttg ccggggcggt ggaagccgaa gatgatcggg   1500
gggatcgggg gcttcatcaa ggtgcggcag tacgaccaga tcctcatcga gatctgcggg   1560
cacaaggcga tcgggacggt cctcgtcggc ccgacgccgg tcaacatcat cgggcggaac   1620
ctgttgaccc cagatcggctg caccttgaac ttccccatca gccctattga gacggtgccc   1680
gtgaagttga agccggggat ggacggcccc aaggtcaagc aatggccatt gacggaggag   1740
aagatcaagg cccttagtcga aatctgtaca gagatggaga aggaagggaa gatcagcaag   1800
atcgggcctg agaaccccta caacactcca gtcttcgcaa tcaagaagaa ggacagtacc   1860
aagtggagaa agctggtgga cttcagagag ctgaacaaga gaactcagga cttctgggaa   1920
gttcagctgg gcatcccaca tcccgctggg ttgaagaaga gaaagtcagt gacagtgctg   1980
gatgtgggtg atgcctactt ctccgttccc ttggacgagg acttcaggaa gtacactgcc   2040
ttcacgatac ctagcatcaa caacgagaca ccaggcatcc gctaccagta caacgtgctg   2100
ccacagggat ggaagggatc accagccatc tttcaatcgt cgatgaccaa gatcctggag   2160 ccccttccgca agcaaaaccc agacatcgtg atctatcagc tctacgtagg aagtgacctg   2220
gagatcgggc agcacaggac caagatcgag gagctgagac agcatctgtt gaggtgggga   2280
ctgaccacac cagacaagaa gcaccagaag gaacctccct tcctgtggat gggctacgaa   2340
ctgcatcctg acaagtggac agtgcagccc atcgtgctgc ctgagaagga cagctggact   2400
gtgaacgaca tacagaagct cgtgggcaag ttgaactggg caagccagat ctacccaggc   2460
atcaaagtta ggcagctgtg caagctgctt cgaggaacca aggcactgac agaagtgatc   2520
ccactgacag aggaagcaga gctagaactg gcagagaacc gagagatcct gaaggagcca   2580
gtacatggag tgtactacga cccaagcaag gacctgatcg cagagatcca gaagcagggg   2640
caaggccaat ggacctacca aatctaccag gagcccttca gaaacctgaa gacaggcaag   2700
tacgcaagga tgagggggtgc ccacaccaac gatgtgaagc agctgacaga ggcagtgcag   2760
aagatcacca cagagagcat cgtgatctgg ggcaagactc ccaagttcaa gctgcccata   2820
cagaaggaga catgggagac atggtggacc gagtactggc aagccacctg gatccctgag   2880
```

```
tgggagttcg tgaacacccc tcccttggtg aaactgtggt atcagctgga gaaggaaccc    2940
atcgtgggag cagagacctt ctacgtggat ggggcagcca cagggagac caagctgggc     3000 aaggcaggct acgtgaccaa ccgaggacga cagaaagtgg tgaccctgac tgacaccacc    3060
aaccagaaga ctctgcaagc catctaccta gctctgcaag acagcggact ggaagtgaac    3120
atcgtgacag actcacagta cgcactgggc atcatccaag cacaaccaga ccaatccgag    3180
tcagagctgg tgaaccagat catcgagcag ctgatcaaga aggagaaagt gtacctggca    3240
tgggtcccgg cgcacaaggg gatcggggg aacgagcagg tcgacaagtt ggtctcggcg     3300
gggatccgga aggtgctgtt cctggacggg atcgataagg cccaagatga acatgagaag    3360
taccactcca actggcgcgc tatggccagc gacttcaacc tgccgccggt cgtcgcgaag    3420
gagatcgtcg ccagctgcga caagtgccag ctcaagggg aggccatgca cgggcaagtc     3480
gactgcagtc cggggatctg gcagctgtgc acgcacctgg aggggaaggt gatcctggtc    3540
gcggtccacg tcgccagcgg gtatatcgag gcggaggtca tcccggctga cgggggcag    3600 gagacggcgt acttcctctt gaagctcgcg gggcggtggc cggtcaagac gatccacacg    3660
aacgggagca acttcacggg ggcgacggtc aaggccgcct gttggtgggc gggaatcaag    3720
caggaatttg gaattcccta caatccccaa tcgcaaggag tcgtgagcat gaacaaggag    3780
ctgaagaaga tcatcggaca aagggatcag gctgagcacc tgaagacagc agtgcagatg    3840
gcagtgttca tccacaactt caaaagaaaa gggggattg ggggtacag tgcgggggaa      3900 cggatcgtgg acatcatcgc caccgacatc caaaccaagg agctgcagaa gcagatcacc    3960
aagatccaga acttccgggt gtactaccgc gacagccgca cccactgtg gaagggacca     4020 gcaaagctcc tctggaaggg agaggggca gtggtgatcc aggacaacag tgacatcaaa     4080
gtggtgccaa ggcgcaaggc caagatcatc cgcgactatg gaaaacagat ggcaggggat    4140
gattgtgtgg caagtagaca ggatgaggat ggcgcctag                           4179
```

<210> SEQ ID NO 29
<211> LENGTH: 1392
<212> TYPE: PRT
<213> ORGANISM: Artificial Sequence
<220> FEATURE:
<223> OTHER INFORMATION: Description of Artificial Sequence:fusion
      protein HIV gagpol

<400> SEQUENCE: 29

```
Met Gly Ala Arg Ala Ser Val Leu Ser Gly Gly Glu Leu Asp Arg Trp
  1               5                  10                  15

Glu Lys Ile Arg Leu Arg Pro Gly Gly Lys Lys Tyr Lys Leu Lys
             20                  25                  30

His Ile Val Trp Ala Ser Arg Glu Leu Glu Arg Phe Ala Val Asn Pro
         35                  40                  45

Gly Leu Leu Glu Thr Ser Glu Gly Cys Arg Gln Ile Leu Gly Gln Leu
     50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Asp Lys Ile Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
```

```
              130                 135                 140
Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
                195                 200                 205

Ala Ala Glu Trp Asp Arg Val His Pro Val His Ala Gly Pro Ile Ala
            210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
            290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
            370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Asp Arg Gln
            435                 440                 445

Gly Thr Val Ser Phe Asn Phe Pro Gln Ile Thr Leu Trp Gln Arg Pro
            450                 455                 460

Leu Val Thr Ile Lys Ile Gly Gly Gln Leu Lys Glu Ala Leu Leu Ala
465                 470                 475                 480

Asp Asp Thr Val Leu Glu Glu Met Ser Leu Pro Gly Arg Trp Lys Pro
                485                 490                 495

Lys Met Ile Gly Gly Ile Gly Gly Phe Ile Lys Val Arg Gln Tyr Asp
                500                 505                 510

Gln Ile Leu Ile Glu Ile Cys Gly His Lys Ala Ile Gly Thr Val Leu
            515                 520                 525

Val Gly Pro Thr Pro Val Asn Ile Ile Gly Arg Asn Leu Leu Thr Gln
            530                 535                 540

Ile Gly Cys Thr Leu Asn Phe Pro Ile Ser Pro Ile Glu Thr Val Pro
545                 550                 555                 560
```

-continued

Val Lys Leu Lys Pro Gly Met Asp Gly Pro Lys Val Lys Gln Trp Pro
                565                 570                 575

Leu Thr Glu Glu Lys Ile Lys Ala Leu Val Glu Ile Cys Thr Glu Met
            580                 585                 590

Glu Lys Glu Gly Lys Ile Ser Lys Ile Gly Pro Glu Asn Pro Tyr Asn
        595                 600                 605

Thr Pro Val Phe Ala Ile Lys Lys Lys Asp Ser Thr Lys Trp Arg Lys
    610                 615                 620

Leu Val Asp Phe Arg Glu Leu Asn Lys Arg Thr Gln Asp Phe Trp Glu
625                 630                 635                 640

Val Gln Leu Gly Ile Pro His Pro Ala Gly Leu Lys Lys Lys Lys Ser
                645                 650                 655

Val Thr Val Leu Asp Val Gly Asp Ala Tyr Phe Ser Val Pro Leu Asp
            660                 665                 670

Glu Asp Phe Arg Lys Tyr Thr Ala Phe Thr Ile Pro Ser Ile Asn Asn
        675                 680                 685

Glu Thr Pro Gly Ile Arg Tyr Gln Tyr Asn Val Leu Pro Gln Gly Trp
    690                 695                 700

Lys Gly Ser Pro Ala Ile Phe Gln Ser Ser Met Thr Lys Ile Leu Glu
705                 710                 715                 720

Pro Phe Arg Lys Gln Asn Pro Asp Ile Val Ile Tyr Gln Leu Tyr Val
                725                 730                 735

Gly Ser Asp Leu Glu Ile Gly Gln His Arg Thr Lys Ile Glu Glu Leu
            740                 745                 750

Arg Gln His Leu Leu Arg Trp Gly Leu Thr Thr Pro Asp Lys Lys His
        755                 760                 765

Gln Lys Glu Pro Pro Phe Leu Trp Met Gly Tyr Glu Leu His Pro Asp
    770                 775                 780

Lys Trp Thr Val Gln Pro Ile Val Leu Pro Glu Lys Asp Ser Trp Thr
785                 790                 795                 800

Val Asn Asp Ile Gln Lys Leu Val Gly Lys Leu Asn Trp Ala Ser Gln
                805                 810                 815

Ile Tyr Pro Gly Ile Lys Val Arg Gln Leu Cys Lys Leu Leu Arg Gly
            820                 825                 830

Thr Lys Ala Leu Thr Glu Val Ile Pro Leu Thr Glu Glu Ala Glu Leu
        835                 840                 845

Glu Leu Ala Glu Asn Arg Glu Ile Leu Lys Glu Pro Val His Gly Val
    850                 855                 860

Tyr Tyr Asp Pro Ser Lys Asp Leu Ile Ala Glu Ile Gln Lys Gln Gly
865                 870                 875                 880

Gln Gly Gln Trp Thr Tyr Gln Ile Tyr Gln Glu Pro Phe Lys Asn Leu
                885                 890                 895

Lys Thr Gly Lys Tyr Ala Arg Met Arg Gly Ala His Thr Asn Asp Val
            900                 905                 910

Lys Gln Leu Thr Glu Ala Val Gln Lys Ile Thr Thr Glu Ser Ile Val
        915                 920                 925

Ile Trp Gly Lys Thr Pro Lys Phe Lys Leu Pro Ile Gln Lys Glu Thr
    930                 935                 940

Trp Glu Thr Trp Trp Thr Glu Tyr Trp Gln Ala Thr Trp Ile Pro Glu
945                 950                 955                 960

Trp Glu Phe Val Asn Thr Pro Pro Leu Val Lys Leu Trp Tyr Gln Leu
                965                 970                 975

Glu Lys Glu Pro Ile Val Gly Ala Glu Thr Phe Tyr Val Asp Gly Ala
            980                 985                 990

```
Ala Asn Arg Glu Thr Lys Leu Gly Lys Ala Gly Tyr Val Thr Asn Arg
            995                1000                1005

Gly Arg Gln Lys Val Val Thr Leu Thr Asp Thr Thr Asn Gln Lys Thr
    1010                1015                1020

Leu Gln Ala Ile Tyr Leu Ala Leu Gln Asp Ser Gly Leu Glu Val Asn
1025                1030                1035                1040

Ile Val Thr Asp Ser Gln Tyr Ala Leu Gly Ile Ile Gln Ala Gln Pro
            1045                1050                1055

Asp Gln Ser Glu Ser Glu Leu Val Asn Gln Ile Ile Glu Gln Leu Ile
        1060                1065                1070

Lys Lys Glu Lys Val Tyr Leu Ala Trp Val Pro Ala His Lys Gly Ile
    1075                1080                1085

Gly Gly Asn Glu Gln Val Asp Lys Leu Val Ser Ala Gly Ile Arg Lys
1090                1095                1100

Val Leu Phe Leu Asp Gly Ile Asp Lys Ala Gln Asp Glu His Glu Lys
1105                1110                1115                1120

Tyr His Ser Asn Trp Arg Ala Met Ala Ser Asp Phe Asn Leu Pro Pro
            1125                1130                1135

Val Val Ala Lys Glu Ile Val Ala Ser Cys Asp Lys Cys Gln Leu Lys
        1140                1145                1150

Gly Glu Ala Met His Gly Gln Val Asp Cys Ser Pro Gly Ile Trp Gln
    1155                1160                1165

Leu Cys Thr His Leu Glu Gly Lys Val Ile Leu Val Ala Val His Val
1170                1175                1180

Ala Ser Gly Tyr Ile Glu Ala Glu Val Ile Pro Ala Glu Thr Gly Gln
1185                1190                1195                1200

Glu Thr Ala Tyr Phe Leu Leu Lys Leu Ala Gly Arg Trp Pro Val Lys
            1205                1210                1215

Thr Ile His Thr Asn Gly Ser Asn Phe Thr Gly Ala Thr Val Lys Ala
        1220                1225                1230

Ala Cys Trp Trp Ala Gly Ile Lys Gln Glu Phe Gly Ile Pro Tyr Asn
    1235                1240                1245

Pro Gln Ser Gln Gly Val Val Ser Met Asn Lys Glu Leu Lys Lys Ile
1250                1255                1260

Ile Gly Gln Arg Asp Gln Ala Glu His Leu Lys Thr Ala Val Gln Met
1265                1270                1275                1280

Ala Val Phe Ile His Asn Phe Lys Arg Lys Gly Gly Ile Gly Gly Tyr
            1285                1290                1295

Ser Ala Gly Glu Arg Ile Val Asp Ile Ile Ala Thr Asp Ile Gln Thr
        1300                1305                1310

Lys Glu Leu Gln Lys Gln Ile Thr Lys Ile Gln Asn Phe Arg Val Tyr
    1315                1320                1325

Tyr Arg Asp Ser Arg Asn Pro Leu Trp Lys Gly Pro Ala Lys Leu Leu
1330                1335                1340

Trp Lys Gly Glu Gly Ala Val Val Ile Gln Asp Asn Ser Asp Ile Lys
1345                1350                1355                1360

Val Val Pro Arg Arg Lys Ala Lys Ile Ile Arg Asp Tyr Gly Lys Gln
            1365                1370                1375

Met Ala Gly Asp Asp Cys Val Ala Ser Arg Gln Asp Glu Asp Gly Ala
        1380                1385                1390

<210> SEQ ID NO 30
<211> LENGTH: 2568
<212> TYPE: DNA
```

<213> ORGANISM: Human immunodeficiency virus
<220> FEATURE:
<223> OTHER INFORMATION: HIV envelope protein env (98H)

<400> SEQUENCE: 30

| | | | | | |
|---|---|---|---|---|---|
| atgagggcca | aggagatgag | gaagagctgc | cagcacctga | gaaagtgggg | catcctgctg | 60 |
| ttcggcgtgc | tgatgatctg | cagcgccgag | gagaagctgt | gggtgacagt | gtactacggc | 120 |
| gtgcctgtgt | ggaaggaggc | caccaccacc | ctgttctgtg | cctcggacgc | caaggcccac | 180 |
| cacgccgagg | cccataatgt | gtgggctacc | cacgcctgtg | tgcccaccga | tcccaatcct | 240 |
| caggaggtga | tcctggagaa | cgtgaccgag | aagtacaaca | tgtggaagaa | caacatggtg | 300 |
| gaccagatgc | acgaggacat | catcagcctg | tgggaccaga | gcctgaagcc | ctgtgtgaag | 360 |
| ctgaccccc | tgtgtgtgac | cctgaactgt | accaacgcca | cctacaccaa | cagcgacagc | 420 |
| aagaacagca | ccagcaacag | cagcctggag | gacagcggca | agggcgacat | gaactgtagc | 480 |
| ttcgacgtga | ccacctccat | cgacaagaag | aagaaaaccg | agtacgccat | cttcgacaag | 540 |
| ctggacgtga | tgaacatcgg | caacggccgc | tacaccctgc | tgaactgtaa | caccagcgtg | 600 |
| atcacccagg | cctgccccaa | gatgagcttc | gagcccatcc | ccatccacta | ctgtacccct | 660 |
| gccggctacg | ccatcctgaa | gtgtaacgac | aacaagttca | acggcaccgg | ccctgtacc | 720 |
| aacgtcagca | ccatccagtg | tacccacggc | atcaagcctg | tggtgtccac | ccagctgctg | 780 |
| ctgaacggca | gcctggccga | gggcggcgag | gtgatcatca | ggagcgagaa | cctgaccgac | 840 |
| aacgccaaga | ccatcatcgt | gcagctgaag | gagcccgtgg | agatcaactg | tacccggccc | 900 |
| aacaacaaca | cccggaagag | catccacatg | ggccctggag | ccgccttcta | cgctcggggc | 960 |
| gaagtgatcg | gcgacatcag | acaggccac | tgtaacatca | gcggggcag | gtggaatgat | 1020 |
| accctgaagc | agatcgccaa | gaagctgagg | gagcagttca | caagaccat | ctccctgaac | 1080 |
| cagagcagcg | gcggagacct | ggagatcgtg | atgcacacct | tcaactgtgg | cggcgagttc | 1140 |
| ttctactgta | acacaaccca | gctgttcaac | tccacctgga | cgagaacga | caccacctgg | 1200 |
| aataataccg | ccggcagcaa | caacaacagg | accatcacac | tgccctgccg | gatcaagcag | 1260 |
| atcatcaacc | ggtggcagga | agtgggcaag | gctatgtacg | cccctcccat | cagcggccct | 1320 |
| atcaactgcc | tgagcaacat | caccggcctg | ctgctgacca | gagatggcgg | cgacaacaac | 1380 |
| aataccatcg | agaccttcag | acctggcggc | ggagatatga | gagacaactg | gcggagcgag | 1440 |
| ctgtacaagt | acaaggttgt | gaggatcgag | cccctgggca | tcgcccccac | caaggccaag | 1500 |
| agaagagtgg | tgcagcggga | gaagagagct | gtgggcatcg | gcgccatgtt | tctgggcttt | 1560 |
| ctggagccg | ccggaagcac | aatgggagcc | gcctcggtga | ccctgaccgt | gcaggccaga | 1620 |
| ctgctgctgt | ccggcattgt | gcagcagcag | aacaacctgc | tgagagccat | cgaggccag | 1680 |
| cagcacctgc | tccagctgac | agtgtggggc | atcaagcagc | tccaggccag | ggtgctggcc | 1740 |
| atggagagat | acctgaagga | ccagcaactg | ctcggcatct | ggggctgtag | cggcaagctg | 1800 |
| atctgtacca | ccaacgtgcc | ctggaacgcc | agctggagca | acaagagcct | ggacaagatc | 1860 |
| tggcacaaca | tgacctggat | ggagtgggac | cgggagatcg | acaactacac | aaagctgatc | 1920 |
| tacaccctga | tcgaggccag | ccagatccag | caggagaaga | acgagcagga | gctgctggag | 1980 |
| ctggacagct | gggccagcct | gtggagctgg | ttcgacatca | gcaagtggct | gtggtacatc | 2040 |
| ggcgtgttca | tcatcgtgat | cggcggcctg | gttggtctga | gatcgtgtt | cgccgtgctg | 2100 |
| tccatcgtga | acagagtgag | gcagggctac | agccccctga | gcttcagac | cagactgcct | 2160 |
| gctccgcggg | gccccgatag | acccgagggc | atcgaggagg | gcgaggaga | gagagacagg | 2220 |

-continued

```
gacaggagcg accagctggt gacaggcttc ctggccctga tctgggacga tctgaggagc    2280
ctgtgcctgt tcagctacca ccggctgaga gatctgctgc tgatcgtggc cagaatcgtg    2340
gaactgctgg gcagaagagg ctgggaggcc ctgaagtact ggtggaatct gctccagtac    2400
tggattcagg agctgaagaa cagcgccgtg tccctgctga atgccaccgc catcgccgtg    2460
gccgagggaa ccgacagaat catcgaggtg gtgcagagaa tcggcagagc catcctgcac    2520
atccccggga gaatcagaca gggcctggaa agagccctgc tgtgatga                 2568
```

<210> SEQ ID NO 31
<211> LENGTH: 854
<212> TYPE: PRT
<213> ORGANISM: Human immunodeficiency virus
<220> FEATURE:
<223> OTHER INFORMATION: HIV envelope protein env (98H)

<400> SEQUENCE: 31

```
Met Arg Ala Lys Glu Met Arg Lys Ser Cys Gln His Leu Arg Lys Trp
  1               5                  10                  15

Gly Ile Leu Leu Phe Gly Val Leu Met Ile Cys Ser Ala Glu Glu Lys
             20                  25                  30

Leu Trp Val Thr Val Tyr Tyr Gly Val Pro Val Trp Lys Glu Ala Thr
         35                  40                  45

Thr Thr Leu Phe Cys Ala Ser Asp Ala Lys Ala His His Ala Glu Ala
     50                  55                  60

His Asn Val Trp Ala Thr His Ala Cys Val Pro Thr Asp Pro Asn Pro
 65                  70                  75                  80

Gln Glu Val Ile Leu Glu Asn Val Thr Glu Lys Tyr Asn Met Trp Lys
                 85                  90                  95

Asn Asn Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Ala Thr Tyr Thr Asn Ser Asp Ser Lys Asn Ser Thr
    130                 135                 140

Ser Asn Ser Ser Leu Glu Asp Ser Gly Lys Gly Asp Met Asn Cys Ser
145                 150                 155                 160

Phe Asp Val Thr Thr Ser Ile Asp Lys Lys Lys Thr Glu Tyr Ala
                165                 170                 175

Ile Phe Asp Lys Leu Asp Val Met Asn Ile Gly Asn Gly Arg Tyr Thr
            180                 185                 190

Leu Leu Asn Cys Asn Thr Ser Val Ile Thr Gln Ala Cys Pro Lys Met
        195                 200                 205

Ser Phe Glu Pro Ile Pro Ile His Tyr Cys Thr Pro Ala Gly Tyr Ala
    210                 215                 220

Ile Leu Lys Cys Asn Asp Asn Lys Phe Asn Gly Thr Gly Pro Cys Thr
225                 230                 235                 240

Asn Val Ser Thr Ile Gln Cys Thr His Gly Ile Lys Pro Val Val Ser
                245                 250                 255

Thr Gln Leu Leu Leu Asn Gly Ser Leu Ala Glu Gly Gly Glu Val Ile
            260                 265                 270

Ile Arg Ser Glu Asn Leu Thr Asp Asn Ala Lys Thr Ile Ile Val Gln
        275                 280                 285

Leu Lys Glu Pro Val Glu Ile Asn Cys Thr Arg Pro Asn Asn Asn Thr
    290                 295                 300

Arg Lys Ser Ile His Met Gly Pro Gly Ala Ala Phe Tyr Ala Arg Gly
```

```
            305                 310                 315                 320
Glu Val Ile Gly Asp Ile Arg Gln Ala His Cys Asn Ile Ser Arg Gly
                    325                 330                 335

Arg Trp Asn Asp Thr Leu Lys Gln Ile Ala Lys Lys Leu Arg Glu Gln
                    340                 345                 350

Phe Asn Lys Thr Ile Ser Leu Asn Gln Ser Ser Gly Gly Asp Leu Glu
                    355                 360                 365

Ile Val Met His Thr Phe Asn Cys Gly Gly Glu Phe Phe Tyr Cys Asn
                370                 375                 380

Thr Thr Gln Leu Phe Asn Ser Thr Trp Asn Glu Asn Asp Thr Thr Trp
385                 390                 395                 400

Asn Asn Thr Ala Gly Ser Asn Asn Glu Thr Ile Thr Leu Pro Cys
                    405                 410                 415

Arg Ile Lys Gln Ile Ile Asn Arg Trp Gln Glu Val Gly Lys Ala Met
                    420                 425                 430

Tyr Ala Pro Pro Ile Ser Gly Pro Ile Asn Cys Leu Ser Asn Ile Thr
                    435                 440                 445

Gly Leu Leu Leu Thr Arg Asp Gly Gly Asp Asn Asn Asn Thr Ile Glu
450                 455                 460

Thr Phe Arg Pro Gly Gly Gly Asp Met Arg Asp Asn Trp Arg Ser Glu
465                 470                 475                 480

Leu Tyr Lys Tyr Lys Val Val Arg Ile Glu Pro Leu Gly Ile Ala Pro
                    485                 490                 495

Thr Lys Ala Lys Arg Arg Val Val Gln Arg Glu Lys Arg Ala Val Gly
                    500                 505                 510

Ile Gly Ala Met Phe Leu Gly Phe Leu Gly Ala Ala Gly Ser Thr Met
                    515                 520                 525

Gly Ala Ala Ser Val Thr Leu Thr Val Gln Ala Arg Leu Leu Leu Ser
                    530                 535                 540

Gly Ile Val Gln Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                    565                 570                 575

Arg Val Leu Ala Met Glu Arg Tyr Leu Lys Asp Gln Gln Leu Leu Gly
                    580                 585                 590

Ile Trp Gly Cys Ser Gly Lys Leu Ile Cys Thr Thr Asn Val Pro Trp
                    595                 600                 605

Asn Ala Ser Trp Ser Asn Lys Ser Leu Asp Lys Ile Trp His Asn Met
                    610                 615                 620

Thr Trp Met Glu Trp Asp Arg Glu Ile Asp Asn Tyr Thr Lys Leu Ile
625                 630                 635                 640

Tyr Thr Leu Ile Glu Ala Ser Gln Ile Gln Gln Glu Lys Asn Glu Gln
                    645                 650                 655

Glu Leu Leu Glu Leu Asp Ser Trp Ala Ser Leu Trp Ser Trp Phe Asp
                    660                 665                 670

Ile Ser Lys Trp Leu Trp Tyr Ile Gly Val Phe Ile Ile Val Ile Gly
                    675                 680                 685

Gly Leu Val Gly Leu Lys Ile Val Phe Ala Val Leu Ser Ile Val Asn
                    690                 695                 700

Arg Val Arg Gln Gly Tyr Ser Pro Leu Ser Phe Gln Thr Arg Leu Pro
705                 710                 715                 720

Ala Pro Arg Gly Pro Asp Arg Pro Glu Gly Ile Glu Glu Gly Gly Gly
                    725                 730                 735
```

-continued

```
Glu Arg Asp Arg Asp Arg Ser Asp Gln Leu Val Thr Gly Phe Leu Ala
            740                 745                 750

Leu Ile Trp Asp Asp Leu Arg Ser Leu Cys Leu Phe Ser Tyr His Arg
            755                 760                 765

Leu Arg Asp Leu Leu Leu Ile Val Ala Arg Ile Val Glu Leu Leu Gly
            770                 775                 780

Arg Arg Gly Trp Glu Ala Leu Lys Tyr Trp Trp Asn Leu Leu Gln Tyr
785                 790                 795                 800

Trp Ile Gln Glu Leu Lys Asn Ser Ala Val Ser Leu Leu Asn Ala Thr
                805                 810                 815

Ala Ile Ala Val Ala Glu Gly Thr Asp Arg Ile Ile Glu Val Val Gln
            820                 825                 830

Arg Ile Gly Arg Ala Ile Leu His Ile Pro Arg Arg Ile Arg Gln Gly
            835                 840                 845

Leu Glu Arg Ala Leu Leu
    850

<210> SEQ ID NO 32
<211> LENGTH: 957
<212> TYPE: PRT
<213> ORGANISM: Artificial Sequence
<220> FEATURE:
<223> OTHER INFORMATION: Description of Artificial Sequence:fusion
      protein HIV mIP10hMCP-3 env (clade B)

<400> SEQUENCE: 32

Met Asn Pro Ser Ala Ala Val Ile Phe Cys Leu Ile Leu Leu Gly Leu
  1               5                  10                  15

Ser Gly Thr Gln Gly Ile Leu Asp Ala Gln Pro Val Gly Ile Asn Thr
             20                  25                  30

Ser Thr Thr Cys Cys Tyr Arg Phe Ile Asn Lys Lys Ile Pro Lys Gln
         35                  40                  45

Arg Leu Glu Ser Tyr Arg Arg Thr Thr Ser Ser His Cys Pro Arg Glu
     50                  55                  60

Ala Val Ile Phe Lys Thr Lys Leu Asp Lys Glu Ile Cys Ala Asp Pro
 65                  70                  75                  80

Thr Gln Lys Trp Val Gln Asp Phe Met Lys His Leu Asp Lys Lys Thr
                 85                  90                  95

Gln Thr Pro Lys Leu Ala Ser Gly Arg Ala Lys Glu Met Arg Lys Ser
            100                 105                 110

Cys Gln His Leu Arg Lys Trp Gly Ile Leu Leu Phe Gly Val Leu Met
        115                 120                 125

Ile Cys Ser Ala Glu Glu Lys Leu Trp Val Thr Val Tyr Tyr Gly Val
    130                 135                 140

Pro Val Trp Lys Glu Ala Thr Thr Thr Leu Phe Cys Ala Ser Asp Ala
145                 150                 155                 160

Lys Ala His His Ala Glu Ala His Asn Val Trp Ala Thr His Ala Cys
                165                 170                 175

Val Pro Thr Asp Pro Asn Pro Gln Glu Val Ile Leu Glu Asn Val Thr
            180                 185                 190

Glu Lys Tyr Asn Met Trp Lys Asn Asn Met Val Asp Gln Met His Glu
        195                 200                 205

Asp Ile Ile Ser Leu Trp Asp Gln Ser Leu Lys Pro Cys Val Lys Leu
    210                 215                 220

Thr Pro Leu Cys Val Thr Leu Asn Cys Thr Asn Ala Thr Tyr Thr Asn
225                 230                 235                 240
```

-continued

Ser Asp Ser Lys Asn Ser Thr Ser Asn Ser Ser Leu Glu Asp Ser Gly
            245                 250                 255

Lys Gly Asp Met Asn Cys Ser Phe Asp Val Thr Ser Ile Asp Lys
            260                 265                 270

Lys Lys Lys Thr Glu Tyr Ala Ile Phe Asp Lys Leu Asp Val Met Asn
            275                 280                 285

Ile Gly Asn Gly Arg Tyr Thr Leu Leu Asn Cys Asn Thr Ser Val Ile
            290                 295                 300

Thr Gln Ala Cys Pro Lys Met Ser Phe Glu Pro Ile Pro Ile His Tyr
305                 310                 315                 320

Cys Thr Pro Ala Gly Tyr Ala Ile Leu Lys Cys Asn Asp Asn Lys Phe
                    325                 330                 335

Asn Gly Thr Gly Pro Cys Thr Asn Val Ser Thr Ile Gln Cys Thr His
                    340                 345                 350

Gly Ile Lys Pro Val Val Ser Thr Gln Leu Leu Asn Gly Ser Leu
                    355                 360                 365

Ala Glu Gly Gly Glu Val Ile Ile Arg Ser Glu Asn Leu Thr Asp Asn
            370                 375                 380

Ala Lys Thr Ile Ile Val Gln Leu Lys Glu Pro Val Glu Ile Asn Cys
385                 390                 395                 400

Thr Arg Pro Asn Asn Asn Thr Arg Lys Ser Ile His Met Gly Pro Gly
                    405                 410                 415

Ala Ala Phe Tyr Ala Arg Gly Glu Val Ile Gly Asp Ile Arg Gln Ala
                    420                 425                 430

His Cys Asn Ile Ser Arg Gly Arg Trp Asn Asp Thr Leu Lys Gln Ile
            435                 440                 445

Ala Lys Lys Leu Arg Glu Gln Phe Asn Lys Thr Ile Ser Leu Asn Gln
450                 455                 460

Ser Ser Gly Gly Asp Leu Glu Ile Val Met His Thr Phe Asn Cys Gly
465                 470                 475                 480

Gly Glu Phe Phe Tyr Cys Asn Thr Thr Gln Leu Phe Asn Ser Thr Trp
                    485                 490                 495

Asn Glu Asn Asp Thr Thr Trp Asn Asn Thr Ala Gly Ser Asn Asn Asn
            500                 505                 510

Glu Thr Ile Thr Leu Pro Cys Arg Ile Lys Gln Ile Ile Asn Arg Trp
            515                 520                 525

Gln Glu Val Gly Lys Ala Met Tyr Ala Pro Pro Ile Ser Gly Pro Ile
530                 535                 540

Asn Cys Leu Ser Asn Ile Thr Gly Leu Leu Leu Thr Arg Asp Gly Gly
545                 550                 555                 560

Asp Asn Asn Asn Thr Ile Glu Thr Phe Arg Pro Gly Gly Gly Asp Met
                    565                 570                 575

Arg Asp Asn Trp Arg Ser Glu Leu Tyr Lys Tyr Lys Val Val Arg Ile
            580                 585                 590

Glu Pro Leu Gly Ile Ala Pro Thr Lys Ala Lys Arg Arg Val Val Gln
            595                 600                 605

Arg Glu Lys Arg Ala Val Gly Ile Gly Ala Met Phe Leu Gly Phe Leu
            610                 615                 620

Gly Ala Ala Gly Ser Thr Met Gly Ala Ala Ser Val Thr Leu Thr Val
625                 630                 635                 640

Gln Ala Arg Leu Leu Leu Ser Gly Ile Val Gln Gln Asn Asn Leu
                    645                 650                 655

Leu Arg Ala Ile Glu Ala Gln Gln His Leu Leu Gln Leu Thr Val Trp
                    660                 665                 670

Gly Ile Lys Gln Leu Gln Ala Arg Val Leu Ala Met Glu Arg Tyr Leu
675 680 685

Lys Asp Gln Gln Leu Leu Gly Ile Trp Gly Cys Ser Gly Lys Leu Ile
690 695 700

Cys Thr Thr Asn Val Pro Trp Asn Ala Ser Trp Ser Asn Lys Ser Leu
705 710 715 720

Asp Lys Ile Trp His Asn Met Thr Trp Met Glu Trp Asp Arg Glu Ile
725 730 735

Asp Asn Tyr Thr Lys Leu Ile Tyr Thr Leu Ile Glu Ala Ser Gln Ile
740 745 750

Gln Gln Glu Lys Asn Glu Gln Glu Leu Leu Glu Leu Asp Ser Trp Ala
755 760 765

Ser Leu Trp Ser Trp Phe Asp Ile Ser Lys Trp Leu Trp Tyr Ile Gly
770 775 780

Val Phe Ile Ile Val Ile Gly Gly Leu Val Gly Leu Lys Ile Val Phe
785 790 795 800

Ala Val Leu Ser Ile Val Asn Arg Val Arg Gln Gly Tyr Ser Pro Leu
805 810 815

Ser Phe Gln Thr Arg Leu Pro Ala Pro Arg Gly Pro Asp Arg Pro Glu
820 825 830

Gly Ile Glu Glu Gly Gly Gly Glu Arg Asp Arg Asp Arg Ser Asp Gln
835 840 845

Leu Val Thr Gly Phe Leu Ala Leu Ile Trp Asp Asp Leu Arg Ser Leu
850 855 860

Cys Leu Phe Ser Tyr His Arg Leu Arg Asp Leu Leu Leu Ile Val Ala
865 870 875 880

Arg Ile Val Glu Leu Leu Gly Arg Arg Gly Trp Glu Ala Leu Lys Tyr
885 890 895

Trp Trp Asn Leu Leu Gln Tyr Trp Ile Gln Glu Leu Lys Asn Ser Ala
900 905 910

Val Ser Leu Leu Asn Ala Thr Ala Ile Ala Val Ala Glu Gly Thr Asp
915 920 925

Arg Ile Ile Glu Val Val Gln Arg Ile Gly Arg Ala Ile Leu His Ile
930 935 940

Pro Arg Arg Ile Arg Gln Gly Leu Glu Arg Ala Leu Leu
945 950 955

<210> SEQ ID NO 33
<211> LENGTH: 953
<212> TYPE: PRT
<213> ORGANISM: Artificial Sequence
<220> FEATURE:
<223> OTHER INFORMATION: Description of Artificial Sequence:fusion
protein HIV hIP10hMCP-3 env (clade B)

<400> SEQUENCE: 33

Met Asn Gln Thr Ala Ile Leu Ile Cys Cys Leu Ile Phe Leu Thr Leu
1 5 10 15

Ser Gly Ile Gln Gly Gln Pro Val Gly Ile Asn Thr Ser Thr Thr Cys
20 25 30

Cys Tyr Arg Phe Ile Asn Lys Lys Ile Pro Lys Gln Arg Leu Glu Ser
35 40 45

Tyr Arg Arg Thr Thr Ser Ser His Cys Pro Arg Glu Ala Val Ile Phe
50 55 60

Lys Thr Lys Leu Asp Lys Glu Ile Cys Ala Asp Pro Thr Gln Lys Trp
65 70 75 80

-continued

Val Gln Asp Phe Met Lys His Leu Asp Lys Lys Thr Gln Thr Pro Lys
                85                  90                  95

Leu Ala Ser Gly Arg Ala Lys Glu Met Arg Lys Ser Cys Gln His Leu
            100                 105                 110

Arg Lys Trp Gly Ile Leu Leu Phe Gly Val Leu Met Ile Cys Ser Ala
        115                 120                 125

Glu Glu Lys Leu Trp Val Thr Val Tyr Tyr Gly Val Pro Val Trp Lys
    130                 135                 140

Glu Ala Thr Thr Thr Leu Phe Cys Ala Ser Asp Ala Lys Ala His His
145                 150                 155                 160

Ala Glu Ala His Asn Val Trp Ala Thr His Ala Cys Val Pro Thr Asp
                165                 170                 175

Pro Asn Pro Gln Glu Val Ile Leu Glu Asn Val Thr Glu Lys Tyr Asn
            180                 185                 190

Met Trp Lys Asn Asn Met Val Asp Gln Met His Glu Asp Ile Ile Ser
        195                 200                 205

Leu Trp Asp Gln Ser Leu Lys Pro Cys Val Lys Leu Thr Pro Leu Cys
    210                 215                 220

Val Thr Leu Asn Cys Thr Asn Ala Thr Tyr Thr Asn Ser Asp Ser Lys
225                 230                 235                 240

Asn Ser Thr Ser Asn Ser Ser Leu Glu Asp Ser Gly Lys Gly Asp Met
                245                 250                 255

Asn Cys Ser Phe Asp Val Thr Thr Ser Ile Asp Lys Lys Lys Lys Thr
            260                 265                 270

Glu Tyr Ala Ile Phe Asp Lys Leu Asp Val Met Asn Ile Gly Asn Gly
        275                 280                 285

Arg Tyr Thr Leu Leu Asn Cys Asn Thr Ser Val Ile Thr Gln Ala Cys
    290                 295                 300

Pro Lys Met Ser Phe Glu Pro Ile Pro Ile His Tyr Cys Thr Pro Ala
305                 310                 315                 320

Gly Tyr Ala Ile Leu Lys Cys Asn Asp Asn Lys Phe Asn Gly Thr Gly
                325                 330                 335

Pro Cys Thr Asn Val Ser Thr Ile Gln Cys Thr His Gly Ile Lys Pro
            340                 345                 350

Val Val Ser Thr Gln Leu Leu Leu Asn Gly Ser Leu Ala Glu Gly Gly
        355                 360                 365

Glu Val Ile Ile Arg Ser Glu Asn Leu Thr Asp Asn Ala Lys Thr Ile
    370                 375                 380

Ile Val Gln Leu Lys Glu Pro Val Glu Ile Asn Cys Thr Arg Pro Asn
385                 390                 395                 400

Asn Asn Thr Arg Lys Ser Ile His Met Gly Pro Gly Ala Ala Phe Tyr
                405                 410                 415

Ala Arg Gly Glu Val Ile Gly Asp Ile Arg Gln Ala His Cys Asn Ile
            420                 425                 430

Ser Arg Gly Arg Trp Asn Asp Thr Leu Lys Gln Ile Ala Lys Lys Leu
        435                 440                 445

Arg Glu Gln Phe Asn Lys Thr Ile Ser Leu Asn Gln Ser Ser Gly Gly
    450                 455                 460

Asp Leu Glu Ile Val Met His Thr Phe Asn Cys Gly Gly Glu Phe Phe
465                 470                 475                 480

Tyr Cys Asn Thr Thr Gln Leu Phe Asn Ser Thr Trp Asn Glu Asn Asp
                485                 490                 495

Thr Thr Trp Asn Asn Thr Ala Gly Ser Asn Asn Asn Glu Thr Ile Thr

```
                500             505             510
Leu Pro Cys Arg Ile Lys Gln Ile Ile Asn Arg Trp Gln Glu Val Gly
        515                 520                 525
Lys Ala Met Tyr Ala Pro Pro Ile Ser Gly Pro Ile Asn Cys Leu Ser
        530                 535                 540
Asn Ile Thr Gly Leu Leu Leu Thr Arg Asp Gly Gly Asp Asn Asn Asn
545                 550                 555                 560
Thr Ile Glu Thr Phe Arg Pro Gly Gly Gly Asp Met Arg Asp Asn Trp
                565                 570                 575
Arg Ser Glu Leu Tyr Lys Tyr Lys Val Val Arg Ile Glu Pro Leu Gly
                580                 585                 590
Ile Ala Pro Thr Lys Ala Lys Arg Arg Val Val Gln Arg Glu Lys Arg
                595                 600                 605
Ala Val Gly Ile Gly Ala Met Phe Leu Gly Phe Leu Gly Ala Ala Gly
                610                 615                 620
Ser Thr Met Gly Ala Ala Ser Val Thr Leu Thr Val Gln Ala Arg Leu
625                 630                 635                 640
Leu Leu Ser Gly Ile Val Gln Gln Gln Asn Asn Leu Leu Arg Ala Ile
                645                 650                 655
Glu Ala Gln Gln His Leu Leu Gln Leu Thr Val Trp Gly Ile Lys Gln
                660                 665                 670
Leu Gln Ala Arg Val Leu Ala Met Glu Arg Tyr Leu Lys Asp Gln Gln
                675                 680                 685
Leu Leu Gly Ile Trp Gly Cys Ser Gly Lys Leu Ile Cys Thr Thr Asn
                690                 695                 700
Val Pro Trp Asn Ala Ser Trp Ser Asn Lys Ser Leu Asp Lys Ile Trp
705                 710                 715                 720
His Asn Met Thr Trp Met Glu Trp Asp Arg Glu Ile Asp Asn Tyr Thr
                725                 730                 735
Lys Leu Ile Tyr Thr Leu Ile Glu Ala Ser Gln Ile Gln Gln Glu Lys
                740                 745                 750
Asn Glu Gln Glu Leu Leu Glu Leu Asp Ser Trp Ala Ser Leu Trp Ser
                755                 760                 765
Trp Phe Asp Ile Ser Lys Trp Leu Trp Tyr Ile Gly Val Phe Ile Ile
                770                 775                 780
Val Ile Gly Gly Leu Val Gly Leu Lys Ile Val Phe Ala Val Leu Ser
785                 790                 795                 800
Ile Val Asn Arg Val Arg Gln Gly Tyr Ser Pro Leu Ser Phe Gln Thr
                805                 810                 815
Arg Leu Pro Ala Pro Arg Gly Pro Asp Arg Pro Glu Gly Ile Glu Glu
                820                 825                 830
Gly Gly Gly Glu Arg Asp Arg Asp Arg Ser Asp Gln Leu Val Thr Gly
                835                 840                 845
Phe Leu Ala Leu Ile Trp Asp Asp Leu Arg Ser Leu Cys Leu Phe Ser
                850                 855                 860
Tyr His Arg Leu Arg Asp Leu Leu Leu Ile Val Ala Arg Ile Val Glu
865                 870                 875                 880
Leu Leu Gly Arg Arg Gly Trp Glu Ala Leu Lys Tyr Trp Trp Asn Leu
                885                 890                 895
Leu Gln Tyr Trp Ile Gln Glu Leu Lys Asn Ser Ala Val Ser Leu Leu
                900                 905                 910
Asn Ala Thr Ala Ile Ala Val Ala Glu Gly Thr Asp Arg Ile Ile Glu
                915                 920                 925
```

```
Val Val Gln Arg Ile Gly Arg Ala Ile Leu His Ile Pro Arg Arg Ile
            930             935                 940

Arg Gln Gly Leu Glu Arg Ala Leu Leu
945                 950

<210> SEQ ID NO 34
<211> LENGTH: 955
<212> TYPE: PRT
<213> ORGANISM: Artificial Sequence
<220> FEATURE:
<223> OTHER INFORMATION: Description of Artificial Sequence:fusion
      protein HIV huMCP-3 env

<400> SEQUENCE: 34

Met Lys Ala Ser Ala Ala Leu Leu Cys Leu Leu Leu Thr Ala Ala Ala
  1               5                  10                  15

Phe Ser Pro Gln Gly Leu Ala Gly Gln Pro Val Gly Ile Asn Thr Ser
                 20                  25                  30

Thr Thr Cys Cys Tyr Arg Phe Ile Asn Lys Lys Ile Pro Lys Gln Arg
             35                  40                  45

Leu Glu Ser Tyr Arg Arg Thr Thr Ser Ser His Cys Pro Arg Glu Ala
     50                  55                  60

Val Ile Phe Lys Thr Lys Leu Asp Lys Glu Ile Cys Ala Asp Pro Thr
 65                  70                  75                  80

Gln Lys Trp Val Gln Asp Phe Met Lys His Leu Asp Lys Lys Thr Gln
                 85                  90                  95

Thr Pro Lys Leu Ala Ser Arg Ala Lys Glu Met Arg Lys Ser Cys Gln
                100                 105                 110

His Leu Arg Lys Trp Gly Ile Leu Leu Phe Gly Val Leu Met Ile Cys
            115                 120                 125

Ser Ala Glu Glu Lys Leu Trp Val Thr Val Tyr Tyr Gly Val Pro Val
130                 135                 140

Trp Lys Glu Ala Thr Thr Thr Leu Phe Cys Ala Ser Asp Ala Lys Ala
145                 150                 155                 160

His His Ala Glu Ala His Asn Val Trp Ala Thr His Ala Cys Val Pro
                165                 170                 175

Thr Asp Pro Asn Pro Gln Glu Val Ile Leu Glu Asn Val Thr Glu Lys
            180                 185                 190

Tyr Asn Met Trp Lys Asn Asn Met Val Asp Gln Met His Glu Asp Ile
        195                 200                 205

Ile Ser Leu Trp Asp Gln Ser Leu Lys Pro Cys Val Lys Leu Thr Pro
    210                 215                 220

Leu Cys Val Thr Leu Asn Cys Thr Asn Ala Thr Tyr Thr Asn Ser Asp
225                 230                 235                 240

Ser Lys Asn Ser Thr Ser Asn Ser Ser Leu Glu Asp Ser Gly Lys Gly
                245                 250                 255

Asp Met Asn Cys Ser Phe Asp Val Thr Thr Ser Ile Asp Lys Lys Lys
            260                 265                 270

Lys Thr Glu Tyr Ala Ile Phe Asp Lys Leu Asp Val Met Asn Ile Gly
        275                 280                 285

Asn Gly Arg Tyr Thr Leu Leu Asn Cys Asn Thr Ser Val Ile Thr Gln
    290                 295                 300

Ala Cys Pro Lys Met Ser Phe Glu Pro Ile Pro Ile His Tyr Cys Thr
305                 310                 315                 320

Pro Ala Gly Tyr Ala Ile Leu Lys Cys Asn Asp Asn Lys Phe Asn Gly
                325                 330                 335
```

-continued

```
Thr Gly Pro Cys Thr Asn Val Ser Thr Ile Gln Cys Thr His Gly Ile
            340                 345                 350

Lys Pro Val Val Ser Thr Gln Leu Leu Asn Gly Ser Leu Ala Glu
            355                 360                 365

Gly Gly Glu Val Ile Ile Arg Ser Glu Asn Leu Thr Asp Asn Ala Lys
370                 375                 380

Thr Ile Ile Val Gln Leu Lys Glu Pro Val Glu Ile Asn Cys Thr Arg
385                 390                 395                 400

Pro Asn Asn Asn Thr Arg Lys Ser Ile His Met Gly Pro Gly Ala Ala
                    405                 410                 415

Phe Tyr Ala Arg Gly Glu Val Ile Gly Asp Ile Arg Gln Ala His Cys
            420                 425                 430

Asn Ile Ser Arg Gly Arg Trp Asn Asp Thr Leu Lys Gln Ile Ala Lys
            435                 440                 445

Lys Leu Arg Glu Gln Phe Asn Lys Thr Ile Ser Leu Asn Gln Ser Ser
450                 455                 460

Gly Gly Asp Leu Glu Ile Val Met His Thr Phe Asn Cys Gly Gly Glu
465                 470                 475                 480

Phe Phe Tyr Cys Asn Thr Thr Gln Leu Phe Asn Ser Thr Trp Asn Glu
                    485                 490                 495

Asn Asp Thr Thr Trp Asn Asn Thr Ala Gly Ser Asn Asn Asn Glu Thr
            500                 505                 510

Ile Thr Leu Pro Cys Arg Ile Lys Gln Ile Ile Asn Arg Trp Gln Glu
            515                 520                 525

Val Gly Lys Ala Met Tyr Ala Pro Pro Ile Ser Gly Pro Ile Asn Cys
530                 535                 540

Leu Ser Asn Ile Thr Gly Leu Leu Leu Thr Arg Asp Gly Gly Asp Asn
545                 550                 555                 560

Asn Asn Thr Ile Glu Thr Phe Arg Pro Gly Gly Gly Asp Met Arg Asp
                    565                 570                 575

Asn Trp Arg Ser Glu Leu Tyr Lys Tyr Lys Val Val Arg Ile Glu Pro
            580                 585                 590

Leu Gly Ile Ala Pro Thr Lys Ala Lys Arg Arg Val Val Gln Arg Glu
            595                 600                 605

Lys Arg Ala Val Gly Ile Gly Ala Met Phe Leu Gly Phe Leu Gly Ala
610                 615                 620

Ala Gly Ser Thr Met Gly Ala Ala Ser Val Thr Leu Thr Val Gln Ala
625                 630                 635                 640

Arg Leu Leu Leu Ser Gly Ile Val Gln Gln Gln Asn Asn Leu Leu Arg
                    645                 650                 655

Ala Ile Glu Ala Gln Gln His Leu Leu Gln Leu Thr Val Trp Gly Ile
            660                 665                 670

Lys Gln Leu Gln Ala Arg Val Leu Ala Met Glu Arg Tyr Leu Lys Asp
            675                 680                 685

Gln Gln Leu Leu Gly Ile Trp Gly Cys Ser Gly Lys Leu Ile Cys Thr
690                 695                 700

Thr Asn Val Pro Trp Asn Ala Ser Trp Ser Asn Lys Ser Leu Asp Lys
705                 710                 715                 720

Ile Trp His Asn Met Thr Trp Met Glu Trp Asp Arg Glu Ile Asp Asn
                    725                 730                 735

Tyr Thr Lys Leu Ile Tyr Thr Leu Ile Glu Ala Ser Gln Ile Gln Gln
            740                 745                 750

Glu Lys Asn Glu Gln Glu Leu Leu Glu Leu Asp Ser Trp Ala Ser Leu
            755                 760                 765
```

```
Trp Ser Trp Phe Asp Ile Ser Lys Trp Leu Tyr Ile Gly Val Phe
    770                 775                 780
Ile Ile Val Ile Gly Gly Leu Val Gly Leu Lys Ile Val Phe Ala Val
785             790                 795                 800
Leu Ser Ile Val Asn Arg Val Arg Gln Gly Tyr Ser Pro Leu Ser Phe
                805                 810                 815
Gln Thr Arg Leu Pro Ala Pro Arg Gly Pro Asp Arg Pro Glu Gly Ile
            820                 825                 830
Glu Glu Gly Gly Gly Glu Arg Asp Arg Asp Arg Ser Asp Gln Leu Val
        835                 840                 845
Thr Gly Phe Leu Ala Leu Ile Trp Asp Asp Leu Arg Ser Leu Cys Leu
    850                 855                 860
Phe Ser Tyr His Arg Leu Arg Asp Leu Leu Leu Ile Val Ala Arg Ile
865                 870                 875                 880
Val Glu Leu Leu Gly Arg Arg Gly Trp Glu Ala Leu Lys Tyr Trp Trp
                885                 890                 895
Asn Leu Leu Gln Tyr Trp Ile Gln Glu Leu Lys Asn Ser Ala Val Ser
            900                 905                 910
Leu Leu Asn Ala Thr Ala Ile Ala Val Ala Glu Gly Thr Asp Arg Ile
        915                 920                 925
Ile Glu Val Val Gln Arg Ile Gly Arg Ala Ile Leu His Ile Pro Arg
    930                 935                 940
Arg Ile Arg Gln Gly Leu Glu Arg Ala Leu Leu
945                 950                 955

<210> SEQ ID NO 35
<211> LENGTH: 4089
<212> TYPE: DNA
<213> ORGANISM: Artificial Sequence
<220> FEATURE:
<223> OTHER INFORMATION: Description of Artificial Sequence:fusion
      protein HIV LAMPpol

<400> SEQUENCE: 35
atggcgcccc gcagcgcccg gcgacccctg ctgctgctac tgctgttgct gctgctcggc      60
ctcatgcatt gtgcgtcagc agcaatgttt atggtgaaaa atggcaacgg accgcgtgc     120 ataatggcca acttctctgc tgccttctca gtgaactacg acaccaagag tggccctaag    180
aacatgaccc ttgacctgcc atcagatgcc acagtggtgc tcaaccgcag ctcctgtgga    240
aaagagaaca cttctgaccc cagtctcgtg attgcttttg aagaggacac atactcact    300 ctcaatttca cgagaaatgc aacacgttac agcgtccagc tcatgagttt tgtttataac    360
ttgtcagaca cacaccttt tccccaatgcg agctccaaag aaatcaagac tgtggaatct    420
ataactgaca tcagggcaga tatagataaa aaatacagat gtgttagtgg caccccaggtc    480 cacatgaaca acgtgaccgt aacgctccat gatgccacca tccaggcgta cctttccaac    540
agcagcttca gcaggggaga gacacgctgt gaacaagaca ggccttcccc aaccacagcg    600
ccccctgcgc cacccagccc ctcgccctca cccgtgccca gagccctc tgtggacaag    660 tacaacgtga gcggcaccaa cggacctgc ctgctggcca gcatggggct gcagctgaac    720
ctcacctatg agaggaagga caacacgacg gtgacaaggc ttctcaacat caaccccaac    780
aagacctcgg ccagcgggag ctgcggcgcc cacctggtga ctctggagct gcacagcgag    840
ggcaccaccg tcctgcttct ccagttcggg atgaatgcaa gttctagccg gtttttccta    900
caaggaatcc agttgaatac aattcttcct gacgccagag accctgcctt taaagctgcc    960
```

```
aacggctccc tgcgagcgct gcaggccaca gtcggcaatt cctacaagtg caacgcggag    1020
gagcacgtcc gtgtcacgaa ggcgttttca gtcaatatat tcaaagtgtg ggtccaggct    1080
ttcaaggtgg aaggtggcca gtttggctct gtggaggagt gtctgctgga cgagaacagc    1140
ctcgaggata tcggccctca gatcacgctc tggcagcggc cgctcgtcac agtacggatc    1200 gggggcaac tcaaggaggc gctgctcgcg gacgacacgg tcttggagga gatgtcgttg     1260
ccggggcggt ggaagccgaa gatgatcggg gggatcgggg gcttcatcaa ggtgcggcag    1320
tacgaccaga tcctcatcga gatctgcggg cacaaggcga tcgggacggt cctcgtcggc    1380
ccgacgccgg tcaacatcat cgggcggaac ctgttgaccc agatcggctg cacccttgaac  1440 ttccccatca gccctattga cggtgcccc gtgaagttga agccggggat ggacggcccc     1500
aaggtcaagc aatggccatt gacgaaagag aagatcaagg ccttagtcga aatctgtaca    1560
gagatggaga aggaagggaa gatcagcaag atcgggcctg agaacccta caacactcca     1620 gtcttcgcaa tcaagaagaa ggacagtacc aagtggagaa agctggtgga cttcagagag    1680
ctgaacaaga gaactcagga cttctgggaa gttcagctgg gcatcccaca tcccgctggg    1740
ttgaagaaga gaagtcagt gacagtgctg gatgtgggtg atgcctactt ctccgttccc      1800
ttggacgagg acttcaggaa gtacactgcc ttcacgatac ctagcatcaa caacgagaca    1860
ccaggcatcc gctaccagta caacgtgctg ccacagggat ggaagggatc accagccatc    1920
tttcaatcgt cgatgaccaa gatcctggag ccttccgca agcaaaaccc agacatcgtg    1980
atctatcagc tctacgtagg aagtgacctg gagatcgggc agcacaggac caagatcgag    2040
gagctgagac agcatctgtt gaggtgggga ctgaccacac cagacaagaa gcaccagaag    2100 gaacctcct tcctgtggat gggctacgaa ctgcatcctg acaagtggac agtgcagccc     2160
atcgtgctgc ctgagaagga cagctggact gtgaacgaca tacagaagct cgtgggcaag    2220
ttgaactggg caagccagat ctacccaggc atcaaagtta ggcagctgtg caagctgctt    2280
cgaggaacca aggcactgac agaagtgatc ccactgacag aggaagcaga gctagaactg    2340
gcagagaacc gagagatcct gaaggagcca gtacatggag tgtactacga cccaagcaag    2400
gacctgatcg cagagatcca gaagcagggg caaggccaat ggacctacca aatctaccag    2460
gagcccttca agaacctgaa gacaggcaag tacgcaagga tgaggggtgc ccacaccaac    2520
gatgtgaagc agctgacaga ggcagtgcag aagatcacca cagagagcat cgtgatctgg    2580
ggcaagactc ccaagttcaa gctgcccata cagaaggaga catgggagac atggtggacc    2640
gagtactggc aagccacctg gatccctgag tgggagttcg tgaacacccc tcccttggtg    2700
aaactgtggt atcagctgga aaggaaccc atcgtgggag cagagacctt ctacgtggat     2760
ggggcagcca acagggagac caagctgggc aaggcaggct acgtgaccaa ccgaggacga    2820
cagaaagtgg tgaccctgac tgacaccacc aaccagaaga ctctgcaagc catctaccta    2880
gctctgcaag acagcggact ggaagtgaac atcgtgacag actcacagta cgcactgggc    2940
atcatccaag cacaaccaga ccaatccgag tcagagctgg tgaaccagat catcgagcag    3000
ctgatcaaga aggagaaagt gtacctggca tgggtcccgg cgcacaaggg gatcgggggg    3060
aacgagcagg tcgacaagtt ggtctcggcg gggatccgga aggtgctgtt cctggacggg    3120
atcgataagg cccaagatga acatgagaag taccactcca actggcgcgc tatggccagc    3180
gacttcaacc tgccgccggt cgtcgcgaag gagatcgtcg ccagctgcga caagtgccag    3240
ctcaaggggg aggccatgca cgggcaagtc gactgcagtc cggggatctg gcagctgtgc    3300
acgcacctgg aggggaaggt gatcctggtc gcggtccacg tcgccagcgg gtatatcgag    3360
```

```
gcggaggtca tcccggctga cacggggcag gagacggcgt acttcctctt gaagctcgcg    3420
gggcggtggc cggtcaagac gatccacacg aacgggagca acttcacggg ggcgacggtc    3480
aaggccgcct gttggtgggc gggaatcaag caggaatttg gaattcccta caatccccaa    3540
tcgcaaggag tcgtgagcat gaacaaggag ctgaagaaga tcatcggaca aagggatcag    3600
gctgagcacc tgaagacagc agtgcagatg gcagtgttca tccacaactt caaaagaaaa    3660
ggggggattg gggggtacag tgcggggaa cggatcgtgg acatcatcgc caccgacatc    3720
caaaccaagg agctgcagaa gcagatcacc aagatccaga acttccgggt gtactaccgc    3780
gacagccgca acccactgtg gaagggacca gcaaagctcc tctggaaggg agagggggca    3840
gtggtgatcc aggacaacag tgacatcaaa gtggtgccaa ggcgcaaggc caagatcatc    3900
cgcgactatg gaaaacagat ggcagggat gattgtgtgg caagtagaca ggatgaggat    3960
gctagcggat ccgaattcac gctgatcccc atcgctgtgg gtggtgccct ggcggggctg    4020
gtcctcatcg tcctcatcgc ctacctcgtc ggcaggaaga ggagtcacgc aggctaccag    4080
actatctag                                                           4089
```

<210> SEQ ID NO 36
<211> LENGTH: 1362
<212> TYPE: PRT
<213> ORGANISM: Artificial Sequence
<220> FEATURE:
<223> OTHER INFORMATION: Description of Artificial Sequence:fusion
      protein HIV LAMPpol

<400> SEQUENCE: 36

```
Met Ala Pro Arg Ser Ala Arg Arg Pro Leu Leu Leu Leu Leu Leu
 1               5                  10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
        50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Ala Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
```

```
                225                 230                 235                 240
Leu Thr Tyr Glu Arg Lys Asp Asn Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
            275                 280                 285

Phe Gly Met Asn Ala Ser Ser Ser Arg Phe Phe Leu Gln Gly Ile Gln
            290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
            355                 360                 365

Gly Ser Val Glu Glu Cys Leu Leu Asp Glu Asn Ser Leu Glu Asp Ile
            370                 375                 380

Gly Pro Gln Ile Thr Leu Trp Gln Arg Pro Leu Val Thr Val Arg Ile
385                 390                 395                 400

Gly Gly Gln Leu Lys Glu Ala Leu Leu Ala Asp Asp Thr Val Leu Glu
                405                 410                 415

Glu Met Ser Leu Pro Gly Arg Trp Lys Pro Lys Met Ile Gly Gly Ile
            420                 425                 430

Gly Gly Phe Ile Lys Val Arg Gln Tyr Asp Gln Ile Leu Ile Glu Ile
            435                 440                 445

Cys Gly His Lys Ala Ile Gly Thr Val Leu Val Gly Pro Thr Pro Val
            450                 455                 460

Asn Ile Ile Gly Arg Asn Leu Leu Thr Gln Ile Gly Cys Thr Leu Asn
465                 470                 475                 480

Phe Pro Ile Ser Pro Ile Glu Thr Val Pro Val Lys Leu Lys Pro Gly
                485                 490                 495

Met Asp Gly Pro Lys Val Lys Gln Trp Pro Leu Thr Lys Glu Lys Ile
            500                 505                 510

Lys Ala Leu Val Glu Ile Cys Thr Glu Met Glu Lys Glu Gly Lys Ile
            515                 520                 525

Ser Lys Ile Gly Pro Glu Asn Pro Tyr Asn Thr Pro Val Phe Ala Ile
            530                 535                 540

Lys Lys Lys Asp Ser Thr Lys Trp Arg Lys Leu Val Asp Phe Arg Glu
545                 550                 555                 560

Leu Asn Lys Arg Thr Gln Asp Phe Trp Glu Val Gln Leu Gly Ile Pro
                565                 570                 575

His Pro Ala Gly Leu Lys Lys Lys Lys Ser Val Thr Val Leu Asp Val
            580                 585                 590

Gly Asp Ala Tyr Phe Ser Val Pro Leu Asp Glu Asp Phe Arg Lys Tyr
            595                 600                 605

Thr Ala Phe Thr Ile Pro Ser Ile Asn Asn Glu Thr Pro Gly Ile Arg
            610                 615                 620

Tyr Gln Tyr Asn Val Leu Pro Gln Gly Trp Lys Gly Ser Pro Ala Ile
625                 630                 635                 640

Phe Gln Ser Ser Met Thr Lys Ile Leu Glu Pro Phe Arg Lys Gln Asn
                645                 650                 655
```

-continued

```
Pro Asp Ile Val Ile Tyr Gln Leu Tyr Val Gly Ser Asp Leu Glu Ile
            660                 665                 670

Gly Gln His Arg Thr Lys Ile Glu Glu Leu Arg Gln His Leu Leu Arg
            675                 680                 685

Trp Gly Leu Thr Thr Pro Asp Lys Lys His Gln Lys Glu Pro Pro Phe
690                 695                 700

Leu Trp Met Gly Tyr Glu Leu His Pro Asp Lys Trp Thr Val Gln Pro
705                 710                 715                 720

Ile Val Leu Pro Glu Lys Asp Ser Trp Thr Val Asn Asp Ile Gln Lys
                725                 730                 735

Leu Val Gly Lys Leu Asn Trp Ala Ser Gln Ile Tyr Pro Gly Ile Lys
            740                 745                 750

Val Arg Gln Leu Cys Lys Leu Leu Arg Gly Thr Lys Ala Leu Thr Glu
            755                 760                 765

Val Ile Pro Leu Thr Glu Glu Ala Glu Leu Glu Leu Ala Glu Asn Arg
            770                 775                 780

Glu Ile Leu Lys Glu Pro Val His Gly Val Tyr Tyr Asp Pro Ser Lys
785                 790                 795                 800

Asp Leu Ile Ala Glu Ile Gln Lys Gln Gly Gln Gly Gln Trp Thr Tyr
                805                 810                 815

Gln Ile Tyr Gln Glu Pro Phe Lys Asn Leu Lys Thr Gly Lys Tyr Ala
            820                 825                 830

Arg Met Arg Gly Ala His Thr Asn Asp Val Lys Gln Leu Thr Glu Ala
            835                 840                 845

Val Gln Lys Ile Thr Thr Glu Ser Ile Val Ile Trp Gly Lys Thr Pro
            850                 855                 860

Lys Phe Lys Leu Pro Ile Gln Lys Glu Thr Trp Glu Thr Trp Trp Thr
865                 870                 875                 880

Glu Tyr Trp Gln Ala Thr Trp Ile Pro Glu Trp Glu Phe Val Asn Thr
                885                 890                 895

Pro Pro Leu Val Lys Leu Trp Tyr Gln Leu Glu Lys Glu Pro Ile Val
            900                 905                 910

Gly Ala Glu Thr Phe Tyr Val Asp Gly Ala Ala Asn Arg Glu Thr Lys
            915                 920                 925

Leu Gly Lys Ala Gly Tyr Val Thr Asn Arg Gly Arg Gln Lys Val Val
930                 935                 940

Thr Leu Thr Asp Thr Thr Asn Gln Lys Thr Leu Gln Ala Ile Tyr Leu
945                 950                 955                 960

Ala Leu Gln Asp Ser Gly Leu Glu Val Asn Ile Val Thr Asp Ser Gln
                965                 970                 975

Tyr Ala Leu Gly Ile Ile Gln Ala Gln Pro Asp Gln Ser Glu Ser Glu
            980                 985                 990

Leu Val Asn Gln Ile Ile Glu Gln Leu Ile Lys Lys Glu Lys Val Tyr
            995                 1000                1005

Leu Ala Trp Val Pro Ala His Lys Gly Ile Gly Gly Asn Glu Gln Val
        1010                1015                1020

Asp Lys Leu Val Ser Ala Gly Ile Arg Lys Val Leu Phe Leu Asp Gly
1025                1030                1035                1040

Ile Asp Lys Ala Gln Asp Glu His Glu Lys Tyr His Ser Asn Trp Arg
                1045                1050                1055

Ala Met Ala Ser Asp Phe Asn Leu Pro Pro Val Val Ala Lys Glu Ile
            1060                1065                1070

Val Ala Ser Cys Asp Lys Cys Gln Leu Lys Gly Glu Ala Met His Gly
        1075                1080                1085
```

```
Gln Val Asp Cys Ser Pro Gly Ile Trp Gln Leu Cys Thr His Leu Glu
    1090                1095                1100

Gly Lys Val Ile Leu Val Ala Val His Val Ala Ser Gly Tyr Ile Glu
1105                1110                1115                1120

Ala Glu Val Ile Pro Ala Glu Thr Gly Gln Thr Ala Tyr Phe Leu
            1125                1130                1135

Leu Lys Leu Ala Gly Arg Trp Pro Val Lys Thr Ile His Thr Asn Gly
        1140                1145                1150

Ser Asn Phe Thr Gly Ala Thr Val Lys Ala Ala Cys Trp Trp Ala Gly
        1155                1160                1165

Ile Lys Gln Glu Phe Gly Ile Pro Tyr Asn Pro Gln Ser Gln Gly Val
    1170                1175                1180

Val Ser Met Asn Lys Glu Leu Lys Lys Ile Ile Gly Gln Arg Asp Gln
1185                1190                1195                1200

Ala Glu His Leu Lys Thr Ala Val Gln Met Ala Val Phe Ile His Asn
            1205                1210                1215

Phe Lys Arg Lys Gly Gly Ile Gly Gly Tyr Ser Ala Gly Glu Arg Ile
        1220                1225                1230

Val Asp Ile Ile Ala Thr Asp Ile Gln Thr Lys Glu Leu Gln Lys Gln
        1235                1240                1245

Ile Thr Lys Ile Gln Asn Phe Arg Val Tyr Tyr Arg Asp Ser Arg Asn
    1250                1255                1260

Pro Leu Trp Lys Gly Pro Ala Lys Leu Leu Trp Lys Gly Glu Gly Ala
1265                1270                1275                1280

Val Val Ile Gln Asp Asn Ser Asp Ile Lys Val Val Pro Arg Arg Lys
            1285                1290                1295

Ala Lys Ile Ile Arg Asp Tyr Gly Lys Gln Met Ala Gly Asp Asp Cys
        1300                1305                1310

Val Ala Ser Arg Gln Asp Glu Asp Ala Ser Gly Ser Glu Phe Thr Leu
        1315                1320                1325

Ile Pro Ile Ala Val Gly Gly Ala Leu Ala Gly Leu Val Leu Ile Val
    1330                1335                1340

Leu Ile Ala Tyr Leu Val Gly Arg Lys Arg Ser His Ala Gly Tyr Gln
1345                1350                1355                1360

Thr Ile

<210> SEQ ID NO 37
<211> LENGTH: 2763
<212> TYPE: DNA
<213> ORGANISM: Artificial Sequence
<220> FEATURE:
<223> OTHER INFORMATION: Description of Artificial Sequence:fusion
      protein HIV LAMP-NTV

<400> SEQUENCE: 37
atggcgcccc gcagcgcccg gcgaccccctg ctgctgctac tgctgttgct gctgctcggc      60
ctcatgcatt gtgcgtcagc agcaatgttt atggtgaaaa atggcaacgg gaccgcgtgc    120
ataatggcca acttctctgc tgccttctca gtgaactacg acaccaagag tggccctaag    180
aacatgaccc ttgacctgcc atcagatgcc acagtggtgc tcaaccgcag ctcctgtgga    240
aaagagaaca cttctgaccc cagtctcgtg attgcttttg gaagaggaca tactcactca    300
ctcaatttca cgagaaatgc aacacgttac agcgtccagc tcatgagttt tgtttataac    360
ttgtcagaca caccttttt ccccaatgcg agctccaaag aaatcaagac tgtggaatct    420
ataactgaca tcagggcaga tatagataaa aaatacagat gtgttagtgg cacccaggtc    480
```

```
cacatgaaca acgtgaccgt aacgctccat gatgccacca tccaggcgta cctttccaac    540
agcagcttca gcaggggaga gacacgctgt gaacaagaca ggccttcccc aaccacagcg    600
cccccctgcgc cacccagccc ctcgccctca cccgtgccca agagccccctc tgtggacaag   660
tacaacgtga gcggcaccaa cgggacctgc ctgctggcca gcatggggct gcagctgaac    720
ctcacctatg agaggaagga caacacgacg gtgacaaggc ttctcaacat caaccccaac    780
aagacctcgg ccagcgggag ctgcggcgcc cacctggtga ctctggagct gcacagcgag    840
ggcaccaccg tcctgctctt ccagttcggg atgaatgcaa gttctagccg gttttttccta   900
caaggaatcc agttgaatac aattcttcct gacgccagag accctgcctt taaagctgcc    960
aacggctccc tgcgagcgct gcaggccaca gtcggcaatt cctacaagtg caacgcggag   1020
gagcacgtcc gtgtcacgaa ggcgttttca gtcaatatat tcaaagtgtg gtccaggct   1080
ttcaaggtgg aagtggcca gtttggctct gtggaggagt gtctgctgga cgagaacagc   1140
ctcgaggata tcgggaagtg gtcgaagtcg tcggtgatcg ggtggccgac tgttcgggag   1200
cggatgcggc gggcggagcc ggcggcggat cgggtgggag cggcgtcgcg ggaccttgag   1260
aagcacgggg cgatcacgtc gagcaacacg gcggcgacga atgcggcgtg tgcctggcta   1320
gaggcgcaag aggaggagga agtgggtttt ccggtcacgc cgcaggtccc gcttcggccg   1380
atgacgtaca aggcagcggt cgacctcagc cacttcctca aggagaaggg gggactggag   1440
gggctcatcc actcccagcg gcggcaggac atccttgacc tgtggatcta ccacacacaa   1500
ggctacttcc cggattggca gaactacacg ccggggccgg gggtccggta tccgctgacc   1560
tttggatggt gctacaagct agtaccggtt gagccggata agatcgagga ggccaacaag   1620
ggagagaaca ccagcttgtt gcaccctgtg agcctgcatg gaatggatga cccggagcgg   1680
gaggtgcttg agtggcggtt tgacagccgc ctagcgtttc atcacgtggc ccgagagctg   1740
catccggagt acttcaagaa ctgcggatcc gagccagtag atcctagact agagccctgg   1800
aagcatccag gatcgcagcc gaagacggcg tgcaccaact gctactgcaa gaagtgcttc   1860
caccaggtct gcttcatgac gaaggccttg ggcatctcct atggccggaa gaagcggaga   1920
cagcgacgaa gagctcatca gaactcgcag acgcaccagg cgtcgctatc gaagcaaccc   1980
acctcccaat cccgagggga cccgacaggc ccgaaggaat cgaagaagga ggtggagaga   2040
gagacagaga cagatccgtt cgactggtct agagagaacc ggtggcaggt gatgattgtg   2100
tggcaggtcg accggatgcg gattcggacg tggaagtcgc ttgtcaagca ccacatgtac   2160
atctcgggga aggcgaaggg gtggttctac cggcaccact atgagtcgac gcaccccgcgg   2220
atctcgtcgg aggtccacat cccgctaggg gacgcgaagc ttgtcatcac gacgtactgg   2280
ggtctgcata cgggagagcg ggactggcat ttgggtcagg gagtctccat agagtggagg   2340
aaaaagcggt atagcacgca agtagacccg gacctagcgg accagctaat ccacctgtac   2400
tacttcgact cgttctcgga gtcggcgata cggaatacca tccttgggcg gatcgtttcg   2460
ccgcggagtg agtatcaagc ggggcacaac aaggtcgggt cgctacagta cttggcgctc   2520
gcggcgttga tcacgccgaa gcagataaag ccgccgttgc cgtcggttac gaaactgacg   2580
gaggaccggt ggaacaagcc ccagaagacc aagggccacc gggggagcca cacaatgaac   2640
gggcacgaat tcacgctgat ccccatcgct gtgggtggtg ccctggcggg gctggtcctc   2700
atcgtcctca tcgcctacct cgtcggcagg aagaggagtc acgcaggcta ccagactatc   2760
tag                                                                 2763
```

-continued

```
<210> SEQ ID NO 38
<211> LENGTH: 920
<212> TYPE: PRT
<213> ORGANISM: Artificial Sequence
<220> FEATURE:
<223> OTHER INFORMATION: Description of Artificial Sequence:fusion
      protein HIV LAMP-NTV

<400> SEQUENCE: 38
```

Met Ala Pro Arg Ser Ala Arg Arg Pro Leu Leu Leu Leu Leu Leu
 1               5                  10                  15

Leu Leu Leu Gly Leu Met His Cys Ala Ser Ala Met Phe Met Val
             20                  25                  30

Lys Asn Gly Asn Gly Thr Ala Cys Ile Met Ala Asn Phe Ser Ala Ala
             35                  40                  45

Phe Ser Val Asn Tyr Asp Thr Lys Ser Gly Pro Lys Asn Met Thr Leu
 50                  55                  60

Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
                100                 105                 110

Gln Leu Met Ser Phe Val Tyr Asn Leu Ser Asp Thr His Leu Phe Pro
            115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Gly Thr Thr Val Leu Leu Phe Gln
        275                 280                 285

Phe Gly Met Asn Ala Ser Ser Ser Arg Phe Phe Leu Gln Gly Ile Gln
290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Asp Ile

```
                370             375             380
Gly Lys Trp Ser Lys Ser Val Ile Gly Trp Pro Thr Val Arg Glu
385             390             395             400

Arg Met Arg Arg Ala Glu Pro Ala Ala Asp Arg Val Gly Ala Ala Ser
                405             410             415

Arg Asp Leu Glu Lys His Gly Ala Ile Thr Ser Ser Asn Thr Ala Ala
                420             425             430

Thr Asn Ala Ala Cys Ala Trp Leu Glu Ala Gln Glu Glu Glu Val
                435             440             445

Gly Phe Pro Val Thr Pro Gln Val Pro Leu Arg Pro Met Thr Tyr Lys
450             455             460

Ala Ala Val Asp Leu Ser His Phe Leu Lys Glu Lys Gly Gly Leu Glu
465             470             475             480

Gly Leu Ile His Ser Gln Arg Arg Gln Asp Ile Leu Asp Leu Trp Ile
                485             490             495

Tyr His Thr Gln Gly Tyr Phe Pro Asp Trp Gln Asn Tyr Thr Pro Gly
                500             505             510

Pro Gly Val Arg Tyr Pro Leu Thr Phe Gly Trp Cys Tyr Lys Leu Val
                515             520             525

Pro Val Glu Pro Asp Lys Ile Glu Glu Ala Asn Lys Gly Glu Asn Thr
                530             535             540

Ser Leu Leu His Pro Val Ser Leu His Gly Met Asp Asp Pro Glu Arg
545             550             555             560

Glu Val Leu Glu Trp Arg Phe Asp Ser Arg Leu Ala Phe His His Val
                565             570             575

Ala Arg Glu Leu His Pro Glu Tyr Phe Lys Asn Cys Gly Ser Glu Pro
                580             585             590

Val Asp Pro Arg Leu Glu Pro Trp Lys His Pro Gly Ser Gln Pro Lys
                595             600             605

Thr Ala Cys Thr Asn Cys Tyr Cys Lys Lys Cys Phe His Gln Val Cys
610             615             620

Phe Met Thr Lys Ala Leu Gly Ile Ser Tyr Gly Arg Lys Lys Arg Arg
625             630             635             640

Gln Arg Arg Arg Ala His Gln Asn Ser Gln Thr His Gln Ala Ser Leu
                645             650             655

Ser Lys Gln Pro Thr Ser Gln Ser Arg Gly Asp Pro Thr Gly Pro Lys
                660             665             670

Glu Ser Lys Lys Glu Val Glu Arg Glu Thr Glu Thr Asp Pro Phe Asp
                675             680             685

Trp Ser Arg Glu Asn Arg Trp Gln Val Met Ile Val Trp Gln Val Asp
690             695             700

Arg Met Arg Ile Arg Thr Trp Lys Ser Leu Val Lys His His Met Tyr
705             710             715             720

Ile Ser Gly Lys Ala Lys Gly Trp Phe Tyr Arg His His Tyr Glu Ser
                725             730             735

Thr His Pro Arg Ile Ser Ser Glu Val His Ile Pro Leu Gly Asp Ala
                740             745             750

Lys Leu Val Ile Thr Thr Tyr Trp Gly Leu His Thr Gly Glu Arg Asp
                755             760             765

Trp His Leu Gly Gln Gly Val Ser Ile Glu Trp Arg Lys Lys Arg Tyr
                770             775             780

Ser Thr Gln Val Asp Pro Asp Leu Ala Asp Gln Leu Ile His Leu Tyr
785             790             795             800
```

-continued

```
Tyr Phe Asp Ser Phe Ser Glu Ser Ala Ile Arg Asn Thr Ile Leu Gly
            805                 810                 815

Arg Ile Val Ser Pro Arg Ser Glu Tyr Gln Ala Gly His Asn Lys Val
        820                 825                 830

Gly Ser Leu Gln Tyr Leu Ala Leu Ala Ala Leu Ile Thr Pro Lys Gln
        835                 840                 845

Ile Lys Pro Pro Leu Pro Ser Val Thr Lys Leu Thr Glu Asp Arg Trp
    850                 855                 860

Asn Lys Pro Gln Lys Thr Lys Gly His Arg Gly Ser His Thr Met Asn
865                 870                 875                 880

Gly His Glu Phe Thr Leu Ile Pro Ile Ala Val Gly Gly Ala Leu Ala
                885                 890                 895

Gly Leu Val Leu Ile Val Leu Ile Ala Tyr Leu Val Gly Arg Lys Arg
            900                 905                 910

Ser His Ala Gly Tyr Gln Thr Ile
        915                 920
```

<210> SEQ ID NO 39
<211> LENGTH: 450
<212> TYPE: DNA
<213> ORGANISM: Artificial Sequence
<220> FEATURE:
<223> OTHER INFORMATION: Description of Artificial Sequence:fusion
      protein Human IL-15tPA6 opt (AG59)

<400> SEQUENCE: 39

```
atggatgcaa tgaagagagg gctctgctgt gtgctgctgc tgtgtggagc agtcttcgtt      60
tcgcccagcc aggaaatcca tgcccgattc agaagaggag ccagaaactg ggtgaacgtg     120
atctcggacc tgaagaagat cgaggacctc atccagtcga tgcacatcga cgcgacgctg     180
tacacggagt cggacgtcca cccgtcgtgc aaggtcacgg cgatgaagtg cttcctcctg     240
gagctccaag tcatctcgct cgagtcgggg gacgcgtcga tccacgacac ggtggagaac     300
ctgatcatcc tggcgaacaa ctcgctgtcg tcgaacggga acgtcacgga gtcgggctgc     360
aaggagtgcg aggagctgga ggagaagaac atcaaggagt cctgcagtc gttcgtgcac     420
atcgtccaga tgttcatcaa cacgtcgtga                                      450
```

<210> SEQ ID NO 40
<211> LENGTH: 149
<212> TYPE: PRT
<213> ORGANISM: Artificial Sequence
<220> FEATURE:
<223> OTHER INFORMATION: Description of Artificial Sequence:fusion
      protein Human IL-15tPA6

<400> SEQUENCE: 40

```
Met Asp Ala Met Lys Arg Gly Leu Cys Cys Val Leu Leu Leu Cys Gly
 1               5                  10                  15

Ala Val Phe Val Ser Pro Ser Gln Glu Ile His Ala Arg Phe Arg Arg
            20                  25                  30

Gly Ala Arg Asn Trp Val Asn Val Ile Ser Asp Leu Lys Lys Ile Glu
        35                  40                  45

Asp Leu Ile Gln Ser Met His Ile Asp Ala Thr Leu Tyr Thr Glu Ser
    50                  55                  60

Asp Val His Pro Ser Cys Lys Val Thr Ala Met Lys Cys Phe Leu Leu
65                  70                  75                  80

Glu Leu Gln Val Ile Ser Leu Glu Ser Gly Asp Ala Ser Ile His Asp
                85                  90                  95
```

-continued

```
Thr Val Glu Asn Leu Ile Ile Leu Ala Asn Asn Ser Leu Ser Ser Asn
                100                 105                 110
Gly Asn Val Thr Glu Ser Gly Cys Lys Glu Cys Glu Leu Glu Glu
        115                 120                 125
Lys Asn Ile Lys Glu Phe Leu Gln Ser Phe Val His Ile Val Gln Met
130                 135                 140
Phe Ile Asn Thr Ser
145

<210> SEQ ID NO 41
<211> LENGTH: 930
<212> TYPE: PRT
<213> ORGANISM: Artificial Sequence
<220> FEATURE:
<223> OTHER INFORMATION: Description of Artificial Sequence:fusion
      protein HIV MCP-3env

<400> SEQUENCE: 41

Met Asn Pro Ser Ala Ala Val Ile Phe Cys Leu Ile Leu Leu Gly Leu
  1               5                  10                  15
Ser Gly Thr Gln Gly Ile Leu Asp Ala Gln Pro Val Gly Ile Asn Thr
             20                  25                  30
Ser Thr Thr Cys Cys Tyr Arg Phe Ile Asn Lys Lys Ile Pro Lys Gln
         35                  40                  45
Arg Leu Glu Ser Tyr Arg Arg Thr Thr Ser Ser His Cys Pro Arg Glu
     50                  55                  60
Ala Val Ile Phe Lys Thr Lys Leu Asp Lys Glu Ile Cys Ala Asp Pro
 65                  70                  75                  80
Thr Gln Lys Trp Val Gln Asp Phe Met Lys His Leu Asp Lys Lys Thr
                 85                  90                  95
Gln Thr Pro Lys Leu Ile Cys Ser Ala Glu Glu Lys Leu Trp Val Thr
            100                 105                 110
Val Tyr Tyr Gly Val Pro Val Trp Lys Glu Ala Thr Thr Thr Leu Phe
        115                 120                 125
Cys Ala Ser Asp Ala Lys Ala His His Ala Glu Ala His Asn Val Trp
130                 135                 140
Ala Thr His Ala Cys Val Pro Thr Asp Pro Asn Pro Gln Glu Val Ile
145                 150                 155                 160
Leu Glu Asn Val Thr Glu Lys Tyr Asn Met Trp Lys Asn Asn Met Val
                165                 170                 175
Asp Gln Met His Glu Asp Ile Ile Ser Leu Trp Asp Gln Ser Leu Lys
            180                 185                 190
Pro Cys Val Lys Leu Thr Pro Leu Cys Val Thr Leu Asn Cys Thr Asn
        195                 200                 205
Ala Thr Tyr Thr Asn Ser Asp Ser Lys Asn Ser Thr Ser Asn Ser Ser
210                 215                 220
Leu Glu Asp Ser Gly Lys Gly Asp Met Asn Cys Ser Phe Asp Val Thr
225                 230                 235                 240
Thr Ser Ile Asp Lys Lys Lys Thr Glu Tyr Ala Ile Phe Asp Lys
                245                 250                 255
Leu Asp Val Met Asn Ile Gly Asn Gly Arg Tyr Thr Leu Leu Asn Cys
            260                 265                 270
Asn Thr Ser Val Ile Thr Gln Ala Cys Pro Lys Met Ser Phe Glu Pro
        275                 280                 285
Ile Pro Ile His Tyr Cys Thr Pro Ala Gly Tyr Ala Ile Leu Lys Cys
        290                 295                 300
```

-continued

```
Asn Asp Asn Lys Phe Asn Gly Thr Gly Pro Cys Thr Asn Val Ser Thr
305                 310                 315                 320

Ile Gln Cys Thr His Gly Ile Lys Pro Val Val Ser Thr Gln Leu Leu
                325                 330                 335

Leu Asn Gly Ser Leu Ala Glu Gly Gly Glu Val Ile Ile Arg Ser Glu
            340                 345                 350

Asn Leu Thr Asp Asn Ala Lys Thr Ile Ile Val Gln Leu Lys Glu Pro
        355                 360                 365

Val Glu Ile Asn Cys Thr Arg Pro Asn Asn Asn Thr Arg Lys Ser Ile
370                 375                 380

His Met Gly Pro Gly Ala Ala Phe Tyr Ala Arg Gly Glu Val Ile Gly
385                 390                 395                 400

Asp Ile Arg Gln Ala His Cys Asn Ile Ser Arg Gly Arg Trp Asn Asp
                405                 410                 415

Thr Leu Lys Gln Ile Ala Lys Lys Leu Arg Glu Gln Phe Asn Lys Thr
            420                 425                 430

Ile Ser Leu Asn Gln Ser Ser Gly Gly Asp Leu Glu Ile Val Met His
        435                 440                 445

Thr Phe Asn Cys Gly Gly Glu Phe Phe Tyr Cys Asn Thr Thr Gln Leu
    450                 455                 460

Phe Asn Ser Thr Trp Asn Glu Asn Asp Thr Thr Trp Asn Asn Thr Ala
465                 470                 475                 480

Gly Ser Asn Asn Asn Glu Thr Ile Thr Leu Pro Cys Arg Ile Lys Gln
                485                 490                 495

Ile Ile Asn Arg Trp Gln Glu Val Gly Lys Ala Met Tyr Ala Pro Pro
            500                 505                 510

Ile Ser Gly Pro Ile Asn Cys Leu Ser Asn Ile Thr Gly Leu Leu Leu
        515                 520                 525

Thr Arg Asp Gly Gly Asp Asn Asn Thr Ile Glu Thr Phe Arg Pro
    530                 535                 540

Gly Gly Gly Asp Met Arg Asp Asn Trp Arg Ser Glu Leu Tyr Lys Tyr
545                 550                 555                 560

Lys Val Val Arg Ile Glu Pro Leu Gly Ile Ala Pro Thr Lys Ala Lys
                565                 570                 575

Arg Arg Val Val Gln Arg Glu Lys Arg Ala Val Gly Ile Gly Ala Met
            580                 585                 590

Phe Leu Gly Phe Leu Gly Ala Ala Gly Ser Thr Met Gly Ala Ala Ser
        595                 600                 605

Val Thr Leu Thr Val Gln Ala Arg Leu Leu Leu Ser Gly Ile Val Gln
    610                 615                 620

Gln Gln Asn Asn Leu Leu Arg Ala Ile Glu Ala Gln Gln His Leu Leu
625                 630                 635                 640

Gln Leu Thr Val Trp Gly Ile Lys Gln Leu Gln Ala Arg Val Leu Ala
                645                 650                 655

Met Glu Arg Tyr Leu Lys Asp Gln Gln Leu Leu Gly Ile Trp Gly Cys
            660                 665                 670

Ser Gly Lys Leu Ile Cys Thr Thr Asn Val Pro Trp Asn Ala Ser Trp
        675                 680                 685

Ser Asn Lys Ser Leu Asp Lys Ile Trp His Asn Met Thr Trp Met Glu
    690                 695                 700

Trp Asp Arg Glu Ile Asp Asn Tyr Thr Lys Leu Ile Tyr Thr Leu Ile
705                 710                 715                 720

Glu Ala Ser Gln Ile Gln Gln Glu Lys Asn Glu Gln Glu Leu Leu Glu
                725                 730                 735
```

```
Leu Asp Ser Trp Ala Ser Leu Trp Ser Trp Phe Asp Ile Ser Lys Trp
                740                 745                 750

Leu Trp Tyr Ile Gly Val Phe Ile Val Ile Gly Gly Leu Val Gly
            755                 760                 765

Leu Lys Ile Val Phe Ala Val Leu Ser Ile Val Asn Arg Val Arg Gln
    770                 775                 780

Gly Tyr Ser Pro Leu Ser Phe Gln Thr Arg Leu Pro Ala Pro Arg Gly
785                 790                 795                 800

Pro Asp Arg Pro Glu Gly Ile Glu Glu Gly Gly Glu Arg Asp Arg
                805                 810                 815

Asp Arg Ser Asp Gln Leu Val Thr Gly Phe Leu Ala Leu Ile Trp Asp
                820                 825                 830

Asp Leu Arg Ser Leu Cys Leu Phe Ser Tyr His Arg Leu Arg Asp Leu
                835                 840                 845

Leu Leu Ile Val Ala Arg Ile Val Glu Leu Leu Gly Arg Arg Gly Trp
    850                 855                 860

Glu Ala Leu Lys Tyr Trp Trp Asn Leu Leu Gln Tyr Trp Ile Gln Glu
865                 870                 875                 880

Leu Lys Asn Ser Ala Val Ser Leu Leu Asn Ala Thr Ala Ile Ala Val
                885                 890                 895

Ala Glu Gly Thr Asp Arg Ile Ile Glu Val Val Gln Arg Ile Gly Arg
                900                 905                 910

Ala Ile Leu His Ile Pro Arg Arg Ile Arg Gln Gly Leu Glu Arg Ala
            915                 920                 925

Leu Leu
    930

<210> SEQ ID NO 42
<211> LENGTH: 660
<212> TYPE: DNA
<213> ORGANISM: Artificial Sequence
<220> FEATURE:
<223> OTHER INFORMATION: Description of Artificial Sequence:Human IL-12
      p35opt

<400> SEQUENCE: 42
atgtgcccgg cgcgctccct gctgctcgtg gcgacgctgg tcctgctcga ccacctgagc      60
ctggcgcgga acctgccggt ggcgacgccg gacccgggga tgttcccgtg cctgcaccac     120
agccagaacc tgctgcgggc ggtgtcgaac atgctgcaga aggcgcggca gacgctggag     180
ttctacccgt gcacgagcga ggagatcgac acgaggaca tcacgaagga caagaccagc     240
acggtggagg cgtgcctgcc gctggagctg acgaagaacg agtcgtgcct gaactcgagg     300
gagacgtcgt tcatcacgaa cgggtcgtgc ctggcgtcgc ggaagacgtc gttcatgatg     360
gcgctgtgcc tgtcgtcgat ctacgaggac ctgaagatgt accaggtgga gttcaagacg     420
atgaacgcga agctgctgat ggacccgaag cggcagatct tcctcgacca gaacatgctg     480
gcggtgatcg acgagctcat gcaggcgctc aacttcaaca gcgagacggt gccgcagaag     540
tcgtcgctcg aggagccgga cttctacaag acgaagatca agctctgcat cctgctgcac     600
gctttccgga tccgggcggt gacgatcgac cgggtgatgt cgtacctgaa cgcttcgtaa     660

<210> SEQ ID NO 43
<211> LENGTH: 219
<212> TYPE: PRT
<213> ORGANISM: Homo sapiens
<220> FEATURE:
<223> OTHER INFORMATION: human IL-12 p35
```

<400> SEQUENCE: 43

```
Met Cys Pro Ala Arg Ser Leu Leu Leu Val Ala Thr Leu Val Leu Leu
 1               5                  10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215
```

<210> SEQ ID NO 44
<211> LENGTH: 987
<212> TYPE: DNA
<213> ORGANISM: Artificial Sequence
<220> FEATURE:
<223> OTHER INFORMATION: Description of Artificial Sequence:Human IL-12 p40opt

<400> SEQUENCE: 44

```
atgtgccacc agcagctggt catcagctgg ttcagcctcg ttttcctcgc ctcgccgctg      60
gtcgccatat gggagctcaa gaaggacgta tacgtggtgg agctggactg gtaccccgac     120
gcgccgggcg agatggtcgt cctgacgtgc gacacgccgg aggaggacgg catcacgtgg     180
acgctggacc agtccagcga ggtcctcggc tccggcaaga cgctgacgat ccaggtcaag     240
gagttcggcg acgcgggcca gtacacgtgc cacaagggcg cgaggtcctc gagccactcc     300
ctcctcctgc tacacaagaa ggaggacggg atctggagca cggacatcct caaggaccag     360
aaggagccga gaacaagac cttcctgcgc tgcgaggcga agaattactc gggccggttc     420
acgtgctggt ggctcaccac gatcagcacg gacctgacgt tctcggtcaa gtcgtcgcgg     480
ggctcgtcgg accccagg ggtgacctgc ggcgcggcga cgctgtcggc ggagcgggtg     540
cggggcgaca acaaggagta cgagtactcg gtcgagtgcc aggaggactc ggcgtgcccg     600
gcggcggagg agtcgctgcc gatcgaggtg atggtcgacg cggtccacaa gctgaagtac     660
gagaactaca cgtcgtcgtt cttcatccgg gacatcatca gccggacccc gccgaagaac     720
```

-continued

```
ctgcagctga agccgctgaa gaactcgcgg caggtcgagg tctcgtggga gtacccggac      780
acgtggtcga cgccgcactc gtacttctcg ctgacgttct gcgtccaagt gcagggcaag      840
tcgaagcggg agaagaagga ccgggtgttc accgacaaga cgagcgcgac ggtgatctgc      900
cggaagaacg cgtcgatctc ggtgcgggcg caggaccggt actactcgtc gtcgtggtcg      960
gagtgggcgt cggtgccgtg cagctag                                          987
```

<210> SEQ ID NO 45
<211> LENGTH: 328
<212> TYPE: PRT
<213> ORGANISM: Homo sapiens
<220> FEATURE:
<223> OTHER INFORMATION: human IL-12 p40

<400> SEQUENCE: 45

```
Met Cys His Gln Gln Leu Val Ile Ser Trp Phe Ser Leu Val Phe Leu
  1               5                  10                  15

Ala Ser Pro Leu Val Ala Ile Trp Glu Leu Lys Lys Asp Val Tyr Val
             20                  25                  30

Val Glu Leu Asp Trp Tyr Pro Asp Ala Pro Gly Glu Met Val Val Leu
         35                  40                  45

Thr Cys Asp Thr Pro Glu Glu Asp Gly Ile Thr Trp Thr Leu Asp Gln
     50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320
```

Glu Trp Ala Ser Val Pro Cys Ser
              325

<210> SEQ ID NO 46
<211> LENGTH: 465
<212> TYPE: DNA
<213> ORGANISM: Artificial Sequence
<220> FEATURE:
<223> OTHER INFORMATION: Description of Artificial Sequence:Human
      IL-2opt

<400> SEQUENCE: 46
atgtaccgca tgcagctgct ctcgtgcatc gcgctcagcc tcgcgctggt gacgaactcg      60
gcgcccacgt cctcgtccac gaagaagacc cagctgcagc tggagcacct gctcctggac     120
ctccagatga tcctgaacgg catcaacaac tacaagaacc ccaagctcac ccggatgctg     180
acgttcaagt tctacatgcc gaagaaggcc acggagctga agcaccttca gtgcttggag     240
gaggagttga agcccctgga ggaggtcctc aacctggccc agagcaagaa cttccacctg     300
aggccccggg acctcatctc caacatcaac gtgatcgtcc tggagttgaa gggcagcgag     360
acgaccttca gtgcgagta cgccgacgag acggcgacca tcgtcgagtt cctgaaccgg     420
tggatcacct tctgccagtc gatcatcagc acgctgacct gataa                    465

<210> SEQ ID NO 47
<211> LENGTH: 153
<212> TYPE: PRT
<213> ORGANISM: Homo sapiens
<220> FEATURE:
<223> OTHER INFORMATION: human IL-2

<400> SEQUENCE: 47

Met Tyr Arg Met Gln Leu Leu Ser Cys Ile Ala Leu Ser Leu Ala Leu
 1               5                  10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 48
<211> LENGTH: 396
<212> TYPE: DNA
<213> ORGANISM: Artificial Sequence
<220> FEATURE:
<223> OTHER INFORMATION: Description of Artificial Sequence:fusion
      protein Human IL-15GM-CSF opt (AG146)

<400> SEQUENCE: 48

```
atgtggctcc agggcctgct actcctgggg acggtggcct gcagcatctc gaactgggtg    60
aacgtgatct cggacctgaa gaagatcgag gacctcatcc agtcgatgca catcgacgcg   120
acgctgtaca cggagtcgga cgtccacccg tcgtgcaagg tcacggcgat gaagtgcttc   180
ctcctggagc tccaagtcat ctcgctcgag tcggggacg cgtcgatcca cgacacggtg    240
gagaacctga tcatcctggc gaacaactcg ctgtcgtcga acgggaacgt cacggagtcg   300
ggctgcaagg agtgcgagga gctggaggag aagaacatca aggagttcct gcagtcgttc   360
gtgcacatcg tccagatgtt catcaacacg tcgtga                             396
```

<210> SEQ ID NO 49
<211> LENGTH: 131
<212> TYPE: PRT
<213> ORGANISM: Artificial Sequence
<220> FEATURE:
<223> OTHER INFORMATION: Description of Artificial Sequence:fusion
      protein Human IL-15GM-CSF opt

<400> SEQUENCE: 49

```
Met Trp Leu Gln Gly Leu Leu Leu Gly Thr Val Ala Cys Ser Ile
 1               5                  10                  15

Ser Asn Trp Val Asn Val Ile Ser Asp Leu Lys Lys Ile Glu Asp Leu
            20                  25                  30

Ile Gln Ser Met His Ile Asp Ala Thr Leu Tyr Thr Glu Ser Asp Val
        35                  40                  45

His Pro Ser Cys Lys Val Thr Ala Met Lys Cys Phe Leu Leu Glu Leu
    50                  55                  60

Gln Val Ile Ser Leu Glu Ser Gly Asp Ala Ser Ile His Asp Thr Val
65                  70                  75                  80

Glu Asn Leu Ile Ile Leu Ala Asn Asn Ser Leu Ser Ser Asn Gly Asn
                85                  90                  95

Val Thr Glu Ser Gly Cys Lys Glu Cys Glu Glu Leu Glu Glu Lys Asn
            100                 105                 110

Ile Lys Glu Phe Leu Gln Ser Phe Val His Ile Val Gln Met Phe Ile
        115                 120                 125

Asn Thr Ser
    130
```

<210> SEQ ID NO 50
<211> LENGTH: 399
<212> TYPE: DNA
<213> ORGANISM: Artificial Sequence
<220> FEATURE:
<223> OTHER INFORMATION: Description of Artificial Sequence:fusion
      protein Human IL-15IgE opt (AG54)

<400> SEQUENCE: 50

```
atggactgga cgtggatcct tttccttgtc gcggcggcga cgcgggtcca ctcgaactgg    60
gtgaacgtga tctcggacct gaagaagatc gaggacctca tccagtcgat gcacatcgac   120
gcgacgctgt acacggagtc ggacgtccac ccgtcgtgca aggtcacggc gatgaagtgc   180
ttcctcctgg agctccaagt catctcgctc gagtcggggg acgcgtcgat ccacgacacg   240
gtggagaacc tgatcatcct ggcgaacaac tcgctgtcgt cgaacgggaa cgtcacggag   300
tcgggctgca aggagtgcga ggagctggag gagaagaaca tcaaggagtt cctgcagtcg   360
ttcgtgcaca tcgtccagat gttcatcaac acgtcgtga                          399
```

<210> SEQ ID NO 51

```
<211> LENGTH: 132
<212> TYPE: PRT
<213> ORGANISM: Artificial Sequence
<220> FEATURE:
<223> OTHER INFORMATION: Description of Artificial Sequence:fusion
      protein Human IL-15IgE opt (AG54)

<400> SEQUENCE: 51

Met Asp Trp Thr Trp Ile Leu Phe Leu Val Ala Ala Ala Thr Arg Val
  1               5                  10                  15

His Ser Asn Trp Val Asn Val Ile Ser Asp Leu Lys Lys Ile Glu Asp
             20                  25                  30

Leu Ile Gln Ser Met His Ile Asp Ala Thr Leu Tyr Thr Glu Ser Asp
         35                  40                  45

Val His Pro Ser Cys Lys Val Thr Ala Met Lys Cys Phe Leu Leu Glu
     50                  55                  60

Leu Gln Val Ile Ser Leu Glu Ser Gly Asp Ala Ser Ile His Asp Thr
 65                  70                  75                  80

Val Glu Asn Leu Ile Ile Leu Ala Asn Asn Ser Leu Ser Ser Asn Gly
                 85                  90                  95

Asn Val Thr Glu Ser Gly Cys Lys Glu Cys Glu Glu Leu Glu Glu Lys
            100                 105                 110

Asn Ile Lys Glu Phe Leu Gln Ser Phe Val His Ile Val Gln Met Phe
        115                 120                 125

Ile Asn Thr Ser
        130

<210> SEQ ID NO 52
<211> LENGTH: 807
<212> TYPE: DNA
<213> ORGANISM: Artificial Sequence
<220> FEATURE:
<223> OTHER INFORMATION: Description of Artificial Sequence:Human
      interleukin-15 (IL-15) receptor alpha

<400> SEQUENCE: 52
atggccccga ggcgggcgcg aggctgccgg accctcggtc tcccggcgct gctactgctc      60
ctgctgctcc ggccgccggc gacgcggggc atcacgtgcc cgccccccat gtccgtggag     120
cacgcagaca tctgggtcaa gagctacagc ttgtactccc gggagcggta catctgcaac     180
tcgggtttca agcggaaggc cggcacgtcc agcctgacgg agtgcgtgtt gaacaaggcc     240
acgaatgtcg cccactggac gacccccctcg ctcaagtgca tccgcgaccc ggccctggtt     300
caccagcggc ccgcgccacc ctccaccgta acgacggcgg gggtgacccc gcagccggag     360
agcctctccc gtcgggaaa ggagcccgcc gcgtcgtcgc ccagctcgaa caacacggcg     420
gccacaactg cagcgatcgt cccgggctcc cagctgatgc cgtcgaagtc gccgtccacg     480
ggaaccacgg agatcagcag tcatgagtcc tcccacggca cccctcgca acgacggcc     540 aagaactggg aactcacggc gtccgcctcc accagccgc cggggtgta tccgcaaggc     600 cacagcgaca ccacggtggc gatctccacg tccacggtcc tgctgtgtgg gctgagcgcg     660
gtgtcgctcc tggcgtgcta cctcaagtcg aggcagactc cccgctggc cagcgttgag     720 atggaggcca tggaggctct gccggtgacg tgggggacca gcagcaggga tgaggacttg     780
gagaactgct cgcaccacct ataatga                                         807

<210> SEQ ID NO 53
<211> LENGTH: 267
<212> TYPE: PRT
<213> ORGANISM: Homo sapiens
```

```
<220> FEATURE:
<223> OTHER INFORMATION: human interleukin-15 (IL-15) receptor alpha

<400> SEQUENCE: 53

Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265

<210> SEQ ID NO 54
<211> LENGTH: 489
<212> TYPE: DNA
<213> ORGANISM: Homo sapiens
<220> FEATURE:
<223> OTHER INFORMATION: human wild-type interleukin 15 (IL-15)

<400> SEQUENCE: 54
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtgaatgtaa taagtgattt gaaaaaaatt     180
gaagatctta ttcaatctat gcatattgat gctactttat atacggaaag tgatgttcac     240
cccagttgca aagtaacagc aatgaagtgc tttctcttgg agttacaagt tatttcactt     300
gagtctggag atgcaagtat tcatgataca gtagaaaatc tgatcatcct agcaaacaac     360
agtttgtctt ctaatgggaa tgtaacagaa tctggatgca aagaatgtga ggaactggag     420
```

```
gaaaaaaata ttaaagaatt tttgcagagt tttgtacata ttgtccaaat gttcatcaac      480
acttcttga                                                              489

<210> SEQ ID NO 55
<211> LENGTH: 162
<212> TYPE: PRT
<213> ORGANISM: Homo sapiens
<220> FEATURE:
<223> OTHER INFORMATION: human wild-type interleukin 15 (IL-15)

<400> SEQUENCE: 55

Met Arg Ile Ser Lys Pro His Leu Arg Ser Ile Ser Ile Gln Cys Tyr
  1               5                  10                  15

Leu Cys Leu Leu Leu Asn Ser His Phe Leu Thr Glu Ala Gly Ile His
             20                  25                  30

Val Phe Ile Leu Gly Cys Phe Ser Ala Gly Leu Pro Lys Thr Glu Ala
         35                  40                  45

Asn Trp Val Asn Val Ile Ser Asp Leu Lys Lys Ile Glu Asp Leu Ile
     50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 56
<211> LENGTH: 489
<212> TYPE: DNA
<213> ORGANISM: Artificial Sequence
<220> FEATURE:
<223> OTHER INFORMATION: Description of Artificial Sequence:human
      improved IL-15 opt

<400> SEQUENCE: 56
atgcggatct cgaagccgca cctgcggtcg atatcgatcc agtgctacct gtgcctgctc      60
ctgaactcgc acttcctcac ggaggccggt atacacgtct tcatcctggg ctgcttctcg     120
gcggggctgc cgaagacgga ggcgaactgg gtgaacgtga tctcggacct gaagaagatc     180
gaggacctca tccagtcgat gcacatcgac gcgacgctgt acacggagtc ggacgtccac     240
ccgtcgtgca aggtcacggc gatgaagtgc ttcctcctgg agctcaagt catctcgctc      300 gagtcggggg acgcgtcgat ccacgacacg gtggagaacc tgatcatcct ggcgaacaac     360
tcgctgtcgt cgaacgggaa cgtcacggag tcgggctgca aggagtgcga ggagctggag     420
gagaagaaca tcaaggagtt cctgcagtcg ttcgtgcaca tcgtccagat gttcatcaac     480
acgtcgtga                                                             489

<210> SEQ ID NO 57
<211> LENGTH: 489
<212> TYPE: DNA
<213> ORGANISM: Artificial Sequence
```

```
<220> FEATURE:
<223> OTHER INFORMATION: Description of Artificial Sequence:human
      improved IL-15 opt2

<400> SEQUENCE: 57
atgaggatca gcaagcccca cctgaggagc atcagcatcc agtgctacct gtgcctgctg       60
ctgaacagcc acttcctgac cgaggccggt atacacgtgt tcatcctggg ctgctttagc      120
gccggactgc ccaagaccga ggccaattgg gtgaacgtga tcagcgacct gaagaagatc      180
gaggacctca tccagagcat gcacatcgac gccaccctgt acaccgagag cgatgtgcac      240
cccagctgta aggtgaccgc catgaagtgc tttctgctgg agctgcaagt gatcagcctg      300
gagagcggcg acgccagcat ccacgacacc gtggagaacc tgatcatcct ggccaacaac      360
agcctgagca gcaacggcaa tgtgaccgag agcggctgta aggagtgtga ggagctggag      420
gagaagaaca tcaaggagtt tctgcagagc ttcgtgcaca tcgtgcagat gttcatcaac      480
accagctga                                                              489

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence:targeting
      signal cyclin destruction box motif
<220> FEATURE:
<221> NAME/KEY: MOD_RES
<222> LOCATION: (2)
<223> OTHER INFORMATION: Xaa = Ala or Thr
<220> FEATURE:
<221> NAME/KEY: MOD_RES
<222> LOCATION: (6)
<223> OTHER INFORMATION: Xaa = any amino acid
<220> FEATURE:
<221> NAME/KEY: MOD_RES
<222> LOCATION: (7)
<223> OTHER INFORMATION: Xaa = Ile or Val
<220> FEATURE:
<221> NAME/KEY: MOD_RES
<222> LOCATION: (8)
<223> OTHER INFORMATION: Xaa = Gly or Thr

<400> SEQUENCE: 58

Arg Xaa Ala Leu Gly Xaa Xaa Xaa Asn
  1               5

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence:beta-catenin
      destabilization sequence amino acids 18-47

<400> SEQUENCE: 59

Arg Lys Ala Ala Val Ser His Trp Gln Gln Gln Ser Tyr Leu Asp Ser
  1               5                  10                  15

Gly Ile His Ser Gly Ala Thr Thr Thr Ala Pro Ser Leu Ser
             20                  25                  30

<210> SEQ ID NO 60
<211> LENGTH: 102
<212> TYPE: PRT
<213> ORGANISM: Artificial Sequence
<220> FEATURE:
<223> OTHER INFORMATION: Description of Artificial Sequence:murine IP10
      linked to mature human MCP3
```

-continued

```
<400> SEQUENCE: 60

Met Asn Pro Ser Ala Ala Val Ile Phe Cys Leu Ile Leu Leu Gly Leu
1               5                   10                  15

Ser Gly Thr Gln Gly Ile Leu Asp Met Ala Gln Pro Val Gly Ile Asn
            20                  25                  30

Thr Ser Thr Thr Cys Cys Tyr Arg Phe Ile Asn Lys Lys Ile Pro Lys
        35                  40                  45

Gln Arg Leu Glu Ser Tyr Arg Arg Thr Thr Ser Ser His Cys Pro Arg
    50                  55                  60

Glu Ala Val Ile Phe Lys Thr Lys Leu Asp Lys Glu Ile Cys Ala Asp
65                  70                  75                  80

Pro Thr Gln Lys Trp Val Gln Asp Phe Met Lys His Leu Asp Lys Lys
                85                  90                  95

Thr Gln Thr Pro Lys Leu
            100

<210> SEQ ID NO 61
<211> LENGTH: 97
<212> TYPE: PRT
<213> ORGANISM: Artificial Sequence
<220> FEATURE:
<223> OTHER INFORMATION: Description of Artificial Sequence:human IP10
      linked to mature human MCP3

<400> SEQUENCE: 61

Met Asn Gln Thr Ala Ile Leu Ile Cys Cys Leu Ile Phe Leu Thr Leu
1               5                   10                  15

Ser Gly Ile Gln Gly Gln Pro Val Gly Ile Asn Thr Ser Thr Thr Cys
            20                  25                  30

Cys Tyr Arg Phe Ile Asn Lys Lys Ile Pro Lys Gln Arg Leu Glu Ser
        35                  40                  45

Tyr Arg Arg Thr Thr Ser Ser His Cys Pro Arg Glu Ala Val Ile Phe
    50                  55                  60

Lys Thr Lys Leu Asp Lys Glu Ile Cys Ala Asp Pro Thr Gln Lys Trp
65                  70                  75                  80

Val Gln Asp Phe Met Lys His Leu Asp Lys Lys Thr Gln Thr Pro Lys
                85                  90                  95

Leu

<210> SEQ ID NO 62
<211> LENGTH: 99
<212> TYPE: PRT
<213> ORGANISM: Homo sapiens
<220> FEATURE:
<223> OTHER INFORMATION: human MCP3 signal peptide and mature human MCP3

<400> SEQUENCE: 62

Met Lys Ala Ser Ala Ala Leu Leu Cys Leu Leu Leu Thr Ala Ala Ala
1               5                   10                  15

Phe Ser Pro Gln Gly Leu Ala Gln Pro Val Gly Ile Asn Thr Ser Thr
            20                  25                  30

Thr Cys Cys Tyr Arg Phe Ile Asn Lys Lys Ile Pro Lys Gln Arg Leu
        35                  40                  45

Glu Ser Tyr Arg Arg Thr Thr Ser Ser His Cys Pro Arg Glu Ala Val
    50                  55                  60

Ile Phe Lys Thr Lys Leu Asp Lys Glu Ile Cys Ala Asp Pro Thr Gln
65                  70                  75                  80

Lys Trp Val Gln Asp Phe Met Lys His Leu Asp Lys Lys Thr Gln Thr
```

85                  90                  95

Pro Lys Leu

<210> SEQ ID NO 63
<211> LENGTH: 35
<212> TYPE: PRT
<213> ORGANISM: Artificial Sequence
<220> FEATURE:
<223> OTHER INFORMATION: Description of Artificial Sequence:human tissue
      plasminogen activator (tPA) signal peptide and
      propeptide, tPA secretory signal

<400> SEQUENCE: 63

Met Asp Ala Met Lys Arg Gly Leu Cys Cys Val Leu Leu Leu Cys Gly
 1               5                  10                  15

Ala Val Phe Val Ser Pro Ser Gln Glu Ile His Ala Arg Phe Arg Arg
            20                  25                  30

Gly Ala Arg
        35

<210> SEQ ID NO 64
<211> LENGTH: 380
<212> TYPE: PRT
<213> ORGANISM: Artificial Sequence
<220> FEATURE:
<223> OTHER INFORMATION: Description of Artificial Sequence:human
      lysosomal associated membrane protein 1 (LAMP-1) signal
      peptide and luminal domain

<400> SEQUENCE: 64

Met Ala Pro Arg Ser Ala Arg Arg Pro Leu Leu Leu Leu Leu Leu Leu
 1               5                  10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Ala Pro Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn

```
                            225                 230                 235                 240
Leu Thr Tyr Glu Arg Lys Asp Asn Thr Thr Val Thr Arg Leu Leu Asn
                    245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser
    370                 375                 380

<210> SEQ ID NO 65
<211> LENGTH: 36
<212> TYPE: PRT
<213> ORGANISM: Artificial Sequence
<220> FEATURE:
<223> OTHER INFORMATION: Description of Artificial Sequence:human
      lysosomal associated membrane protein 1 (LAMP-1)
      transmembrane domain and cytoplasmic tail

<400> SEQUENCE: 65

Thr Leu Ile Pro Ile Ala Val Gly Gly Ala Leu Ala Gly Leu Val Leu
  1               5                  10                  15

Ile Val Leu Ile Ala Tyr Leu Val Gly Arg Lys Arg Ser His Ala Gly
             20                  25                  30

Tyr Gln Thr Ile
         35
```